(12) United States Patent
Yun et al.

(10) Patent No.: US 10,053,458 B2
(45) Date of Patent: Aug. 21, 2018

(54) PYRIMIDINE-2,4-DIAMINE DERIVATIVE AND ANTICANCER PHARMACEUTICAL COMPOSITION COMPRISING SAME AS EFFECTIVE INGREDIENT

(71) Applicant: KOREA RESEARCH INSTITUTE OF CHEMICAL TECHNOLOGY, Daejeon (KR)

(72) Inventors: Chang Soo Yun, Daejeon (KR); Hyoung Rae Kim, Daejeon (KR); Sung Yun Cho, Daejeon (KR); Hee Jung Jung, Daejeon (KR); Kwangho Lee, Daejeon (KR); Chong Hak Chae, Daejeon (KR); Chong Ock Lee, Seoul (KR); Chi Hoon Park, Daejeon (KR); Pilho Kim, Daejeon (KR); Jong Yeon Hwang, Jeollabuk-do (KR); Jae Du Ha, Daejeon (KR); Sun Joo Ahn, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/319,151

(22) PCT Filed: May 21, 2015

(86) PCT No.: PCT/KR2015/005118
§ 371 (c)(1),
(2) Date: Dec. 15, 2016

(87) PCT Pub. No.: WO2015/194764
PCT Pub. Date: Dec. 23, 2015

(65) Prior Publication Data
US 2017/0145007 A1 May 25, 2017

(30) Foreign Application Priority Data

Jun. 17, 2014 (KR) ........................ 10-2014-0073555

(51) Int. Cl.
*C07D 471/04* (2006.01)
*C07D 405/14* (2006.01)
*C07D 401/14* (2006.01)
*C07D 403/12* (2006.01)
*C07D 401/12* (2006.01)

(52) U.S. Cl.
CPC ......... *C07D 471/04* (2013.01); *C07D 401/12* (2013.01); *C07D 401/14* (2013.01); *C07D 403/12* (2013.01); *C07D 405/14* (2013.01)

(58) Field of Classification Search
CPC .. C07D 471/04; C07D 405/14; C07D 401/12; C07D 401/14; C07D 403/12
See application file for complete search history.

(56) References Cited

U.S. PATENT DOCUMENTS 8,148,391 B2 * 4/2012 Ahmed ................ C07D 239/48
514/275
8,148,392 B2 4/2012 Huesca et al.

FOREIGN PATENT DOCUMENTS

| WO | 2008/073687 A2 | 6/2008 |
| WO | 2008073687 | * 6/2008 |
| WO | 2009/126515 A1 | 10/2009 |
| WO | 2009/143389 A1 | 11/2009 |
| WO | 2012106540 | * 4/2012 |
| WO | 2012/106540 A1 | 8/2012 |

OTHER PUBLICATIONS

Achary Raghavendra et al., Discovery of novel tetrahydroisoquinoline-containing pyrimidines as ALK inhibitors; Bio & Drug Discovery Division, Korean Research Institute of Chemical Technology, Deajeon, 305-600, S. Korea; Bioorganic & Medicinal Chemistry (2016), 24 (2), 207-219.*
Gregory R. Ott, et al, "Discovery of a Potent Inhibitor of Anaplastic Lymphoma Kinase with in Vivo Antitumor Activity", ACS Medicinal Chemistry Letters, vol. 1, pp. 493-498, Published on Web Date: Sep. 1, 2010.
International Search Report dated Feb. 29, 2016; PCT/KR2015/005118.

* cited by examiner

*Primary Examiner* — Alexander R Pagano
*Assistant Examiner* — Ebenezer O Sackey
(74) *Attorney, Agent, or Firm* — Ladas & Parry LLP; Loren K. Thompson

(57) ABSTRACT

The present invention relates to a pyrimidine-2,4-diamine derivative or a pharmaceutically acceptable salt thereof, and a pharmaceutical composition for prevention or treatment of cancer comprising the same as an effective ingredient. A compound according to the present invention has the good effect of inhibiting anaplastic lymphoma kinase (ALK) activity, whereby a therapeutic effect on cancer cells having an anaplastic lymphoma kinase (ALK) fusion protein such as EML4-ALK, NPM-ALK, etc. can be enhanced and it is expected that a recurrence of cancer will be effectively inhibited. As such, the compound can be effectively used in a pharmaceutical composition for prevention or treatment of cancer.

10 Claims, No Drawings

PYRIMIDINE-2,4-DIAMINE DERIVATIVE AND ANTICANCER PHARMACEUTICAL COMPOSITION COMPRISING SAME AS EFFECTIVE INGREDIENT

TECHNICAL FIELD

The present invention relates to a pyrimidine-2,4-diamine derivative or a pharmaceutically acceptable salt thereof, and a pharmaceutical composition for preventing or treating cancer comprising the same as an effective ingredient.

BACKGROUND ART

Cancer is a cell mass composed of undifferentiated cells that ignore necessary conditions in tissue and undergo unlimited proliferation unlike normal cells that are capable of performing regular and temperate proliferation and inhibition according to the individual's needs, and is also called tumor. Cancer cells with the unlimited proliferation penetrate into surrounding tissue, and in more serious cases, the cancer cells involve metastasis to other organs of the body, accompanied by severe pain, which results in an incurable disease eventually causing death.

The American Cancer Society reported that there are 12 million patients or more newly diagnosed with cancer globally in 2007, with 7.6 million deaths, and about 20,000 deaths every day from cancer. In Korea, National Statistical Office reported in 2006 that the leading cause of death was from cancer. Accordingly, development of a tumor treatment agent having excellent therapeutic effect is urgently required to reduce mental and physical pain caused by cancer development and disease, and to improve the quality of life.

Despite many efforts, a mechanism in which normal cells are transformed into cancer cells has not been correctly identified. However, external factors such as environmental factors, chemical substances, radiation, viruses, etc., and internal factors such as genetic and immunological factors, etc., are complexly entangled, resulting in cancer. Genes involved in the development of cancer include oncogenes and tumor suppressor genes, and cancer occurs when balance between the oncogenes and the tumor suppressor genes are collapsed by external factors or internal factors as described above.

Cancer is largely classified into blood cancer and solid cancer, and occurs in almost all parts of the body such as lung cancer, stomach cancer, breast cancer, oral cancer, liver cancer, uterine cancer, esophageal cancer, skin cancer, etc. As treatment methods thereof, a small number of target therapeutic agents such as Gleevec or Herceptin have been used for treatment of specific cancers. However, surgery, radiation therapy, and chemotherapy that inhibits cell proliferation have been main anticancer treatment methods until now. However, since these main methods are not target therapeutic agents, the biggest problems of conventional chemotherapy are cytotoxic side effects and drug resistance, which are main factors that eventually result in failure of the treatment despite successful initial response by a chemotherapeutic agent. Therefore, in order to overcome the limitations of these chemotherapeutic agents, it is necessary to continuously develop a target therapeutic agent with clear anticancer mechanism.

Accordingly, many studies on specific molecular biologic factors involved in tumorigenesis for developing the target therapeutic agent have been conducted, and in particular, molecular biological factors are variously used to predict prognosis of cancer, or to determine performance of chemotherapy and radiation therapy.

Gleevec is one of the representative drugs that most inhibit a tyrosine kinase receptor, one of the specific molecular biological factors. Gleevec has an anticancer effect by inhibiting an action of the Bcr-Abl fusion gene formed by chromosome translocation in the Philadelphia chromosome observed in chronic myelogenous leukemia, and has achieved satisfactory results in patients with chronic myeloid leukemia, as a tyrosine kinase inhibitor. Then, the drugs that have anticancer effects as the tyrosine kinase inhibitors, include gefitinib and erlotinib that are epidermal growth factor receptor (EGFR) tyrosine kinase inhibitors used as non-small cell lung cancer therapeutic agents, and sorafenib and sunitinib used as kidney cell carcinoma therapeutic agents. However, these drugs are known to have side effects such as hemorrhaging, heart attack, heart failure, liver failure, etc.

Recently, anaplastic lymphoma kinase (ALK) has been found in many human tumors and has been studied as a target of target treatment.

The carcinogenic process of the ALK is known to be a fusion gene of ALK-NPM (nucleophosmin), which is mainly observed in anaplastic large cell lymphoma. When the ALK is activated by gene fusion, tyrosine kinase in the ALK acts abnormally and causes cancer. Specifically, the abnormally activated ALK induces cell proliferation, and interferes with apoptosis, thereby preventing cell death, and rearranges cell skeletons, and modifies cell morphology. Cancer geneticization of the ALK is made by interaction with a downstream molecule which is a target material of the ALK, wherein the downstream molecule is a material that mediates intracellular signaling. The ALK is linked to other tyrosine kinases that are normal or are subjected to cancer geneticization to induce interaction or to activate a variety of other pathways.

In particular, the ALK gene is fused with EML4 (echinoderm microtubule-associated protein-like 4) gene in lung cancer cell to produce active tyrosine kinase (EML4-ALK), wherein it has been known that a cancerous ability of the EML4-ALK is dependent on enzyme activity, and further, Mosse et al., have reported about 26% of the ALK gene amplification in 491 neuroblastoma specimens. In addition, the ALK gene has been found to be expressed in a number of non-hematopoietic cell tumors such as large B-cell lymphoma, systemic histiocytosis, inflammatory myoblastic sarcoma, esophageal squamous cell carcinoma, non-small cell lung cancer, rhabdomyosarcoma, myoblastoma, breast cancer, and melanoma cell lines. Various kinds of the ALK fusion proteins have been commonly found in an inflammatory bone marrow fibroblastoma tumor which is a rare disease, and thus, these fusion proteins are thought to be deeply involved in the development of tumors.

Thus, a therapeutic agent targeting the ALK-NPM that aims the treatment of cancer has been developed by blocking an activation pathway of the ALK. Recently, Crizotinib (PF-02341066), one of the small molecule tyrosine kinase inhibitor which was developed as a selective inhibitor of tumorigenic mutation by Pfizer, is known to be effective in the treatment of non-small cell lung cancer as ATP-competent c-Met/HGFR and the ALK inhibitor, and was approved by the FDA in 2011 as a new drug.

Further, NVP-TAE684, LDK-378 from Novartis, and CH5424802 from Chugai are known to have an effect of reducing a tumor size in neuroblastoma cell lines in addition to anaplastic large cell lymphoma cell lines.

Patent Document 1 developed a therapeutic candidate material having various skeletons has been developed for the purpose of inhibiting an activity of conventional ALK, and disclosed that a pyrimidine derivative selectively inhibits the ALK, which is capable of being developed as an anticancer agent.

Therefore, the present inventors have made efforts to develop a compound exhibiting the effect of inhibiting an ALK activity, and found that a pyrimidine-2,4-diamine derivative having a specific structure had a remarkably excellent effect of inhibiting the ALK activity to be useful as an agent for preventing or treating cancer, and as a result, completed the present invention.

RELATED ART DOCUMENT (Patent Document 1) WO 2009143389 A1

DISCLOSURE

Technical Problem

An object of the present invention is to provide a pyrimidine-2,4-diamine derivative, an optical isomer thereof, or a pharmaceutically acceptable salt thereof.

Another object of the present invention is to provide a method of preparing the pyrimidine-2,4-diamine derivative.

Still another aspect of the present invention provides a pharmaceutical composition for preventing or treating cancer containing the pyrimidine-2,4-diamine derivative, an optical isomer thereof, or a pharmaceutically acceptable salt thereof, as an effective ingredient.

Still another aspect of the present invention provides a pharmaceutical composition for preventing or treating diseases caused by an anaplastic lymphoma kinase (ALK) hyperactivity, containing the pyrimidine-2,4-diamine derivative, an optical isomer thereof, or a pharmaceutically acceptable salt thereof, as an effective ingredient.

Still another aspect of the present invention provides an anaplastic lymphoma kinase (ALK) inhibitor containing the pyrimidine-2,4-diamine derivative, an optical isomer thereof, or a pharmaceutically acceptable salt thereof, as an effective ingredient.

Technical Solution

In one general aspect, there are provided a compound represented by Chemical Formula 1 below, an optical isomer thereof, or a pharmaceutically acceptable salt thereof:

[Chemical Formula 1]

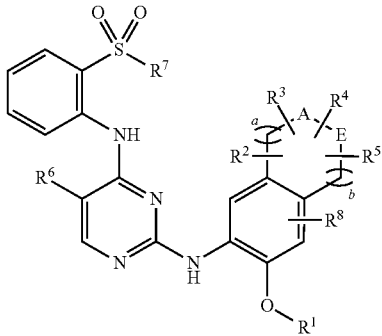

in Chemical Formula 1,

A and E are independently C, O, N, or S;

a and b are independently an integer of 0 to 4;

$R^1$ is —H, —OH, halogen, or $C_{1-10}$ straight or branched chain alkyl unsubstituted or substituted with at least one halogen;

$R^2$, $R^3$, $R^4$ are $R^5$ are independently —H, —OH, =O, $C_{1-10}$ straight or branched chain alkyl unsubstituted or substituted with at least one halogen, $C_{1-10}$ straight or branched chain alkyl unsubstituted or substituted with at least one hydroxy group, $C_{1-10}$ straight or branched chain alkoxy, unsubstituted or substituted 3-10 membered heterocycloalkyl including at least one heteroatom selected from the group consisting of N, O, and S, $C_{1-10}$ straight or branched chain alkyl substituted with unsubstituted $C_{6-10}$ aryl, —C(=O)$R^9$, —C(=O)NH$R^{10}$, —C(=O)(CH$_2$)$_r$OH, —SO$_2$NR$^{11}$R$^{12}$, —(CH$_2$)$_p$NR$^{13}$R$^{14}$, —(CH$_2$)$_q$C(=O)NR$^{15}$R$^{16}$, or —C(=O)(CH$_2$)$_k$NR$^{17}$R$^{18}$, wherein the $R^9$, $R^{10}$, $R^{11}$, $R^{12}$, $R^{13}$, $R^{14}$, $R^{15}$, $R^{16}$, $R^{17}$ and $R^{18}$ are independently —H or $C_{1-10}$ straight or branched chain alkyl unsubstituted or substituted with at least one halogen, the r, p, q and k are independently an integer of 0 to 10, and the substituted 3-10 membered heterocycloalkyl is 3-10 membered heterocycloalkyl substituted with at least one substituent selected from the group consisting of $C_{1-5}$ straight or branched chain alkyl unsubstituted or substituted with at least one halogen, halogen, nitrile and nitro;

two substituents of the $R^2$, $R^3$, $R^4$, and $R^5$ may be simultaneously substituted on carbon atoms at the same position to form unsubstituted $C_{3-10}$ cycloalkyl, together with the carbon atoms to which they are connected;

two substituents of the $R^2$, $R^3$, $R^4$, and $R^5$ may be each substituted on adjacent atoms to form unsubstituted or substituted 5-10 membered heterocycloalkyl including at least one heteroatom selected from the group consisting of N, O, and S, together with the atoms to which they are connected;

wherein the substituted 5-10 membered heterocycloalkyl is 5-10 membered heterocycloalkyl substituted with one =O;

$R^6$ is —H, halogen, or $C_{1-10}$ straight or branched chain alkyl unsubstituted or substituted with at least one halogen;

$R^7$ is $C_{1-10}$ straight or branched chain alkyl; and $R^8$ is halogen.

In another general aspect, there is provided a method of preparing the compound represented by Chemical Formula 1 as shown in Reaction Scheme 1 below, the method including:

reacting a compound represented by Chemical Formula 2 with a compound represented by Chemical Formula 3 to prepare a compound represented by Chemical Formula 4 (Step 1);

substituting a -Boc group of the compound represented by Chemical Formula 4 obtained in step 1 with hydrogen to prepare a compound represented by Chemical Formula 5 (Step 2); and reacting the compound represented by Chemical Formula obtained in step 2 with a compound represented by Chemical Formula 6 to prepare the compound represented by Chemical Formula 1 (Step 3):

[Reaction Scheme 1]

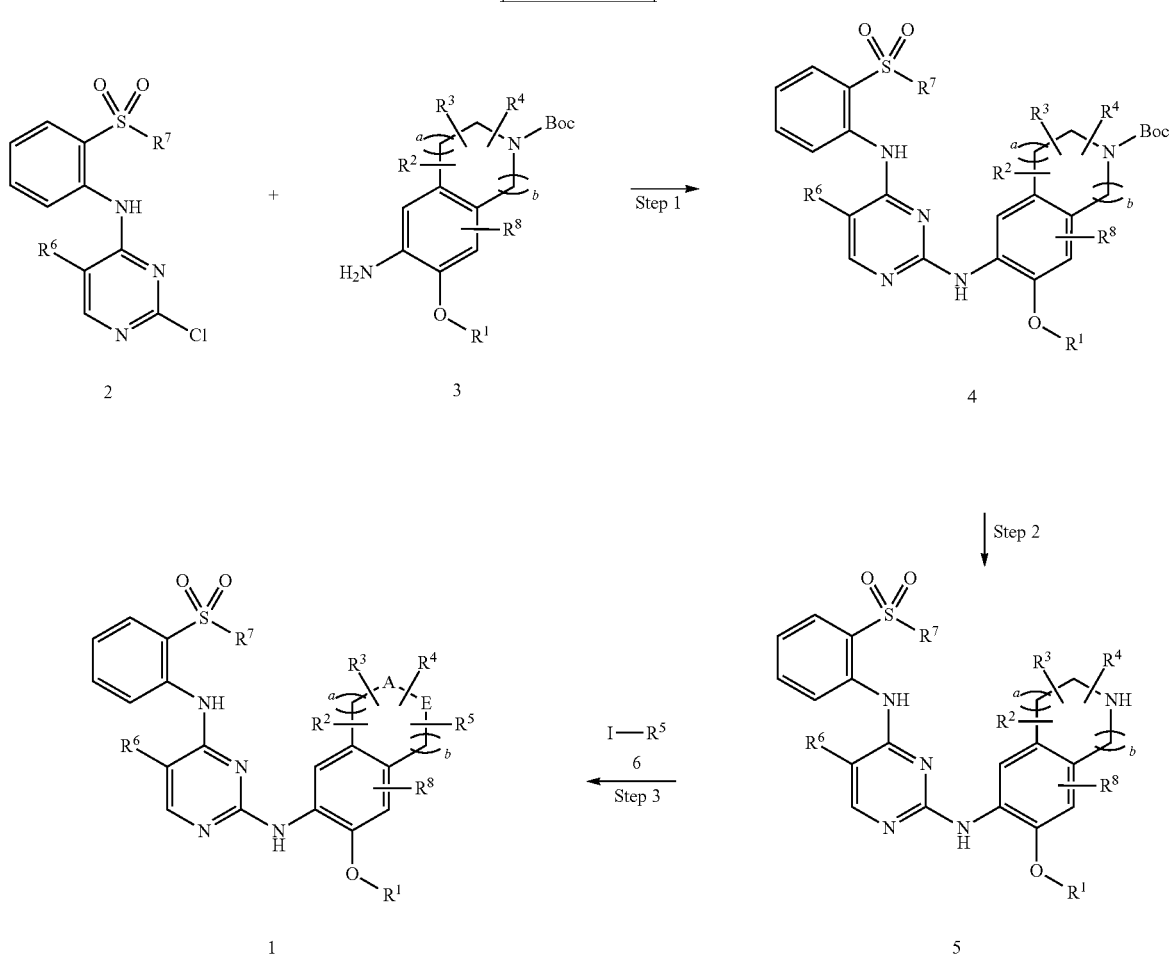

in Reaction Scheme 1,
-Boc is

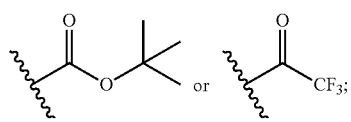

and
$R^1, R^2, R^3, R^4, R^5, R^6, R^7, R^8$, A, E, a, and b are the same as defined in Chemical Formula 1 above.

Further, in another general aspect, there is provided a pharmaceutical composition for preventing or treating cancer containing the compound represented by Chemical Formula 1 above, an optical isomer thereof, or a pharmaceutically acceptable salt thereof, as an effective ingredient.

In addition, in another general aspect, there is provided a pharmaceutical composition for preventing or treating diseases caused by an anaplastic lymphoma kinase (ALK) hyperactivity, containing the compound represented by Chemical Formula 1 above, an optical isomer thereof, or a pharmaceutically acceptable salt thereof, as an effective ingredient.

Further, in another general aspect, there is provided an anaplastic lymphoma kinase (ALK) inhibitor containing the compound represented by Chemical Formula 1 above, an optical isomer thereof, or a pharmaceutically acceptable salt thereof, as an effective ingredient.

Advantageous Effects

The compound according to the present invention has the remarkably excellent effect of inhibiting the activity of the anaplastic lymphoma kinase (ALK) to have an improved therapeutic effect on cancer cells having the ALK fusion protein such as EML4-ALK, NPM-ALK, etc., and to be effectively used in preventing recurrence of cancer. Therefore, the compound of the present invention may be useful as a pharmaceutical composition for preventing or treating cancer.

BEST MODE

Hereinafter, the present invention will be described in detail.

The present invention provides a compound represented by Chemical Formula 1 below, an optical isomer thereof, or a pharmaceutically acceptable salt thereof.

[Chemical Formula 1]

in Chemical Formula 1,

A and E are independently C, O, N, or S;

a and b are independently an integer of 0 to 4;

$R^1$ is —H, —OH, halogen, or $C_{1-10}$ straight or branched chain alkyl unsubstituted or substituted with at least one halogen;

$R^2$, $R^3$, $R^4$ are $R^5$ are independently —H, —OH, =O, $C_{1-10}$ straight or branched chain alkyl unsubstituted or substituted with at least one halogen, $C_{1-10}$ straight or branched chain alkyl unsubstituted or substituted with at least one hydroxy group, $C_{1-10}$ straight or branched chain alkoxy, unsubstituted or substituted 3-10 membered heterocycloalkyl including at least one heteroatom selected from the group consisting of N, O, and S, $C_{1-10}$ straight or branched chain alkyl substituted with unsubstituted $C_{6-10}$ aryl, —C(=O)$R^9$, —C(=O)NHR$^{10}$, —C(=O)(CH$_2$)$_r$OH, —SO$_2$NR$^{11}$R$^{12}$, —(CH$_2$)$_p$NR$^{13}$R$^{14}$, —(CH$_2$)$_q$C(=O)NR$^{15}$R$^{16}$ or —C(=O)(CH$_2$)$_k$NR$^{17}$R$^{18}$, wherein the $R^9$, $R^{10}$, $R^{11}$, $R^{12}$, $R^{13}$, $R^{14}$, $R^{15}$, $R^{16}$, $R^{17}$ and $R^{18}$ are independently —H or $C_{1-10}$ straight or branched chain alkyl unsubstituted or substituted with at least one halogen, the r, p, q and k are independently an integer of 0 to 10, and the substituted 3-10 membered heterocycloalkyl is 3-10 membered heterocycloalkyl substituted with at least one substituent selected from the group consisting of $C_{1-5}$ straight or branched chain alkyl unsubstituted or substituted with at least one halogen, halogen, nitrile and nitro;

two substituents of the $R^2$, $R^3$, $R^4$, and $R^5$ may be simultaneously substituted on carbon atoms at the same position to form unsubstituted $C_{3-10}$ cycloalkyl, together with the carbon atoms to which they are connected;

two substituents of the $R^2$, $R^3$, $R^4$, and $R^5$ may be each substituted on adjacent atoms to form unsubstituted or substituted 5-10 membered heterocycloalkyl including at least one heteroatom selected from the group consisting of N, O, and S, together with the atoms to which they are connected;

wherein the substituted 5-10 membered heterocycloalkyl is 5-10 membered heterocycloalkyl substituted with one =O;

$R^6$ is —H, halogen, or $C_{1-10}$ straight or branched chain alkyl unsubstituted or substituted with at least one halogen;

$R^7$ is $C_{1-10}$ straight or branched chain alkyl; and $R^8$ is halogen.

Preferably,

A and E are independently C, N, or S;

a and b are independently an integer of 0 to 3; and $R^1$ is —H, —OH, halogen, or $C_{1-5}$ straight or branched chain alkyl unsubstituted or substituted with at least one halogen;

$R^2$, $R^3$, $R^4$ are $R^5$ are independently —H, —OH, =O, $C_{1-5}$ straight or branched chain alkyl unsubstituted or substituted with at least one halogen, $C_{1-5}$ straight or branched chain alkyl unsubstituted or substituted with at least one hydroxy group, $C_{1-5}$ straight or branched chain alkoxy, unsubstituted or substituted 3-8 membered heterocycloalkyl including at least one heteroatom selected from the group consisting of N, O, and S, $C_{1-5}$ straight or branched chain alkyl substituted with unsubstituted $C_{6-8}$ aryl, —C(=O)$R^9$, —C(=O)NHR$^{10}$, —C(=O)(CH$_2$)$_r$OH, —SO$_2$NR$^{11}$R$^{12}$, —(CH$_2$)$_p$NR$^{13}$R$^{14}$, —(CH$_2$)$_q$C(=O)NR$^{15}$R$^{16}$, or —C(=O)(CH$_2$)$_k$NR$^{17}$R$^{18}$, wherein the $R^9$, $R^{10}$, $R^{11}$, $R^{12}$, $R^{13}$, $R^{14}$, $R^{15}$, $R^{16}$, $R^{17}$ and $R^{18}$ are independently —H or $C_{1-5}$ straight or branched chain alkyl unsubstituted or substituted with at least one halogen, the r, p, q and k are independently an integer of 0 to 5, and the substituted 3-8 membered heterocycloalkyl is 3-8 membered heterocycloalkyl substituted with at least one substituent selected from the group consisting of $C_{1-5}$ straight or branched chain alkyl unsubstituted or substituted with at least one halogen, halogen, nitrile and nitro;

two substituents of the $R^2$, $R^3$, $R^4$, and $R^5$ may be simultaneously substituted on carbon atoms at the same position to form unsubstituted $C_{3-8}$ cycloalkyl, together with the carbon atoms to which they are connected;

two substituents of the $R^2$, $R^3$, $R^4$, and $R^5$ may be each substituted on adjacent atoms to form unsubstituted or substituted 5-8 membered heterocycloalkyl including at least one heteroatom selected from the group consisting of N, O, and S, together with the atoms to which they are connected;

wherein the substituted 5-8 membered heterocycloalkyl is 5-8 membered heterocycloalkyl substituted with one =O;

$R^6$ is —H, halogen, or $C_{1-5}$ straight or branched chain alkyl unsubstituted or substituted with at least one halogen;

$R^7$ is $C_{1-5}$ straight or branched chain alkyl; and $R^8$ is —F, —Cl or —Br.

More preferably,

A and E are independently C, or N;

a and b are independently an integer of 0 to 2;

$R^1$ is methyl, difluoromethyl, ethyl, isopropyl, isobutyl or sec-butyl;

$R^2$, $R^3$, $R^4$ and $R^5$ are independently —H, methyl, ethyl, n-propyl, isopropyl, trifluoromethyl, benzyl, =O, -continued

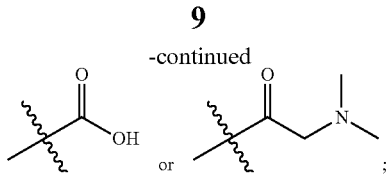

two substituents of the R², R³, R⁴, and R⁵ may be simultaneously substituted on carbon atoms at the same position to form unsubstituted cyclopropyl, cyclopentyl or cyclohexyl, together with the carbon atoms to which they are connected;

two substituents of the R², R³, R⁴, and R⁵ may be each substituted on adjacent atoms to form unsubstituted or substituted 6 membered heterocycloalkyl including at least one heteroatom selected from the group consisting of N, O, and S, together with the atoms to which they are connected;

wherein the substituted 6 membered heterocycloalkyl is 6 membered heterocycloalkyl substituted with one =O;

R⁶ is —Cl;
R⁷ is isopropyl; and
R⁸ is —Cl or —Br.

Preferable examples of the compound represented by Chemical Formula 1 according to the present invention include the following compounds:

(1) 5-chloro-N4-(2-(isopropylsulfonyl)phenyl)-N2-(6-methoxyisoindolin-5-yl)pyrimidine-2,4-diamine;
(2) 5-chloro-N4-(2-(isopropylsulfonyl)phenyl)-N2-(7-methoxy-1,2,3,4-tetrahydroisoquinolin-6-yl)pyrimidine-2,4-diamine;
(3) 5-chloro-N4-(2-(isopropylsulfonyl)phenyl)-N2-(7-methoxy-2-methyl-1,2,3,4-tetrahydroisoquinolin-6-yl)pyrimidine-2,4-diamine;
(4) 5-chloro-N4-(2-(isopropylsulfonyl)phenyl)-N2-(7-methoxy-2-ethyl-1,2,3,4-tetrahydroisoquinolin-6-yl)pyrimidine-2,4-diamine;
(5) 5-chloro-N4-(2-(isopropylsulfonyl)phenyl)-N2-(7-methoxy-2-hydroxyethyl-1,2,3,4-tetrahydroisoquinolin-6-yl)pyrimidine-2,4-diamine;
(6) 5-chloro-N4-(2-(isopropylsulfonyl)phenyl)-N2-(7-methoxy-2-acetyl-1,2,3,4-tetrahydroisoquinolin-6-yl)pyrimidine-2,4-diamine;
(7) 6-(5-chloro-4-(2-(isopropylsulfonyl)phenylamino)pyrimidin-2-yl)amino-N-ethyl-7-methoxy-3,4-dihydroisoquinoline-2(1H)-carboxamide;
(8) 1-6-(5-chloro-4-(2-(isopropylsulfonyl)phenylamino)pyrimidin-2-yl)amino-7-methoxy-3,4-dihydroisoquinolin-2(1H)-yl-2-hydroxyethane-1-one;
(9) 6-(5-chloro-4-(2-(isopropylsulfonyl)phenylamino)pyrimidin-2-yl)amino-7-methoxy-3,4-dihydroisoquinoline-2(1H)-sulfonamide;
(10) 2-(6-(5-chloro-4-(2-(isopropylsulfonyl)phenylamino)pyrimidin-2-yl)amino-7-methoxy-3,4-dihydroisoquinolin-2(1H)-yl)-N,N-dimethylacetamide;
(11) 1-(6-(5-chloro-4-(2-(isopropylsulfonyl)phenylamino)pyrimidin-2-yl)amino-7-methoxy-4,4-dimethyl-3,4-dihydroisoquinolin-2(1H)-yl)-2,2,2-trifluoroethane-1-one;
(12) 5-chloro-N4-(2-(isopropylsulfonyl)phenyl)-N2-(7-methoxy-4,4-dimethyl-1,2,3,4-tetrahydroisoquinolin-6-yl)pyrimidine-2,4-diamine;
(13) 1-(6'-(5-chloro-4-(2-(isopropylsulfonyl)phenylamino)pyrimidin-2-yl)amino-7-methoxy-1'H-spiro[cyclopentane-1,4'-isoquinoline]-2'(3'H)-yl)-2,2,2-trifluoroethane-1-one;
(14) 5-chloro-N4-(2-(isopropylsulfonyl)phenyl)-N2-(7-methoxy-2',3'-dihydro-1'H-spiro[cyclopentane-1,4'-isoquinoline]-6'-yl)pyrimidine-2,4-diamine;
(15) 1-(6-(5-chloro-4-(2-(isopropylsulfonyl)phenylamino)pyrimidin-2-yl)amino-7-methoxy-1'H-spiro[cyclohexane-1,4'-isoquinoline]-2'(3'H)-yl)-2,2,2-trifluoroethane-1-one;
(16) 5-chloro-N4-(2-(isopropylsulfonyl)phenyl)-N2-(7-methoxy-2',3'-dihydro-1'H-spiro[cyclohexane-1,4'-isoquinoline]-6'-yl)pyrimidine-2,4-diamine;
(17) 1-(6-(5-chloro-4-(2-(isopropylsulfonyl)phenylamino)pyrimidin-2-yl)amino-7-isopropoxy-3,4-dihydroisoquinolin-2(1H)-yl)-2,2,2-trifluoroethane-1-one;
(18) 5-chloro-N4-(2-(isopropylsulfonyl)phenyl)-N2-(7-isopropoxy-1,2,3,4-tetrahydroisoquinolin-6-yl)pyrimidine-2,4-diamine;
(19) 1-(6-(5-chloro-4-(2-(isopropylsulfonyl)phenylamino)pyrimidine-2-yl)amino-7-isobutoxy-3,4-dihydroisoquinolin-2(1H)-yl)-2,2,2-trifluoroethane-1-one;
(20) 5-chloro-N4-(2-(isopropylsulfonyl)phenyl)-N2-(7-isobutoxy-1,2,3,4-tetrahydroisoquinolin-6-yl)pyrimidine-2,4-diamine;
(21) 1-(7-(sec-butoxy)-6-(5-chloro-4-(2-(isopropylsulfonyl)phenylamino)pyrimidin-2-yl)amino-3,4-dihydroisoquinolin-2(1H)-yl)-2,2, 2-trifluoroethane-1-one;
(22) 5-chloro-N2-(7-(sec-butoxy)-1,2,3,4-tetrahydroisoquinolin-6-yl)-N4-(2-(isopropylsulfonyl)phenyl)pyrimidine-2,4-diamine;
(23) 5-chloro-N2-(2-(2-(dimethylaminoethyl)-7-methoxy-1,2,3,4-tetrahydroisoquinolin-6-yl)-N4-2-(isopropylsulfonyl)phenyl)pyrimidine-2,4-diamine;
(24) 5-chloro-N4-2-(isopropylsulfonyl)phenyl)-N2-(7-methoxy-2-(piperidine-4-yl)-1,2,3,4-tetrahydroisoquinolin-6-yl)pyrimidine-2,4-diamine;
(25) 5-chloro-N4-(2-(isopropylsulfonyl)phenyl)-N2-(7-methoxy-1-methyl-1,2,3,4-tetrahydroisoquinolin-6-yl)pyrimidine-2,4-diamine;
(26) 5-chloro-N4-(2-(isopropylsulfonyl)phenyl)-N2-(7-methoxy-1-trifluoromethyl-1,2,3,4-tetrahydroisoquinolin-6-yl)pyrimidine-2,4-diamine;
(27) 5-chloro-N4-2-(isopropylsulfonyl)phenyl)-N2-(7-methoxy-1-ethyl-1,2,3,4-tetrahydroisoquinolin-6-yl)pyrimidine-2,4-diamine;
(28) 5-chloro-N4-2-(isopropylsulfonyl)phenyl)-N2-(7-methoxy-1-isopropyl-1,2,3,4-tetrahydroisoquinolin-6-yl)pyrimidine-2,4-diamine;
(29) 1-(6'-(5-chloro-4-(2-(isopropylsulfonyl)phenylamino)pyrimidin-2-yl)amino-7'-methoxy-1'-methyl-1',4'-dihydro-2'H-spiro[cyclopropane-1,3'-isoquinoline]-2'-yl)-2, 2, 2-trifluoroethane-1-one;
(30) 5-chloro-N4-(2-(isopropylsulfonyl)phenyl)-N2-(7-methoxy-1'methyl-1',4'-dihydro-2'H-spiro[cyclopropane-1,3'-isoquinoline]-6'-yl)pyrimidine-2,4-diamine;
(31) 5-chloro-N4-(2-(isopropylsulfonyl)phenyl)-N2-(2-benzyl-7-methoxy-1,1-dimethyl-1,2,3,4-tetrahydroisoquinolin-6-yl)pyrimidine-2,4-diamine;
(32) 1-(6-(5-chloro-4-(2-(isopropylsulfonyl)phenylamino)pyrimidin-2-yl)amino-7-methoxy-1,1-dimethyl-3,4-dihydroisoquinolin-2(1H)-yl)-2,2,2-trifluoroethane-1-one;
(33) 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine;
(34) 5-chloro-N4-(2-(isopropylsulfonyl)phenyl)-N2-(6-methoxy-1,2,3,4-tetrahydroisoquinolin-7-yl)pyrimidine-2,4-diamine;
(35) 5-chloro-N4-(2-(isopropylsulfonyl)phenyl)-N2-(6-methoxy-2-methyl-1,2,3,4-tetrahydroisoquinolin-7-yl)pyrimidine-2,4-diamine;

(36) 2-(7-(5-chloro-4-(2-(isopropylsulfonyl)phenylamino)pyrimidin-2-yl)amino)-6-methoxy-3,4-dihydroisoquinolin-2(1H)-yl)-ethane-1-ol;
(37) 1-(7-(5-chloro-4-(2-(isopropylsulfonyl)phenylamino)pyrimidin-2-yl)amino)-6-methoxy-3,4-dihydroisoquinolin-2(1H)-yl)ethane-1-one;
(38) 7-(5-chloro-4-(2-(isopropylsulfonyl)phenylamino)pyrimidin-2-yl)amino)-N-ethyl-6-methoxy-3,4-dihydroisoquinolin-2(1H)-carboxamide;
(39) 1-(7-(5-chloro-4-(2-(isopropylsulfonyl)phenylamino)pyrimidin-2-yl)amino)-6-methoxy-3,4-dihydroisoquinolin-2(1H)-yl)-2-hydroxyethane-1-one;
(40) 7-(5-chloro-4-(2-(isopropylsulfonyl)phenylamino)pyrimidin-2-yl)amino)-6-methoxy-3,4-dihydroisoquinoline-2(1H)-sulfonamide;
(41) 5-chloro-N4-(2-(isopropylsulfonyl)phenyl)-N2-(6-methoxy-2-ethyl-1,2,3,4-tetrahydroisoquinolin-7-yl)pyrimidine-2,4-diamine;
(42) 2-(7-(5-chloro-4-(2-(isopropylsulfonyl)phenylamino)pyrimidin-2-yl)amino)-6-methoxy-3,4-dihydroisoquinolin-2(1H)-yl)-N,N-dimethylacetamide;
(43) 5-chloro-N4-(2-(isopropylsulfonyl)phenyl)-N2-(2-(2-(dimethylaminoethyl)-6-methoxy-1,2,3,4-tetrahydroquinolin-7-yl)pyrimidine-2,4-diamine;
(44) 7-(5-chloro-4-(2-(isopropylsulfonyl)phenylamino)pyrimidin-2-yl)amino)-6-methoxy-3,4-dihydroisoquinoline-1(2H)-one;
(45) 5-chloro-N4-(2-(isopropylsulfonyl)phenyl)-N2-(6-methoxy-2-(piperidine-4-yl)-1,2,3,4-tetrahydroquinolin-7-yl)pyrimidine-2,4-diamine;
(46) 5-chloro-N4-(2-(isopropylsulfonyl)phenyl)-N2-(6-methoxy-1-methyl-1,2,3,4-tetrahydroquinolin-7-yl)pyrimidine-2,4-diamine;
(47) 5-chloro-N4-(2-(isopropylsulfonyl)phenyl)-N2-(6-methoxy-2,3,4,5-tetrahydro-1H-benzo[d]azepin-7-yl)pyrimidine-2,4-diamine;
(48) 7-((5-chloro-4-(2-(isopropylsulfonyl)phenylamino)pyrimidin-2-yl)amino)-8-methoxy-2,3,4,5-tetrahydro-1H-benzo[c]azepin-1-one;
(49) 5-chloro-N4-(2-(isopropylsulfonyl)phenyl)-N2-(3-ethyl-6-methoxy-2,3,4,5-tetrahydro-1H-benzo[d]azepin-7-yl)pyrimidine-2,4-diamine;
(50) 1-(7-((5-chloro-4-(2-(isopropylsulfonyl)phenylamino)pyrimidin-2-yl)amino)-6-methoxy-4,5-dihydro-1H-benzo[d]azepin-3(2H)-yl)ethanone;
(51) 1-(7-((5-chloro-4-(2-(isopropylsulfonyl)phenylamino)pyrimidin-2-yl)amino)-6-methoxy-4,5-dihydro-1H-benzo[d]azepin-3(2H)-yl)-2-hydroxyethanone;
(52) 2-(7-((5-chloro-4-(2-(isopropylsulfonyl)phenylamino)pyrimidin-2-yl)amino)-8-methoxy-4,5-dihydro-1H-benzo[d]azepin-3(2H)-yl) ethanol;
(53) 5-chloro-N4-(2-(isopropylsulfonyl)phenyl)-N2-(6-methoxy-3-(piperidine-4-yl)-2,3,4,5-tetrahydro-1H-benzo[d]azepin-7-yl)pyrimidine-2,4-diamine;
(54) 5-chloro-N4-(2-(isopropylsulfonyl)phenyl)-N2-(6-methoxy-3-(tetrahydro-2H-pyran-4yl)-2,3,4,5-tetrahydro-1H-benzo[d]azepin-7-yl)pyrimidine-2,4-diamine;
(55) 5-chloro-N4-(2-(isopropylsulfonyl)phenyl)-N2-(3-cyclobutyl-6-methoxy-2,3,4,5-tetrahydro-1H-benzo[d]azepin-7-yl)pyrimidine-2,4-diamine;
(56) 5-chloro-N4-(2-(isopropylsulfonyl)phenyl)-N2-(7-methoxy-2,3,4,5-tetrahydro-1H-benzo[c]azepin-8-yl)pyrimidine-2,4-diamine;
(57) 8-((5-chloro-4-(2-(isopropylsulfonyl)phenylamino)pyrimidine-2-yl)amino)-7-methoxy-2,3,4,5-tetrahydro-1H-benzo Ed azepin-1-one;
(58) 5-chloro-N4-(2-(isopropylsulfonyl)phenyl)-N2-(2-ethyl-7-methoxy-2,3,4,5-tetrahydro-1H-benzo[c]azepin-8-yl)pyrimidine-2,4-diamine;
(59) 1-(8-((5-chloro-4-(2-(isopropylsulfonyl)phenylamino)pyrimidin-2-yl)amino)-7-methoxy-4,5-dihydro-1H-benzo[c]azepin-2 (3H)-yl) ethanone;
(60) 1-(8-((5-chloro-4-(2-(isopropylsulfonyl)phenylamino)pyrimidin-2-yl)amino)-7-methoxy-4,5-dihydro-1H-benzo[c]azepin-2 (3H)-yl)-2-hydroxyethanone;
(61) 2-(8-((5-chloro-4-(2-(isopropylsulfonyl)phenylamino)pyrimidin-2-yl)amino)-7-methoxy-4,5-dihydro-1H-benzo[c]azepin-2 (3H)-yl)ethanol;
(62) 5-chloro-N4-(2-(isopropylsulfonyl)phenyl)-N2-(7-methoxy-2-(piperidin-4-yl)-2,3,4,5-tetrahydro-1H-benzo[c]azepin-8-yl)pyrimidine-2,4-diamine;
(63) 5-chloro-N4-(2-(isopropylsulfonyl)phenyl)-N2-(7-methoxy-2-(tetrahydro-2H-pyran-4-yl)-2,3,4,5-tetrahydro-1H-benzo[c]azepin-8-yl)pyrimidine-2,4-diamine;
(64) 5-chloro-N4-(2-(isopropylsulfonyl)phenyl)-N2-(7-methoxy-2-(oxetan-3-yl)-2,3,4,5-tetrahydro-1H-benzo[c]azepin-8-yl)pyrimidine-2,4-diamine;
(65) 5-chloro-N4-(2-(isopropylsulfonyl)phenyl)-N2-(8-methoxy-2,3,4,5-tetrahydro-1H-benzo[d]azepin-7-yl)pyrimidine-2,4-diamine;
(66) 7-((5-chloro-4-(2-(isopropylsulfonyl)phenylamino)pyrimidin-2-yl)amino)-8-methoxy-4,5-dihydro-1H-benzo[d]azepin-2 (3H)-one;
(67) 5-chloro-N4-(2-(isopropylsulfonyl)phenyl)-N2-(3-ethyl-8-methoxy-2,3,4,5-tetrahydro-1H-benzo[d]azepin-7-yl)pyrimidine-2,4-diamine;
(68) 1-(7-((5-chloro-4-(2-(isopropylsulfonyl)phenylamino)pyrimidin-2-yl)amino)-6-methoxy-4,5-dihydro-1H-benzo[d]azepin-3(2H)-yl)-2-hydroxyethanone;
(69) 5-chloro-N4-(2-(isopropylsulfonyl)phenylamino)pyrimidin-2-yl)amino)-N2-8-methoxy-4,5-dihydro-1H-benzo[d]azepin-3(2H)-yl)ethanol;
(70) 5-chloro-N4-(2-(isopropylsulfonyl)phenyl)-N2-(7-isopropoxy-1-methyl-1,2,3,4-tetrahydroisoquinolin-6-yl)pyrimidine-2,4-diamine;
(71) 5-chloro-N4-(2-(isopropylsulfonyl)phenyl)-N2-(7-isopropoxy-1,1-dimethyl-1,2,3,4-tetrahydroisoquinolin-6-yl)pyrimidine-2,4-diamine;
(72) 5-chloro-N4-(2-(isopropylsulfonyl)phenyl)-N2-(6-methoxy-1,1-dimethyl-1,2,3,4-tetrahydroisoquinolin-7-yl)pyrimidine-2,4-diamine;
(73) 5-chloro-N4-(2-(isopropylsulfonyl)phenyl)-N2-(1-ethyl-7-methoxy-1-methyl-1,2,3,4-tetrahydroisoquinolin-6-yl)pyrimidine-2,4-diamine;
(74) 5-chloro-N4-(2-(isopropylsulfonyl)phenyl)-N2-(1,1-diethyl-7-methoxy-1,2,3,4-tetrahydroisoquinolin-6-yl)pyrimidine-2,4-diamine;
(75) 5-chloro-N4-(2-(isopropylsulfonyl)phenyl)-N2-(6-methoxy-4,4-dimethyl-1,2,3,4-tetrahydroisoquinolin-7-yl)pyrimidine-2,4-diamine;
(76) 6-(5-chloro-4-(2-(isopropylsulfonyl)phenylamino)pyrimidin-2-yl)amino-7-methoxy-1,2,3,4-dihydroisoquinoline-1-carboxylic acid;
(77) 5-chloro-N4-(2-(isopropylsulfonyl)phenyl)-N2-(2-ethyl-7-methoxy-1,1-dimethyl-1,2,3,4-tetrahydroisoquinolin-6-yl)pyrimidine-2,4-diamine;
(78) 1-6-(5-chloro-4-(2-(isopropylsulfonyl)phenylamino)pyrimidin-2-yl)amino-7-methoxy-1,1-dimethyl-3,4-dihydroisoquinolin-2(1H)-yl-2-hydroxyethane-1-one;
(79) 5-chloro-N4-(2-(isopropylsulfonyl)phenyl)-N2-(2-ethyl-7-isopropoxy-1,1-dimethyl-1,2,3,4-tetrahydroisoquinolin-6-yl)pyrimidine-2,4-diamine;

(80) 5-chloro-N4-(2-(isopropylsulfonyl)phenyl)-N2-(6-isopropoxy-4,4-dimethyl-1,2,3,4-tetrahydroisoquinolin-7-yl)pyrimidine-2,4-diamine;
(81) 5-chloro-N4-(2-(isopropylsulfonyl)phenyl)-N2-(6-ethoxy-2-ethyl-4,4-dimethyl-1,2,3,4-tetrahydroisoquinolin-7-yl)pyrimidine-2,4-diamine;
(82) 5-chloro-N4-(2-(isopropylsulfonyl)phenyl)-N2-(2-ethyl-6-isopropoxy-4,4-dimethyl-1,2,3,4-tetrahydroisoquinolin-7-yl)pyrimidine-2,4-diamine;
(83) 5-chloro-N4-(2-(isopropylsulfonyl)phenyl)-N2-(6-methoxy-2,3-dihydro-1H-spiro(cyclopentane-1,4-isoquinoline)-7-yl)pyrimidine-2,4-diamine;
(84) 9-((5-chloro-4-(2-(isopropylsulfonyl)phenyl)aminopyrimidin-2-yl)amino-10-methoxy-2,3,6,7-tetrahydro-1H-pyrazino[2,1-a]isoquinoline)-4 (11bH)-one;
(85) 10-((5-chloro-4-(2-(isopropylsulfonyl)phenyl)aminopyrimidin-2-yl)amino)-9-methoxy-7,7-dimethyl-1,2,3,6,7,11b-hexahydro-4H-pyrazino[2,1-a]isoquinoline)-4-one;
(86) 5-chloro-N4-(2-(isopropylsulfonyl)phenyl)-N2-(9-methoxy-7,7-dimethyl-1,3,4,6,7,11b-hexahydro-2H-pyrazino[2,1-a]isoquinolin-10-yl)pyrimidine-2,4-diamine;
(87) 5-chloro-N4-(2-(isopropylsulfonyl)phenyl)-N2-(5-bromo-7-methoxy-1,1-dimethyl-1,2,3,4-tetrahydroisoquinolin-6-yl)pyrimidine-2,4-diamine;
(88) 5-chloro-N4-(2-(isopropylsulfonyl)phenyl)-N2-(5-chloro-7-methoxy-1,1-dimethyl-1,2,3,4-tetrahydroisoquinolin-6-yl)pyrimidine-2,4-diamine;
(89) 5-chloro-N4-(2-(isopropylsulfonyl)phenyl)-N2-(8-bromo-7-methoxy-1,1-dimethyl-1,2,3,4-tetrahydroisoquinolin-6-yl)pyrimidine-2,4-diamine;
(90) 5-chloro-N4-(2-(isopropylsulfonyl)phenyl)-N2-(8-chloro-7-methoxy-1,1-dimethyl-1,2,3,4-tetrahydroisoquinolin-6-yl)pyrimidine-2,4-diamine;
(91) 5-chloro-N4-(2-(isopropylsulfonyl)phenyl)-N2-(6-methoxy-2,4,4-trimethyl-1,2,3,4-tetrahydroisoquinolin-7-yl)pyrimidine-2,4-diamine;
(92) 5-chloro-N4-(2-(isopropylsulfonyl)phenyl)-N2-(2-ethyl-6-methoxy-4,4-trimethyl-1,2,3,4-tetrahydroisoquinolin-7-yl)pyrimidine-2,4-diamine;
(93) 2-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)ethane-1-ol;
(94) 1-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)-2-(dimethylamino)ethane-1-one;
(95) 1-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)-2-hydroxyethane-1-one;
(96) 5-chloro-N4-(2-(isopropylsulfonyl)phenyl)-N2-(6-methoxy-2,3-dihydro-1H-spiro(cyclopropane-1,4-isoquinoline)-7-yl)pyrimidine-2,4-diamine;
(97) 10-((5-chloro-4-(2-(isopropylsulfonyl)phenyl)aminopyrimidine-2-yl)amino)-9-methoxy-1,2,3,6,7,11b-hexahydro-4H-pyrazino[2,1-a]isoquinoline)-4-one;
(98) 5-chloro-N4-(2-(isopropylsulfonyl)phenyl)-N2-(9-methoxy-1,3,4,6,7-11b-hexahydro-2H-pyrazino[2,1-a]isoquinolin-10-yl)pyrimidine-2,4-diamine;
(99) 5-chloro-N4-(2-(isopropylsulfonyl)phenyl)-N2-(7-ethoxy-1,1-dimethyl-1,2,3,4-tetrahydroisoquinolin-6-yl)pyrimidine-2,4-diamine;
(100) 5-chloro-N4-(2-(isopropylsulfonyl)phenyl)-N2-(7-difluoromethoxy-1,1-dimethyl-1,2,3,4-tetrahydroisoquinolin-6-yl)pyrimidine-2,4-diamine;
(101) 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine hydrochloride;
(102) 5-chloro-N4-(2-(isopropylsulfonyl)phenyl)-N2-(7-methoxy-1-propyl-1,2,3,4-tetrahydroisoquinolin-6-yl)pyrimidine-2,4-diamine;
(103) 6-((5-chloro-4-((2-(isopropylsulfonyl)phenyl)amino)pyridin-2-yl)amino)-7-methoxy-2,2-dimethyl-1,2,3,4-tetrahydroisoquinolin-2-ium iodide;
(104) 5-chloro-N4-(2-(isopropylsulfonyl)phenyl)-N2-(8-methoxy-1,1-dimethyl-2,3,4,5-tetrahydro-1H-benzo[c]azepin-7-yl)pyrimidine-2,4-diamine;
(105) 5-chloro-N4-(2-(isopropylsulfonyl)phenyl)-N2-(8-methoxy-1,1-dimethyl-2,3,4,5-tetrahydro-1H-benzo[d]azepin-7-yl)pyrimidine-2,4-diamine; and
(106) 5-chloro-N4-(2-(isopropylsulfonyl)phenyl)-N2-(6-methoxy-1,1-dimethylisoindolin-5-yl)pyrimidine-2,4-diamine.

The pyrimidine-2,4-diamine derivative represented by Chemical Formula 1 of the present invention is usable in a form of a pharmaceutically acceptable salt. As an example of the salt, an acid addition salt formed by pharmaceutically acceptable free acid is useful. The acid addition salt is obtained from inorganic acids such as hydrochloric acid, nitric acid, phosphoric acid, sulfuric acid, hydrobromic acid, hydriodic acid, nitrous acid or phosphorous acid, non-toxic organic acids such as aliphatic mono and dicarboxylate, phenyl-substituted alkanoate, hydroxy alkanoate and alkanedioate, aromatic acids, aliphatic and aromatic sulfonic acids, and organic acids such as acetic acid, benzoic acid, citric acid, lactic acid, maleic acid, gluconic acid, methanesulfonic acid, 4-toluenesulfonic acid, tartaric acid, and fumaric acid. An example of the pharmaceutically non-toxic salt includes sulfate, pyrosulfate, bisulfate, sulfite, bisulfite, nitrate, phosphate, mono-hydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propioleate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenyl propionate, phenyl butyrate, citrate, lactate, β-hydroxybutyrate, glycolate, maleate, tartrate, methane sulfonate, propane sulfonate, naphthalene-1-sulfonate, naphthalene-2-sulfonate or mandelate.

The acid addition salt according to the present invention may be prepared by generally known methods. For example, the acid addition salt may be prepared by dissolving the pyrimidine-2,4-diamine derivative in an organic solvent such as methanol, ethanol, acetone, methylene chloride, acetonitrile, or the like, and adding organic acid or inorganic acid thereto to thereby obtain a precipitate, then filtering and drying the produced precipitate, or may be prepared by distillation under reduced pressure with a solvent and excessive amounts of acids, followed by drying process or crystallization in the presence of the organic solvent.

Further, the present invention includes not only the pyrimidine-2,4-diamine derivative represented by Chemical Formula 1 above and pharmaceutically acceptable salts thereof, but also all of solvates, optical isomers, hydrates, etc., that are capable of being prepared therefrom.

In addition, as shown in Reaction Scheme 1 below, the present invention provides a method of preparing the compound represented by Chemical Formula 1 including: reacting a compound represented by Chemical Formula 2 with a compound represented by Chemical Formula 3 to prepare a compound represented by Chemical Formula 4 (Step 1);

substituting a -Boc group of the compound represented by Chemical Formula 4 obtained in step 1 with hydrogen to prepare a compound represented by Chemical Formula 5 (Step 2); and reacting the compound represented by Chemical Formula obtained in step 2 with a compound represented by Chemical Formula 6 to prepare the compound represented by Chemical Formula 1 (Step 3):

Formula 3 to prepare the compound represented by Chemical Formula 4, and more specifically, a step of performing an alkylation reaction of the compound represented by Chemical Formula 2 with the compound represented by Chemical Formula 3 in the presence of an organic solvent and a base to prepare the compound represented by Chemical Formula 4.

Here, the solvent may be ether solvents including tetrahydrofuran; dioxane; ethyl ether, 1,2-dimethoxyethane, etc.; lower alcohols including methanol, ethanol, propanol and butanol; dimethylformamide (DMF), dimethylsulfoxide

[Reaction Scheme 1]

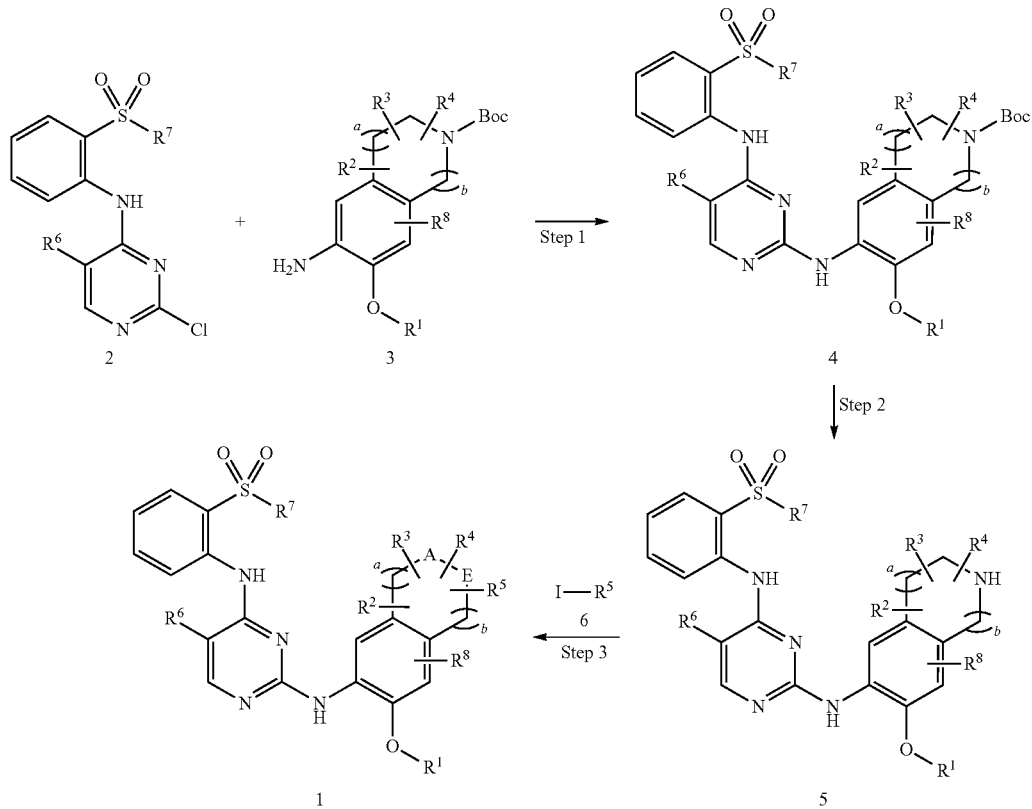

in Reaction Scheme 1,
-Boc is

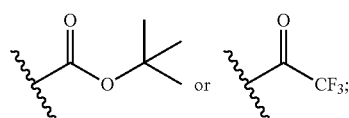

and
$R^1$, $R^2$, $R^3$, $R^4$, $R^5$, $R^6$, $R^7$, $R^8$, A, E, a, and b are the same as defined in Chemical Formula 1 above.

Hereinafter, the method of preparing the compound represented by Chemical Formula 1 according to the present invention is described in detail step by step.

In the method of preparing the compound represented by Chemical Formula 1 according to the present invention, step 1 is a step of reacting the compound represented by Chemical Formula 2 with the compound represented by Chemical (DMSO); acetonazenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methane sulfonate, propane sulfonate, naphthalene-1-sulfonate, naphthalene-2-sulfonate, mandelate, etc.

In addition, the base may be an organic base such as pyridine, triethylamine, N,N-diisopropylethylamine (DIPEA), 1,8-diazabicyclo[5.4.0]-7-undecene (DBU), etc.; or an inorganic base such as sodium hydroxide, sodium carbonate, potassium carbonate, cesium carbonate, sodium hydride, etc. The organic base or the inorganic base may be used in an equivalent amount or in an excess amount.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 1 according to the present invention, step 2 is a step of substituting the -Boc group of the compound represented by Chemical Formula 4 obtained in step 1 with hydrogen to prepare the compound represented by Chemical Formula 5.

Here, the solvent may be ether solvents including tetrahydrofuran; dioxane; ethyl ether, 1,2-dimethoxyethane, etc.; lower alcohols including methanol, ethanol, propanol and butanol; dichloromethane, dimethylformamide (DMF), dimethylsulfoxide (DMSO); acetonazenesulfonate, toluenesulfonate, chlorobenzenesulfonate, xylenesulfonate, phenylacetate, phenylpropionate, phenylbutyrate, secrate, lactate, β-hydroxybutyrate, glycolate, malate, tartrate, methane sulfonate, propane sulfonate, naphthalene-1-sulfonate, naphthalene-2-sulfonate, mandelate, etc.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 1 according to the present invention, step 3 is a step of reacting the compound represented by Chemical Formula 5 obtained in step 2 with the compound represented by Chemical Formula 6 to obtain the compound represented by Chemical Formula 1, and more specifically, a step of dissolving the compound represented by Chemical Formula 5 in an organic solvent, and adding the compound represented by Chemical Formula 6 and diisopropylamine, followed by stirring to obtain the compound represented by Chemical Formula 1.

Here, the solvent may be ether solvents including tetrahydrofuran; dioxane; ethyl ether, 1,2-dimethoxyethane, etc.; lower alcohols including methanol, ethanol, propanol and butanol; dichloromethane, dimethylformamide (DMF), dimethylsulfoxide (DMSO); acetonazenesulfonate, toluenesulfonate, chlorobenzenesulfonate, xylenesulfonate, phenylacetate, phenylpropionate, phenylbutyrate, secrate, lactate, β-hydroxybutyrate, glycolate, malate, tartrate, methane sulfonate, propane sulfonate, naphthalene-1-sulfonate, naphthalene-2-sulfonate, mandelate, etc.

Further, a reaction temperature is preferably a temperature between 0° C. and a boiling point of the solvent, and a reaction time is not particularly limited, but preferably 0.5 to 10 hours.

Preparation Method 1 of Starting Material (Compound Represented by Chemical Formula 3)

The compound represented by Chemical Formula 3, which is a starting material of the Reaction Scheme 1, may be prepared and used as shown in Reaction Scheme 2 below.

The compound represented by Chemical Formula 3 may be prepared by a preparation method including: protecting an amine group of a compound represented by Chemical Formula 7 with a trifluoroacetyl group in the presence of a base to obtain a compound represented by Chemical Formula 8 (Step 1);

substituting the compound represented by Chemical Formula 8 obtained in step 1 with a nitro group to prepare a compound represented by Chemical Formula 9 (Step 2);

performing intramolecular cyclization of the compound represented by Chemical Formula 9 obtained in step 2 in the presence of an acid to obtain a compound represented by Chemical Formula 10 (Step 3);

removing the trifluoroacetyl group from the compound represented by Chemical Formula 10 obtained in step 3 in the presence of a base to obtain a compound represented by Chemical Formula 11 (Step 4);

protecting an amine of the compound represented by Chemical Formula 11 obtained in step 4 with a -Boc group to obtain a compound represented by Chemical Formula 12 (Step 5); and reducing the nitro group of the compound represented by Chemical Formula 12 obtained in step 5 to an amine group to obtain the compound represented by Chemical Formula 3 (Step 6).

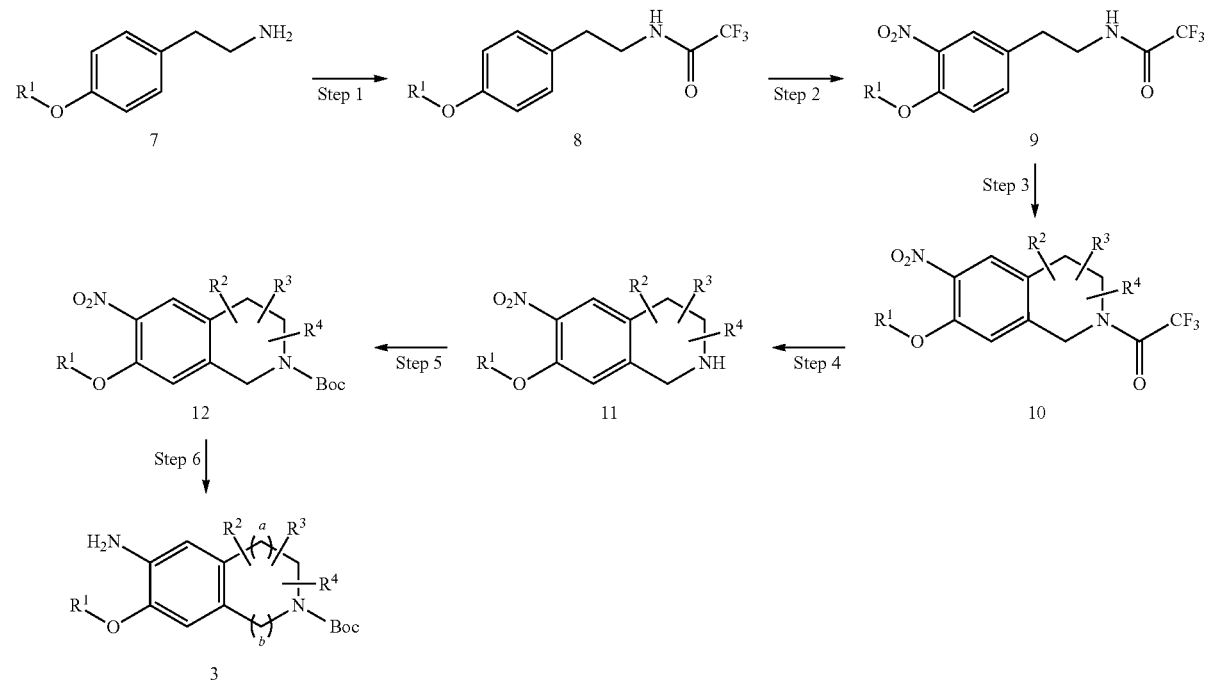

in Reaction Scheme 2,
-Boc is

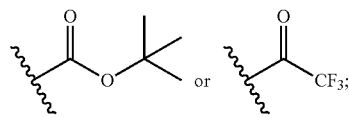

and $R^1$, $R^2$, $R^3$, $R^4$, a, and b are the same as defined in Chemical Formula 1 above.

Hereinafter, the method of preparing the compound represented by Chemical Formula 3 is described in detail step by step.

In the method of preparing the compound represented by Chemical Formula 3 according to the present invention, step 1 is a step of protecting the amine group of the compound represented by Chemical Formula 7 with the trifluoroacetyl group in the presence of the base to obtain the compound represented by Chemical Formula 8.

Here, the base to be usable may be an organic base such as pyridine, triethylamine, N,N-diisopropylethylamine, 1,8-diazabicyclo[5.4.0]-7-undecene (DBU), etc; or an inorganic base such as NaOH, $Na_2CO_3$, $K_2CO_3$, $Cs_2CO_3$, etc. The organic base or the inorganic base may be used in an equivalent amount or in an excess amount.

In addition, as a reaction solvent, an ether solvent such as tetrahydrofuran, dioxane, dichloromethane (DCM), 1,2-dimethoxyethane, etc.; and dimethylformamide (DMF), dimethylsulfoxide, acetonitrile, etc., may be used alone or may be mixed to be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step 2 is a step of substituting the compound represented by Chemical Formula 8 obtained in step 1 with the nitro group to obtain the compound represented by Chemical Formula 9.

Here, the acid to be usable may be hydrochloric acid, sulfuric acid, methanesulfonic acid, polyphosphoric acid, nitric acid, etc., preferably, nitric acid.

In addition, as the reaction solvent, an ether solvent such as acetic anhydride, nitromethane, tetrahydrofuran, dioxane, dichloromethane (DCM), or 1,2-dimethoxyethane, etc.; dimethylformamide (DMF), dimethylsulfoxide, acetonitrile, etc., may be used alone or may be mixed to be used, and preferably, acetic anhydride and nitromethane may be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step 3 is a step of performing intramolecular cyclization of the compound represented by Chemical Formula 9 obtained in step 2 in the presence of the acid to obtain the compound represented by Chemical Formula 10.

Here, the acid to be usable may be hydrochloric acid, sulfuric acid, methanesulfonic acid, acetic acid, polyphosphoric acid, nitric acid, etc., preferably, sulfuric acid.

In addition, as the reaction solvent, an ether solvent such as acetic anhydride, nitromethane, tetrahydrofuran, dioxane, dichloromethane (DCM), or 1,2-dimethoxyethane, etc.; dimethylformamide (DMF), dimethylsulfoxide, acetonitrile, etc., may be used alone or may be mixed to be used, and preferably, acetic anhydride and nitromethane may be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, the step 4 is a step of removing the trifluoroacetyl group from the compound represented by Chemical Formula 10 obtained in step 3 in the presence of the base to obtain the compound represented by Chemical Formula 11.

Here, the base to be usable may be an organic base such as pyridine, triethylamine, N,N-diisopropylethylamine, 1,8-diazabicyclo[5.4.0]-7-undecene (DBU), etc.; or an inorganic base such as NaOH, $Na_2CO_3$, $K_2CO_3$, $Cs_2CO_3$, etc. The organic base or the inorganic base may be used in an equivalent amount or in an excess amount.

In addition, as a reaction solvent, an ether solvent such as tetrahydrofuran, dioxane, dichloromethane (DCM), 1,2-dimethoxyethane, etc.; and dimethylformamide (DMF), dimethylsulfoxide, acetonitrile, etc., may be used alone or may be mixed to be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step is a step of protecting the amine of the compound represented by Chemical Formula 11 obtained in step 4 with the -Boc group to obtain the compound represented by Chemical Formula 12.

Here, -Boc group-substituted reagents to be usable may be

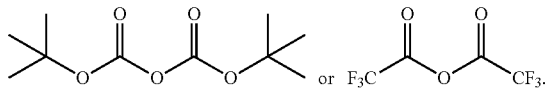

In addition, the base to be usable may be an organic base such as triethylamine (TEA), pyridine, triethylamine, N,N-diisopropylethylamine, 1,8-diazabicyclo[5.4.0]-7-undecene (DBU), etc.; or an inorganic base such as NaOH, $Na_2CO_3$, $K_2CO_3$, $Cs_2CO_3$, etc. The organic base or the inorganic base may be used in an equivalent amount or in an excess amount. The base may be preferably TEA.

In addition, as a reaction solvent, an ether solvent such as tetrahydrofuran, dioxane, dichloromethane (DCM), 1,2-dimethoxyethane, etc.; and dimethylformamide (DMF), dimethylsulfoxide, acetonitrile, etc., may be used alone or may be mixed to be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, the step 6 is a step of reducing the nitro group of the compound represented by Chemical Formula 12 obtained in step 5 to an amine group to obtain the compound represented by Chemical Formula 3.

Here, a catalyst to be usable may be a palladium catalyst (Pd/C).

In addition, the reaction solvent may be an ether solvent such as methanol; tetrahydrofuran; dioxane, dichloromethane (DCM), 1,2-dimethoxyethane, etc.; dimethylformamide (DMF), dimethylsulfoxide, acetonitrile, etc., preferably, methanol.

Further, a reaction temperature is preferably a temperature between 0° C. and a boiling point of the solvent, and a reaction time is not particularly limited, but preferably 0.5 to 10 hours.

Preparation Method 2 of Starting Material (Compound Represented by Chemical Formula 3)

The compound represented by Chemical Formula 3, which is a starting material of the Reaction Scheme 1, may be prepared and used as shown in Reaction Scheme 3 below.

The compound represented by Chemical Formula 3 may be prepared by a preparation method including: protecting an amine group of a compound represented by Chemical Formula 13 with carbamate in the presence of a base to obtain a compound represented by Chemical Formula 14 (Step 1);

performing intramolecular cyclization of the compound represented by Chemical Formula 14 obtained in step 1 in the presence of an acid to obtain a compound represented by Chemical Formula 15 (Step 2);

substituting the compound represented by Chemical Formula 15 obtained in step 2 with a nitro group to prepare a compound represented by Chemical Formula 16 (Step 3);

substituting a carbonyl group of the compound represented by Chemical Formula 16 obtained in step 3 with hydrogen to obtain a compound represented by Chemical Formula 17 (Step 4);

substituting an amine of the compound represented by Chemical Formula 17 obtained in step 4 with a -Boc group to obtain a compound represented by Chemical Formula 18 (Step 5); and adding a catalyst to the compound represented by Chemical Formula 18 obtained in step 5 to reduce the nitro group to an amine group, thereby obtaining the compound represented by Chemical Formula 3 (step 6).

[Reaction Scheme 3]

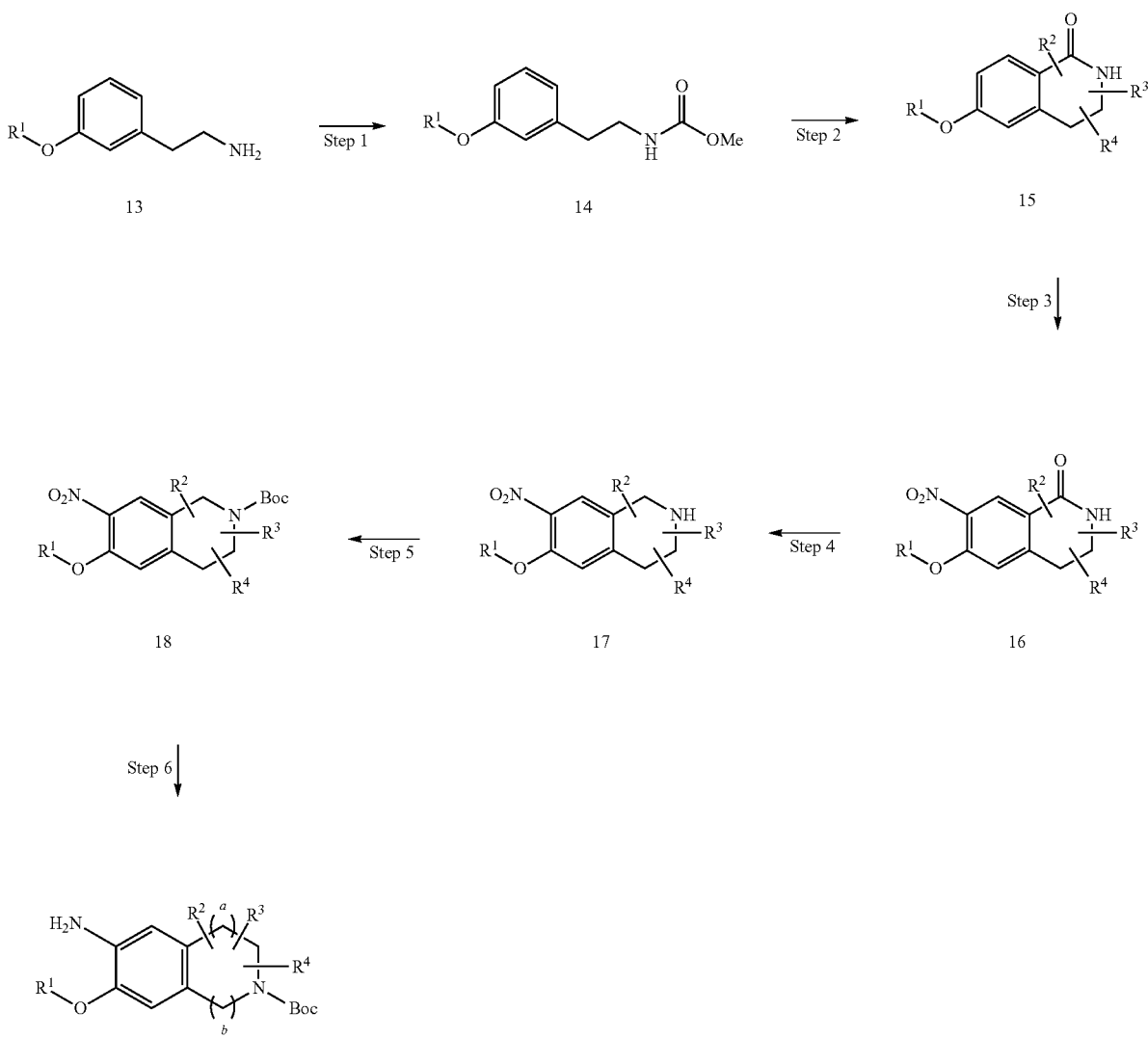

in Reaction Scheme 3,
-Boc is

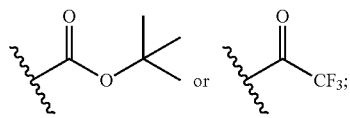

and $R^1$, $R^2$, $R^3$, $R^4$, a, and b are the same as defined in Chemical Formula 1 above.

Hereinafter, the method of preparing the compound represented by Chemical Formula 3 is described in detail step by step.

In the method of preparing the compound represented by Chemical Formula 3 according to the present invention, the step 1 is a step of protecting the amine group of the compound represented by Chemical Formula 13 with carbamate in the presence of the base to obtain the compound represented by Chemical Formula 14.

Here, the solvent to be usable may be an ether solvent such as triethylamine (TEA), tetrahydrofuran, dioxane, dichloromethane (DCM), 1,2-dimethoxyethane, etc.; dimethylformamide (DMF), dimethylsulfoxide, acetonitrile, etc., preferably, triethylamine (TEA) and DCM.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, the step 2 is a step of performing intramolecular cyclization of the compound represented by Chemical Formula 14 obtained in step 1 in the presence of the acid to obtain the compound represented by Chemical Formula 15.

Here, the acid to be usable may be polyphosphoric acid, nitric acid and trifluoroacetic acid (TFA).

In addition, as a solvent, an ether solvent such as tetrahydrofuran, dioxane, dichloromethane (DCM), 1,2-dimethoxyethane, etc.; and dimethylformamide (DMF), dimethylsulfoxide, acetonitrile, etc., may be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step 3 is a step of substituting the compound represented by Chemical Formula 15 obtained in step 2 with the nitro group to obtain the compound represented by Chemical Formula 16.

Here, the solvent to be usable may be an ether solvent such as ethanol, tetrahydrofuran, dioxane, dichloromethane (DCM), 1,2-dimethoxyethane, etc.; dimethylformamide (DMF), dimethylsulfoxide, acetonitrile, etc., preferably, ethanol.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step 4 is a step of substituting the carbonyl group of the compound represented by Chemical Formula 16 obtained in step 3 with hydrogen to obtain the compound represented by Chemical Formula 17.

Here, the base to be usable may be an organic base such as pyridine, triethylamine, N,N-diisopropylethylamine, DBU, etc.; or an inorganic base such as NaOH, $Na_2CO_3$, $K_2CO_3$, $Cs_2CO_3$, etc. The organic base or the inorganic base may be used in an equivalent amount or in an excess amount. The base may be preferably $K_2CO_3$.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step 5 is a step of substituting the amine of the compound represented by Chemical Formula 17 obtained in step 4 with the -Boc group to obtain the compound represented by Chemical Formula 18.

Here, -Boc group-substituted reagents to be usable may be

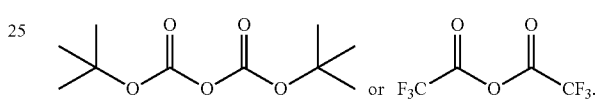

In addition, the base to be usable may be an organic base such as triethylamine (TEA), pyridine, triethylamine, N,N-diisopropylethylamine, 1,8-diazabicyclo[5.4.0]-7-undecene (DBU), etc; or an inorganic base such as NaOH, $Na_2CO_3$, $K_2CO_3$, $Cs_2CO_3$, etc. The organic base or the inorganic base may be used in an equivalent amount or in an excess amount. The base may be preferably TEA.

In addition, as a reaction solvent, an ether solvent such as tetrahydrofuran, dioxane, dichloromethane (DCM), 1,2-dimethoxyethane, etc.; and dimethylformamide (DMF), dimethylsulfoxide, acetonitrile, etc., may be used alone or may be mixed to be used.

Further, a reaction temperature is preferably a temperature between 0° C. and a boiling point of the solvent, and a reaction time is not particularly limited, but preferably 0.5 to 10 hours.

In the method of preparing the compound represented by Chemical Formula 3 according to the present invention, step 6 is a step of adding the catalyst to the compound represented by Chemical Formula 18 obtained in step 5 to reduce the nitro group to the amine group, thereby obtaining the compound represented by Chemical Formula 3.

Here, a catalyst to be usable may be a palladium catalyst (Pd/C).

In addition, the reaction solvent may be an ether solvent such as methanol; tetrahydrofuran; dioxane, dichloromethane (DCM), 1,2-dimethoxyethane, etc.; dimethylformamide (DMF), dimethylsulfoxide, acetonitrile, etc., preferably, methanol.

Further, a reaction temperature is preferably a temperature between 0° C. and a boiling point of the solvent, and a reaction time is not particularly limited, but preferably 0.5 to 10 hours.

Further, the present invention provides a pharmaceutical composition for preventing or treating cancer containing the compound represented by Chemical Formula 1 above, an optical isomer thereof, or a pharmaceutically acceptable salt thereof, as an effective ingredient.

In addition, the present invention provides a pharmaceutical composition for preventing or treating diseases caused by an anaplastic lymphoma kinase (ALK) hyperactivity, the pharmaceutical composition containing the compound represented by Chemical Formula 1 above, an optical isomer thereof, or a pharmaceutically acceptable salt thereof, as an effective ingredient.

Further, the present invention provides an anaplastic lymphoma kinase (ALK) inhibitor containing the compound represented by Chemical Formula 1 above, an optical isomer thereof, or a pharmaceutically acceptable salt thereof, as an effective ingredient.

The pharmaceutical composition and the inhibitor according to the present invention are characterized by inhibiting the activity of anaplastic lymphoma kinase (ALK) to inhibit expression and growth of cancer cells.

The ALK is a gene that induces cell proliferation of cancer present in cancer cells. The ALK is activated by a gene fusion process, wherein tyrosine kinase in the ALK acts abnormally to induce cell proliferation, and interferes with apoptosis, thereby preventing cell death, and rearranges cell skeletons and modifies cell morphology. Moreover, the ALK is linked to other tyrosine kinases that are normal or are subjected to cancer geneticization to interact or activate a variety of other pathways.

Accordingly, an experiment was performed to measure a proliferation inhibitory activity of the ALK of the compound represented by Chemical Formula 1 according to the present invention at an enzyme level, and as a result, it was found that most of the compounds of the Examples according to the present invention had an excellent ability of inhibiting an ALK enzyme activity and a cell activity of L1196M which was a non-small cell lung cancer cell including an ALK enzyme (see Table 2 of Experimental Example 1).

Further, an experiment was performed to figure out a cancer cell proliferation inhibitory ability of the compound represented by Chemical Formula 1 according to the present invention, and as a result, it was found that the compounds of the Examples according to the present invention had an excellent ability of inhibiting ALKs of H2228 and H3122 which were non-small cell lung cancer cell lines, thereby reducing a proliferation activity thereof (see Table 3 of Experimental Example 2).

In addition, an experiment was performed to measure cytotoxicity on BaF3 EML4-ALK L1196M and BaF3 EML4-ALK WT cells of the compound represented by Chemical Formula 1 according to the present invention, and as a result, it was found that most of the compounds of the Examples according to the present invention had low cytotoxic $IC_{50}$ values in BaF3 EML4-ALK wild-type (WT) cell and BaF3 EML4-ALK L1196M cells that were resistant to crizotinib (see Table 4 of Experimental Example 3).

Therefore, the compound represented by Chemical Formula 1 according to the present invention may be used to prevent or treat cancer by inhibiting the activity of the ALK. For example, the compound represented by Chemical Formula 1 according to the present invention may be used for non-small cell lung cancer, neuroblastoma, inflammatory myelofibroblastoma tumor, longitudinal rhabdomyosarcoma, myofibroblastoma, breast cancer, stomach cancer, lung cancer, melanoma, large B-cell lymphoma, systemic histiocytosis, inflammatory myofibroblastic sarcoma, esophageal squamous cell carcinoma, uterine cancer, prostate cancer, etc.

When the composition of the present invention is used as pharmaceuticals, the pharmaceutical composition containing the compound represented by Chemical Formula 1, an optical isomer thereof, or a pharmaceutically acceptable salt thereof, as an effective ingredient, may be formulated and administered in a variety of oral or parenteral dosage forms below at the time of clinical administration, but these forms are not limited thereto.

Examples of formulations for oral administration include tablets, pills, light/soft capsules, liquids, suspensions, emulsions, syrups, granules, elixirs, troches, etc., and these formulations contain diluent (for example: lactose, dextrose, sucrose, mannitol, sorbitol, cellulose and/or glycine), lubricant (for example: silica, talc, stearic acid and magnesium thereof or calcium salt and/or polyethylene glycol) in addition to the effective ingredient. The tablets may also contain binders such as magnesium aluminum silicate, starch paste, gelatin, methylcellulose, sodium carboxymethylcellulose and/or polyvinylpyrrolidine, and in some cases, the tablets may contain disintegrating agents such as starch, agar, alginic acid or sodium salt thereof, or boiling mixture and/or an absorbent, a coloring agent, a flavoring agent and a sweetening agent.

The pharmaceutical composition containing the compound represented by Chemical Formula 1 as an effective ingredient may be administered parenterally, and the parenteral administration may be performed by subcutaneous injection, intravenous injection, intramuscular injection, or intrathoracic injection.

Here, in order to prepare the formulation for parenteral administration, the compound represented by Chemical Formula 1, an optical isomer thereof, or a pharmaceutically acceptable salt thereof may be mixed with water together with a stabilizer or a buffer to prepare a solution or suspension, and then, may be prepared in an ampoule or a vial unit dosage. The composition may be sterilized and/or contain adjuvants such as preservatives, stabilizers, wettable or emulsifying accelerators, salts for controlling osmotic pressure and/or buffers, and other therapeutically useful materials, and may be formulated according to general methods such as mixing, granulating, or coating methods.

The dosage for human body of the pharmaceutical composition containing the compound represented by Chemical Formula 1 as an effective ingredient may vary depending on patient's age, body weight, sex, dosage form, health condition and disease degree. Preferably, the dosage may be 0.01 to 1000 mg/kg/day depending on the judgment of a physician or pharmacist, through an oral or parenteral administration route at a predetermined divided time, for example, several times a day, preferably once or three times a day.

Hereinafter, the method of preparing the compound represented by Chemical Formula 1 according to the present invention is described in detail through Preparation Examples or Examples. The following Examples are merely provided for illustrative purposes as examples of the method of preparing the compound represented by Chemical Formula 1, but it is not intended to limit the scope of the present invention. The preparation method described by Examples below may be obtained by using synthetic conditions well-known in the art of organic synthesis, suitable reagents and the like.

PREPARATION EXAMPLE 1

Preparation of tert-butyl-6-amino-7-methoxy-3,4-dihydroisoquinoline-2(1H)-carboxylate

Step 1: Preparation of 2,2,2-trifluoro-N-(4-methoxyphenethyl)acetamide

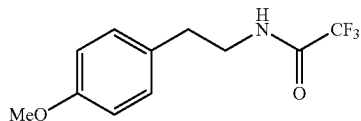 [SMILES: COc1ccc(CCNC(=O)C(F)(F)F)cc1]

4-methoxyphenethylamine (12.0 g, 79.4 mmol) was dissolved in dichloromethane, and then trifluoroacetic anhydride (13.5 mL, 95.2 mmol) was added thereto. The temperature was lowered to 0° C., and triethylamine (27.6 mL, 198 mmol) was slowly added thereto, and the reaction mixture was stirred at room temperature for 3 hours. After completion of the reaction, water was added to dilute the mixture, and the mixture was extracted twice with ethyl acetate and dried over anhydrous magnesium sulfate, and concentrated under reduced pressure. The filtrate concentrated under reduced pressure was purified by column chromatography to obtain the title compound (19 g, 97%).

$^1$H-NMR (300 MHz, DMSO-d6) δ 2.72 (t, J=7.2 Hz, 2H), 3.35-3.39 (m, 2H), 3.71 (s, 3H), 6.87 (d, J=8.4 Hz, 2H), 7.11 (d, J=8.7 Hz, 2H), 9.46 (s, 1H);

LC/MS 248.30 [M$^+$+H].

Step 2: Preparation of 2,2,2-trifluoro-N-(4-methoxy-3-nitrophenethyl)acetamide

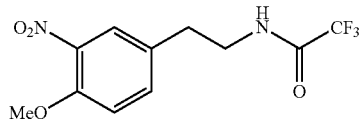 [SMILES: COc1ccc(CCNC(=O)C(F)(F)F)cc1[N+](=O)[O-]]

The 2,2,2-trifluoro-N-(4-methoxyphenethyl)acetamide (20 g, 80.1 mmol) obtained in step 1 was dissolved in trifluoroacetic acid (206 mL), and concentrated nitric acid solution (5.09 g, 80.1 mmol) was added at 0° C. After reaction for 2 hours at 0° C., the trifluoroacetic acid was removed under reduced pressure and the obtained product was extracted twice with ethyl acetate. The organic layer was washed twice with distilled water and a saturated aqueous sodium chloride solution, dried over anhydrous magnesium sulfate, and concentrated under reduced pressure. The filtrate concentrated under reduced pressure was purified by column chromatography to obtain the title compound (19.2 g, 81%).

$^1$H-NMR (300 MHz, DMSO-d6) δ 2.82 (t, J=6.9 Hz, 2H), 3.42 (q, J=6.9, 12.9 Hz, 2H), 3.89 (s, 3H), 7.29 (d, J=8.7 Hz, 1H), 7.49 (dd, J=1.8, 8.4 Hz, 1H), 7.72 (d, J=1.8 Hz, 1H), 9.46 (s, 1H);

LC/MS 293.28 [M$^+$+H].

Step 3: Preparation of 2,2,2-trifluoro-1-(7-methoxy-6-nitro-3,4-dihydroisoquinoline-2(1H)-yl)ethane-1-one

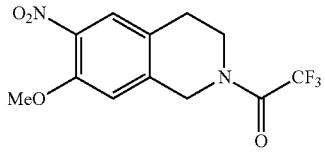 [SMILES: COc1cc2c(cc1[N+](=O)[O-])CCN(C(=O)C(F)(F)F)C2]

To a mixed solution of sulfuric acid (150 mL) and acetic acid (100 mL), the 2,2,2-trifluoro-N-(4-methoxy-3-nitrophenethyl)acetamide (25.0 g, 85.6 mmol) obtained in step 2 and paraformaldehyde (14.5 g) were added and heated at 50° C. for 4 hours. The reaction solution was poured into ice water, extracted twice with ethyl acetate, dried over anhydrous magnesium sulfate, and concentrated under reduced pressure. The filtrate concentrated under reduced pressure was purified by column chromatography to obtain the title compound (15.1 g, 58%).

$^1$H-NMR (300 MHz, DMSO-d6) δ 2.86-2.92 (m, 2H), 3.80 (m, 2H), 3.88 (s, 3H), 4.81 (s, 1.3H), 4.85 (s, 0.7H), 7.33 (s, 0.6H), 7.38 (s, 0.4H), 7.76 (s, 1H);

LC/MS 305.40 [M$^+$+H].

Step 4: Preparation of 7-methoxy-6-nitro-1,2,3,4-tetrahydroisoquinoline

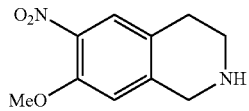

The 2,2,2-trifluoro-1-(7-methoxy-6-nitro-3,4-dihydroisoquinoline-2(1H)-yl)ethane-1-one (15.0 g, 49.3 mmol) obtained in step 3 was dissolved in ethanol (125 mL), and a solution of potassium carbonate (27.2 g, 197 mmol) dissolved in distilled water (25 mL) was added thereto. The reaction solution was reacted at 90° C. for 1 hour and then cooled to room temperature. Ethanol was removed under reduced pressure, and the solution was extracted twice with ethyl acetate, dried over anhydrous magnesium sulfate, and concentrated under reduced pressure. The filtrate concentrated under reduced pressure was purified by column chromatography to obtain the title compound (8.1 g, 79%).

$^1$H-NMR (300 MHz, CDCl$_3$) δ 2.76 (t, J=5.7 Hz, 2H), 3.14 (t, J=5.7 Hz, 2H), 3.92 (s, 3H), 4.04 (s, 2H), 6.71 (s, 1H), 7.65 (s, 1H);

LC/MS 209.41 [M$^+$+H]

Step 5: Preparation of tert-butyl-7-methoxy-6-nitro-3,4-dihydroisoquinoline-2(1H)-carboxylate

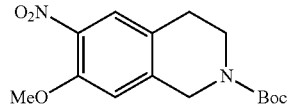

The 7-methoxy-6-nitro-1,2,3,4-tetrahydroisoquinoline (7.0 g, 33.6 mmol) obtained in step 4 was dissolved in dichloromethane and di-tert-butyl dicarbonate (11 g, 46.1 mmol) and triethylamine (21.2 g, 210 mmol) were added thereto at 0° C. After reaction for 4 hours at room temperature, the reaction solution was diluted with water, extracted with dichloromethane, and washed with a saturated aqueous sodium chloride solution. The organic layer was dried over anhydrous magnesium sulfate, concentrated under reduced pressure, and then purified by column chromatography to obtain the title compound (8.9 g, 86%).

$^1$H-NMR (300 MHz, CDCl$_3$) δ 1.50 (s, 9H), 2.81 (t, J=5.7 Hz, 2H), 3.66 (t, J=5.7 Hz, 2H), 3.94 (s, 3H), 4.61 (s, 2H), 6.80 (s, 1H), 7.68 (s, 1H);

LC/MS 309.38 [M$^+$+H].

Step 6: Preparation of tert-butyl-6-amino-7-methoxy-3,4-dihydroisoquinoline-2(1H)-carboxylate

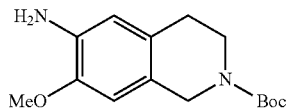 [SMILES: COc1cc2c(cc1N)CCN(C(=O)OC(C)(C)C)C2]

The tert-butyl-7-methoxy-6-nitro-3,4-dihydroisoquinoline-2(1H)-carboxylate (8.5 g, 27.6 mmol) obtained in step 5 was dissolved in ethyl acetate (90 mL) and palladium activated on carbon (0.80 g) was added thereto, followed by stirring at room temperature under hydrogen gas. After the reaction for 16 hours, the reaction solution was filtered using a celite pad to remove the palladium catalyst. The filtrate was concentrated under reduced pressure and purified by column chromatography to obtain the title compound (6.0 g, 75%).

$^1$H-NMR (300 MHz, DMSO-d6) δ 1.41 (s, 9H), 2.54 (t, J=5.8 Hz, 2H), 3.46 (t, J=5.8 Hz, 2H), 3.71 (s, 3H), 4.32 (s, 2H), 4.54 (s, 2H), 6.37 (s, 1H), 6.56 (s, 1H);

LC/MS 279.34 [M$^+$+H].

PREPARATION EXAMPLE 2

Preparation of tert-butyl-7-amino-6-methoxy-3,4-dihydroisoquinoline-2(1H)-carboxylate Step 1: Preparation of methyl 3-methoxyphenethylcarbamate

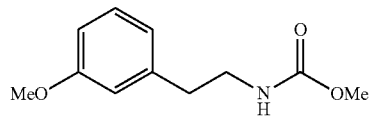 [SMILES: COC(=O)NCCc1cccc(OC)c1]

3-methoxyphenethylamine (30.0 g, 198 mmol) was dissolved in dichloromethane, and then sodium carbonate (42.1 g, 396 mmol) was added thereto. Methyl chloroformate (18.6 mL, 238 mmol) was slowly added at 0° C., and the reaction mixture was stirred for 2 hours. After completion of the reaction, water was added thereto, and the organic layer was separated and dried over anhydrous magnesium sulfate. The reaction mixture was concentrated under reduced pressure to obtain the title compound (35 g, 86%).

$^1$H NMR (300 MHz, CDCl$_3$) δ 2.76 (t, J=6.9 Hz, 2H), 3.41 (t, J=6.9 Hz, 2H), 3.66 (s, 3H), 3.80 (s, 3H), 3.92 (s, 3H), 4.69 (brs, 1H), 6.74-6.79 (m, 3H), 7.20-7.26 (m, 1H)

EI/MS 209.1 [M$^+$].

Step 2: Preparation of 6-methoxy-3,4-dihydroisoquinoline-1(2H)-one

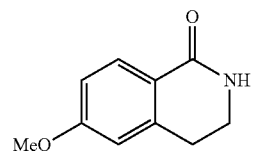 [SMILES: COc1ccc2c(c1)CCNC2=O]

Polyphosphoric acid (184 mL, 184 mmol) was added to the reaction vessel and the temperature was raised to 120° C. The methyl 3-methoxyphenethylcarbamate (35.0 g, 167 mmol) obtained in step 1 was slowly added thereto, and stirred at room temperature for 6 hours. The reaction mixture was poured into ice water, diluted with water, neutralized with potassium carbonate, extracted with dichloromethane, and washed with brine. The organic layer was dried over anhydrous magnesium sulfate and concentrated under reduced pressure to obtain the title compound (22.0 g, 65%).

$^1$H NMR (300 MHz, CDCl$_3$) δ 2.91-2.99 (m, 2H), 3.53-3.58 (m, 2H), 3.85 (s, 3H), 6.71 (m, 1H), 6.79-6.91 (m, 1H), 8.00-8.03 (m, 1H);

EI/MS 177.1 [M$^+$].

Step 3: Preparation of 6-methoxy-7-nitro-3,4-dihydroisoquinoline-1(2H)-one

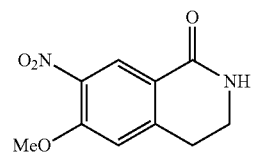

The 6-methoxy-3,4-dihydroisoquinoline-1(2H)-one (22.0 g, 124 mmol) obtained in step 2 was dissolved in acetonitrile, and trifluoroacetic anhydride (69.0 mL, 197 mmol) was added thereto at 0° C. Potassium nitrate (10.6 g, 90.3 mmol) was slowly added to the reaction solution and reacted at 0° C. for 1 hour, and then slowly heated to room temperate. The reaction solution was diluted by pouring it slowly into ice water, neutralized with potassium carbonate, and extracted with dichloromethane. The organic layer was dried over anhydrous magnesium sulfate and concentrated under reduced pressure to obtain the title compound (22.0 g, 65%).

$^1$H NMR (300 MHz, CDCl$_3$) δ 8.57 (s, 1H), 8.23 (d, J=8.7 Hz, 1H), 7.06 (d, J=8.7 Hz, 1H), 6.90 (s, 1H), 6.02 (br s, 1H), 5.95 (br s, 1H), 4.02 (s, 3H), 3.97 (s, 3H), 3.64-3.53 (m, 4H), 3.09 (t, J=6.6 Hz, 2H), 3.00 (q, J=6.9 Hz, 2H);

EI/MS 222 [M$^+$].

Step 4 Preparation of 6-methoxy-7-nitro-1,2,3,4-tetrahydroisoquinoline

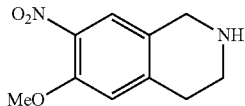

The 6-methoxy-7-nitro-3,4-dihydroisoquinoline-1(2H)-one (14.0 g, 63.0 mmol) obtained in step 3 was dissolved in tetrahydrofuran (100 mL), and BH$_3$-THF complex (1M solution in THF, 315 mL, 315 mmol) was added at 0° C., and the reaction mixture was refluxed with stirring for 12 hours. Methanol was slowly added to the reaction solution at 0° C., and the reaction solution was concentrated under reduced pressure. To the reaction mixture, 2N aqueous hydrochloric acid solution was added. The reaction solution was heated for 3 hours, then extracted with dichloromethane, and washed with a saturated aqueous sodium chloride solution. The organic layer was dried over anhydrous magnesium sulfate and concentrated under reduced pressure to obtain the title compound (8.0 g, 66%).

$^1$H NMR (300 MHz, CDCl$_3$) δ 7.59 (s, 1H), 7.05 (d, J=8.7 Hz, 1H), 6.83 (d, J=8.7 Hz, 1H), 6.78 (s, 1H), 3.98 (s, 4H), 3.93 (s, 3H), 3.87 (s, 3H), 3.14-3.12 (m, 4H), 2.82-2.86 (m, 4H), 2.68-2.69 (m, 2H);

EI/MS 208 [M$^+$].

Step 5: Preparation of Tert-butyl-6-methoxy-7-nitro-3,4-dihydroisoquinoline-2(1H)-carboxylate

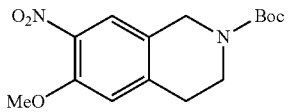

The 6-methoxy-7-nitro-1,2,3,4-tetrahydroisoquinoline (8.0 g, 38.4 mmol) obtained in step 4 was dissolved in dichloromethane, and triethylamine (13.4 mL, 96.1 mmol) was added thereto. Di-tert-butyl dicarbonate (10.1 g, 46.1 mmol) was added at 0-C, and the reaction solution was stirred at room temperature overnight. The reaction solution was diluted with water, extracted with dichloromethane and washed with a saturated aqueous sodium chloride solution. The organic layer was dried over anhydrous magnesium sulfate, concentrated under reduced pressure, and then purified by column chromatography to obtain the title compound (4.6 g, 39%).

18: $^1$H NMR (300 MHz, CDCl$_3$) δ 7.01 (s, 1H), 6.83 (s, 1H), 4.54 (s, 2H), 3.94 (s, 3H), 3.68 (t, J=5.4 Hz, 2H), 2.90 (t, J=5.4 Hz, 2H), 1.49 (s, 9H);

EI/MS 308 [M$^+$].

Step 6: Preparation of Tert-butyl-7-amino-6-methoxy-3,4-dihydroisoquinoline-2(1H)-carboxylate

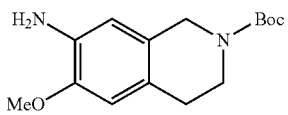

The tert-butyl-6-methoxy-7-nitro-3,4-dihydroisoquinoline-2(1H)-carboxylate (4.5 g, 14.6 mmol) obtained in step 5 was dissolved in methanol and palladium activated on carbon (0.50 g) was added thereto, followed by stirring at room temperature under hydrogen gas. After the reaction for 16 hours, the reaction solution was filtered using a celite pad to remove the palladium catalyst. The filtrate was concentrated under reduced pressure and purified by column chromatography to obtain the title compound (3.3 g, 81%).

$^1$H NMR (300 MHz, CDCl$_3$) δ 6.53 (s, 1H), 6.46 (s, 1H), 4.43 (s, 2H), 3.83 (s, 3H), 3.71 (brs, 2H), 3.61 (m, 2H), 2.72 (m, 2H), 1.48 (s, 9H);

LC/MS 279 [M$^+$+H].

EXAMPLE 1

Preparation of 5-chloro-n4-(2-(Isopropylsulfonyl)Phenyl)-n2-(6-methoxyisoindolin-5-yl)Pyrimidine-2,4-diamine

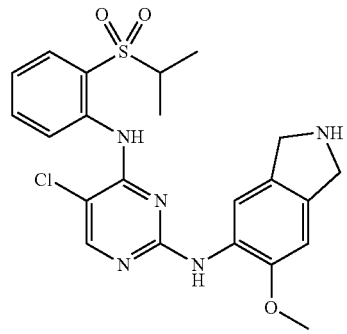 [SMILES: COc1cc2c(cc1Nc1ncc(Cl)c(Nc3ccccc3S(=O)(=O)C(C)C)n1)CNC2]

Step 1: Preparation of Tert-butyl 5-(5-chloro-4-(2-(isopropylsulfonyl)phenylamino)Pyrimidin-2-ylamino)-6-methoxyisoindoline-2-carboxylate 2,5-dichloro-N-(2-(isopropylsulfonyl)phenyl)pyrimidine-4-amine (1.01 g, 2.92 mmol) was dissolved in THF (50 mL), and tert-butyl 5-amino-6-methoxyisoindoline-2-carboxylate (814 mg, 2.92 mmol) was added thereto, and xantphos (65.5 mg, 0.29 mmol), Cs$_2$CO$_3$ (3.1 g, 8.76 mmol), and Pd(OAc)$_2$ (84.5 mg, 0.15 mmol) were sequentially added thereto. The resulting product was degassed by charging with nitrogen, followed by stirring at 130° C. for 18 hours. After completion of the reaction, the reaction mixture was extracted with EA/H$_2$O, and the organic layer was dried over MgSO$_4$, filtered and concentrated. The obtained product was purified by column chromatography (Hx:EA, 3:1) to obtain the title compound (524 mg, 31%).

Step 2: Preparation of 5-chloro-N4-(2-(isopropylsulfonyl)phenyl)-N2-(6-methoxyisoindolin-5-yl)pyrimidine-2,4-diamine The tert-butyl 5-(5-chloro-4-(2-(isopropylsulfonyl)phenylamino)pyrimidine-2-ylamino)-6-methoxyisoindoline-2-carboxylate (524 mg, 0.89 mmol) obtained by step 1 above was dissolved in dichloromethane (3 mL), and 3 mL of dioxane in which 4M HCl was dissolved was added thereto, and the reaction mixture was stirred at room temperature for 2 hours. After completion of the reaction, the HCl solution was removed under reduced pressure to obtain the title compound (510 mg, 95%).

¹H-NMR (300 MHz, CDCl₃) δ 9.47 (s, 1H), 8.50 (d, J=9 Hz, 1H), 8.16 (s, 1H), 7.91 (d, J=9 Hz, 1H), 7.66-7.59 (m, 2H), 6.80 (s, 1H), 4.25-4.11 (m, 2H), 3.93-3.64 (m, 1H), 3.01-2.94 (m, 11H), 1.42-1.38 (m, 8H);
LC/MS 474 (M⁺+H).

EXAMPLE 2

Preparation of 5-chloro-N4-(2-(isopropylsulfonyl)phenyl-N2-(7-methoxy-1,2,3,4-tetrahydroisoquinolin-6-yl)pyrimidine-2,4-diamine

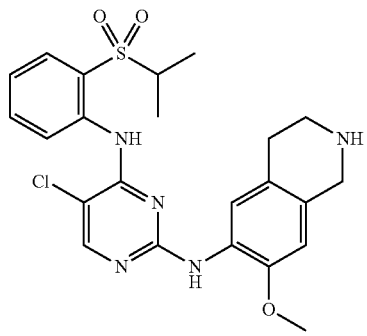 [SMILES: COc1cc2c(cc1Nc1ncc(Cl)c(Nc3ccccc3S(=O)(=O)C(C)C)n1)CCNC2]

Step 1: Preparation of 6-((5-chloro-4-((2-(isopropylsulfonyl)phenylamino)pyrimidin-2-yl)amino-7-methoxy-3,4-dihydroisoquinoline-2(1H)-carboxylate 2,5-dichloro-N-(2-(isopropylsulfonyl)phenyl)pyrimidine-4-amine (1.01 g, 2.92 mmol) was dissolved in THF (50 mL), and tert-butyl-6-amino-7-methoxy-3,4-dihydroisoquinoline-2(1H)-carboxylate (814 mg, 2.92 mmol) obtained in Step 6 of Preparation Example 1 was added thereto, and xantphos (65.5 mg, 0.29 mmol), Cs₂CO₃ (3.1 g, 8.76 mmol), and Pd(OAc)₂ (84.5 mg, 0.15 mmol) were sequentially added thereto. The resulting product was degassed by charging with nitrogen, followed by stirring at 130° C. for 18 hours. After completion of the reaction, the reaction mixture was extracted with EA/H₂O, and the organic layer was dried over MgSO₄, filtered and concentrated. The obtained product was purified by column chromatography (Hx:EA, 3:1) to obtain the title compound (524 mg, 31%).

Step 2: Preparation of 5-chloro-N4-(2-(isopropylsulfonyl)phenyl)-N2-(7-methoxy-1,2,3,4-tetrahydroisoquinolin-6-yl)pyrimidine-2,4-diamine The 6-((5-chloro-4-((2-(isopropylsulfonyl)phenylamino)pyrimidin-2-yl)amino-7-methoxy-3,4-dihydroisoquinoline-2(1H)-carboxylate (524 mg, 0.89 mmol) obtained by step 1 above was dissolved in dichloromethane (3 mL), and 3 mL of dioxane in which 4M HCl was dissolved was added thereto, and the reaction mixture was stirred at room temperature for 2 hours. After completion of the reaction, the HCl solution was removed under reduced pressure to obtain the title compound (510 mg, 95%).
¹H NMR (300 MHz, CD3OD) δ 8.29 (s, 1H), 8.12 (d, J=7.4 Hz, 1H), 8.05 (d, J=8.0 Hz, 1H), 7.82 (t, J=7.7 Hz, 1H), 7.62 (t, J=7.5 Hz, 1H), 7.43 (s, 1H), 6.95 (s, 1H), 4.34 (s, 2H), 3.89 (s, 3H), 3.50-3.35 (m, 3H), 2.83 (t, J=6.0 Hz, 2H), 1.25 (d, J=6.0 Hz, 6H);
LC/MS 488.1 (M⁺+H).

EXAMPLE 3

Preparation of 5-chloro-N4-(2-(isopropylsulfonyl)phenyl)-N2-(7-methoxy-2-methyl-1,2,3,4-tetrahydroisoquinolin-6-yl)pyrimidine-2,4-diamine

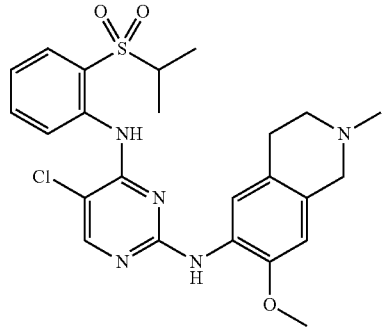 [SMILES: COc1cc2c(cc1Nc1ncc(Cl)c(Nc3ccccc3S(=O)(=O)C(C)C)n1)CCN(C)C2]

The 5-chloro-N4-(2-(isopropylsulfonyl)phenyl)-N2-(7-methoxy-1,2,3,4-tetrahydroisoquinolin-6-yl)pyrimidine-2,4-diamine (50 mg, 0.10 mmol) obtained in Example 2 was dissolved in ethanol (1 mL), diisopropylamine (0.04 mL, 0.25 mmol) and methyl iodide (0.01 mL, 0.15 mmol) were added at 0° C., followed by stirring at room temperature for 18 hours. The reaction solution was diluted with water, extracted three times with dichloromethane, and then washed with a saturated aqueous sodium chloride solution. The organic layer was dried over anhydrous magnesium sulfate, concentrated under reduced pressure, and purified by column chromatography to obtain the title compound (38 mg, 75%).
¹H NMR (300 MHz, CDCl₃) δ 9.56 (s, 1H), 8.50 (d, J=9.0 Hz, 1H), 8.14 (s, 1H), 7.95-7.80 (m, 2H), 7.53 (s, 1H), 7.37 (t, J=7.6 Hz, 1H), 6.75 (s, 1H), 4.60 (s, 2H), 4.14 (t, J=6.08 Hz, 2H), 3.92 (s, 3), 3.30-3.15 (m, 5H), 1.30 (d, J=6.8 Hz, 6H);
LC/MS 501.1 (M⁺).

EXAMPLE 4

Preparation of 5-chloro-N4-(2-(isopropylsulfonyl)phenyl)-N2-(7-methoxy-2-ethyl-1,2,3,4-tetrahydroisoquinolin-6-yl)pyrimidine-2,4-diamine

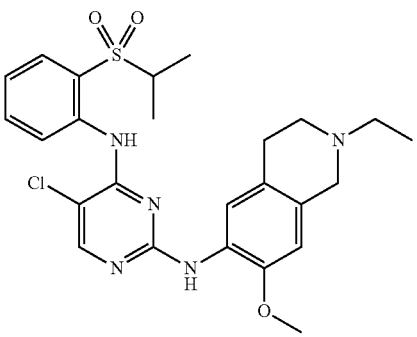 [SMILES: CCN1CCc2cc(Nc3ncc(Cl)c(Nc4ccccc4S(=O)(=O)C(C)C)n3)c(OC)cc2C1]

The title compound was obtained by performing the same method as Example 3 except that ethyl iodide was used instead of using the methyl iodide.

$^1$H NMR (300 MHz, CDCl$_3$) δ 9.46 (s, 1H), 8.49 (d, J=8.3 Hz, 1H), 8.15 (s, 1H), 7.95 (s, 1H), 7.92 (s, 1H), 7.69 (t, J=7.8 Hz, 1H), 7.55 (s, 1H), 7.32-7.26 (m, 1H), 6.61 (s, 1H), 3.87 (s, 3H), 3.57 (s, 2H), 3.33-3.16 (m, 1H), 2.90 (dd, J=5.1, 15.9 Hz, 4H), 2.71 (q, J=6.9 Hz, 2H), 1.38-1.21 (m, 9H);

LC/MS 516.2 (M$^+$+H).

EXAMPLE 5

Preparation of 5-chloro-N4-(2-(isopropylsulfonyl)phenyl)-N2-(7-methoxy-2-hydroxyethyl-1,2,3,4-tetrahydroisoquinolin-6-yl)pyrimidine-2,4-diamine

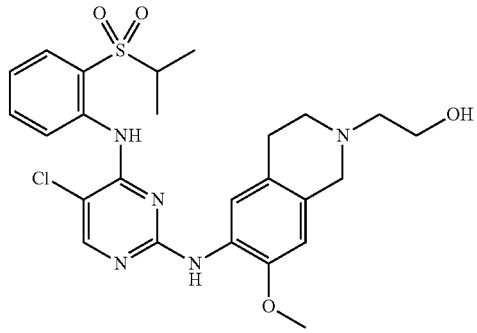 [SMILES: COc1cc2c(cc1Nc1ncc(Cl)c(Nc3ccccc3S(=O)(=O)C(C)C)n1)CCN(CCO)C2]

The title compound was obtained by performing the same method as Example 3 except that 2-bromoethanol was used instead of using the methyl iodide.

$^1$H NMR (300 MHz, CDCl$_3$) δ 9.56 (s, 1H), 8.48 (q, J=3.8 Hz, 1H), 8.15 (d, J=10.1 Hz, 2H), 7.90 (d, J=7.4 Hz, 1H), 7.70 (t, J=8.0 Hz, H), 7.57 (s, 1H), 7.36-7.28 (m, 1H), 6.71 (s, 1H), 4.21 (s, 2H), 4.21 (s, 4H), 4.05-3.77 (m, 8H), 3.31-3.16 (m, 1H), 3.06 (s, 1H), 1.30 (d, J=6.6 Hz, 6H);

LC/MS 531.2 (M$^+$).

EXAMPLE 6

Preparation of 5-chloro-N4-(2-(isopropylsulfonyl)phenyl)-N2-(7-methoxy-2-acetyl-1,2,3,4-tetrahydroisoquinolin-6-yl)pyrimidine-2,4-diamine

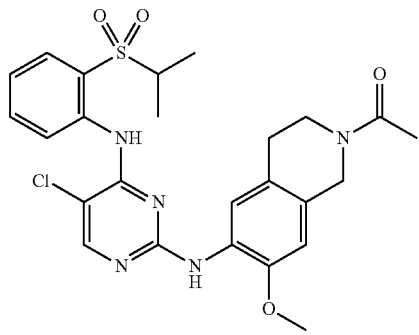 [SMILES: COc1cc2c(cc1Nc1ncc(Cl)c(Nc3ccccc3S(=O)(=O)C(C)C)n1)CCN(C(C)=O)C2]

The title compound was obtained by performing the same method as Example 3 except that acetic anhydride was used instead of using the methyl iodide.

$^1$H NMR (300 MHz, CDCl$_3$) δ 9.52 (s, 1H), 8.53 (dd, J=8.6, 11.9 Hz, 1H), 8.17 (s, 1H), 8.05 (d, J=4.0 Hz, 1H), 7.93 (d, J=7.9 Hz, 1H), 7.70-750 (m, 2H), 7.35-7.26 (m, 1H), 6.63 (d, J=12.7 Hz, 1H), 4.68 (s, 1H), 4.58 (s, 1H), 3.87 (s, 3H), 3.79 (t, J=5.7 Hz, 1H), 3.65 (t, J=5.6 Hz, 1H), 3.32-3.18 (m, 1H), 2.70 (dt, J=5.4, 27.2 Hz, 2H), 2.18 (s, 3H), 1.31 (d, J=6.8 Hz, 6H);

LC/MS 530.2 (M$^+$+H).

EXAMPLE 7

Preparation of 6-(5-chloro-4-(2-(isopropylsulfonyl)phenylamino)pyrimidin-2-yl)amino-N-ethyl-7-methoxy-3,4-dihydroisoquinoline-2(1H)-carboxamide

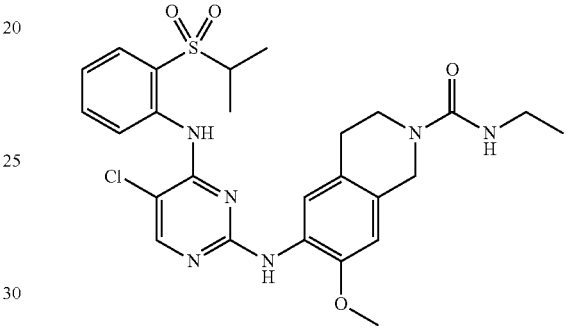

The title compound was obtained by performing the same method as Example 3 except that ethyl isocyanate was used instead of using the methyl iodide.

$^1$H NMR (300 MHz, CDCl$_3$) δ 9.52 (s, 1H), 8.53 (d, J=8.4 Hz, 1H), 8.17 (s, 1H), 8.04 (s, 1H), 7.93 (d, J=8.0 Hz, 1H), 7.62 (t, J=7.7 Hz, 1H), 7.56 (s, 1H), 7.36-7.20 (m, 1H), 6.64 (s, 1H), 4.55-4.37 (m, 2H), 3.87 (s, 3H), 3.70-3.53 (m, 2H), 3.40-3.16 (m, 3H), 2.67 (t, J=5.5 Hz, 2H), 1.31 (d, J=6.8 Hz, 6H), 1.18 (t, J=7.2 Hz, 3H);

LC/MS 559.1 (M$^+$+H).

EXAMPLE 8

Preparation of 1-6-(5-chloro-4-(2-(isopropylsulfonyl)phenylamino)pyrimidin-2-yl)amino-7-methoxy-3,4-dihydroisoquinoline-2(1H)-yl-2-hydroxyethane-1-one

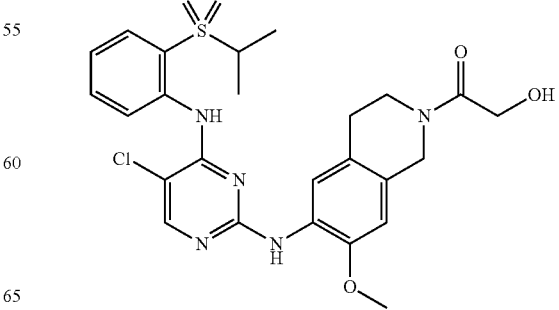

The title compound was obtained by performing the same method as Example 3 except that glycolic acid was used instead of using the methyl iodide.

$^1$H NMR (300 MHz, CDCl$_3$) δ 9.53 (s, 1H), 8.53 (t, J=8.5 Hz, 1H), 8.17 (s, 1H), 8.08 (d, J=3.6 Hz, 1H), 7.93 (d, J=7.9 Hz, 1H), 7.68-7.3 (m, 2H), 7.35-7.34 (m, 1H), 6.62 (d, J=18.1 Hz, 1H), 4.73 (s, 1H), 4.39 (s, 1H), 4.25 (s, 2H), 3.89 (s, 3H), 3.80-3.56 (m, 2H), 3.48 (t, J=5.6 Hz, 1H), 3.24 (q, J=6.9 Hz, 1H), 2.80-2.62 (m, 2H), 1.31 (d, J=6.0 Hz, 6H); LC/MS 546.1 (M$^+$+H).

EXAMPLE 9

Preparation of 6-(5-chloro-4-(2-(isopropylsulfonyl) phenylamino)pyrimidin-2-yl)amino-7-methoxy-3,4-dihydroisoquinoline-2(1H)-sulfonamide

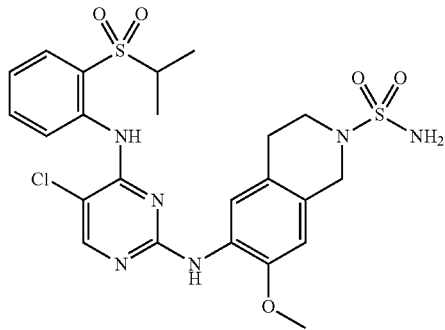 [SMILES: COc1cc2c(cc1Nc1ncc(Cl)c(Nc3ccccc3S(=O)(=O)C(C)C)n1)CCN(S(N)(=O)=O)C2]

The title compound was obtained by performing the same method as Example 3 except that sulfonamide was used instead of using the methyl iodide.

$^1$H NMR (300 MHz, CDCl$_3$) δ 9.52 (s, 1H), 8.52 (d, J=8.3 Hz, 1H), 8.17 (s, 1H), 8.06 (s, 1H), 7.94 (d, J=7.7 Hz, 1H), 7.70-7.53 (m, 2H), 7.33-7.27 (m, 1H), 6.58 (s, 1H), 4.48 (s, 2H), 4.37 (s, 2H), 3.97 (s, 1H), 3.87 (s, 3H), 3.64 (s, 1H), 3.50 (t, J=5.9 Hz, 2H), 3.32-3.16 (m, 1H), 2.87-2.75 (m, 2H) 1.31 (d, J=6.8 Hz, 6H);
LC/MS 567.1 (M$^+$+H).

EXAMPLE 10

Preparation of 2-(6-(5-chloro-4-(2-(isopropylsulfonyl)phenylamino)pyrimidin-2-yl)amino-7-methoxy-3,4-dihydroisoquinoline-2(1H)-yl-N,N-dimethylacetamide

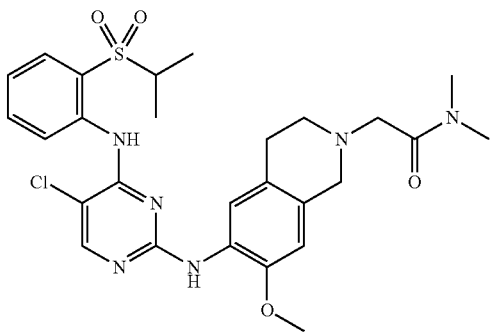 [SMILES: COc1cc2c(cc1Nc1ncc(Cl)c(Nc3ccccc3S(=O)(=O)C(C)C)n1)CCN(CC(=O)N(C)C)C2]

The title compound was obtained by performing the same method as Example 3 except that 2-chloro-N,N-dimethylacetamide was used instead of using the methyl iodide.

$^1$H NMR (300 MHz, CDCl$_3$) δ 9.58 (s, 1H), 8.46 (d, J=8.4 Hz, 1H), 8.18 (s, 1H), 8.14 (s, 1H), 7.94 (d, J=8.0 Hz, 1H), 7.87 (t, J=7.7 Hz, 1H), 7.61 (s, 1H), 7.33 (t, J=7.7 Hz, 1H), 6.66 (s, 1H), 5.47-5.23 (m, 4H), 5.10 (d, J=16.1 Hz, 2H), 4.78-4.60 (m, 2H), 3.91 (s, 3H), 3.35-3.20 (m, 1H), 3.09 (s, 3H), 2.98 (s, 3H), 1.33 (d, J=6.8 Hz, 6H);
LC/MS 573.1 (M$^+$+H).

EXAMPLE 11

Preparation of 1-(6-(5-chloro-4-(2-(isopropylsulfonyl)phenylamino)pyrimidin-2-yl)amino-7-methoxy-4,4-dimethyl-3,4-dihydroisoquinolin-2(1H)-yl)-2,2,2-trifluoroethane-1-one

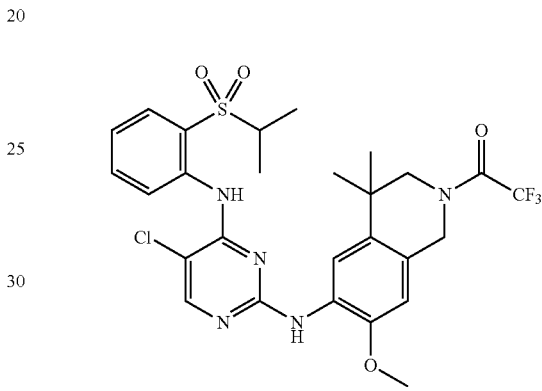

Step 1: Preparation of 5-chloro-N4-(2-(isopropylsulfonyl)phenyl)-N2-(7-methoxy-4,4-dimethyl-1,2,3,4-tetrahydroisoquinolin-6-yl)pyrimidine-2,4-diamine The title compound was obtained by performing the same method as Example 2 except that tert-butyl 6-amino-7-methoxy-4,4-dimethyl-3,4-dihydroisoquinoline-2(1H)-carboxylate was used instead of using the tert-butyl 6-amino-7-methoxy-3,4-dihydroisoquinoline-2(1H)-carboxylate.

Step 2: Preparation of 1-(6-(5-chloro-4-(2-(isopropylsulfonyl)phenylamino)pyrimidin-2-yl)amino-7-methoxy-4,4-dimethyl-3,4-dihydroisoquinolin-2(1H)-yl)-2,2,2-trifluoroethane-1-one The title compound was obtained by performing the same method as Example 3 except that the 5-chloro-N4-(2-(isopropylsulfonyl)phenyl)-N2-(7-methoxy-4,4-dimethyl-1,2,3,4-tetrahydroisoquinolin-6-yl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, DMSO-d6) δ 1.01 (s, 6H), 1.12 (d, J=6.6 Hz, 6H), 3.42 (hept, J=6.6 Hz, 1H), 3.45-3.48 (m, 2H), 3.72 (s, 3H), 4.73 (s, 1H), 4.79 (s, 1H), 6.96 (d, J=5.4 Hz, 1H), 7.35-7.37 (m, 1H), 7.52-7.62 (m, 2H), 7.82 (d, J=8.4 Hz, 1H), 8.28 (s, 2H), 8.93 (br, 1H), 9.69 (s, 1H);
LC/MS 611.84 (M$^+$+H).

EXAMPLE 12

Preparation of 5-chloro-N4-(2-(isopropylsulfonyl)phenyl)-N2-(7-methoxy-4,4-dimethyl-1,2,3,4-tetrahydroisoquinolin-6-yl)pyrimidine-2,4-diamine

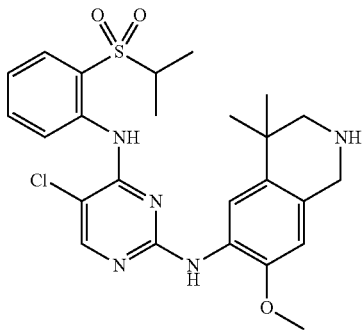 [SMILES: COc1cc2c(cc1Nc1ncc(Cl)c(Nc3ccccc3S(=O)(=O)C(C)C)n1)C(C)(C)CNC2]

The title compound was obtained by performing the same method as Example 2 except that tert-butyl 6-amino-7-methoxy-4,4-dimethyl-3,4-dihydroisoquinoline-2(1H)-carboxylate was used instead of using the tert-butyl 6-amino-7-methoxy-3,4-dihydroisoquinoline-2(1H)-carboxylate.

¹H-NMR (300 MHz, DMSO-d6) δ 1.08 (s, 6H), 1.31 (d, J=6.9 Hz, 6H), 1.85 (s, 1H), 2.79 (s, 2H), 3.28 (hept, J=6.9 Hz, 1H), 3.85 (s, 3H), 3.95 (s, 2H), 7.21-7.26 (m, 1H), 7.46 (s, 1H), 7.59-7.64 (m, 1H), 7.91 (dd, J=1.5 Hz, 8.1 Hz, 1H), 8.18 (s, 1H), 8.19 (s, 1H), 8.46 (d, J=8.1 Hz, 1H), 9.44 (s, 1H);

LC/MS 515.76 (M⁺+H).

EXAMPLE 13

Preparation of 1-(6-(5-chloro-4-(2-(isopropylsulfonyl)phenylamino)pyrimidin-2-yl)amino-7-methoxy-1H-spiro[cyclopentane-1,4-isoquinoline]-2(3H)-yl)-2,2,2-trifluoroethane-1-one

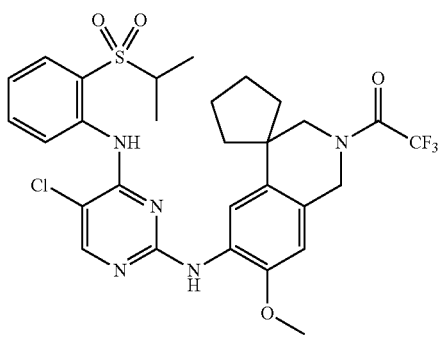 [SMILES: COc1cc2c(cc1Nc1ncc(Cl)c(Nc3ccccc3S(=O)(=O)C(C)C)n1)C1(CCCC1)CN(C(=O)C(F)(F)F)C2]

Step 1: Preparation of 5-chloro-N4-(2-(isopropylsulfonyl)phenyl)-N2-(7-methoxy-2,3-dihydro-1H-spiro[cyclopentane-1,4-isoquinoline]-6-yl)pyrimidine-2,4-diamine The title compound was obtained by performing the same method as Example 2 except that

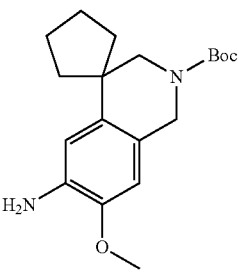

was used instead of using the tert-butyl-6-amino-7-methoxy-3,4-dihydroisoquinoline-2(1H)-carboxylate.

Step 2: Preparation of 1-(6-(5-chloro-4-(2-(isopropylsulfonyl)phenylamino)pyrimidin-2-yl)amino-7-methoxy-1H-spiro[cyclopentane-1,4-isoquinoline]-2(3H)-yl)-2,2,2-trifluoroethane-1-one The title compound was obtained by performing the same method as Example 3 except that the 5-chloro-N4-(2-(isopropylsulfonyl)phenyl)-N2-(7-methoxy-2,3-dihydro-1H-spiro[cyclopentane-1,4-isoquinoline]-6-yl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H-NMR (300 MHz, DMSO-d6) δ 9.79 (s, 1H), 9.09 (br, 1H), 8.30 (s, 2H), 7.81 (d, J=7.5 Hz, 1H), 7.54-7.57 (m, 1H), 7.45 (s, 1H), 7.34 (t, J=7.5 Hz, 1H), 6.98 (d, J=3.3 Hz, 1H), 4.79 (s, 1H), 4.72 (s, 1H), 3.58 (s, 3H), 3.48 (s, 2H), 3.35 (hept, J=6.9 Hz, 1H), 1.52-1.57 (m, 8H), 1.13 (d, J=6.9 Hz, 6H);

LC/MS 337.76 (M⁺+H).

EXAMPLE 14

Preparation of 5-chloro-N4-(2-(isopropylsulfonyl)phenyl)-N2-(7-methoxy-2,3-dihydro-1H-spiro[cyclopentane-1,4-isoquinoline]-6-yl)pyrimidine-2,4-diamine

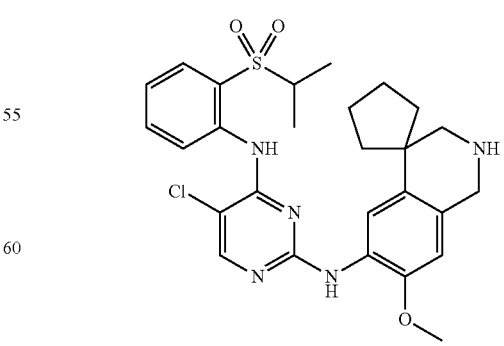

The title compound was obtained by performing the same method as Example 2 except that

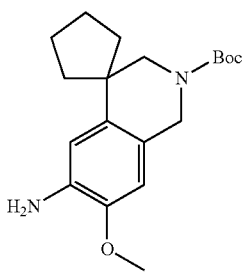

was used instead of using the tert-butyl-6-amino-7-methoxy-3,4-dihydroisoquinoline-2(1H)-carboxylate.

¹H-NMR (300 MHz, CDCl₃) δ 9.59 (s, 1H), 8.56 (d, J=8.4 Hz, 1H), 8.19 (s, 1H), 8.16 (s, 1H), 7.90 (d, J=7.8 Hz, 1H), 7.59 (t, J=7.5 Hz, 1H), 7.43 (s, 1H), 7.22 (t, J=7.2 Hz, 1H), 6.48 (s, 1H), 3.98 (s, 2H), 3.86 (s, 3H), 3.29 (hept, J=6.9 Hz, 1H), 2.82 (s, 2H), 1.59-1.72 (m, 8H), 1.33 (d, J=6.9 Hz, 6H); LC/MS 541.87 (M⁺+H).

EXAMPLE 15

Preparation of 1-(6-(5-chloro-4-(2-(isopropylsulfonyl)phenylamino)pyrimidin-2-yl)amino-7-methoxy-1H-spiro[cyclohexane-1,4-isoquinoline]-2(3H)-yl)-2,2,2-trifluoroethane-1-one

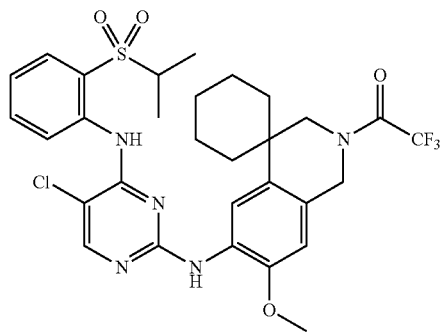 [SMILES: COc1cc2c(cc1Nc1ncc(Cl)c(Nc3ccccc3S(=O)(=O)C(C)C)n1)C1(CCCCC1)CN(C(=O)C(F)(F)F)C2]

Step 1: Preparation of 5-chloro-N4-(2-(isopropylsulfonyl)phenyl)-N2-(7-methoxy-2,3-dihydro-1H-spiro[cyclohexane-1,4-isoquinoline]-6-yl)pyrimidine-2,4-diamine The title compound was obtained by performing the same method as Example 2 except that

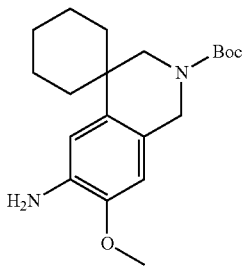 [SMILES: COc1cc2c(cc1N)C1(CCCCC1)CN(C(=O)OC(C)(C)C)C2]

was used instead of using the tert-butyl-6-amino-7-methoxy-3,4-dihydroisoquinoline-2(1H)-carboxylate.

Step 2: Preparation of 1-(6-(5-chloro-4-(2-(isopropylsulfonyl)phenylamino)pyrimidin-2-yl)amino-7-methoxy-1H-spiro[cyclopentane-1,4-isoquinoline]-2(3H)-yl)-2,2,2-trifluoroethane-1-one The title compound was obtained by performing the same method as Example 3 except that the 5-chloro-N4-(2-(isopropylsulfonyl)phenyl)-N2-(7-methoxy-2,3-dihydro-1H-spiro[cyclohexane-1,4-isoquinoline]-6-yl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H-NMR (300 MHz, DMSO-d6) δ 9.78 (s, 1H), 9.04 (br, 1H), 8.30 (s, 2H), 7.81 (d, J=8.1 Hz, 1H), 7.55-7.58 (m, 2H), 7.32 (t, J=7.8 Hz, 1H), 6.98 (s, 1H), 4.78 (s, 1.6H), 4.69 (s, 0.4H), 3.81 (s, 2H), 3.73 (s, 3H), 3.44 (hept, J=6.9 Hz, 1H), 1.15-1.63 (m, 10H), 1.14 (d, J=6.9 Hz, 6H); LC/MS 651.80 (M⁺+H).

EXAMPLE 16

Preparation of 5-chloro-N4-(2-(isopropylsulfonyl)phenyl)-N2-(7-methoxy-2,3-dihydro-1H-spiro[cyclohexane-1,4-isoquinoline]-6-yl)pyrimidine-2,4-diamine

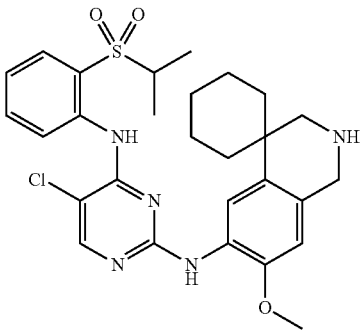 [SMILES: COc1cc2c(cc1Nc1ncc(Cl)c(Nc3ccccc3S(=O)(=O)C(C)C)n1)C1(CCCCC1)CNC2]

The title compound was obtained by performing the same method as Example 2 except that

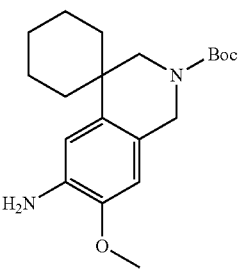

was used instead of using the tert-butyl-6-amino-7-methoxy-3,4-dihydroisoquinoline-2(1H)-carboxylate.

¹H-NMR (300 MHz, CDCl₃) δ 9.59 (s, 1H), 8.56 (d, J=8.4 Hz, 1H), 8.25 (s, 1H), 8.21 (s, 1H), 7.90 (d, J=8.1 Hz, 1H), 7.58 (t, J=7.8 Hz, 1H), 7.42 (s, 1H), 7.21 (t, J=7.5 Hz, 1H), 6.49 (s, 1H), 3.98 (s, 2H), 3.86 (s, 3H), 3.31 (hept, J=6.9 Hz, 1H), 2.26 (s, 2H), 2.72 (br, 1H), 1.38-1.59 (m, 10H), 1.34 (d, J=6.9 Hz, 6H);

LC/MS 555.77 (M$^+$+H).

EXAMPLE 17

Preparation of 1-(6-(5-chloro-4-(2-(isopropylsulfonyl)phenylamino)pyrimidin-2-yl)amino-7-isopropoxy-3,4-dihydroisoquinolin-2(1H)-yl)-2,2,2-trifluoroethane-1-one

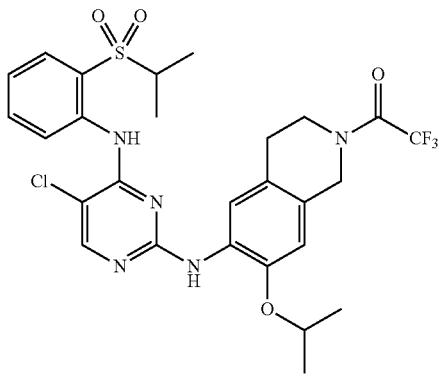 [SMILES: CC(C)Oc1cc2c(cc1Nc1ncc(Cl)c(Nc3ccccc3S(=O)(=O)C(C)C)n1)CCN(C(=O)C(F)(F)F)C2]

Step 1: Preparation of 5-chloro-N4-(2-(isopropylsulfonyl)phenyl)-N2-(7-isopropoxy-1,2,3,4-tetrahydroisoquinolin-6-yl)pyrimidine-2,4-diamine The title compound was obtained by performing the same method as Example 2 except that tert-butyl 6-amino-7-isopropoxy-3,4-dihydroisoquinoline-2(1H)-carboxylate was used instead of using the tert-butyl 6-amino-7-methoxy-3,4-dihydroisoquinoline-2(1H)-carboxylate.

Step 2: Preparation of 1-(6-(5-chloro-4-(2-(isopropylsulfonyl)phenylamino)pyrimidin-2-yl)amino-7-isopropoxy-3,4-dihydroisoquinolin-2(1H)-yl)-2,2,2-trifluoroethane-1-one The title compound was obtained by performing the same method as Example 3 except that the 5-chloro-N4-(2-(isopropylsulfonyl)phenyl)-N2-(7-isopropoxy-1,2,3,4-tetrahydroisoquinolin-6-yl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.53 (s, 1H), 8.52 (t, J=7.8 Hz, 1H), 8.18 (s, 1H), 8.09 (d, J=9.9 Hz, 1H), 7.95 (d, J=7.2 Hz, 1H), 7.58-7.62 (m, 2H), 7.26-7.32 (m, 1H) 6.65 (s, 0.4H), 6.62 (s, 0.6H), 4.73 (s, 1H), 4.68 (s, 1H), 4.58 (hept, J=6.0 Hz, 1H), 3.79-3.88 (m, 2H), 3.26 (hept J=6.9 Hz, 1H), 2.69-2.76 (m, 2H), 4.58 (d, J=6.0 Hz, 6H), 1.32 (d, J=6.9 Hz, 6H);

LC/MS 612.0 (M$^+$+H).

EXAMPLE 18

Preparation of 5-chloro-N4-(2-(isopropylsulfonyl)phenyl)-N2-(7-isopropoxy-1,2,3,4-tetrahydroisoquinolin-6-yl)pyrimidine-2,4-diamine

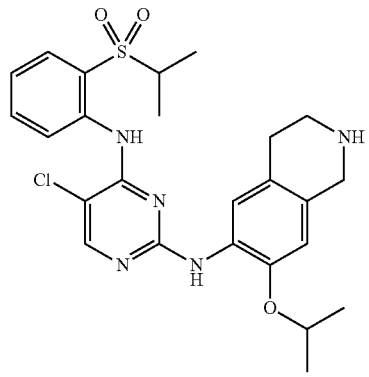 [SMILES: CC(C)Oc1cc2c(cc1Nc1ncc(Cl)c(Nc3ccccc3S(=O)(=O)C(C)C)n1)CCNC2]

The title compound was obtained by performing the same method as Example 2 except that tert-butyl-6-amino-7-isopropoxy-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.48 (br, 1H), 8.54 (d, J=8.1 Hz, 1H), 8.16 (s, 1H), 7.92-7.96 (m, 1H), 7.59-7.66 (m, 2H), 7.24-7.29 (m, 1H), 6.54 (s, 1H), 4.54 (hept, J=6.3 Hz, 1H), 3.95 (s, 2H), 3.26 (hept J=6.9 Hz, 1H), 3.08-3.13 (m, 2H), 2.55-2.59 (m, 2H), 1.93 (br, 1H), 1.37 (d, J=6.3 Hz, 6H), 1.31 (d, J=6.9 Hz, 6H);

LC/MS 516.0 (M$^+$+H).

EXAMPLE 19

Preparation of 1-(6-(5-chloro-4-(2-(isopropylsulfonyl)phenylamino)pyrimidin-2-yl)amino-7-isobutoxy-3,4-dihydroisoquinolin-2(1H)-yl)-2,2,2-trifluoroethane-1-one

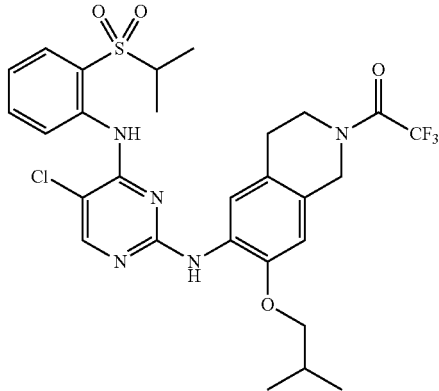 [SMILES: CC(C)COc1cc2c(cc1Nc1ncc(Cl)c(Nc3ccccc3S(=O)(=O)C(C)C)n1)CCN(C(=O)C(F)(F)F)C2]

Step 1: Preparation of 5-chloro-N4-(2-(isopropylsulfonyl)phenyl)-N2-(7-isobutoxy-1,2,3,4-tetrahydroisoquinolin-6-yl)pyrimidine-2,4-diamine The title compound was obtained by performing the same method as Example 2 except that tert-butyl-6-amino-7- isobutoxy-3,4-dihydroisoquinoline-2(1H)-carboxylate was used instead of using the tert-butyl-6-amino-7-methoxy-3,4-dihydroisoquinoline-2(1H)-carboxylate.

Step 2: Preparation of 1-(6-(5-chloro-4-(2-(isopropylsulfonyl)phenylamino)pyrimidin-2-yl)amino-7-isobutoxy-3,4-dihydroisoquinolin-2(1H)-yl)-2,2,2-trifluoroethane-1-one The title compound was obtained by performing the same method as Example 3 except that the 5-chloro-N4-(2-(isopropylsulfonyl)phenyl)-N2-(7-isobutoxy-1,2,3,4-tetrahydroisoquinolin-6-yl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin 6-yl)pyrimidine-2,4-diamine and methyl iodide.

$^1$H-NMR (300 MHz, CDCl$_3$) δ 9.55 (s, 1H), 8.52-8.57 (m, 1H), 8.19 (s, 1H), 8.19 (d, J=9.0 Hz, 1H), 7.94 (d, J=7.8 Hz, 1H), 7.60 (br, 1H), 7.26-7.31 (m, 1H) 6.64 (s, 0.6H), 6.61 (s, 0.4H), 4.73 (s, 1H), 4.69 (s, 1H), 3.79-3.86 (m, 4H), 3.25 (hept, J=6.9 Hz, 1H), 2.77 (br, 2H), 2.14-2.21 (m, 1H), 1.32 (d, J=6.9 Hz, 6H), 1.08 (d, J=6.6 Hz, 6H);

LC/MS 626.0 (M$^+$+H).

EXAMPLE 20

Preparation of 5-chloro-N4-(2-(isopropylsulfonyl)phenyl)-N2-(7-isobutoxy-1,2,3,4-tetrahydroisoquinolin-6-yl)pyrimidine-2,4-diamine

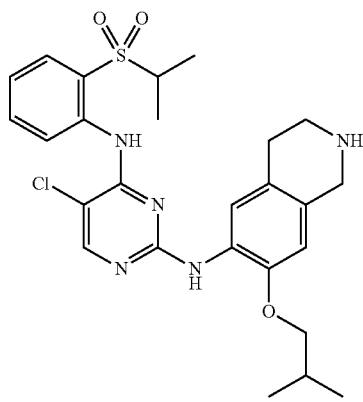 [SMILES: CC(C)COc1cc2c(cc1Nc1ncc(Cl)c(Nc3ccccc3S(=O)(=O)C(C)C)n1)CCNC2]

The title compound was obtained by performing the same method as Example 2 except that tert-butyl-6-amino-7-isobutoxy-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.49 (br, 1H), 8.56 (d, J=8.4 Hz, 1H), 8.16 (s, 1H), 7.91-7.94 (m, 2H), 7.56-7.64 (m, 2H), 7.24-7.26 (m, 1H), 6.52 (s, 1H), 3.96 (s, 2H), 3.76 (d, J=6.3 Hz, 2H), 3.26 (hept, J=6.6 Hz, 1H), 3.10 (br, 2H), 2.59 (br, 2H), 2.14-2.18 (m, 1H), 1.71 (br, 1H), 1.31 (d, J=6.6 Hz, 6H), 1.06 (d, J=6.6 Hz, 6H);

LC/MS 530.0 (M$^+$+H).

EXAMPLE 21

Preparation of 1-(7-(sec-butoxy)-6-((5-chloro-4-(2-(isopropylsulfonyl)phenyl)amino)pyrimidin-2-yl)amino)-3,4-dihydroisoquinolin-2(1H)-yl)-2,2,2-trifluoroethane-1-one

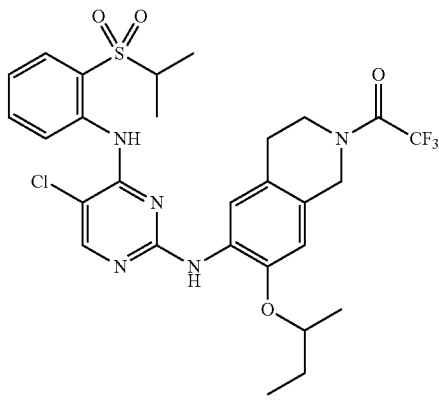 [SMILES: CCC(C)Oc1cc2c(cc1Nc1ncc(Cl)c(Nc3ccccc3S(=O)(=O)C(C)C)n1)CCN(C(=O)C(F)(F)F)C2]

Step 1: Preparation of 5-chloro-N2-(7-(sec-butoxy)-1,2,3,4-tetrahydroisoquinolin-6-yl)-N4-(2-isopropylsulfonyl)phenyl)pyrimidine-2,4-diamine The title compound was obtained by performing the same method as Example 2 except that tert-butyl-6-amino-7-sec-butoxy-3,4-dihydroisoquinoline-2(1H)-carboxylate was used instead of using the tert-butyl-6-amino-7-methoxy-3,4-dihydroisoquinoline-2(1H)-carboxylate.

Step 2: Preparation of 1-(7-(sec-butoxy)-6-((5-chloro-4-(2-(isopropylsulfonyl)phenyl)amino)pyrimidin-2-yl)amino)-3,4-dihydroisoquinolin-2(1H)-yl)-2,2,2-trifluoroethane-1-one The title compound was obtained by performing the same method as Example 3 except that the 5-chloro-N2-(7-sec-butoxy-1, 2,3,4-tetrahydroisoquinolin-6-yl)-N4-(2-isopropylsulfonyl)phenyl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.53 (s, 1H), 8.52-8.55 (m, 1H), 8.18 (s, 1H), 8.09 (d, J=9.3 Hz, 1H), 7.94 (d, J=7.5 Hz, 1H), 7.61-7.66 (m, 2H), 7.26-7.31 (m, 1H) 6.64 (s, 0.7H), 6.61 (s, 0.3H), 4.72 (s, 1H), 4.68 (s, 1H), 4.34-4.35 (m, 1H), 3.81-3.85 (m, 2H), 3.26 (hept, J=6.6 Hz, 1H), 2.75 (br, 2H), 1.69-1.82 (m, 2H), 1.34 (d, J=5.4 Hz, 3H), 1.32 (d, J=6.6 Hz, 6H), 1.02 (t, J=7.5 Hz, 3H);

LC/MS 626.0 (M$^+$+H).

EXAMPLE 22

Preparation of 5-chloro-N2-(7-sec-butoxy-1,2,3,4-tetrahydroisoquinolin-6-yl)-N4-(2-isopropylsulfonyl)phenyl)pyrimidine-2,4-diamine

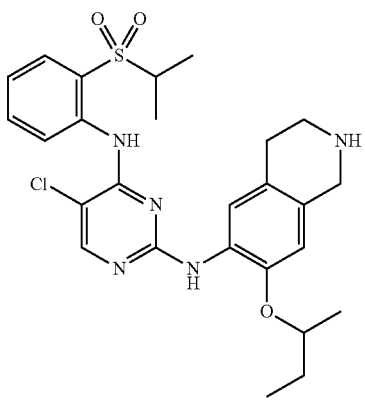 [SMILES: CCC(C)Oc1cc2c(cc1Nc1ncc(Cl)c(Nc3ccccc3S(=O)(=O)C(C)C)n1)CCNC2]

The title compound was obtained by performing the same method as Example 2 except that tert-butyl-6-amino-7-sec-butoxy-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.46 (br, 1H), 8.53 (d, J=8.4 Hz, 1H), 8.15 (s, 1H), 7.90-7.95 (m, 2H), 7.59-7.64 (m, 2H), 7.23-7.28 (m, 1H), 6.52 (s, 1H), 4.29-4.31 (m, 1H), 3.95 (s, 2H), 3.24 (hept J=6.6 Hz, 1H), 3.10 (br, 2H), 2.57 (br, 2H), 2.25 (br, 1H), 1.61-1.83 (m, 2H), 1.30 (d, J=6.6 Hz, 9H), 0.99 (t, J=7.2 Hz, 3H);

LC/MS 530.0 (M$^+$+H).

EXAMPLE 23

Preparation of 5-chloro-N2-(2-(2-(dimethylamino)ethyl)-7-methoxy-1,2,3,4-tetrahydroisoquinolin-6-yl)-N4-2-(isopropylsulfonyl)phenyl)pyrimidine-2,4-diamine

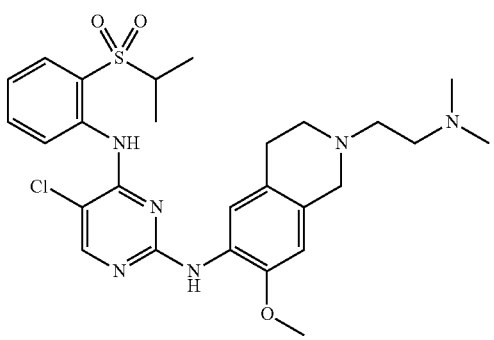 [SMILES: COc1cc2c(cc1Nc1ncc(Cl)c(Nc3ccccc3S(=O)(=O)C(C)C)n1)CCN(CCN(C)C)C2]

The title compound was obtained by performing the same method as Example 3 except that the 5-chloro-N4-(2-(isopropylsulfonyl)phenyl)-N2-(7-methoxy-1,2,3,4-tetrahydroisoquinolin-6-yl)pyrimidine-2,4-diamine obtained in Example 2 and 2-chloro-N,N-dimethylethanamine were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.53 (s, 1H), 8.56-8.50 (m, 1H), 8.27-8.18 (m, 2H), 8.07 (d, J=6.9 Hz, 1H), 7.95-7.93 (m, 1H), 7.66-7.55 (m, 2H), 6.62 (d, J=6.9 Hz, 1H), 4.64-4.51 (m, 2H), 3.89 (s, 3H), 3.79-3.74 (m, 1H), 3.68-3.63 (m, 4H), 3.28-3.23 (m, 1H), 3.13-3.10 (m, 1H), 2.73-2.67 (m, 2H), 1.33 (d, J=6.9 Hz, 6H), 1.26 (s, 6H);

LC/MS 559 (M$^+$+H).

EXAMPLE 24

Preparation of 5-chloro-N4-2-(isopropylsulfonyl)phenyl)-N2-(7-methoxy-2-(piperidin-4-yl)-1,2,3,4-tetrahydroisoquinolin-6-yl)pyrimidine-2,4-diamine

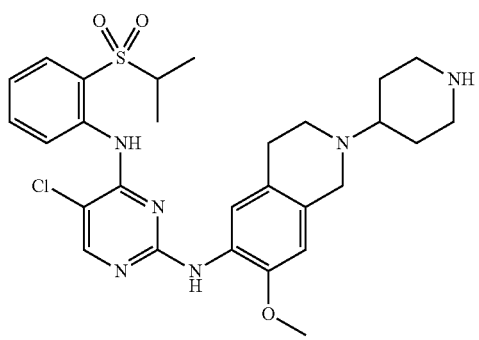 [SMILES: COc1cc2c(cc1Nc1ncc(Cl)c(Nc3ccccc3S(=O)(=O)C(C)C)n1)CCN(C1CCNCC1)C2]

The title compound was obtained by performing the same method as Example 3 except that the 5-chloro-N4-(2-(isopropylsulfonyl)phenyl)-N2-(7-methoxy-1,2,3,4-tetrahydroisoquinolin-6-yl)pyrimidine-2,4-diamine obtained in Example 2 and 4-iodopiperidine were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.53-9.42 (m, 1H), 8.53-8.50 (m, 1H), 8.20-8.16 (m, 1H), 7.97-7.91 (m, 2H), 7.67-7.56 (m, 2H), 6.54 (s, 1H), 3.89-3.85 (m, 5H), 3.68-3.85 (m, 3H), 3.27-3.21 (m, 1H), 2.91 (m, 2H), 2.75 (m, 4H), 1.96-1.93 (m, 2H), 1.60-1.57 (m, 2H), 1.32 (d, J=6.9 Hz, 6H);

LC/MS 571 (M$^+$+H).

EXAMPLE 25

Preparation of 5-chloro-N4-2-(isopropylsulfonyl)phenyl)-N2-(7-methoxy-1-methyl-1,2,3,4-tetrahydroisoquinolin-6-yl)pyrimidine-2,4-diamine

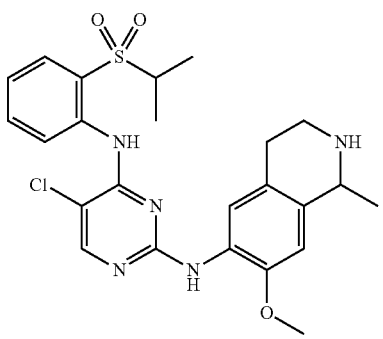 [SMILES: COc1cc2c(cc1Nc1ncc(Cl)c(Nc3ccccc3S(=O)(=O)C(C)C)n1)CCNC2C]

The title compound was obtained by performing the same method as Example 2 except that the tert-butyl 6-amino-7-methoxy-1-methyl-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.49 (br, 1H), 8.55 (d, J=8.1 Hz, 1H), 8.17 (s, 1H), 7.92-7.95 (m, 2H), 7.62-7.68 (m, 1H), 7.55 (br, 1H), 7.24-7.29 (m, 1H), 6.64 (s, 1H), 4.08 (q, J=6.6 Hz, 1H), 3.88 (s, 1H), 3.21-3.30 (m, 1H), 2.65-2.75 (m, 1H), 2.49-2.55 (m, 1H), 1.78 (br, 1H), 1.46 (d, J=6.6 Hz, 3H), 1.31 (dd, J=1.5 Hz, 6.9 Hz, 6H);
LC/MS 501.9 (M$^+$+H).

EXAMPLE 26

Preparation of 5-chloro-N4-2-(isopropylsulfonyl)phenyl)-N2-(7-methoxy-1-trifluoromethyl-1,2,3,4-tetrahydroisoquinolin-6-yl)pyrimidine-2,4-diamine

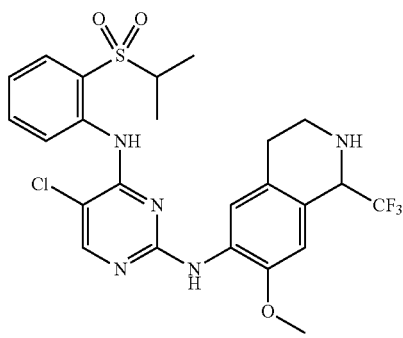 [SMILES: COc1cc2c(cc1Nc1ncc(Cl)c(Nc3ccccc3S(=O)(=O)C(C)C)n1)CCNC2C(F)(F)F]

The title compound was obtained by performing the same method as Example 2 except that tert-butyl-6-amino-7-methoxy-1-(trifluoromethyl)-3,4-dihydroisoquinoline-2(1H)-carboxylate was used instead of using the tert-butyl-6-amino-7-methoxy-3,4-dihydroisoquinoline-2(1H)-carboxylate.

$^1$H NMR (300 MHz, CDCl$_3$) δ 9.44 (s, 1H), 8.45 (d, J=6 Hz, 1H), 8.09 (s, 1H), 7.97 (s, 1H), 7.86 (d, J=6 Hz, 1H), 7.60-7.52 (m, 1H), 6.71 (s, 1H), 4.40-4.32 (m, 1H), 3.86 (s, 3H), 3.30-3.12 (m, 2H), 3.08-2.93 (m, 1H), 2.62-2.49 (m, 1H), 1.98 (s, 1H), 1.29-1.17 (m, 9H);
LC/MS 556.00 (M$^+$).

EXAMPLE 27

Preparation of 5-chloro-N4-2-(isopropylsulfonyl)phenyl)-N2-(7-methoxy-1-ethyl-1,2,3,4-tetrahydroisoquinolin-6-yl)pyrimidine-2,4-diamine

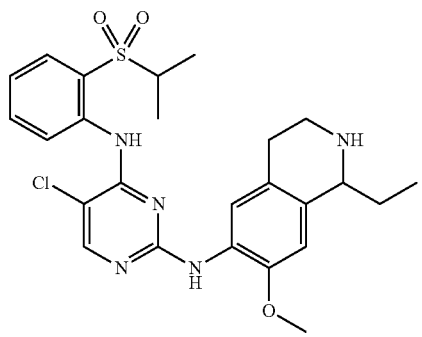 [SMILES: CCC1NCCc2cc(Nc3ncc(Cl)c(Nc4ccccc4S(=O)(=O)C(C)C)n3)c(OC)cc21]

The title compound was obtained by performing the same method as Example 2 except that tert-butyl-6-amino-1-ethyl-7-methoxy-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (500 MHz, CDCl$_3$) δ 8.43-8.40 (s, 1H), 7.92-7.87 (m, 1H), 7.67 (s, 1H), 7.52 (s, 1H), 7.04-7.00 (m, 1H), 6.25-6.19 (m, 1H), 5.85-5.78 (m, 2H), 5.60 (d, J=15 Hz, 1H), 4.90-4.82 (m, 1H), 4.02-4.01 (m, 1H), 3.82 (s, 3H), 3.61-3.52 (m, 1H), 3.35-3.25 (m, 1H), 2.91 (s, 3H), 2.78 (s, 3H);
LC/MS 646.74 (M$^+$).

EXAMPLE 28

Preparation of 5-chloro-N4-2-(isopropylsulfonyl)phenyl)-N2-(7-methoxy-1-isopropyl-1,2,3,4-tetrahydroisoquinolin-6-yl)pyrimidine-2,4-diamine

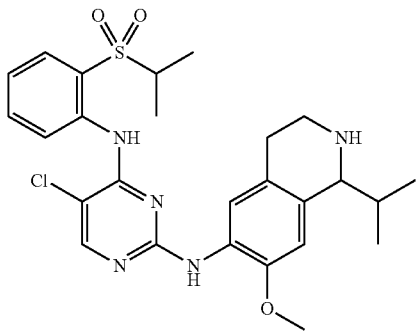 [SMILES: COc1cc2c(cc1Nc1ncc(Cl)c(Nc3ccccc3S(=O)(=O)C(C)C)n1)CCNC2C(C)C]

The title compound was obtained by performing the same method as Example 2 except that tert-butyl-6-amino-1-isopropyl-7-methoxy-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (500 MHz, CDCl$_3$) δ 8.43-8.40 (s, 1H), 7.92-7.87 (m, 1H), 7.67 (s, 1H), 7.52 (s, 1H), 7.04-7.00 (m, 1H), 6.25-6.19 (m, 1H), 5.85-5.78 (m, 2H), 5.60 (d, J=15 Hz, 1H), 4.90-4.82 (m, 1H), 4.02-4.01 (m, 1H), 3.82 (s, 3H), 3.61-3.52 (m, 1H), 3.35-3.25 (m, 1H), 2.91 (s, 3H), 2.78 (s, 3H);
LC/MS 646.74 (M$^+$).

EXAMPLE 29

Preparation of 1-(6-((5-chloro-4-((2-(isopropylsulfonyl)phenylamino)pyrimidin-2-yl)amino)-7-methoxy-1-methyl-1,4-dihydro-2H-spiro[cyclopropane-1,3-isoquinoline]-2-yl)-2,2,2-trifluoroethane-1-one

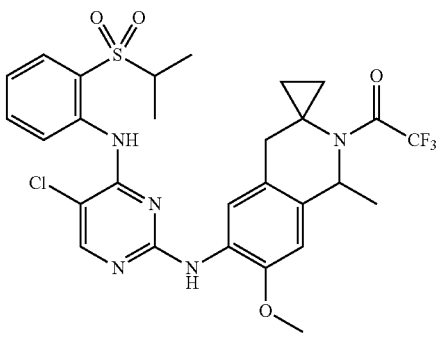 [SMILES: COc1cc2c(cc1Nc1ncc(Cl)c(Nc3ccccc3S(=O)(=O)C(C)C)n1)CC1(CC1)N(C(=O)C(F)(F)F)C2C]

Step 1: Preparation of 5-chloro-N4-(2-(isopropyl-sulfonyl)phenyl)-N2-(7-methoxy-1methyl-1,4-dihydro-2H-spiro[cyclopropane-1,3-isoquinoline]-6-yl)pyrimidine-2,4-diamine The title compound was obtained by performing the same method as Example 2 except that

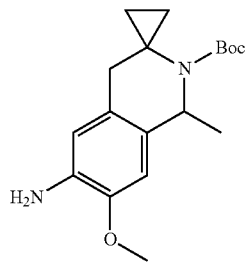 [SMILES: COc1cc2c(cc1N)CC1(CC1)N(C(=O)OC(C)(C)C)C2C]

was used instead of using the tert-butyl-6-amino-7-methoxy-3,4-dihydroisoquinoline-2(1H)-carboxylate.

Step 2: Preparation of 1-(6-((5-chloro-4-((2-(isopropylsulfonyl)phenylamino)pyrimidin-2-yl)amino)-7-methoxy-1-methyl-1,4-dihydro-2H-spiro[cyclopropane-1,3-isoquinoline]-2-yl)-2,2,2-trifluoroethane-1-one The title compound was obtained by performing the same method as Example 3 except that the 5-chloro-N4-(2-(isopropylsulfonyl)phenyl)-N2-(7-methoxy-1-methyl-1,4-dihydro-2H-spiro[cyclopropane-1,3-isoquinoline]-6-yl)pyrimidine-2,4-diamine obtained in step 1 and 2,2,2-trifluoroacetyliodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.51 (s, 1H), 8.50 (d, J=8.1 Hz, 1H), 8.00 (s, 1H), 7.92 (dd, J=8.1, 1.5 Hz, 1H), 7.57-7.62 (m, 2H), 7.23-7.29 (m, 1H), 6.62 (s, 1H), 5.64 (br, 1H), 5.09 (br, 1H), 3.91 (s, 3H), 3.47 (br, 1H), 3.25 (hept, J=6.6 Hz, 1H), 1.89 (br, 1H), 1.70 (d, J=6.3 Hz, 3H), 1.31 (dd, J=6.6, 1.5 Hz, 6H), 1.20-1.25 (m, 1H), 1.02-1.04 (m, 2H), 0.75 (br, 1H);

LC/MS 624.0 (M$^+$+H).

EXAMPLE 30

Preparation of 5-chloro-N4-(2-(isopropylsulfonyl)phenyl)-N2-(7-methoxy-1methyl-1,4-dihydro-2H-spiro[cyclopropane-1,3-isoquinoline]-6-yl)pyrimidine-2,4-diamine

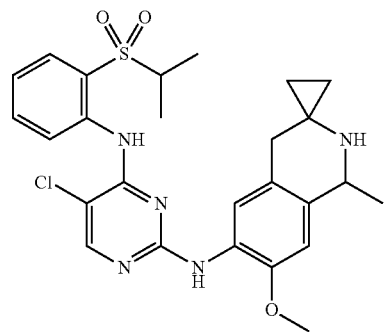 [SMILES: COc1cc2c(cc1Nc1ncc(Cl)c(Nc3ccccc3S(=O)(=O)C(C)C)n1)CC1(CC1)NC2C]

The title compound was obtained by performing the same method as Example 2 except that

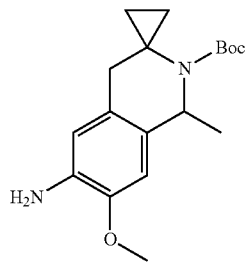 [SMILES: COc1cc2c(cc1N)CC1(CC1)N(C(=O)OC(C)(C)C)C2C]

was used instead of using the tert-butyl-6-amino-7-methoxy-3,4-dihydroisoquinoline-2(1H)-carboxylate.

$^1$H-NMR (300 MHz, CDCl$_3$) δ 9.48 (s, 1H), 8.53 (d, J=8.1 Hz, 1H), 8.16 (s, 1H), 7.94 (s, 1H), 7.07 (d, J=1.8, 1H), 7.58-7.64 (m, 1H), 7.55 (s, 1H), 7.21-7.27 (m, 1H), 6.71 (s, 1H), 4.10 (q J=6.6 Hz, 1H), 3.23 (hept, J=6.9 Hz, 1H), 3.03 (d, J=16.2 Hz, 1H), 2.11 (d, J=15.9 Hz, 1H), 1.69 (br, 1H), 1.46 (d, J=6.6 Hz, 3H), 1.30 (dd, J=6.9, 1.8 Hz, 6H), 0.78-0.85 (m, 1H), 0.54-0.69 (m, 2H), 0.35-0.39 (m, 1H);

LC/MS 528.0 (M$^+$+H).

EXAMPLE 31

Preparation of 5-chloro-N4-(2-(isopropylsulfonyl)phenyl)-N2-(2-benzyl-7-methoxy-1,1-dimethyl-1,2,3,4-tetrahydroisoquinolin-6-yl)pyrimidine-2,4-diamine

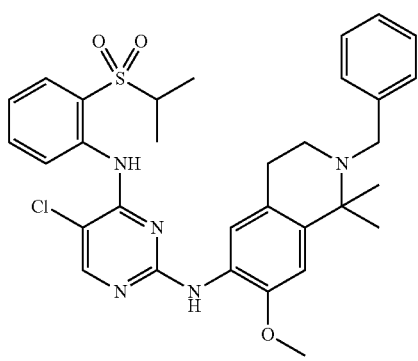 [SMILES: COc1cc2c(cc1Nc1ncc(Cl)c(Nc3ccccc3S(=O)(=O)C(C)C)n1)CCN(Cc1ccccc1)C2(C)C]

Step 1: Preparation of 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine The title compound was obtained by performing the same method as Example 2 except that the tert-butyl-6-amino-7-methoxy-1,1-dimethyl-3,4-dihydroisoquinoline-2(1H)-carboxylate was used instead of using the tert-butyl-6-amino-7-methoxy-3,4-dihydroisoquinoline-2(1H)-carboxylate.

Step 2: Preparation of 5-chloro-N4-(2-(isopropylsulfonyl)phenyl)-N2-(2-benzyl-7-methoxy-1,1-dimethyl-1,2,3,4-tetrahydroisoquinolin-6-yl)pyrimidine-2,4-diamine The title compound was obtained by performing the same method as Example 3 except that the 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine obtained in step 1 and (iodomethyl)benzene were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.47 (s, 1H), 8.52 (d, J=8.4 Hz, 1H), 8.15 (s, 1H), 7.91 (br, 1H), 7.88 (s, 1H), 7.56-7.64 (m, 2H), 7.44 (d, J=7.2 Hz, 2H), 7.34 (t, J=7.5 Hz, 2H), 7.20-7.28 (m, 2H), 6.77 (s, 1H), 3.90 (s, 3H), 3.73 (s, 2H), 3.24 (sept, J=6.9 Hz, 1H), 2.68 (br, 2H), 2.51 (br, 2H), 1.50 (s, 6H), 1.29 (d, J=6.9 Hz, 6H);

LC/MS 606.0 (M$^+$+H).

EXAMPLE 32

Preparation of 1-(6-(5-chloro-4-(2-(isopropylsulfonyl)phenylamino)pyrimidin-2-yl)amino-7-methoxy-1,1-dimethyl-3,4-dihydroisoquinolin-2(1H)-yl)-2,2,2-trifluoroethane-1-one

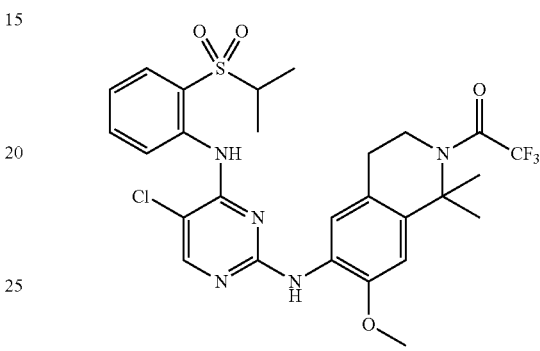

Step 1: Preparation of 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine The title compound was obtained by performing the same method as Example 2 except that tert-butyl-6-amino-7-methoxy-1,1-dimethyl-3,4-dihydroisoquinoline-2(1H)-carboxylate was used instead of using the tert-butyl-6-amino-7-methoxy-3,4-dihydroisoquinoline-2(1H)-carboxylate.

Step 2: Preparation of 5-chloro-N4-(2-(isopropylsulfonyl)phenyl)-N2-(2-benzyl-7-methoxy-1,1-dimethyl-1,2,3,4-tetrahydroisoquinolin-6-yl)pyrimidine-2,4-diamine The title compound was obtained by performing the same method as Example 3 except that the 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine obtained in step 1 and 2,2,2-trifluoroacetyliodide were used instead of using 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.55 (s, 1H), 8.55 (d, J=8.4 Hz, 1H), 8.18 (s, 1H), 8.04 (s, 1H), 7.94 (d, J=7.8 Hz, 1H), 7.64 (t, J=7.2 Hz, 1H), 7.59 (s, 1H), 7.64 (t, J=7.5 Hz, 1H), 6.75 (s, 1H), 3.92 (s, 3H), 3.60 (br, 2H), 3.26 (sept, J=6.9 Hz, 1H), 2.71 (br, 2H), 1.84 s, 6H), 1.31 (d, J=6.9 Hz, 6H);

LC/MS 612.3 (M$^+$+H).

EXAMPLE 33

Preparation of 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine

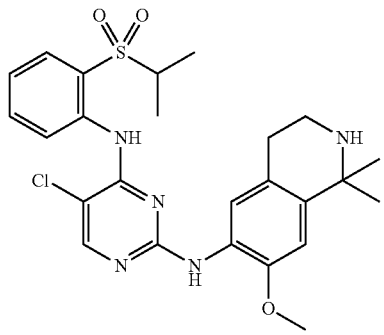 [SMILES: COc1cc2c(cc1Nc1ncc(Cl)c(Nc3ccccc3S(=O)(=O)C(C)C)n1)CCNC2(C)C]

The title compound was obtained by performing the same method as Example 2 except that tert-butyl-6-amino-7-methoxy-1,1-dimethyl-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.49 (s, 1H), 8.54 (d, J=8.4 Hz, 1H), 8.16 (s, 1H), 7.92-7.94 (m, 2H), 7.65 (t, J=6.9 Hz, 1H), 7.55 (s, 1H), 7.24-7.29 (m, 1H), 6.69 (s, 1H), 3.89 (s, 3H), 3.25 (sept, J=6.9 Hz, 1H), 3.12 (t, J=5.7 Hz, 2H), 2.58 (t, J=5.7 Hz, 2H), 1.71 (br, 2H), 1.46 (s, 6H), 1.31 (d, J=6.9 Hz, 6H);

LC/MS 516.2 (M$^+$+H).

EXAMPLE 34

Preparation of 5-chloro-N4-(2-(isopropylsulfonyl)phenyl)-N2-(6-methoxy-1,2,3,4-tetrahydroisoquinolin-7-yl)pyrimidine-2,4-diamine

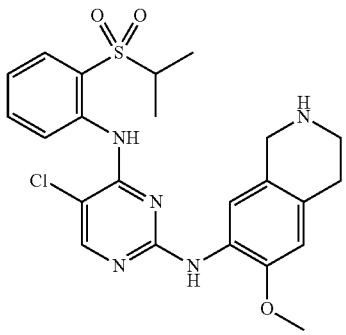 [SMILES: COc1cc2c(cc1Nc1ncc(Cl)c(Nc3ccccc3S(=O)(=O)C(C)C)n1)CNCC2]

The title compound was obtained by performing the same method as Example 2 except that tert-butyl-7-amino-6-methoxy-3,4-dihydroisoquinoline-2(1H)-carboxylate was used instead of using the tert-butyl-6-amino-7-methoxy-3,4-dihydroisoquinoline-2(1H)-carboxylate.

$^1$H NMR (300 MHz, CD3OD) δ 8.27 (s, 1H), 8.18-8.50 (m, 2H), 8.05 (d, J=7.7 Hz, 1H), 7.82 (t, J=7.6 Hz, 1H), 7.63 (t, J=7.7 Hz, 1H), 7.69 (s, 1H), 7.25 (s, 1H), 7.12 (s, 1H), 6.98 (s, 1H), 4034 (s, 2H), 3.89 (s, 3H), 3.57-3.38 (m, 3H), 3.20-3.06 (m, 2H), 1.25 (d, J=6.7 Hz, 6H);

LC/MS 488.5 (M$^+$+H).

EXAMPLE 35

Preparation of 5-chloro-N4-(2-(isopropylsulfonyl)phenyl)-N2-(6-methoxy-2-methyl-1,2,3,4-tetrahydroisoquinolin-7-yl)pyrimidine-2,4-diamine

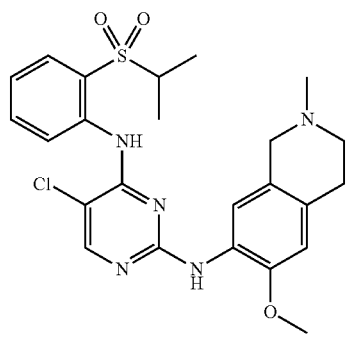 [SMILES: COc1cc2c(cc1Nc1ncc(Cl)c(Nc3ccccc3S(=O)(=O)C(C)C)n1)CN(C)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 was used instead of using the 5-chloro-N4-(2-(isopropylsulfonyl)phenyl)-N2-(7-methoxy-1,2,3,4-tetrahydroisoquinolin-6-yl)pyrimidine-2,4-diamine.

$^1$H NMR (300 MHz, CDCl$_3$) δ 9.56 (s, 1H), 8.50 (d, J=9.0 Hz, 1H), 8.14 (s, 1H), 7.95-7.80 (m, 2H), 7.53 (s, 1H), 7.37 (t, J=7.6 Hz, 1H), 6.75 (s, 1H), 4.60 (s, 2H), 4.14 (t, J=6.08 Hz, 2H), 3.92 (s, 3), 3.30-3.15 (m, 5H), 1.30 (d, J=6.8 Hz, 6H);

LC/MS 501.1 (M$^+$).

EXAMPLE 36

Preparation of 2-(7-(5-chloro-4-(2-(isopropylsulfonyl)phenylamino)pyrimidin-2-yl)amino)-6-methoxy-3,4-dihydroisoquinolin-2(1H)-yl)-ethane-1-ol

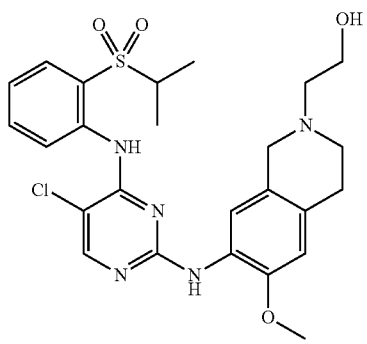 [SMILES: COc1cc2c(cc1Nc1ncc(Cl)c(Nc3ccccc3S(=O)(=O)C(C)C)n1)CN(CCO)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and 2-bromoethanol were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.49 (s, 1H), 8.51 (d, J=8.3 Hz, 1H), 8.15 (s, 2H), 7.93 (s, 2H), 7.67 (t, J=7.67 Hz, 1H), 7.54 (s, 1H), 6.62 (s, 1H), 4.59-4.43 (m, 5H), 3.97-3.79 (m, 3H), 3.79-3.66 (m, 2H), 3.58-3.45 (m, 2H), 2.93-2.67 (m, 3H), 1.30 (d, J=6.6 Hz, 6H);
LC/MS 532.2 (M⁺+H).

EXAMPLE 37

Preparation of 1-(7-(5-chloro-4-(2-(isopropylsulfonyl)phenylamino)pyrimidin-2-yl)amino)-6-methoxy-3,4-dihydroisoquinolin-2(1H)-yl)ethane-1-one

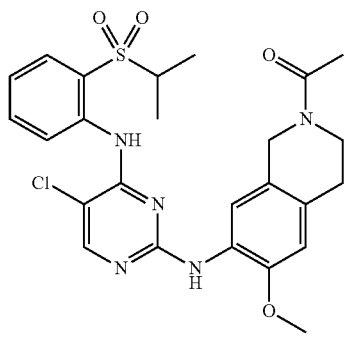 [SMILES: COc1cc2c(cc1Nc1ncc(Cl)c(Nc3ccccc3S(=O)(=O)C(C)C)n1)CN(C(C)=O)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and acetic anhydride were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.
¹H NMR (300 MHz, CDCl₃) δ 9.52 (d, J=6.6 Hz, 1H), 8.50 (dd, J=8.4, 17.7 Hz, 1H), 8.15 (d, J=9.2 Hz, 1H), 8.02 (s, 1H), 7.93 (d, J=7.9 Hz, 1H), 7.81-7.58 (m, 2H), 7.38 (t, J=7.3 Hz, 1H), 6.64 (d, J=6.2 Hz, 1H), 4.53 (s, 1H), 3.88 (s, 3H), 3.81 (t, J=5.1 Hz, 1H), 3.73-3.62 (m, 2H), 3.33-3.16 (m, 1H), 2.84 (dt, J=5.8, 13.4 Hz, 2H), 2.19 (s, 3), 1.31 (d, J=6.7 Hz, 6H);
LC/MS 530.1 (M⁺+H).

EXAMPLE 38

Preparation of 7-(5-chloro-4-(2-(isopropylsulfonyl)phenylamino)pyrimidin-2-yl)amino)-N-ethyl-6-methoxy-3,4-dihydroisoquinoline-2(1H)-carboxamide

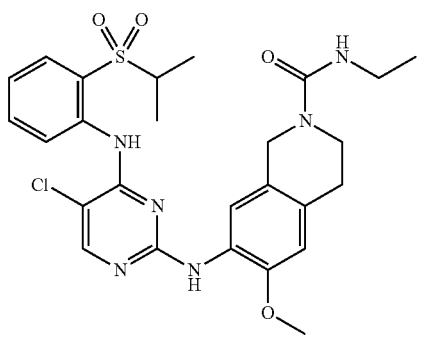 [SMILES: CCNC(=O)N1CCc2cc(OC)c(Nc3ncc(Cl)c(Nc4ccccc4S(=O)(=O)C(C)C)n3)cc2C1]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and ethyl isocyanate were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.
¹H NMR (300 MHz, CDCl₃) δ 9.53 (s, 1H), 8.53 (d, J=8.3 Hz, 1H), 8.15 (s, 1H), 8.04 (s, 1H), 0.7.93 (d, J=7.9 Hz, 1H), 7.71 (t, J=7.8 Hz, 1H), 7.55 (s, 1H), 7.32 (d, J=11.3 Hz, 1H), 6.65 (s, 1H), 4.43 (s, 1H), 4.36 (s, 2H), 3.88 (s, 3H), 3.60 (t, J=5.5 Hz, 2H), 3.42-3.15 (m, 3H), 2.81 (t, J=5.3 Hz, 2H), 1.30 (d, J=6.8 Hz, 6H), 1.85 (t, J=7.1 Hz, 3H);
LC/MS 559.1 (M⁺+H).

EXAMPLE 39

Preparation of 1-(7-(5-chloro-4-(2-(isopropylsulfonyl)phenylamino)pyrimidin-2-yl)amino)-6-methoxy-3,4-dihydroisoquinolin-2(1H)-yl)-2-hydroxyethane-1-one

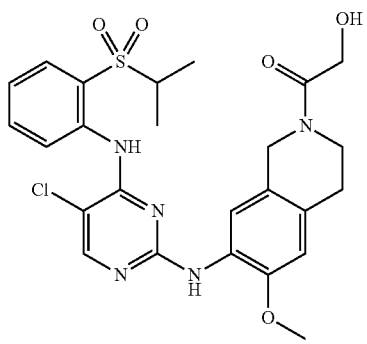 [SMILES: COc1cc2c(cc1Nc1ncc(Cl)c(Nc3ccccc3S(=O)(=O)C(C)C)n1)CN(C(=O)CO)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and glycolic acid were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.
¹H NMR (300 MHz, CDCl₃) δ 9.52 (s, 1H), 8.51 (t, J=7.7 Hz, 1H), 8.18 (d, J=5.8 Hz, 1H), 8.09 (s, 1H), 7.95 (d, J=8.0 Hz, 1H), 7.80-7.52 (m, 2H), 7.40-7.27 (m, 1H), 6.65 (d, J=5.3 Hz, 1H), 4.59 (s, 1H), 4.25 (s, 2H), 4.19 (s, 1H), 3.89 (s, 3H), 3.70-3.54 (m, 2H), 3.45 (t, J=5.8 Hz, 1H), 3.31-3.15 (m, 1H), 2.91-2.76 (m, 2H), 1.32 (d, J=6.8 Hz, 6H);
LC/MS 546.1 (M⁺+H).

EXAMPLE 40

Preparation of 7-(5-chloro-4-(2-(isopropylsulfonyl)phenylamino)pyrimidin-2-yl)amino)-6-methoxy-3,4-dihydroisoquinoline-2(1H)-sulfonamide

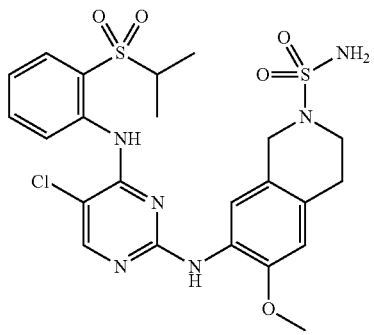 [SMILES: COc1cc2c(cc1Nc1ncc(Cl)c(Nc3ccccc3S(=O)(=O)C(C)C)n1)CN(S(N)(=O)=O)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and sulfonamide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.48 (s, 1H), 8.46 (d, J=8.4 Hz, 1H), 8.13 (s, 1H), 7.98 (s, 1H), 7.91 (d, J=7.9 Hz, 1H), 7.70 (t, J=7.9 Hz, 1H), 7.55 (s, 1H), 7.40-7.28 (m, 1H), 6.62 (s, 1H), 5.00-4.75 (m, 2H), 4.20 (s, 2H), 3.87 (s, 3), 3.47 (t, J=5.6 Hz, 2H), 3.30-3.16 (m, 1H), 2.94 (t, J=5.5 Hz, 2H), 1.30 (d, J=6.9 Hz, 6H);

LC/MS 567.1 (M$^+$+H).

EXAMPLE 41

Preparation of 5-chloro-N4-(2-(isopropylsulfonyl)phenyl)-N2-(6-methoxy-2-ethyl-1,2,3,4-tetrahydroisoquinolin-7-yl)pyrimidine-2,4-diamine

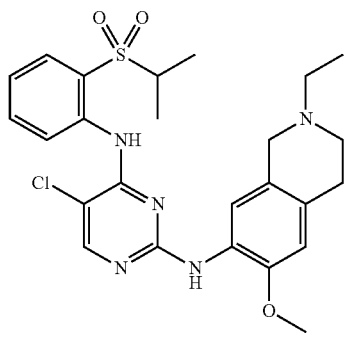 [SMILES: CCN1CCc2cc(OC)c(Nc3ncc(Cl)c(Nc4ccccc4S(=O)(=O)C(C)C)n3)cc2C1]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and ethyl iodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.46 (s, 1H), 8.49 (d, J=8.3 Hz, 1H), 8.15 (s, 1H), 7.95 (s, 1H), 7.92 (s, 1H), 7.69 (t, J=7.8 Hz, 1H), 7.55 (s, 1H), 7.32-7.26 (m, 1H), 6.61 (s, 1H), 3.87 (s, 3H), 3.57 (s, 2H), 3.33-3.16 (m, 1H), 2.90 (dd, J=5.1, 15.9 Hz, 4H), 2.71 (q, J=6.9 Hz, 2H), 1.38-1.21 (m, 9H);

LC/MS 516.2 (M$^+$+H).

EXAMPLE 42

Preparation of 2-(7-(5-chloro-4-(2-(isopropylsulfonyl)phenylamino)pyrimidin-2 yl)amino)-6-methoxy-3,4-dihydroisoquinolin-2(1H)-yl)-N, N-dimethylacetamide

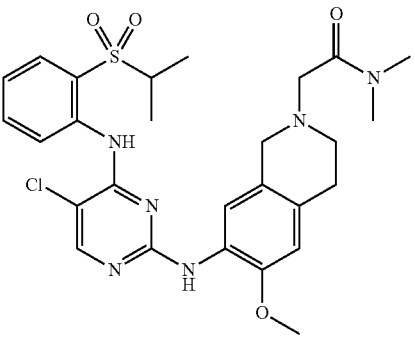 [SMILES: COc1cc2c(cc1Nc1ncc(Cl)c(Nc3ccccc3S(=O)(=O)C(C)C)n1)CN(CC(=O)N(C)C)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and 2-chloro-N,N-dimethylacetamide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.51 (s, 1H), 8.50 (d, J=8.3 Hz, 1H), 8.15 (s, 1H), 8.00-7.88 (m, 2H), 7.71 (t, J=7.8 Hz, 1H), 7.55 (s, 1H), 7.32 (d, J=7.4 Hz, 1H), 6.62 (s, 1H), 7.08 (s, 2H), 3.87 (s, 3H), 3.84 (s, 2H), 3.69-3.53 (m, 4H), 3.33-3.17 (m, 1H), 3.10 (s, 3H), 2.99 (s, 3H), 1.31 (d, J=6.8 Hz, 6H);

LC/MS 573.1 (M$^+$+H).

EXAMPLE 43

Preparation of 5-chloro-N4-(2-(isopropylsulfonyl)phenyl)-N2-(2-(2-(dimethylaminoethyl)-6-methoxy-1,2,3,4-tetrahydroquinolin-7-yl)pyrimidine-2,4-diamine

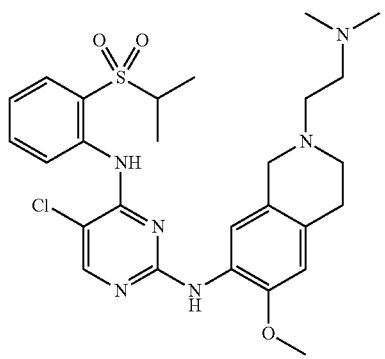 [SMILES: COc1cc2c(cc1Nc1ncc(Cl)c(Nc3ccccc3S(=O)(=O)C(C)C)n1)CN(CCN(C)C)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and 2-iodo-N,N-dimethylethanamine were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.66 (s, 1H), 8.80 (s, 1H), 8.69-8.66 (m, 1H), 8.18 (s, 1H), 7.89-7.87 (s, 1H), 7.73-7.70 (m, 1H), 7.39 (s, 1H), 6.71 (s, 1H), 5.84 (s, 1H), 3.95 (s, 3H), 3.89 (m, 2H), 3.73-3.49 (m, 6H), 3.26-3.21 (m, 1H), 2.99-2.95 (m, 2H), 1.32 (d, J=6.9 Hz, 6H), 1.25 (s, 6H);
LC/MS 559 (M$^+$+H).

EXAMPLE 44

Preparation of 7-(5-chloro-4-(2-(isopropylsulfonyl)phenylamino)pyrimidin-2-yl)amino)-6-methoxy-3,4-dihydroisoquinoline-1(2H)-one

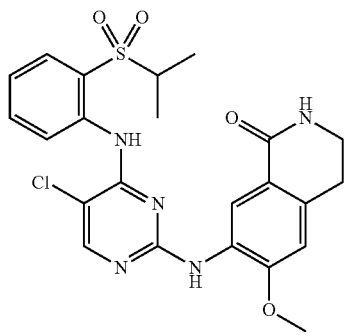 [SMILES: COc1cc2c(cc1Nc1ncc(Cl)c(Nc3ccccc3S(=O)(=O)C(C)C)n1)C(=O)NCC2]

The title compound was obtained by performing the same method as Example 2 except that the tert-butyl 7-amino-6-methoxy-1-oxo-3,4-dihydroisoquinoline-2(1H)-carboxylate was used instead of using the tert-butyl-6-amino-7-methoxy-3,4-dihydroisoquinoline-2(1H)-carboxylate.

$^1$H NMR (300 MHz, CDCl$_3$) δ 9.66 (s, 1H), 8.80 (s, 1H), 8.69 (m, 1H), 8.19 (s, 1H), 7.89 (s, 1H), 7.71 (s, 1H), 7.3 9 (m, 1H), 6.71 (s, 1H), 5.90 (m, 1H), 3.95 (s, 3H), 3.57 (m, 2H), 2.97 (m, 2H), 1.32 (d, J=6.9 Hz, 6H);
LC/MS 552 (M$^+$+H).

EXAMPLE 45

Preparation of 5-chloro-N4-(2-(isopropylsulfonyl)phenyl)-N2-(6-methoxy-2-(piperidine-4-yl)-1,2,3,4-tetrahydroquinolin-7-yl)pyrimidine-2,4-diamine

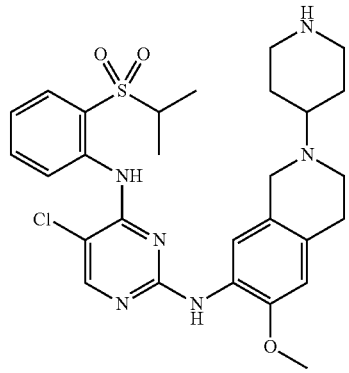 [SMILES: COc1cc2c(cc1Nc1ncc(Cl)c(Nc3ccccc3S(=O)(=O)C(C)C)n1)CN(C1CCNCC1)CC2]

The title compound was obtained by performing the same method as Example 3 except that the 5-chloro-N4-(2-(isopropylsulfonyl)phenyl)-N2-(6-methoxy-1,2,3,4-tetrahydroisoquinolin-7-yl)pyrimidine-2,4-diamine obtained in Example 34 and 4-iodopiperidine were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.48 (s, 1H), 8.53-8.51 (m, 1H), 8.16 (s, 1H), 7.95-7.92 (m, 2H), 7.69-7.64 (m, 1H), 7.55 (m, 1H), 6.61 (s, 1H), 4.22 (s, 2H), 3.86 (s, 3H), 3.74-3.58 (m, 5H), 3.28-3.23 (m, 1H), 2.87-2.65 (m, 6H), 1.88-1.81 (m, 2H), 1.49 (s, 9H), 1.33 (d, J=6.9 Hz, 6H);
LC/MS 671 (M$^+$+H).

EXAMPLE 46

Preparation of 5-chloro-N4-(2-(isopropylsulfonyl)phenyl)-N2-(6-methoxy-1-methyl-1,2,3,4-tetrahydroquinolin-7-yl)pyrimidine-2,4-diamine

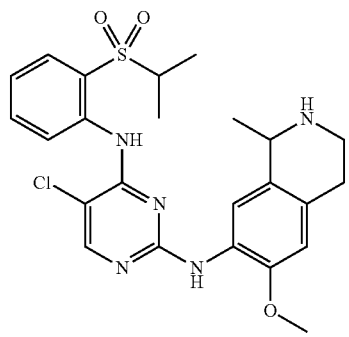 [SMILES: COc1cc2c(cc1Nc1ncc(Cl)c(Nc3ccccc3S(=O)(=O)C(C)C)n1)C(C)NCC2]

The title compound was obtained by performing the same method as Example 2 except that the tert-butyl-7-amino-6-methoxy-1-methyl-3,4-dihydroisoquinoline-2(1H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.44 (br, 1H), 8.45 (d, J=8.1 Hz, 1H), 8.17 (s, 1H), 8.06 (s, 1H), 7.93 (d, J=7.8 Hz, 1H), 7.64 (t, J=7.8 Hz, 1H), 7.56 (br, 1H), 7.24-7.29 (m, 1H), 6.58 (s, 1H), 3.91-3.96 (m, 1H), 3.87 (s, 3H), 3.22-3.28 (m, 2H), 2.96-3.05 (m, 1H), 2.77-2.87 (m, 1H), 2.68-2.70 (m, 1H), 1.78 (br, 1H), 1.34 (d, J=6.9 Hz, 3H), 1.26 (d, J=6.9 Hz, 3H), 1.09 (d, J=6.0 Hz, 3H);
LC/MS 501.9 (M$^+$+H).

EXAMPLE 47

Preparation of 5-chloro-N4-(2-(isopropylsulfonyl)phenyl)-N2-(6-methoxy-2,3,4,5-tetrahydro-1H-benzo[d]azepin-7-yl)pyrimidine-2,4-diamine

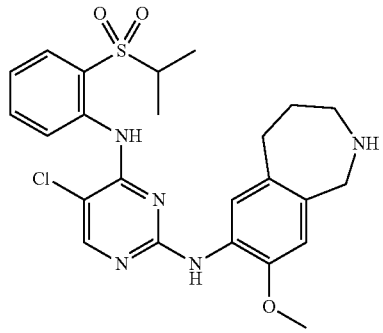 [SMILES: COc1cc2c(cc1Nc1ncc(Cl)c(Nc3ccccc3S(=O)(=O)C(C)C)n1)CCCNC2]

The title compound was obtained by performing the same method as Example 2 except that the tert-butyl-7-amino-8-methoxy-4,5-dihydro-1H-benzo[c]azepin-2(3H)-carboxylate was used instead of using the tert-butyl-6-amino-7-methoxy-3,4-dihydroisoquinoline-2(1H)-carboxylate.

$^1$H NMR (300 MHz, CDCl$_3$) δ 8.31 (s, 1H), 8.09-8.05 (m, 1H), 7.83 (m, 1H), 7.67-7.64 (m, 1H), 7.50 (s, 1H), 7.32-7.29 (s, 1H), 7.14 (s, 1H), 4.36 (s, 1H), 4.01-4.00 (m, 1H), 3.92 (s, 3H), 3.59 (s, 3H), 3.52-3.40 (m, 4H), 1.29-1.15 (m, 6H);
LC/MS 552.10 (M$^+$).

EXAMPLE 48

Preparation of 7-((5-chloro-4-(2-(isopropylsulfonyl)phenylamino)pyrimidin-2-yl)amino)-8-methoxy-2,3,4,5-tetrahydro-1H-benzo[c]azepin-1-one

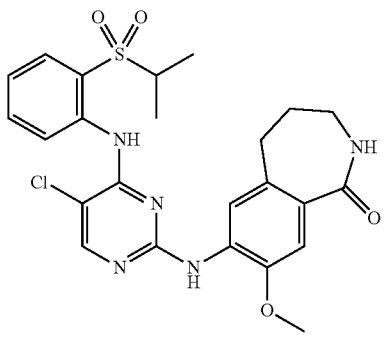 [SMILES: COc1cc2c(cc1Nc1ncc(Cl)c(Nc3ccccc3S(=O)(=O)C(C)C)n1)CCCNC2=O]

The title compound was obtained by performing the same method as Example 2 except that the tert-butyl-7-amino-8-methoxy-1-oxo-4,5-dihydro-1H-benzo[c]azepin-2 (3H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.85 (s, 1H), 8.48 (d, J=9 Hz, 1H), 8.15 (s, 1H), 7.80 (d, J=9 Hz, 1H), 7.65 (s, 1H), 7.55-7.50 (m, 2H), 7.13-7.10 (s, 1H), 3.87 (s, 3H), 3.15-3.05 (m, 2H), 2.65-2.55 (m, 2H), 2.05-2.00 (m, 2H), 1.25 (d, J=6 Hz, 6H);
LC/MS 516.10 (M$^+$).

EXAMPLE 49

Preparation of 5-chloro-N4-(2-(isopropylsulfonyl)phenyl)-N2-(3-ethyl-6-methoxy-2,3,4,5-tetrahydro-1H-benzo[d]azepin-7-yl)pyrimidine-2,4-diamine

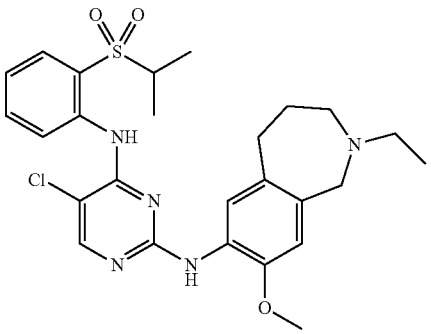 [SMILES: CCN1CCCc2cc(Nc3ncc(Cl)c(Nc4ccccc4S(=O)(=O)C(C)C)n3)c(OC)cc2C1]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and ethyl iodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.49 (s, 1H), 8.55 (d, J=8.49, 1H), 8.16 (s, 1H), 8.04 (s, 1H), 7.92 (d, J=7.86, 1H), 7.65-7.60 (m, 1H), 7.53 (s, 1H), 6.70 (s, 1H), 3.87-3.84 (m, 4H), 3.25-3.23 (m, 3H), 3.08 (s, 2H), 2.53-2.46 (m, 2H), 2.05 (s, 1H), 1.68-1.67 (m, 2H), 1.34-1.14 (m, 6H), 1.11-1.09 (m, 3H);
LC/MS 530.10 (M$^+$).

EXAMPLE 50

Preparation of 1-(7-((5-chloro-4-(2-(isopropylsulfonyl)phenylamino)pyrimidin-2-yl)amino)-6-methoxy-4,5-dihydro-1H-benzo[d]azepin-3(2H)-yl)ethanone

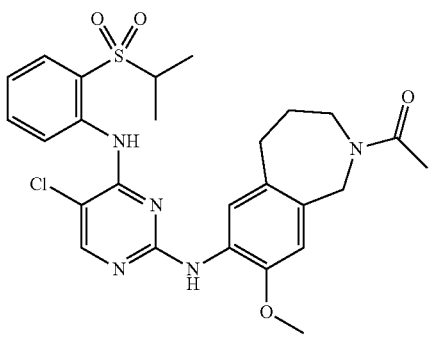 [SMILES: COc1cc2c(cc1Nc1ncc(Cl)c(Nc3ccccc3S(=O)(=O)C(C)C)n1)CCCN(C(C)=O)C2]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and acetic anhydride were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.50 (s, 1H), 8.56-8.50 (m, 1H), 8.15-8.05 (m, 2H), 7.91 (d, 1H), 7.62-7.56 (m, 2H), 6.93 (s, 1H), 6.69 (s, 1H), 4.47 (d, J=18.57, 2H), 3.89 (s, 3H), 3.86-3.84 (m, 3H), 3.28-3.23 (m, 1H), 2.82-2.73 (m, 2H), 2.15 (d, J=9.03, 2H), 2.06 (s, 3H), 1.78 (s, 2H), 1.32-1.25 (m, 6H);
LC/MS 544.10 (M$^+$).

EXAMPLE 51

Preparation of 1-(7-((5-chloro-4-(2-(isopropylsulfonyl)phenylamino)pyrimidin-2-yl)amino)-6-methoxy-4,5-dihydro-1H benzo[d]azepin-3(2H)-yl)-2-hydroxyethanone

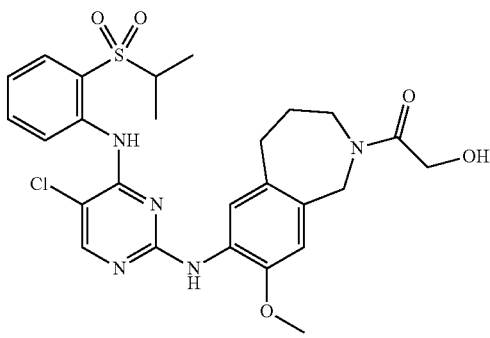 [SMILES: COc1cc2c(cc1Nc1ncc(Cl)c(Nc3ccccc3S(=O)(=O)C(C)C)n1)CCCN(C(=O)CO)C2]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and glycolic acid were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.50 (s, 1H), 8.55-8.49 (m, 1H), 8.16-8.09 (m, 2H), 7.94 (m, 1H), 7.63-7.57 (m, 1H), 6.93 (s, 1H), 6.64 (s, 1H), 4.57 (s, 1H), 4.28 (d, J=13.53 Hz, 1H), 4.15-4.12 (m, 1H), 3.90 (s, 3H), 3.62-3.52 (m, 2H), 3.23 (m, 1H), 2.79-2.75 (m, 2H), 2.04 (s, 1H), 1.83-1.78 (m, 2H), 1.32-1.23 (m, 6H);
LC/MS 560.04 (M$^+$).

EXAMPLE 52

Preparation of 2-(7-((5-chloro-4-(2-(isopropylsulfonyl)phenylamino)pyrimidin-2-yl)amino)-8-methoxy-4,5-dihydro-1H-benzo[d]azepin-3(2H)-yl)ethanol

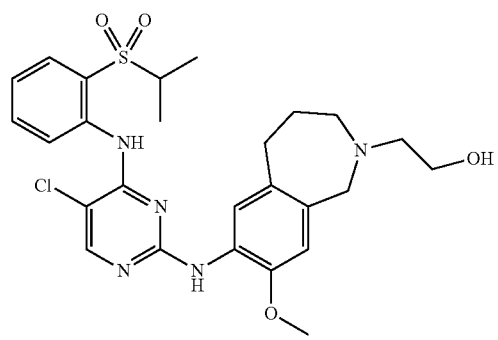 [SMILES: COc1cc2c(cc1Nc1ncc(Cl)c(Nc3ccccc3S(=O)(=O)C(C)C)n1)CCCN(CCO)C2]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and 2-bromoethanol were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.47 (s, 1H), 8.53 (d, J=9 Hz, 1H), 8.15 (s, 1H), 7.98-7.90 (m, 2H), 7.62-7.57 (t, J=6 Hz, 1H), 7.27-7.22 (m, 1H), 6.65 (s, 1H), 3.67 (s, 3H), 3.47 (s, 1H), 3.32-3.20 (q, J=6 Hz, 1H), 3.00-2.86 (m, 5H), 2.71-2.68 (m, 2H), 2.35-2.30 (s, 1H), 1.35 (d, J=6 Hz, 6H);
LC/MS 546.08 (M$^+$).

EXAMPLE 53

Preparation of 5-chloro-N4-(2-(isopropylsulfonyl)phenyl)-N2-(6-methoxy-3-(piperidin-4-yl)-2,3,4,5-tetrahydro-1H-benzo[d]azepin-7-yl)pyrimidine-2,4-diamine

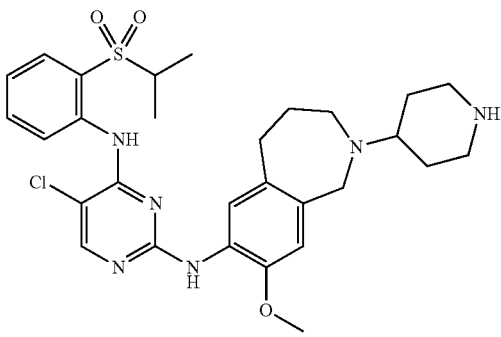 [SMILES: COc1cc2c(cc1Nc1ncc(Cl)c(Nc3ccccc3S(=O)(=O)C(C)C)n1)CCCN(C1CCNCC1)C2]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and 4-iodopiperidine were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.49 (s, 1H), 8.55 (d, J=14.16 Hz, 1H), 8.17-8.13 (m, 1H), 8.07-8.03 (m, 1H), 7.94-7.89 (m, 1H), 7.72-7.51 (m, 1H), 6.70-6.65 (m, 1H), 4.15-3.99 (m, 2H), 3.92-3.77 (m, 3H), 3.66-3.63 (m, 1H), 3.48-3.47 (m, 1H), 2.76-2.44 (m, 4H), 2.05-1.98 (m, 1H), 1.90-1.79 (m, 2H), 1.78-1.62 (m, 2H), 1.37-1.17 (m, 6H), 1.00-0.77 (m, 2H);

LC/MS 546.10 (M$^+$).

EXAMPLE 54

Preparation of 5-chloro-N4-(2-(isopropylsulfonyl)phenyl)-N2-(6-methoxy-3-(tetrahydro-2H-pyran-4-yl)-2,3,4,5-tetrahydro-1H-benzo[d]azepin-7-yl)pyrimidine-2,4-diamine

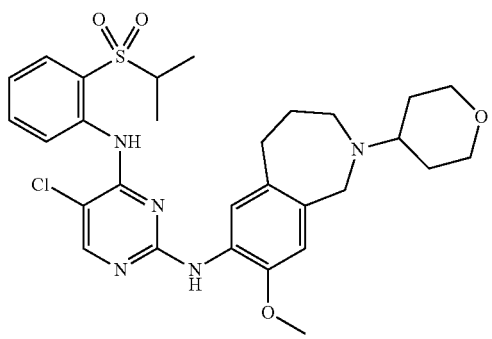 [SMILES: COc1cc2c(cc1Nc1ncc(Cl)c(Nc3ccccc3S(=O)(=O)C(C)C)n1)CCCN(C1CCOCC1)C2]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and 4-iodo-tetrahydro-2H-pyran were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.50 (s, 1H), 8.55 (d, J=8.43 Hz, 1H), 8.16 (s, 1H), 8.07 (s, 1H), 7.91 (s, 1H), 7.65-7.55 (m, 2H), 6.67 (s, 1H), 4.01-3.97 (m, 2H), 3.86 (s, 3H), 3.34-3.16 (m, 4H), 2.74-2.71 (m, 2H), 2.63 (m, 1H), 2.02 (m, 1H), 1.85-1.81 (m, 2H), 1.73-1.60 (m, 3H), 1.37-1.23 (m, 6H);

LC/MS 585.15 (M$^+$).

EXAMPLE 55

Preparation of 5-chloro-N4-(2-(isopropylsulfonyl)phenyl)-N2-(3-cyclobutyl-6-methoxy-2,3,4,5-tetrahydro-1H-benzo[d]azepin-7-yl)pyrimidine-2,4-diamine

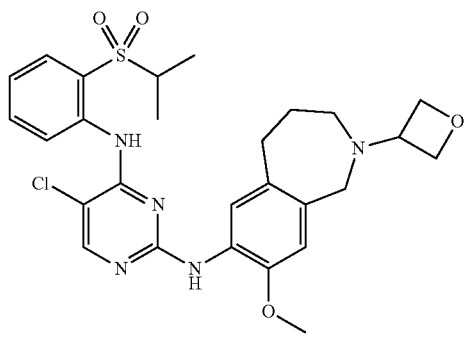 [SMILES: COc1cc2c(cc1Nc1ncc(Cl)c(Nc3ccccc3S(=O)(=O)C(C)C)n1)CCCN(C1COC1)C2]

The title compound was obtained by performing the same method as Example 3 except that the 5-chloro-N4-(2-(isopropylsulfonyl)phenyl)-N2-(6-methoxy-2,3,4,5-tetrahydro-1H-benzo[d]azepin-7-yl)pyrimidine-2,4-diamine obtained in Example 47 and 3-iodooxetane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.50 (s, 1H), 8.54 (d, J=11.97 Hz, 1H), 8.16 (s, 1H), 8.06 (s, 1H), 7.93 (d, J=14.16 Hz, 1H), 7.66-7.53 (m, 2H), 6.58 (s, 1H), 4.59 (s, 3H), 3.86 (s, 3H), 3.77-3.71 (m, 1H), 3.60 (s, 2H), 3.28-3.22 (m, 1H), 2.85-2.78 (m, 2H), 2.74-2.67 (m, 2H), 2.05-2.01 (m, 1H), 1.74-1.66 (m, 2H), 1.33-1.22 (m, 6H);

LC/MS 556.12 (M$^+$).

EXAMPLE 56

Preparation of 5-chloro-N4-(2-(isopropylsulfonyl)phenyl)-N2-(7-methoxy-2,3,4,5-tetrahydro-1H-benzo[c]azepin-8-yl)pyrimidine-2,4-diamine

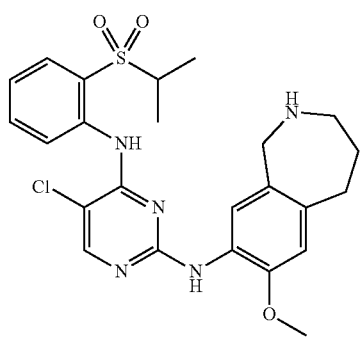 [SMILES: COc1cc2c(cc1Nc1ncc(Cl)c(Nc3ccccc3S(=O)(=O)C(C)C)n1)CNCCC2]

The title compound was obtained by performing the same method as Example 2 except that the tert-butyl 8-amino-7-methoxy-4,5-dihydro-1H-benzo[c]azepin-2(3H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 10.20 (s, 1H), 9.00-8.75 (s. 1H), 8.63 (s, 1H), 8.26 (s, 1H), 7.83 (d, J=6 Hz, 1H), 7.72-7.70 (m, 1H), 7.68 (s, 1H), 7.43-7.40 (m, 1H), 6.98 (s, 1H), 4.05-4.00 (s, 2H), 3.68 (s, 3H), 2.96-2.92 (m, 4H), 1.84-1.81 (m, 4H), 1.17-1.10 (m, 6H);

LC/MS 502.03 (M$^+$).

EXAMPLE 57

Preparation of 8-((5-chloro-4-(2-(isopropylsulfonyl)phenylamino)pyrimidin-2-yl)amino)-7-methoxy-2,3,4,5-tetrahydro-1H-benzo[c]azepin-1-one

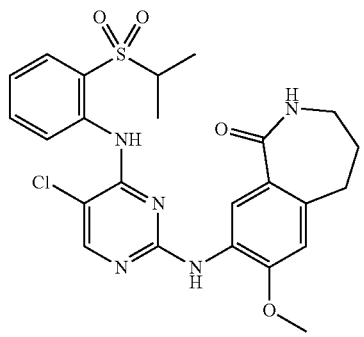 [SMILES: COc1cc2c(cc1Nc1ncc(Cl)c(Nc3ccccc3S(=O)(=O)C(C)C)n1)C(=O)NCCC2]

The title compound was obtained by performing the same method as Example 2 except that the tert-butyl 8-amino-7-methoxy-1-oxo-4,5-dihydro-1H-benzo[c]azepin-2(3H)-carboxylate was used instead of using the tert-butyl-6-amino-7-methoxy-3,4-dihydroisoquinoline-2(1H)-carboxylate.

$^1$H-NMR (300 MHz, CDCl$_3$) δ 9.58 (s, 1H), 8.57-8.55 (m, 1H), 8.15 (s, 1H), 7.88-7.86 (m, 1H), 7.70-7.68 (m, 1H), 7.44 (s, 1H), 6.68 (s, 1H), 6.26 (s, 1H), 3.91 (s, 3H), 3.50-3.47 (m, 1H), 36.15-3.13 (m, 3H), 2.80 (s, 2H), 1.96 (s, 2H), 1.60 (s, 2H), 1.17 (s, 6H);

LC/MS 516.01 (M$^+$).

EXAMPLE 58

Preparation of 5-chloro-N4-(2-(isopropylsulfonyl)phenyl)-N2-(2-ethyl-7-methoxy-2,3,4,5-tetrahydro-1H-benzo[c]azepin-8-yl)pyrimidine-2,4-diamine

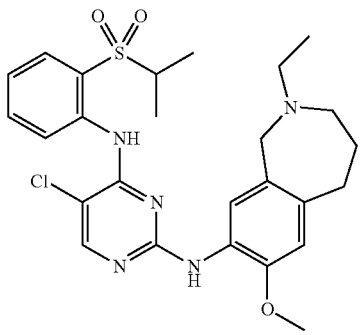 [SMILES: CCN1CCCc2cc(OC)c(Nc3ncc(Cl)c(Nc4ccccc4S(=O)(=O)C(C)C)n3)cc2C1]

The title compound was obtained by performing the same method as Example 3 except that the 5-chloro-N4-(2-(isopropylsulfonyl)phenyl)-N2-(7-methoxy-2,3,4,5-tetrahydro-1H-benzo[c]azepin-8-yl)pyrimidine-2,4-diamine obtained in Example 56 and ethyl iodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.49 (s, 1H), 8.49 (d, J=8.4 Hz, 1H), 8.16 (s, 1H), 8.11 (s, 1H), 7.93 (d, J=8.0 Hz, 1H), 7.68 (t, J=7.9 Hz, 1H), 7.53 (s, 1H), 7.33 (t, J=7.6 Hz, 1H), 6.70 (s, 1H), 3.90 (s, 3H), 3.21-3.12 (m, 2H), 2.94-2.81 (m, 2H), 2.51-2.36 (m, 2H), 1.83-1.71 (m, 2H), 1.30 (d, J=6.8 Hz, 6H), 0.98 (t, J=7.0 Hz, 3H);

LC/MS 530.2 (M$^+$+H).

EXAMPLE 59

Preparation of 1-(8-((5-chloro-4-(2-(isopropylsulfonyl)phenylamino)pyrimidin-2-yl)amino)-7-methoxy-4,5-dihydro-1H-benzo[c]azepin-2(3H)-yl)ethanone

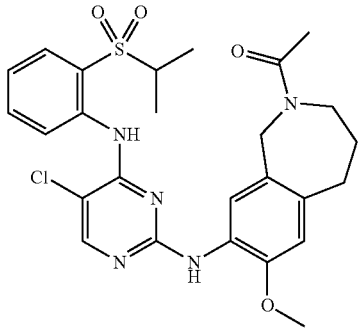 [SMILES: COc1cc2c(cc1Nc1ncc(Cl)c(Nc3ccccc3S(=O)(=O)C(C)C)n1)CN(C(C)=O)CCC2]

The title compound was obtained by performing the same method as Example 3 except that the 5-chloro-N4-(2-(isopropylsulfonyl)phenyl)-N2-(7-methoxy-2,3,4,5-tetrahydro-1H-benzo[c]azepin-8-yl)pyrimidine-2,4-diamine obtained in Example 56 and acetic anhydride were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.56 (s, 0.5H), 9.53 (s, 0.5H), 8.60 (d, J=8.3 Hz, 0.5H), 8.54 (d, J=8.3 Hz, 0.5H), 8.24-8.11 (m, 2H), 7.99-7.86 (m, 1H), 7.77-7.61 (m, 1H), 7.55 (s, 0.5H), 7.46 (s, 0.5H), 7.35-7.20 (m, 1H), 6.72 (s, 0.5H), 6.68 (s, 0.5H), 4.44 (s, 1H), 4.34 (s, 1H), 3.89 (s, 1.5H), 3.87 (s, 1.5H), 3.82 (s, 1H), 3.70-3.62 (m, 1H), 3.34-3.18 (m, 1H), 2.97-2.86 (m, 2H), 2.04 (s, 1.5H), 1.86 (s, 1.5H), 1.84-1.72 (m, 2H), 1.39-1.27 (m, 6H);

LC/MS 544.2 (M⁺+H).

EXAMPLE 60

Preparation of 1-(8-((5-chloro-4-(2-(isopropylsulfonyl)phenylamino)pyrimidin-2-yl)amino)-7-methoxy-4,5-dihydro-1H-benzo[c]azepin-2(3H)-yl)-2-hydroxyethanone

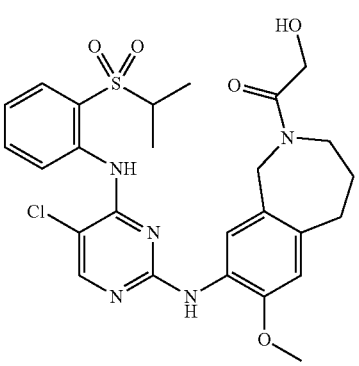 [SMILES: COc1cc2c(cc1Nc1ncc(Cl)c(Nc3ccccc3S(=O)(=O)C(C)C)n1)CN(C(=O)CO)CCC2]

The title compound was obtained by performing the same method as Example 3 except that the 5-chloro-N4-(2-(isopropylsulfonyl)phenyl)-N2-(7-methoxy-2,3,4,5-tetrahydro-1H-benzo[c]azepin-8-yl)pyrimidine-2,4-diamine obtained in Example 56 and glycolic acid were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.61 (s, 0.5H), 9.53 (s, 0.5H), 8.58 (d, J=8.3 Hz, 0.5H), 8.52 (d, J=8.4 Hz, 0.5H), 8.28 (s, 0.5H), 8.26-8.13 (m, 1.5H), 8.21-7.95 (m, 1H), 7.78-7.59 (m, 1H), 7.54 (s, 0.5H), 7.48 (s, 0.5H), 7.35-7.21 (m, 1H), 6.72 (s, 0.5H), 6.69 (s, 0.5H), 4.48 (s, 1H), 4.20 (s, 1H), 4.09 (d, J=4.0 Hz, 1H), 3.89 (m, 3H), 3.58-3.49 (m, 1.5H), 3.43-3.37 (m, 0.5H), 3.37-3.25 (m, 1H), 2.96-2.93 (m, 2H), 1.82 (m, 2H), 1.34 (d, J=6.8 Hz, 6H);

LC/MS 560.2 (M⁺+H).

EXAMPLE 61

Preparation of 2-(8-((5-chloro-4-(2-(isopropylsulfonyl)phenylamino)pyrimidin-2-yl)amino)-7-methoxy-4,5-dihydro-1H-benzo[c]azepin-2(3H)-yl)ethanol

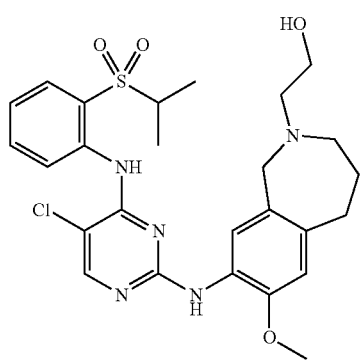 [SMILES: COc1cc2c(cc1Nc1ncc(Cl)c(Nc3ccccc3S(=O)(=O)C(C)C)n1)CN(CCO)CCC2]

The title compound was obtained by performing the same method as Example 3 except that the 5-chloro-N4-(2-(isopropylsulfonyl)phenyl)-N2-(7-methoxy-2,3,4,5-tetrahydro-1H-benzo[c]azepin-8-yl)pyrimidine-2,4-diamine obtained in Example 56 and 2-bromoethanol were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.53 (s, 1H), 8.50 (d, J=8.4 Hz, 1H), 8.17 (s, 1H), 8.07 (s, 1H), 7.95 (d, J=7.9 Hz, 1H), 7.68 (t, J=7.6 Hz, 1H), 7.51 (s, 1H), 7.32 (t, J=7.9 Hz, 1H), 6.71 (s, 1H), 3.90 (s, 3H), 3.86 (s, 2H), 3.50-3.40 (m, 2H), 3.33-3.22 (m, 1H), 3.22-3.15 (m, 2H), 2.96-2.82 (m, 2H), 2.57-2.46 (m, 2H), 1.82-1.68 (m, 2H), 1.32 (d, J=6.8 Hz, 6H);

LC/MS 546.2 (M⁺+H).

EXAMPLE 62

Preparation of 5-chloro-N4-(2-(isopropylsulfonyl)phenyl)-N2-(7-methoxy-2-(piperidin-4-yl)-2,3,4,5-tetrahydro-1H-benzo[c]azepin-8-yl)pyrimidine-2,4-diamine

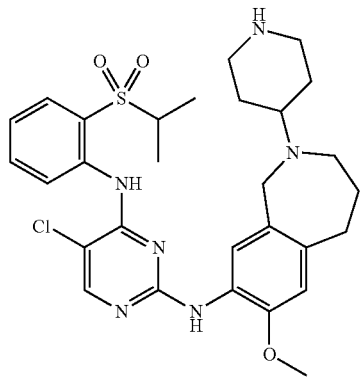 [SMILES: COc1cc2c(cc1Nc1ncc(Cl)c(Nc3ccccc3S(=O)(=O)C(C)C)n1)CN(C1CCNCC1)CCC2]

The title compound was obtained by performing the same method as Example 3 except that the 5-chloro-N4-(2-(isopropylsulfonyl)phenyl)-N2-(7-methoxy-2,3,4,5-tetrahydro- 1H-benzo[c]azepin-8-yl)pyrimidine-2,4-diamine obtained in Example 56 and 4-iodopiperidine were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CD3OD) δ 8.33-8.16 (m, 2H), 8.16-8.00 (m, 1H), 7.90-7.73 (m, 1H), 7.73-7.59 (m, 1H), 7.59-7.42 (m, 1H), 7.12 (s, 1H), 4.60-4.29 (m, 2H), 3.91 (s, 3H), 3.78-3.52 (m, 7H), 3.24-3.00 (m, 3H), 2.38 (m, 2H), 2.17 (m, 4H), 1.41-1.22 (m, 6H);

LC/MS 585.3 (M⁺+H).

EXAMPLE 63

Preparation of 5-chloro-N4-(2-(isopropylsulfonyl)phenyl)-N2-(7-methoxy-2-(tetrahydro-2H-pyran-4-yl)-2,3,4,5-tetrahydro-1H-benzo[c]azepin-8-yl)pyrimidine-2,4-diamine

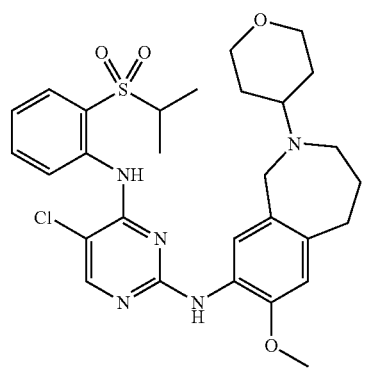 [SMILES: COc1cc2c(cc1Nc1ncc(Cl)c(Nc3ccccc3S(=O)(=O)C(C)C)n1)CN(C1CCOCC1)CCC2]

The title compound was obtained by performing the same method as Example 3 except that the 5-chloro-N4-(2-(isopropylsulfonyl)phenyl)-N2-(7-methoxy-2,3,4,5-tetrahydro-1H-benzo[c]azepin-8-yl)pyrimidine-2,4-diamine obtained in Example 56 and 4-iodo-tetrahydro-2H-pyran were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.54 (s, 1H), 8.54 (d, J=8.2 Hz, 1H), 8.16 (s, 1H), 8.02 (s, 1H), 7.94 (d, J=7.9 Hz, 1H), 7.66 (t, J=7.8 Hz, 1H), 7.48 (s, 1H), 7.31 (d, J=7.5 Hz, 1H), 6.72 (s, 1H), 3.96-3.81 (m, 6H), 3.33-3.14 (m, 5H), 2.94-2.85 (m, 2H), 2.55-2.39 (m, 1H), 1.97 (s, 1H), 1.80-1.65 (m, 4H), 1.53-1.40 (m, 2H), 1.32 (d, J=6.9 Hz, 6H);

LC/MS 586.2 (M⁺+H).

EXAMPLE 64

Preparation of 5-chloro-N4-(2-(isopropylsulfonyl)phenyl)-N2-(7-methoxy-2-(oxetan-3-yl)-2,3,4,5-tetrahydro-1H-benzo[c]azepin-8-yl)pyrimidine-2,4-diamine

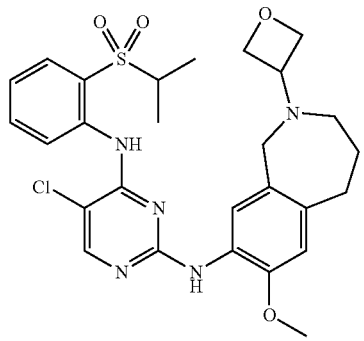 [SMILES: COc1cc2c(cc1Nc1ncc(Cl)c(Nc3ccccc3S(=O)(=O)C(C)C)n1)CN(C1COC1)CCC2]

The title compound was obtained by performing the same method as Example 3 except that the 5-chloro-N4-(2-(isopropylsulfonyl)phenyl)-N2-(7-methoxy-2,3,4,5-tetrahydro-1H-benzo[d]azepin-8-yl)pyrimidine-2,4-diamine obtained in Example 56 and 3-iodooxetane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.57 (s, 1H), 8.53 (d, J=8.2 Hz, 1H), 8.16 (s, 1H), 8.02-7.90 (m, 2H), 7.64 (t, J=7.2 Hz, 1H), 7.51 (s, 1H), 7.34-7.28 (m, 1H), 6.70 (s, 1H), 4.77-4.58 (m, 1H), 4.51-4.33 (m, 3H), 3.89 (s, 3H), 3.70-3.60 (m, 1H), 3.57 (s, 2H), 3.34-3.18 (m, 1H), 2.96-2.79 (m, 4H), 1.80-1.62 (m, 2H), 1.28 (d, J=7.0 Hz, 6H);

LC/MS 558.2 (M⁺+H).

EXAMPLE 65

Preparation of 5-chloro-N4-(2-(isopropylsulfonyl)phenyl)-N2-(8-methoxy-2,3,4,5-tetrahydro-1H-benzo[d]azepin-7-yl)pyrimidine-2,4-diamine

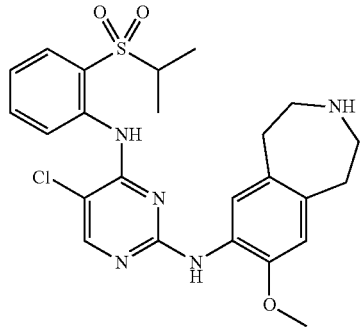 [SMILES: COc1cc2c(cc1Nc1ncc(Cl)c(Nc3ccccc3S(=O)(=O)C(C)C)n1)CCNCC2]

The title compound was obtained by performing the same method as Example 2 except that tert-butyl-7-amino-8-methoxy-1,2,4,5-tetrahydrobenzo[d]azepin-3-carboxylate was used instead of using the tert-butyl-6-amino-7-methoxy-3,4-dihydroisoquinoline-2(1H)-carboxylate.

¹H-NMR (300 MHz, CDCl₃) δ 8.25-8.23 (m, 2H), 8.1.6-8.14 (s, 1H), 7.78-7.74 (s, 1H), 7.60-7.56 (s, 1H), 7.40-7.33 (s, 1H), 7.00-6.98 (s, 1H), 3.84 (s, 3H), 3.70-3.55 (m, 5H), 2.91-2.89 (m, 2H), 2.12 (s, 1H), 1.98 (s, 1H), 1.35-1.13 (m, 6H);
LC/MS 502.03 (M⁺).

EXAMPLE 66

Preparation of 7-((5-chloro-4-(2-(isopropylsulfonyl) phenylamino)pyrimidin-2-yl)amino)-8-methoxy-4,5-dihydro-1H-benzo[d]azepin-2(3H)-one

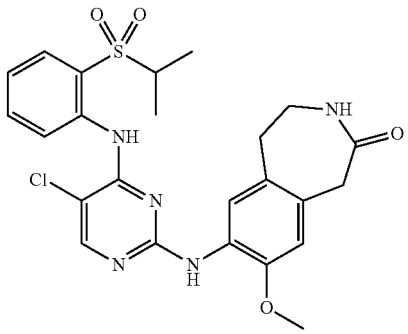 [SMILES: COc1cc2c(cc1Nc1ncc(Cl)c(Nc3ccccc3S(=O)(=O)C(C)C)n1)CCNC(=O)C2]

The title compound was obtained by performing the same method as Example 2 except that tert-butyl 7-amino-8-methoxy-2-oxo-1,2,4,5-tetrahydrobenzo[d]azepin-3-carboxylate was used instead of using the tert-butyl-6-amino-7-methoxy-3,4-dihydroisoquinoline-2(1H)-carboxylate.
¹H-NMR (300 MHz, CDCl₃) δ 9.49 (s, 1H), 8.46 (d, J=3 Hz, 1H), 8.14 (d, J=21 Hz, 1H), 7.89 (d, J=9 Hz, 1H), 7.67-7.64 (m, 1H), 7.25-7.10 (m, 1H), 6.77 (s, 1H), 4.8 (s, 1H), 4.45-4.34 (m, 2H), 3.87 (s, 3H), 3.70-3.61 (m, 2H), 3.24-3.20 (m, 1H), 2.02 (s, 3H), 1.85-1.75 (m, 2H), 1.50-1.45 (m, 2H), 1.38-1.05 (m, 7H);
LC/MS 516.20 (M⁺).

EXAMPLE 67

Preparation of 5-chloro-N4-(2-(isopropylsulfonyl) phenyl)-N2-(3-ethyl-8-methoxy-2,3,4,5-tetrahydro-1H-benzo[d]azepin-7-yl)pyrimidine-2,4-diamine

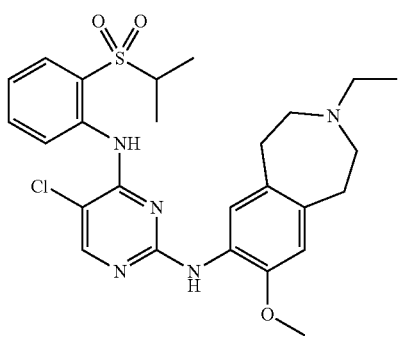 [SMILES: CCN1CCc2cc(Nc3ncc(Cl)c(Nc4ccccc4S(=O)(=O)C(C)C)n3)c(OC)cc2CC1]

The title compound was obtained by performing the same method as Example 3 except that the 5-chloro-N4-(2-(isopropylsulfonyl)phenyl)-N2-(8-methoxy-2,3,4,5-tetrahydro-1H-benzo[d]azepin-7-yl)pyrimidine-2,4-diamine obtained in Example 65 and ethyl iodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.
¹H-NMR (300 MHz, CDCl₃) δ 9.50 (s, 1H), 8.50 (d, J=9 Hz, 1H), 8.25 (s, 1H), 8.00 (s, 1H), 7.90 (d, J=9 Hz, 1H), 7.60-7.57 (m, 1H), 7.50 (s, 1H), 6.65 (s, 1H), 3.85 (s, 3H), 3.28-3.25 (m, 2H), 3.00 (s, 3H), 2.85-2.60 (m, 6H), 1.25-1.20 (m, 9H);
LC/MS 530.08 (M⁺).

EXAMPLE 68

Preparation of 1-(7-((5-chloro-4-(2-(isopropylsulfonyl)phenylamino)pyrimidin-2-yl)amino)-6-methoxy-4,5-dihydro-1H-benzo[d]azepin-3(2H)-yl)-2-hydroxyethanone

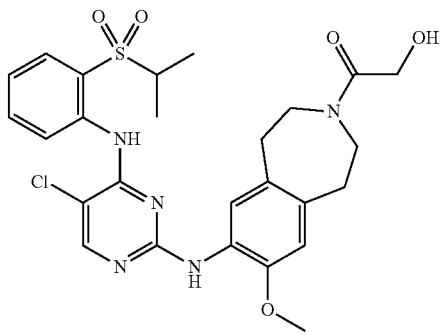 [SMILES: COc1cc2c(cc1Nc1ncc(Cl)c(Nc3ccccc3S(=O)(=O)C(C)C)n1)CCN(C(=O)CO)CC2]

The title compound was obtained by performing the same method as Example 3 except that the 5-chloro-N4-(2-(isopropylsulfonyl)phenyl)-N2-(8-methoxy-2,3,4,5-tetrahydro-1H-benzo[d]azepin-7-yl)pyrimidine-2,4-diamine obtained in Example 65 and glycolic acid were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.
¹H-NMR (300 MHz, CDCl₃) δ 9.53 (d, J=18 Hz, 1H), 8.59-8.52 (m, 1H), 8.16 (d, J=9 Hz, 2H), 7.92 (d, J=9 Hz, 1H), 7.55-7.50 (m, 2H), 7.47 (s, 1H), 6.65 (d, J=9 Hz, 1H), 4.25 (s, 2H), 3.85 (s, 3H11H), 3.70-3.65 (m, 3H), 3.45-3.30 (m, 2H), 3.20-3.15 (m, 2H), 1.38 (s, 6H);
LC/MS 560.06 (M⁺).

EXAMPLE 69

Preparation of 5-chloro-N4-(2-(isopropylsulfonyl) phenylamino)pyrimidin-2-yl)amino)-N2-8-methoxy-4,5-dihydro-1H-benzo[d]azepin-3(2H)-yl)ethanol

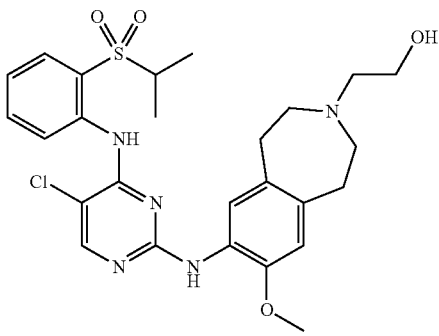 [SMILES: COc1cc2c(cc1Nc1ncc(Cl)c(Nc3ccccc3S(=O)(=O)C(C)C)n1)CCN(CCO)CC2]

The title compound was obtained by performing the same method as Example 3 except that the 5-chloro-N4-(2-(isopropylsulfonyl)phenyl)-N2-(8-methoxy-2,3,4,5-tetrahydro-1H-benzo[d]azepin-7-yl)pyrimidine-2,4-diamine obtained in Example 65 and 2-bromoethanol were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H-NMR (300 MHz, CDCl$_3$) δ 9.47 (s, 1H), 8.53 (d, J=9 Hz, 1H), 8.15 (s, 1H), 7.98-7.90 (m, 2H), 7.62-7.57 (t, J=6 Hz, 1H), 7.27-7.22 (m, 1H), 6.65 (s, 1H), 3.67 (s, 3H), 3.47 (s, 1H), 3.32-3.20 (q, J=6 Hz, 1H), 3.00-2.86 (m, 5H), 2.71-2.68 (m, 2H), 2.35-2.30 (s, 1H), 1.35 (d, J=6 Hz, 6H); LC/MS 546.08 (M$^+$).

EXAMPLE 70

Preparation of 5-chloro-N4-(2-(isopropylsulfonyl) phenyl)-N2-(7-isopropoxy-1-methyl-1,2,3,4-tetrahydroisoquinolin 6 yl)pyrimidine-2,4-diamine

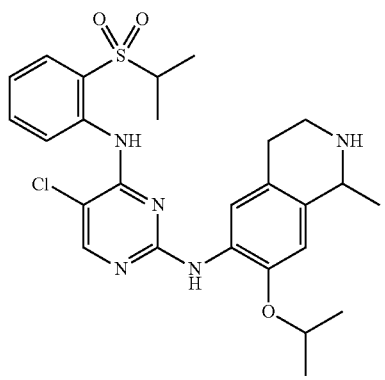 [SMILES: CC(C)Oc1cc2c(cc1Nc1ncc(Cl)c(Nc3ccccc3S(=O)(=O)C(C)C)n1)CCNC2C]

Step 1: Preparation of 1-(6-(5-chloro-4-(2-(isopropylsulfonyl)phenylamino)pyrimidin-2-yl)amino-7-isopropoxy-3,4-dihydroisoquinolin-2(1H)-yl)-2,2,2-trifluoroethane-1-one 2,5-dichloro-N-(2-(isopropylsulfonyl)phenyl)pyrimidine-4-amine (76 mg, 0.22 mmol) was dissolved in isopropyl alcohol (11 mL), and then 1-(6-amino-7-isopropoxy-3,4-dihydroisoquinolin-2(1H)-yl)-2,2,2-trifluoroethane-1-one (63 mg, 0.20 mmol) and p-TsOH (38 mg, 0.20 mmol) were added thereto. Then, the resulting product was degassed by charging with nitrogen, followed by stirring at 90-C for 10 hours. After completion of the reaction, the reaction mixture was extracted with EA/H$_2$O, and the organic layer was dried over MgSO$_4$, filtered and concentrated. The obtained product was purified by column chromatography (Hx:EA, 3:1) to obtain the title compound (48 mg, 38%)

Step 2: Preparation of 5-chloro-N4-(2-(isopropylsulfonyl)phenyl) N2-(7 isopropoxy-1-methyl-1,2,3,4-tetrahydroisoquinolin-6-yl)pyrimidine-2,4-diamine The 1-(6-(5-chloro-4-(2-(isopropylsulfonyl)phenylamino)pyrimidin-2-yl)amino-7-isopropoxy-3,4-dihydroisoquinolin-2(1H)-yl)-2,2,2-trifluoroethane-1-one (40 mg, 0.06 mmol) obtained in step 1 was dissolved in ethanol (1 mL), and 0.5 mL of water in which K$_2$CO$_3$ (35 mg, 0.26 mmol) was dissolved was added thereto, and the reaction mixture was stirred at 90° C. for 4 hours. After completion of the reaction, the reaction mixture was extracted with EA/H$_2$O, and the organic layer was dried over MgSO$_4$, filtered and concentrated. The obtained product was purified by column chromatography (MC:MeOH, 9:1) to obtain the title compound (20 mg, 59%).

$^1$H-NMR (300 MHz, CDCl$_3$) δ 9.47 (s, 1H), 8.53 (d, J=8.4 Hz, 1H), 8.16 (s, 1H), 7.92-7.96 (m, 2H), 7.61-7.67 (m, 2H), 7.26-7.29 (m, 2H), 6.65 (s, 1H), 4.52-4.59 (m, 1H), 4.07-4.09 (m, 1H), 3.23-3.28 (m, 2H), 2.96-3.03 (m, 1H), 2.65-2.71 (m, 1H), 2.48-2.53 (m, 1H), 2.13 (s, br, 1H), 1.46 (d, J=6.6 Hz, 3H), 1.37 (d, J=6.6 Hz, 6H), 1.31 (dd, J=6.9, 1.8 Hz, 6H);

LC/MS 530.4 [M$^+$+H]

EXAMPLE 71

Preparation of 5-chloro-N4-(2-(isopropylsulfonyl) phenyl)-N2-(7-isopropoxy-1,1-dimethyl-1,2,3,4-tetrahydroisoquinolin-6-yl)pyrimidine-2,4-diamine

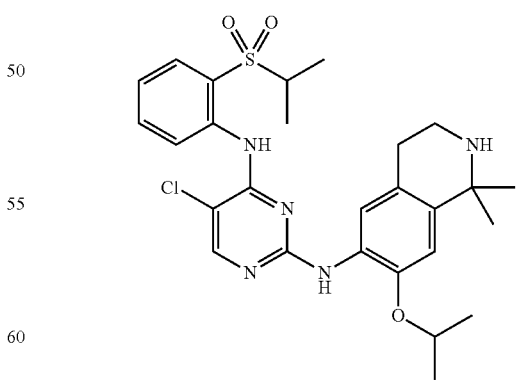

The title compound was obtained by performing the same method as Example 70 except that 1-(6-amino-7-isopropoxy-1,1-dimethyl-3,4-dihydroisoquinolin-2(1H)-yl)-2,2,2-trifluoroethanone

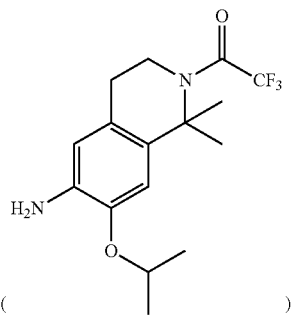 [SMILES: CC(C)Oc1cc2c(cc1N)CCN(C(=O)C(F)(F)F)C2(C)C]

was used instead of using the 1-(6-amino-7-isopropoxy-3,4-dihydroisoquinolin-2(1H)-yl)-2,2,2-trifluoroethane-1-one.

¹H-NMR (300 MHz, CDCl₃) δ 9.48 (s, 1H), 8.53 (d, J=8.1 Hz, 1H), 8.16 (s, 1H), 7.94 (s, 1H), 7.64 (t, J=6.9 Hz, 1H), 7.26-7.30 (m, 1H), 6.71 (s, 1H), 4.56 (sept, J=6.0 Hz, 1H), 3.26 (t, J=6.9 Hz, 1H), 3.11 (t, J=5.4 Hz, 2H), 2.56 (t, J=5.4 Hz, 2H), 1.79 (br, 1H), 1.45 (s, 6H), 1.38 (d, J=6.0 Hz, 6H), 1.31 (d, J=6.9 Hz, 6H);

LC/MS 544.4 [M⁺+H].

EXAMPLE 72

Preparation of 5-chloro-N4-(2-(isopropylsulfonyl)phenyl)-N2-(6-methoxy-1,1-dimethyl-1,2,3,4-tetrahydroisoquinolin-7-yl)pyrimidine-2,4-diamine

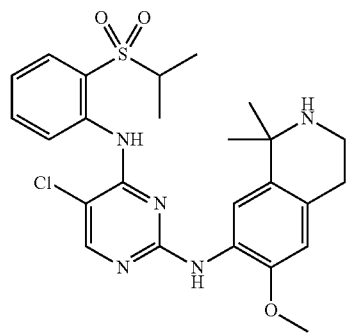 [SMILES: COc1cc2c(cc1Nc1ncc(Cl)c(Nc3ccccc3S(=O)(=O)C(C)C)n1)C(C)(C)NCC2]

The title compound was obtained by performing the same method as Example 70 except that 1-(7-amino-6-methoxy-1,1-dimethyl-3,4-dihydroisoquinolin-2(1H)-yl)-2,2,2-trifluoroethanone

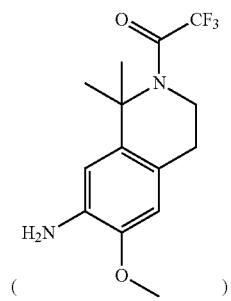 [SMILES: COc1cc2c(cc1N)C(C)(C)N(C(=O)C(F)(F)F)CC2]

was used instead of using the 1-(6-amino-7-isopropoxy-3,4-dihydroisoquinolin-2(1H)-yl)-2,2,2-trifluoroethane-1-one.

¹H-NMR (300 MHz, CDCl₃) δ 9.44 (s, 1H), 8.46 (d, J=8.1 Hz, 1H), 8.18 (s, 1H), 8.08 (s, 1H), 7.91 (d, J=8.1 Hz, 1H), 7.62 (t, J=8.4 Hz, 1H), 7.44 (s, 1H), 7.24 (d, J=7.2 Hz, 1H), 6.55 (s, 1H), 3.86 (s, 3H), 3.27 (sept, J=6.9 Hz, 1H), 3.12 (t, J=5.4 Hz, 2H), 2.73 (t, J=5.4 Hz, 2H), 1.78 (br, 1H), 1.31 (d, J=6.9 Hz, 6H), 1.28 (s, 6H);

LC/MS 516.3 [M⁺+H].

EXAMPLE 73

Preparation of 5-chloro-N4-(2-(isopropylsulfonyl)phenyl)-N2-(1-ethyl-7-methoxy-1-methyl-1,2,3,4-tetrahydroisoquinolin-6-yl)pyrimidine-2,4-diamine

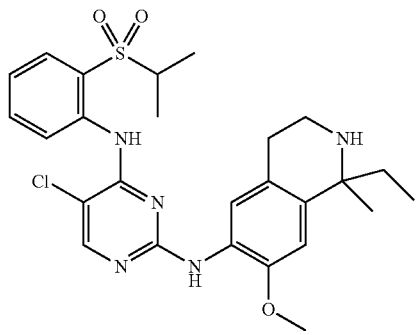 [SMILES: CCC1(C)NCCc2cc(Nc3ncc(Cl)c(Nc4ccccc4S(=O)(=O)C(C)C)n3)c(OC)cc21]

The title compound was obtained by performing the same method as Example 70 except that 1-(6-amino-1-ethyl-7-methoxy-1-methyl-3,4-dihydroisoquinolin-2(1H)-yl)-2,2,2-trifluoroethanone

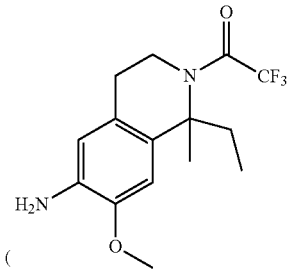

was used instead of using the 1-(6-amino-7-isopropoxy-3,4-dihydroisoquinolin-2(1H)-yl)-2,2,2-trifluoroethane-1-one.

¹H NMR (300 MHz, CDCl₃) δ 9.49 (s, 1H), 8.54 (d, J=8.4 Hz, 1H), 8.16 (s, 1H), 7.92 (br, 2H), 7.64 (t, J=7.5 Hz, 1H), 7.56 (s, 1H), 7.25 (t, J=8.1 Hz, 1H), 6.63 (s, 1H), 1.41 (s, 3H), 3.25 (sept, J=6.9 Hz, 1H), 3.08-3.09 (m, 2H), 2.56 (br, 2H), 2.15 (br, 1H), 1.87-1.90 (m, 1H), 1.69-1.75 (m, 1H), 1.41 (s, 31), 1.31 (d, J=6.9 Hz, 6H), 0.84 (t, J=7.2 Hz, 3H);

LC/MS 530.6 [M⁺+H].

EXAMPLE 74

Preparation of 5-chloro-N4-(2-(isopropylsulfonyl)phenyl)-N2-(1,1-diethyl-7-methoxy-1,2,3,4-tetrahydroisoquinolin-6-yl)pyrimidine-2,4-diamine

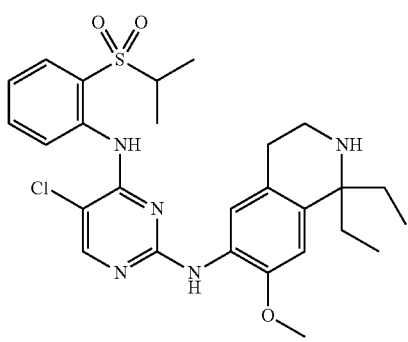 [SMILES: CCC1(CC)NCCc2cc(Nc3ncc(Cl)c(Nc4ccccc4S(=O)(=O)C(C)C)n3)c(OC)cc21]

The title compound was obtained by performing the same method as Example 70 except that 1-(6-amino-1,1-diethyl-7-methoxy-3,4-dihydroisoquinolin-2(1H)-yl)-2,2,2-trifluoroethanone

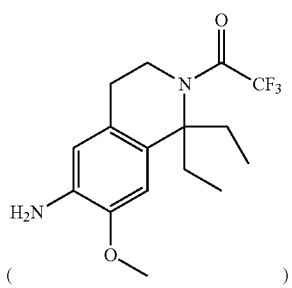

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.51 (s, 1H), 8.54 (d, J=8.1 Hz, 1H), 8.16 (s, 1H), 7.92-7.95 (m, 2H), 7.64 (t, J=7.8 Hz, 1H), 7.57 (s, 1H), 7.26-7.29 (m, 1H), 6.59 (s, 1H), 3.89 (s, 3H), 3.25 (sept, J=6.9 Hz, 1H), 3.15 (br, 2H), 2.95 (br, 1H), 2.62 (br, 2H), 1.73-1.93 (m, 4H), 1.31 (d, J=6.9 Hz, 6H), 0.86 (t, J=7.2 Hz, 6H);

LC/MS 544.6 [M$^+$+H].

EXAMPLE 75

Preparation of 5-chloro-N4-(2-(isopropylsulfonyl)phenyl)-N2-(6-methoxy-4,4-dimethyl-1,2,3,4-tetrahydroisoquinolin-7-yl)pyrimidine-2,4-diamine

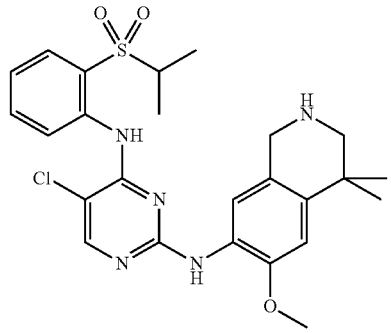 [SMILES: COc1cc2c(cc1Nc1ncc(Cl)c(Nc3ccccc3S(=O)(=O)C(C)C)n1)CNCC2(C)C]

The title compound was obtained by performing the same method as Example 70 except that 1-(7-amino-6-methoxy-4,4-dimethyl-3,4-dihydroisoquinolin-2(1H)-yl)-2,2,2-trifluoroethanone

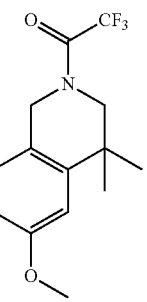

was used instead of using the 1-(6-amino-7-isopropoxy-3,4-dihydroisoquinolin-2(1H)-yl)-2,2,2-trifluoroethane-1-one.

$^1$H NMR (500 MHz, CDCl$_3$) δ 9.49 (s, 1H), 8.52 (d, J=8.3 Hz, 1H), 8.18 (s, 1H), 7.95 (dd, J=8.0, 1.4 Hz, 1H), 7.88 (s, 1H), 7.69 (t, J=7.2 Hz, 1H), 7.59 (s, br, 1H), 7.30 (t, J=8.0 Hz, 1H), 6.83 (s, 1H), 3.92 (s, 3H), 3.83 (s, 2H), 3.26 (sept, J=6.9 Hz, 1H), 2.87 (s, 2H), 1.94 (s, br, 1H), 1.33 (d, J=6.9 Hz, 6H), 1.29 (s, 6H);

LC/MS 516.3 [M$^+$+H].

EXAMPLE 76

Preparation of 6-(5-chloro-4-(2-(isopropylsulfonyl)phenylamino)pyrimidin-2-yl)amino-7-methoxy-1,2,3,4-dihydroisoquinoline-1-carboxylic acid

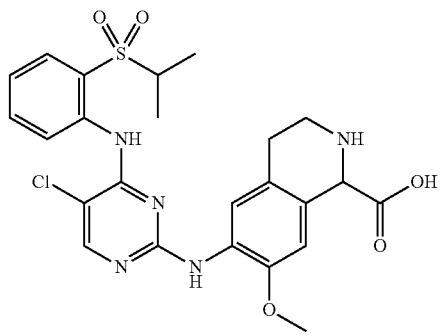 [SMILES: COc1cc2c(cc1Nc1ncc(Cl)c(Nc3ccccc3S(=O)(=O)C(C)C)n1)CCNC2C(=O)O]

The title compound was obtained by performing the same method as Example 70 except that 6-amino-7-methoxy-2-(2,2,2-trifluoroacetyl)-1,2,3,4-tetrahydroisoquinolin-1-carboxylic acid

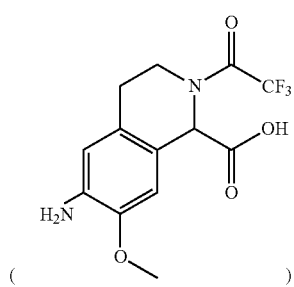

was used instead of using the 1-(6-amino-7-isopropoxy-3,4-dihydroisoquinolin-2(1H)-yl)-2,2,2-trifluoroethane-1-one.

¹H NMR (300 MHz, CDCl₃) δ 9.52 (br, 1H), 8.48 (d, J=8.2 Hz, 1H), 8.35 (s, 1H), 8.26 (s, 1H), 7.82 (d, J=7.6 Hz, 1H), 6.69-7.75 (m, 1H), 7.46 (s, 1H), 7.43 (s, 1H), 7.34 (t, J=7.5 Hz, 1H), 4.43 (s, 1H), 3.77 (s, 3H), 3.10-3.33 (m, 2H), 2.55-2.73 (m, 3H), 1.16 (d, J=6.9 Hz, 6H);

LC/MS 532.2 [M⁺+H].

EXAMPLE 77

Preparation of 5-chloro-N4-(2-(isopropylsulfonyl)phenyl)-N2-(2-ethyl-7-methoxy-1,1-dimethyl-1,2,3,4-tetrahydroisoquinolin-6-yl)pyrimidine-2,4-diamine

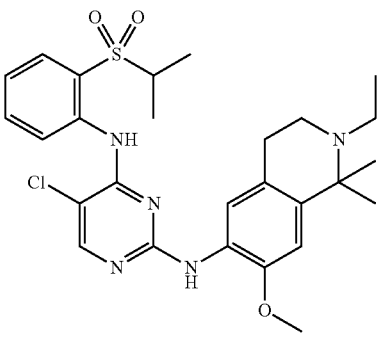 [SMILES: CCN1CCc2cc(Nc3ncc(Cl)c(Nc4ccccc4S(=O)(=O)C(C)C)n3)c(OC)cc2C1(C)C]

Step 1: Preparation of 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine The title compound was obtained by performing the same method as Example 70 except that 1-(6-amino-7-methoxy-3,4-dihydroisoquinolin-2(1H)-yl)-2,2,2-trifluoroethane-1-one was used instead of using the 1-(6-amino-7-isopropoxy-3,4-dihydroisoquinolin-2(1H)-yl)-2,2,2-trifluoroethane-1-one.

Step 2: Preparation of 5-chloro-N4-(2-(isopropylsulfonyl)phenyl)-N2-(2-ethyl-7-methoxy-1,1-dimethyl-1,2,3,4-tetrahydroisoquinolin-6-yl)pyrimidine-2,4-diamine The title compound was obtained by performing the same method as Example 3 except that the 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine obtained in step 1 and iodoethane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

¹H NMR (300 MHz, CDCl₃) δ 9.46 (s, 1H), 8.51 (d, J=8.1 Hz, 1H), 8.15 (s, 1H), 7.92 (dd, J=1.6, 8.0 Hz, 1H), 7.89 (s, br, 1H), 7.64-7.69 (m, 1H), 7.55 (s, 1H), 7.24-7.29 (m, 1H), 6.69 (s, 1H), 3.87 (s, 3H), 3.24 (sept, J=6.8 Hz, 1H), 2.81-2.83 (br, 2H), 2.57-2.64 (m, 4H), 1.45 (s, 6H), 1.30 (d, J=6.8 Hz, 6H) 1.14-1.18 (m, 3H);

LC/MS 544.2 [M⁺+H].

EXAMPLE 78

Preparation of 1-6-(5-chloro-4-(2-(isopropylsulfonyl)phenylamino)pyrimidin-2-yl)amino-7-methoxy-1,1-dimethyl-3,4-dihydroisoquinolin-2(1H)-yl-2-hydroxyethane-1-one

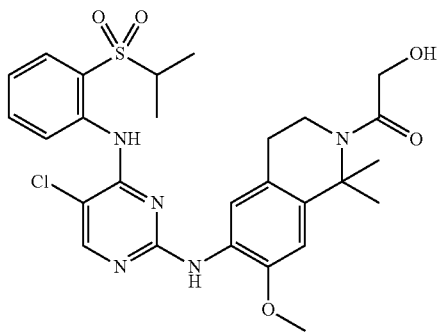 [SMILES: COc1cc2c(cc1Nc1ncc(Cl)c(Nc3ccccc3S(=O)(=O)C(C)C)n1)CCN(C(=O)CO)C2(C)C]

The title compound was obtained by performing the same method as Example 3 except that the 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine and glycolic acid were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.55 (s, 1H), 8.55 (d, J=8.3 Hz, 1H), 8.18 (s, 1H), 8.02 (s, 1H), 7.94 (dd, J=1.2, 8.0 Hz, 1H), 7.58-7.66 (m, 2H), 7.26-7.32 (m, 1H), 4.20 (d, J=3.1 Hz, 2H), 3.92 (s, 3H), 3.60 (br, s, 1H), 3.30-3.34 (m, 2H), 3.25 (sept, J=6.8 Hz, 1H), 2.66-2.69 (m, 2H), 1.85 (s, 6H), 1.30 (d, J=6.8 Hz, 6H);

LC/MS 574.1 [M$^+$+H].

EXAMPLE 79

Preparation of 5-chloro-N4-(2-(isopropylsulfonyl)phenyl)-N2-(2-ethyl-7-isopropoxy-1,1-dimethyl-1,2,3,4-tetrahydroisoquinolin-6-yl)pyrimidine-2,4-diamine

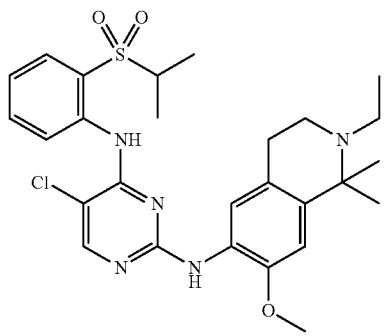 [SMILES: CCN1CCc2cc(Nc3ncc(Cl)c(Nc4ccccc4S(=O)(=O)C(C)C)n3)c(OC)cc2C1(C)C]

The title compound was obtained by performing the same method as Example 3 except that the 5-chloro-N4-(2-(isopropylsulfonyl)phenyl)-N2-(7-isopropoxy-1,1-dimethyl-1,2,3,4-tetrahydroisoquinolin-6-yl)pyrimidine-2,4-diamine obtained in Example 71 and iodoethane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.45 (s, 1H), 8.51 (d, J=8.3 Hz, 1H), 8.15 (s, 1H), 7.93 (dd, J=1.3, 8.0 Hz, 1H), 7.90 (s, 1H), 7.66 (t, J=7.4 Hz, 1H), 7.59 (s, 1H), 7.25-7.30 (m, 1H), 6.72 (s, 1H), 4.54 (sept, J=6.2 Hz, 2H), 3.25 (sept, J=6.9 Hz, 1H), 2.84-2.61 (m, 6H), 1.38 (s, 6H), 1.37 (d, J=6.2 Hz, 6H), 1.30 (d, J=6.9 Hz, 6H), 1.17 (br, 3H);

LC/MS 572.1 [M$^+$+H].

EXAMPLE 80

Preparation of 5-chloro-N4-(2-(isopropylsulfonyl)phenyl)-N2-(6-isopropoxy-4,4-dimethyl-1,2,3,4-tetrahydroisoquinolin-7-yl)pyrimidine-2,4-diamine

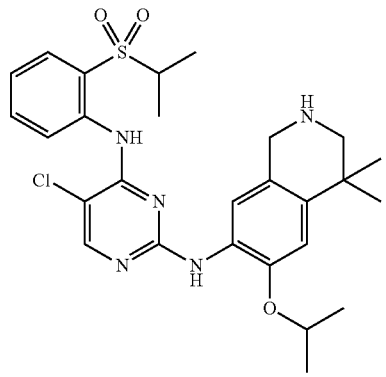 [SMILES: CC(C)Oc1cc2c(cc1Nc1ncc(Cl)c(Nc3ccccc3S(=O)(=O)C(C)C)n1)CNCC2(C)C]

The title compound was obtained by performing the same method as Example 70 except that 1-(7-amino-6-isopropoxy-4,4-dimethyl-3,4-dihydroisoquinolin-2(1H)-yl)-2,2,2-trifluoroethanone

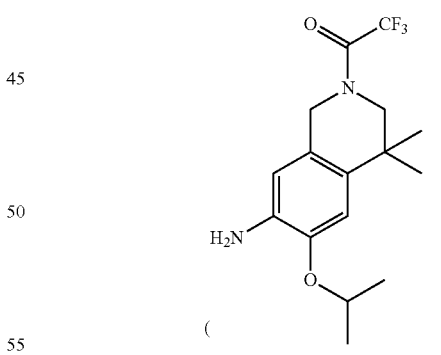

was used instead of using the 1-(6-amino-7-isopropoxy-3,4-dihydroisoquinolin-2(1H)-yl)-2,2,2-trifluoroethane-1-one.

$^1$H NMR (500 MHz, CDCl$_3$) δ 9.47 (s, 1H), 8.51 (d, J=8.3 Hz, 1H), 8.18 (s, 1H), 7.95 (dd, J=1.4, 8.0 Hz, 1H), 7.68 (t, J=7.2 Hz, 1H), 7.65 (s, br, 1H), 7.31 (t, J=7.5 Hz, 1H), 6.85 (s, 1H), 4.60 (sept, J=6.1 Hz, 1H), 3.80 (s, 2H), 3.27 (sept, J=6.9 Hz, 1H) 2.87 (s, 2H), 2.17 (br, s, 1H), 1.41 (d, J=6.1 Hz, 6H), 1.33 (d, J=6.9 Hz, 6H), 1.28 (s, 6H);

LC/MS 544.2 [M$^+$+H].

EXAMPLE 81

Preparation of 5-chloro-N4-(2-(isopropylsulfonyl)phenyl)-N2-(6-ethoxy-2-ethyl-4,4-dimethyl-1,2,3,4-tetrahydroisoquinolin-7-yl)pyrimidine-2,4-diamine

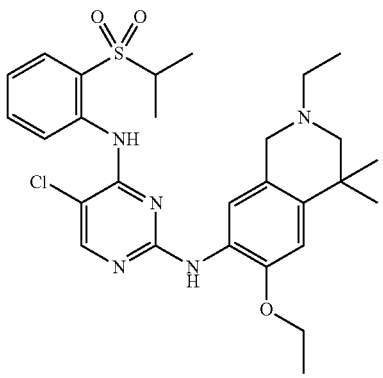 [SMILES: CCOc1cc2c(cc1Nc1ncc(Cl)c(Nc3ccccc3S(=O)(=O)C(C)C)n1)CN(CC)CC2(C)C]

Step 1: Preparation of 5-chloro-N2-(6-ethoxy-2-ethyl-4,4-dimethyl-1,2,3,4-tetrahydroisoquinolin-7-yl)-N4-(2-(isopropylsulfonyl)phenyl)pyrimidine-2,4-diamine The title compound was obtained by performing the same method as Example 70 except that 1-(7-amino-6-ethoxy-4,4-dimethyl-3,4-dihydroisoquinolin-2(1H)-yl)-2,2,2-trifluoroethanone

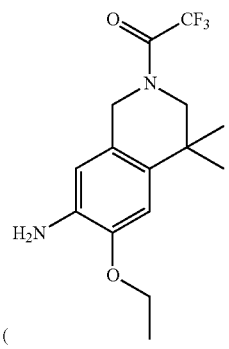

was used instead of using the 1-(6-amino-7-isopropoxy-3,4-dihydroisoquinolin-2(1H)-yl)-2,2,2-trifluoroethane-1-one.

Step 2: Preparation of 5-chloro-N4-(2-(isopropylsulfonyl)phenyl)-N2-(6-ethoxy-2-ethyl-4,4-dimethyl-1,2,3,4-tetrahydroisoquinolin-7-yl)pyrimidine-2,4-diamine The title compound was obtained by performing the same method as Example 3 except that the 5-chloro-N2-(6-ethoxy-2-ethyl-4,4-dimethyl-1,2,3,4-tetrahydroisoquinolin-7-yl)-N4-(2-(isopropylsulfonyl)phenyl)pyrimidine-2,4-diamine obtained in step 1 and iodoethane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (500 MHz, CDCl$_3$) δ 9.46 (s, 1H), 8.51 (d, J=8.3 Hz, 1H), 8.17 (s, 1H), 7.96 (dd, J=1.3, 7.9 Hz, 1H), 7.88 (s, 1H), 7.68-7.71 (m, 1H), 7.61 (s, 1H), 7.28-7.31 (m, 1H), 6.79 (s, 1H), 4.12 (q, J=7.0 Hz, 2H), 3.36 (s, 2H), 3.27 (sept, J=6.9 Hz, 1H), 2.51 (q, J=7.2 Hz, 2H), 2.40 (s, 2H), 1.48 (t, J=7.0 Hz, 3H), 1.33 (d, J=6.9 Hz, 6H), 1.30 (s, 6H), 1.17 (t, J=7.2 Hz, 3H);

LC/MS 558.2 [M$^+$+H].

EXAMPLE 82

Preparation of 5-chloro-N4-(2-(isopropylsulfonyl)phenyl)-N2-(2-ethyl-6-isopropoxy-4,4-dimethyl-1,2,3,4-tetrahydroisoquinolin-7-yl)pyrimidine-2,4-diamine

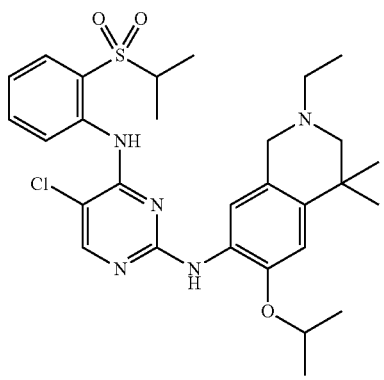 [SMILES: CCN1Cc2cc(Nc3ncc(Cl)c(Nc4ccccc4S(=O)(=O)C(C)C)n3)c(OC(C)C)cc2C(C)(C)C1]

The title compound was obtained by performing the same method as Example 3 except that the 5-chloro-N4-(2-(isopropylsulfonyl)phenyl)-N2-(6-isopropoxy-4,4-dimethyl-1,2,3,4-tetrahydroisoquinolin-7-yl)pyrimidine-2,4-diamine obtained in Example 80 and iodoethane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (500 MHz, CDCl$_3$) δ 9.45 (s, 1H), 8.51 (d, J=8.4 Hz, 1H), 8.17 (s, 1H), 7.96 (dd, J=1.4, 8.0 Hz, 1H), 7.90 (s, 1H), 7.68-7.72 (m, 1H), 7.62 (s, 1H), 7.28-7.31 (m, 1H), 6.82 (s, 1H), 4.59 (sept, J=6.1 Hz, 1H), 3.35 (s, 2H), 3.27 (sept, J=6.9 Hz, 1H), 2.51 (q, J=7.1 Hz, 2H), 2.41 (s, 2H), 1.39 (d, J=6.1 Hz, 6H), 1.33 (d, J=6.9 Hz, 6H), 1.30 (s, 6H), 1.17 (t, J=7.1 Hz, 3H);

LC/MS 572.2 [M$^+$+H].

EXAMPLE 83

Preparation of 5-chloro-N4-(2-(isopropylsulfonyl)phenyl)-N2-(6-methoxy-2,3-dihydro-1H-spiro(cyclopentane-1,4-isoquinolin)-7-yl)pyrimidine-2,4-diamine

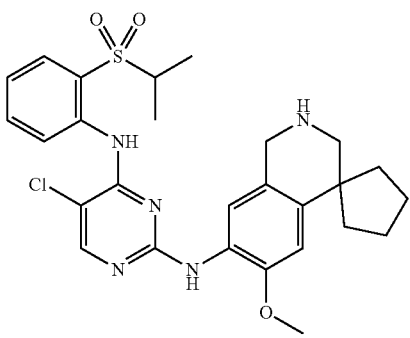 [SMILES: COc1cc2c(cc1Nc1ncc(Cl)c(Nc3ccccc3S(=O)(=O)C(C)C)n1)CNCC21CCCC1]

The title compound was obtained by performing the same method as Example 70 except that

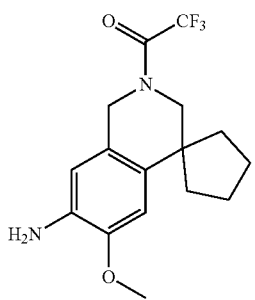 [SMILES: COc1cc2c(cc1N)CN(C(=O)C(F)(F)F)CC21CCCC1]

was used instead of using the 1-(6-amino-7-isopropoxy-3,4-dihydroisoquinolin-2(1H)-yl)-2,2,2-triflucroethane-1-one.

$^1$H NMR (500 MHz, CDCl$_3$) δ 9.48 (s, 1H), 8.51 (d, J=8.3 Hz, 1H), 8.17 (s, 1H), 7.95 (dd, J=1.6, 8.0 Hz, 1H), 7.86 (s, 1H), 7.68 (t, J=7.6 Hz, 1H), 7.59 (s, 1H), 7.30 (t, J=7.8 Hz, 1H), 6.78 (s, 1H), 3.91 (s, 3H), 3.83 (s, 2H), 3.26 (sept, J=6.9 Hz, 1H), 2.87 (s, 2H), 2.20 (s, br, 1H), 1.79-1.88 (m, 8H), 1.33 (d, J=6.9 Hz, 6H);

LC/MS 542.2 [M$^+$+H].

EXAMPLE 84

Preparation of 9-((5-chloro-4-(2-(isopropylsulfonyl)phenyl)aminopyrimidin-2-yl)amino)-10-methoxy-2,3,6,7-tetrahydro-1H-pyrazino[2,1-a]isoquinoline-4(11bH)-one

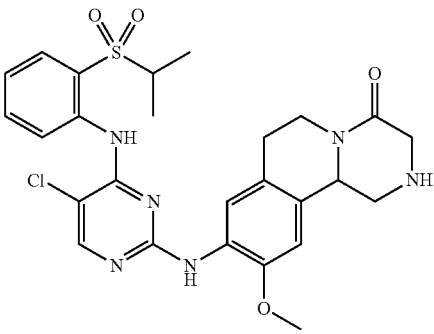 [SMILES: COc1cc2c(cc1Nc1ncc(Cl)c(Nc3ccccc3S(=O)(=O)C(C)C)n1)CCN1C(=O)CNCC21]

The title compound was obtained by performing the same method as Example 70 except that 9-amino-10-methoxy-2-(2,2,2-trifluoroacetyl)-2,3,6,7-tetrahydro-1H-pyrazino[2,1-a]isoquinoline-4(11bH)-one ( 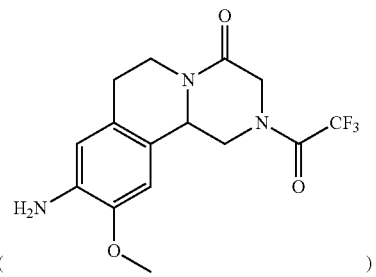 [SMILES: COc1cc2c(cc1N)CCN1C(=O)CN(C(=O)C(F)(F)F)CC21] )

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.52 (s, 1H), 8.50 (d, J=8.3 Hz, 1H), 8.17 (s, 1H), 8.09 (s, 1H), 7.94 (dd, J=1.3, 8.0 Hz, 1H), 7.60-7.66 (m, 2H), 7.29 (t, J=7.9 Hz, 1H), 6.60 (s, 1H), 4.85-4.90 (m, 1H), 4.74-4.78 (m, 1H), 3.89 (s, 3H), 3.52-3.72 (m, 3H), 3.24 (sept, J=6.8 Hz, 1H), 2.76-2.92 (m, 3H), 2.45-2.50 (m, 1H), 1.64 (br, s, 1H), 1.31 (dd, J=4.7, 6.8 Hz, 6H);

LC/MS 557.2 [M$^+$+H].

EXAMPLE 85

Preparation of 10-((5-chloro-4-(2-(isopropylsulfonyl)phenyl)aminopyrimidin-2-yl)amino)-9-methoxy-7,7-dimethyl-1,2,3,6,7,11b-hexahydro-4H-pyrazino[2,1-a]isoquinoline)-4-one

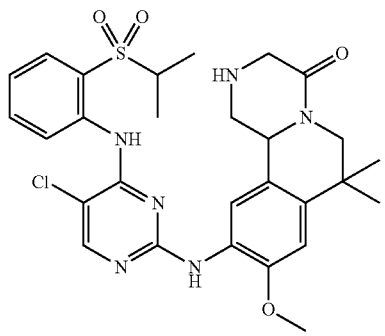 [SMILES: COc1cc2c(cc1Nc1ncc(Cl)c(Nc3ccccc3S(=O)(=O)C(C)C)n1)C1CNCC(=O)N1CC2(C)C]

The title compound was obtained by performing the same method as Example 70 except that 10-amino-9-methoxy-7,7-dimethyl-2-(2,2,2-trifluoroacetyl)-2,3,6,7-tetrahydro-1H-pyrazino[2,1-a]isoquinoline-4 (11bH)-one

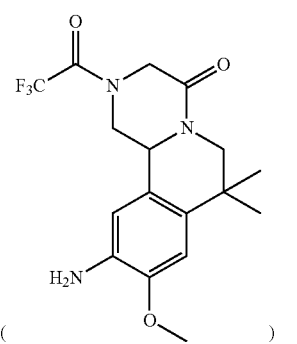 [SMILES: COc1cc2c(cc1N)C1CN(C(=O)C(F)(F)F)CC(=O)N1CC2(C)C]

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.51 (s, 1H), 8.47 (d, J=8.3 Hz, 1H), 8.18 (s, 1H), 8.13 (s, 1H), 7.96 (dd, J=1.2, 7.9 Hz, 1H), 7.69 (t, J=8.4 Hz, 1H), 7.59 (s, 1H), 7.32 (t, J=7.8 Hz, 1H), 6.82 (s, 1H), 4.61-4.69 (m, 2H), 3.92 (s, 3H), 3.46-3.66 (m, 2H), 3.15-3.31 (m, 2H), 2.57-2.64 (m, 2H), 1.61 (s, br, 1H), 1.23-1.36 (m, 12H);

LC/MS 584.8 [M$^+$+H].

EXAMPLE 86

Preparation of 5-chloro-N4-(2-(isopropylsulfonyl)phenyl)-N2-(9-methoxy-7,7-dimethyl-1,3,4,6,7,11b-hexahydro-2H-pyrazino[2,1-a]isoquinolin-10-yl)pyrimidine-2,4-diamine

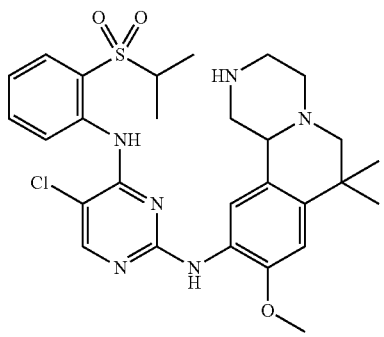 [SMILES: COc1cc2c(cc1Nc1ncc(Cl)c(Nc3ccccc3S(=O)(=O)C(C)C)n1)C1CNCCN1CC2(C)C]

The title compound was obtained by performing the same method as Example 70 except that 1-(10-amino-9-methoxy-7,7-dimethyl-3,4,6,7-tetrahydro-1H-pyrazino[2,1-a]isoquinolin-2(11bH)-yl)-2,2,2-trifluoroethanone

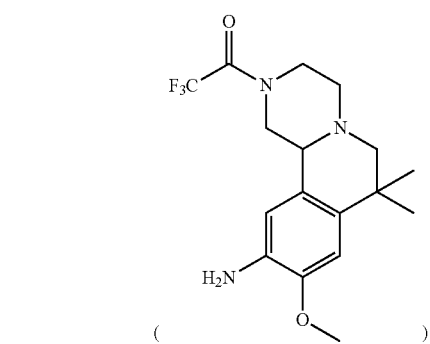 [SMILES: COc1cc2c(cc1N)C1CN(C(=O)C(F)(F)F)CCN1CC2(C)C]

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.51 (s, 1H), 8.50 (d, J=8.4 Hz, 1H), 8.15 (s, 1H), 8.01 (s, 1H), 7.93 (dd, J=1.2, 7.9 Hz, 1H), 7.67 (t, J=7.3 Hz, 1H), 7.48 (s, 1H), 7.28 (t, J=7.9 Hz, 1H), 6.79 (s, 1H), 3.89 (s, 3H), 3.22-3.33 (m, 1H), 2.76-3.09 (m, 5H), 2.32-2.49 (m, 4H), 1.95 (s, br, 1H), 1.23-1.38 (m, 12H);

LC/MS 571.2 [M$^+$+H].

EXAMPLE 87

Preparation of 5-chloro-N4-(2-(isopropylsulfonyl)phenyl)-N2-(5-bromo-7-methoxy-1,1-dimethyl-1,2,3,4-tetrahydroisoquinolin-6-yl)pyrimidine-2,4-diamine

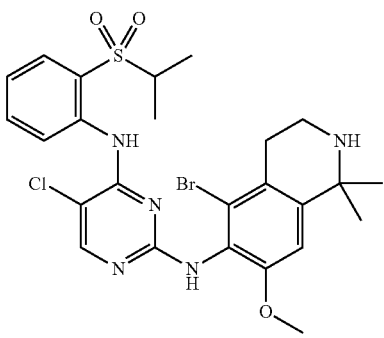 [SMILES: COc1cc2c(c(Br)c1Nc1ncc(Cl)c(Nc3ccccc3S(=O)(=O)C(C)C)n1)CCNC2(C)C]

The title compound was obtained by performing the same method as Example 70 except that 1-(6-amino-5-bromo-7-methoxy-1,1-dimethyl-3,4-dihydroisoquinolin-2(1H)-yl)-2,2,2-trifluoroethanone

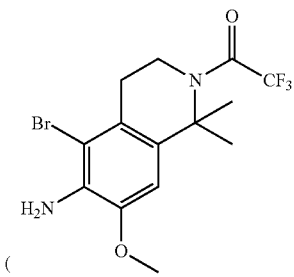

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.66 (s, br, 1H), 8.41 (d, J=8.4 Hz, 1H), 8.10 (s, 1H), 7.82 (d, J=7.9 Hz, 1H), 7.32 (t, J=7.6 Hz, 1H), 7.12 (t, J=7.4 Hz, 1H), 6.80 (s, 1H), 6.56 (s, br, 1H), 3.75 (s, 3H), 3.22 (sept, J=6.9 Hz, 1H), 3.18 (t, J=5.9 Hz, 2H), 2.73 (t, J=5.9 Hz, 2H), 2.03 (s, br, 1H), 1.53 (s, 6H), 1.29 (d, J=6.9 Hz, 6H);

LC/MS 594.1 [M$^+$+H].

EXAMPLE 88

Preparation of 5-chloro-N4-(2-(isopropylsulfonyl)phenyl)-N2-(5-chloro-7-methoxy-1,1-dimethyl-1,2,3,4-tetrahydroisoquinolin-6-yl)pyrimidine-2,4-diamine

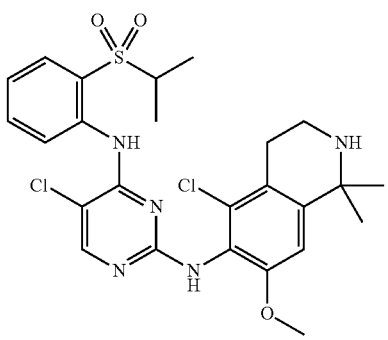 [SMILES: COc1cc2c(c(Cl)c1Nc1ncc(Cl)c(Nc3ccccc3S(=O)(=O)C(C)C)n1)CCNC2(C)C]

The title compound was obtained by performing the same method as Example 70 except that 1-(6-amino-5-chloro-7-methoxy-1,1-dimethyl-3,4-dihydroisoquinolin-2(1H)-yl)-2,2,2-trifluoroethanone was used instead of using the 1-(6-amino-7-isopropoxy-3,4-dihydroisoquinolin-2(1H)-yl)-2,2,2-trifluoroethane-1-one.

$^1$H NMR (500 MHz, CDCl$_3$) δ 9.68 (s, br, 1H), 8.45 (d, J=8.0 Hz, 1H), 8.13 (s, 1H), 7.85 (d, J=7.9 Hz, 1H), 7.35 (t, J=7.1 Hz, 1H), 7.15 (t, J=7.3 Hz, 1H), 6.78 (s, 1H), 6.57 (s, br, 1H), 3.79 (s, 3H), 3.25 (sept, J=6.9 Hz, 1H), 3.20 (t, J=6.0 Hz, 2H), 2.75 (t, J=5.9 Hz, 2H), 1.72 (s, br, 1H), 1.54 (s, 6H), 1.32 (d, J=6.9 Hz, 6H);

LC/MS 550.1 [M$^+$+H].

EXAMPLE 89

Preparation of 5-chloro-N4-(2-(isopropylsulfonyl)phenyl)-N2-(8-bromo-7-methoxy-1,1-dimethyl-1,2,3,4-tetrahydroisoquinolin-6-yl)pyrimidine-2,4-diamine

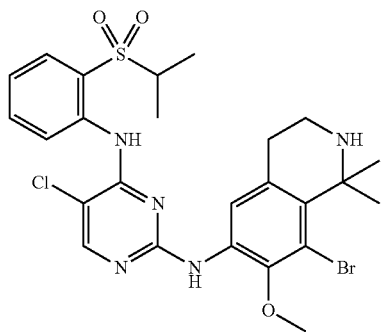 [SMILES: COc1c(Nc2ncc(Cl)c(Nc3ccccc3S(=O)(=O)C(C)C)n2)cc2c(c1Br)C(C)(C)NCC2]

The title compound was obtained by performing the same method as Example 70 except that 1-(6-amino-8-bromo-7-methoxy-1,1-dimethyl-3,4-dihydroisoquinolin-2(1H)-yl)-2,2,2-trifluoroethanone

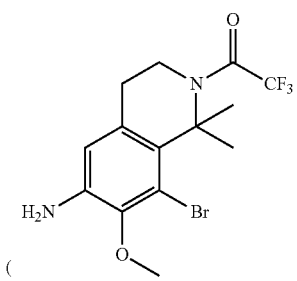

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.57 (s, br, 1H), 8.51 (d, J=8.1 Hz, 1H), 8.18 (s, 1H), 7.96 (s, 1H), 7.94 (d, J=7.9 Hz, 1H), 7.65 (t, J=8.6 Hz, 1H), 7.46 (s, br, 1H), 7.28 (t, J=8.1 Hz, 1H), 3.85 (s, 3H), 3.25 (sept, J=6.9 Hz, 1H), 3.04 (t, J=5.8 Hz, 2H), 2.64 (t, J=5.7 Hz, 2H), 1.71 (s, 6H), 1.32 (d, J=6.9 Hz, 6H);

LC/MS 595.9 [M$^+$+H].

EXAMPLE 90

Preparation of 5-chloro-N4-(2-(isopropylsulfonyl)phenyl)-N2-(8-chloro-7-methoxy-1,1-dimethyl-1,2,3,4-tetrahydroisoquinolin-6-yl)pyrimidine-2,4-diamine

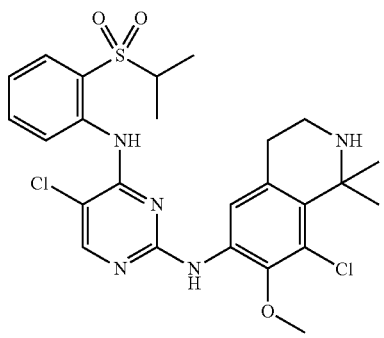 [SMILES: COc1c(Nc2ncc(Cl)c(Nc3ccccc3S(=O)(=O)C(C)C)n2)cc2c(c1Cl)C(C)(C)NCC2]

The title compound was obtained by performing the same method as Example 70 except that 1-(6-amino-8-chloro-7-methoxy-1,1-dimethyl-3,4-dihydroisoquinolin-2(1H)-yl)-2,2,2-trifluoroethanone

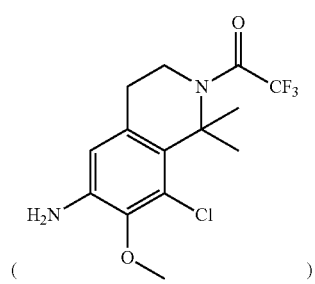 [SMILES: COc1c(N)cc2c(c1Cl)C(C)(C)N(C(=O)C(F)(F)F)CC2]

was used instead of using the 1-(6-amino-7-isopropoxy-3,4-dihydroisoquinolin-2(1H)-yl)-2,2,2-trifluoroethane-1-one.

$^1$H NMR (500 MHz, CDCl$_3$) δ 9.59 (s, br, 1H), 8.54 (d, J=8.3 Hz, 1H), 8.21 (s, 1H), 7.97-7.96 (m, 2H), 7.68 (t, J=7.9 Hz, 1H), 7.51 (s, br, 1H), 7.31 (t, J=7.6 Hz, 1H), 3.89 (s, 3H), 3.28 (sept, J=6.9 Hz, 1H), 3.08 (t, J=5.7 Hz, 2H), 2.65 (t, J=5.7 Hz, 2H), 1.70 (s, 6H), 1.35 (d, J=6.9 Hz, 6H);

LC/MS 550.1 [M$^+$+H].

EXAMPLE 91

Preparation of 5-chloro-N4-(2-(isopropylsulfonyl)phenyl)-N2-(6-methoxy-2,4,4-trimethyl-1,2,3,4-tetrahydroisoquinolin-7-yl)pyrimidine-2,4-diamine

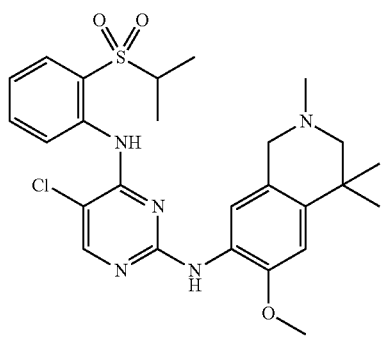 [SMILES: COc1cc2c(cc1Nc1ncc(Cl)c(Nc3ccccc3S(=O)(=O)C(C)C)n1)CN(C)CC2(C)C]

The title compound was obtained by performing the same method as Example 3 except that the 5-chloro-N4-(2-(isopropylsulfonyl)phenyl)-N2-(6-methoxy-4,4-dimethyl-1,2,3,4-tetrahydroisoquinolin-7-yl)pyrimidine-2,4-diamine obtained in Example 75 and methyl iodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.45 (s, br, 1H), 8.49 (d, J=8.3 Hz, 1H), 8.14 (s, 1H), 7.93 (d, J=7.9 Hz, 1H), 7.84 (s, 1H), 7.67 (t, J=7.2 Hz, 1H), 7.52 (s, br, 1H), 7.26 (t, J=7.4 Hz, 1H), 6.78 (s, 1H), 3.88 (s, 3H), 3.32 (s, 2H), 3.24 (sept, J=6.9 Hz 1H), 2.38 (s, 3H), 2.37 (s, 2H), 1.30 (d, J=6.9 Hz, 6H), 1.29 (s, 6H);
LC/MS 530.2 [M$^+$+H].

EXAMPLE 92

Preparation of 5-chloro-N4-(2-(isopropylsulfonyl)phenyl)-N2-(2-ethyl-6-methoxy-4,4-trimethyl-1,2,3,4-tetrahydroisoquinolin-7-yl)pyrimidine-2,4-diamine

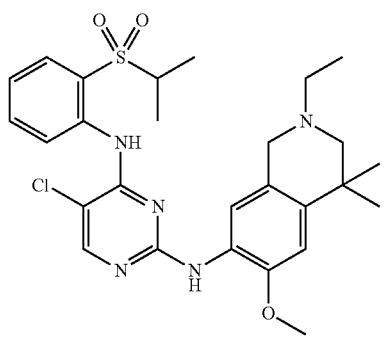 [SMILES: CCN1Cc2cc(Nc3ncc(Cl)c(Nc4ccccc4S(=O)(=O)C(C)C)n3)c(OC)cc2C(C)(C)C1]

The title compound was obtained by performing the same method as Example 3 except that the 5-chloro-N4-(2-(isopropylsulfonyl)phenyl)-N2-(6-methoxy-4,4-dimethyl-1,2,3,4-tetrahydroisoquinolin-7-yl)pyrimidine-2,4-diamine obtained in Example 75 and iodoethane were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.44 (s, br, 1H), 8.49 (d, J=8.3 Hz, 1H), 8.14 (s, 1H), 7.93 (d, J=7.9 Hz, 1H), 7.85 (s, 1H), 7.67 (t, J=8.4 Hz, 1H), 7.53 (s, br, 1H), 7.26 (t, J=8.2 Hz, 1H), 6.77 (s, 1H), 3.88 (s, 3H), 3.36 (s, 2H), 3.24 (sept, J=6.9 Hz, 1H), 2.49 (q, J=7.2 Hz, 2H), 2.38 (s, 2H), 1.30 (d, J=6.9 Hz, 6H), 1.29 (s, 6H), 1.14 (t, J=7.1 Hz, 3H); LC/MS 544.2 [M$^+$+H]

EXAMPLE 93

Preparation of 2-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)ethane-1-ol

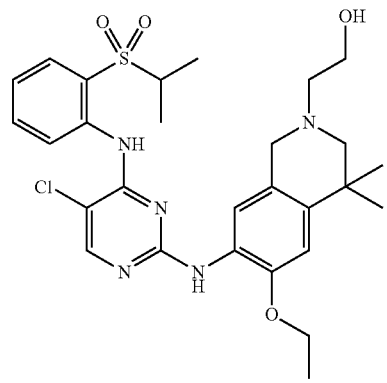 [SMILES: CCOc1cc2c(cc1Nc1ncc(Cl)c(Nc3ccccc3S(=O)(=O)C(C)C)n1)CN(CCO)CC2(C)C]

Step 1: Preparation of 5-chloro-N2-(6-ethoxy-2-ethyl-4,4-dimethyl-1,2,3,4-tetrahydroisoquinolin-7-yl)-N4-(2-(isopropylsulfonyl)phenyl)pyrimidine-2,4-diamine The title compound was obtained by performing the same method as Example 70 except that 1-(7-amino-6-ethoxy-4,4-dimethyl-3,4-dihydroisoquinolin-2(1H)-yl)-2,2,2-trifluoroethanone

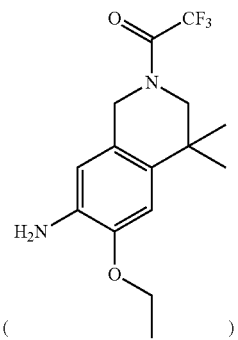 [SMILES: CCOc1cc2c(cc1N)CN(C(=O)C(F)(F)F)CC2(C)C]

was used instead of using the 1-(6-amino-7-isopropoxy-3,4-dihydroisoquinolin-2(1H)-yl)-2,2,2-trifluoroethane-1-one.

Step 2: Preparation of 2-(7-(5-chloro-4-(2-(isopropylsulfonyl)phenylamino)pyrimidin-2-yl)amino)-6-methoxy-4,4-dimethyl-3,4-dihydroisoquinolin-2(1H)-yl)-ethane-1-ol The title compound was obtained by performing the same method as Example 3 except that the 5-chloro-N2-(6-ethoxy-2-ethyl-4,4-dimethyl-1,2,3,4-tetrahydroisoquinolin-7-yl)-N4-(2-(isopropylsulfonyl)phenyl)pyrimidine-2,4-diamine obtained in step 1 and 2-iodoethanol were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.49 (s, br, 1H), 8.52 (d, J=8.3 Hz, 1H), 8.15 (s, 1H), 7.93 (d, J=8.0 Hz, 1H), 7.90 (s, 1H), 7.66 (t, J=8.3 Hz, 1H), 7.54 (s, br, 1H), 7.28 (t, J=7.9 Hz, 1H), 6.79 (s, 1H), 3.89 (s, 3H), 3.69 (t, J=5.1 Hz, 2H), 3.47 (s, 2H), 3.25 (sept, J=6.9 Hz 1H), 2.66 (t, J=5.2 Hz, 2H), 2.50 (s, 2H), 1.32-1.30 (m, 12H);

LC/MS 560.2 [M$^+$+H].

EXAMPLE 94

Preparation of 1-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)-2-(dimethylamino)ethane-1-one

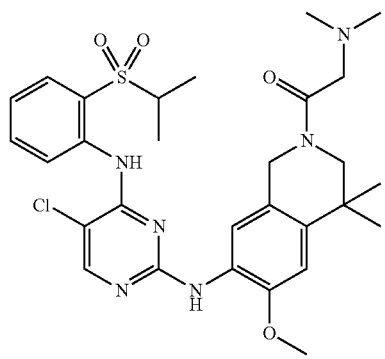 [SMILES: COc1cc2c(cc1Nc1ncc(Cl)c(Nc3ccccc3S(=O)(=O)C(C)C)n1)CN(C(=O)CN(C)C)CC2(C)C]

The title compound was obtained by performing the same method as Example 3 except that the 5-chloro-N4-(2-(isopropylsulfonyl)phenyl)-N2-(6-methoxy-4,4-dimethyl-1,2,3,4-tetrahydroisoquinolin-7-yl)pyrimidine-2,4-diamine obtained in Example 75 and 2-(dimethylamino)acetyl iodide were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.54 (s, br, 0.4H), 9.49 (s, br, 0.5H), 8.56 (d, J=8.6 Hz, 0.4H), 8.47 (d, J=8.3 Hz, 0.6H), 8.18 (s, 0.4H), 8.15 (s, 0.6H), 8.03 (s, 0.6H), 8.01 (s, 0.4H), 7.94 (d, J=8.1 Hz, 1H), 7.79 (t, J=7.3 Hz, 0.6H), 7.68 (t, J=8.3 Hz, 0.4H), 7.58 (s, 0.5H), 7.55 (s, 0.3H), 7.39 (t, J=7.6 Hz, 0.6H), 7.28 (t, J=7.8 Hz, 0.4H), 6.81 (s, 0.4H), 6.78 (s, 0.6H), 4.64 (s, 0.8H), 4.56 (s, 1.2H), 3.90 (s, 3H), 3.59 (s, 0.7H), 3.53 (s, 1.2H), 3.29-3.19 (m, 3H), 2.34 (s, 3.7H), 2.30 (s, 2.3H), 1.32-1.27 (m, 12H);

LC/MS 601.20 [M$^+$+H].

EXAMPLE 95

Preparation of 1-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)-2-hydroxyethane-1-one

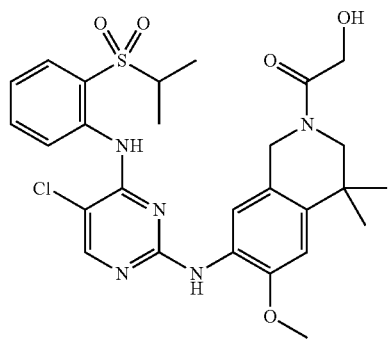 [SMILES: COc1cc2c(cc1Nc1ncc(Cl)c(Nc3ccccc3S(=O)(=O)C(C)C)n1)CN(C(=O)CO)CC2(C)C]

The title compound was obtained by performing the same method as Example 3 except that the 5-chloro-N4-(2-(isopropylsulfonyl)phenyl)-N2-(6-methoxy-4,4-dimethyle-1,2,3,4-tetrahydroisoquinolin-7-yl)pyrimidine-2,4-diamine obtained in Example 75 and glycolic acid were used instead of using the 5-chloro-N4-(2-(isopropylsulfonyl)phenyl)-N2-(7-methoxy-1,2,3,4-tetrahydroisoquinolin-6-yl)pyrimidine-2,4-diamine and methyl iodide.

$^1$H NMR (300 MHz, CDCl$_3$) δ 9.53 (s, br, 0.4H), 9.51 (s, br, 0.5H), 8.50 (t, J=8.6 Hz, 1H), 8.18 (s, 0.4H), 8.17 (s, 0.5H), 8.05 (s, 1H), 7.96 (d, J=7.9 Hz, 1H), 7.76 (t, J=7.2 Hz, 0.6H), 7.65 (t, J=7.1 Hz, 0.4H), 7.58 (s, br, 1H), 7.37 (t, J=7.6 Hz, 0.7H), 7.32 (t, J=7.3 Hz, 0.4H), 6.81 (s, 0.4H), 6.77 (s, 0.6H), 4.62 (s, 1H), 4.28-4.26 (m, 2H), 4.22-4.21 (m, 1H), 3.92 (s, 1.2H), 3.90 (s, 1.7H), 3.69 (t, J=4.1 Hz, 1H), 3.64 (s, 1H), 3.29-3.17 (m, 2H), 1.33-1.28 (m, 12H);

LC/MS 574.20 [M$^+$+H].

EXAMPLE 96

Preparation of 5-chloro-N4-(2-(isopropylsulfonyl)phenyl)-N2-(6-methoxy-2,3-dihydro-1H-spiro(cyclopropane-1,4-isoquinolin)-7-yl)pyrimidine-2,4-diamine

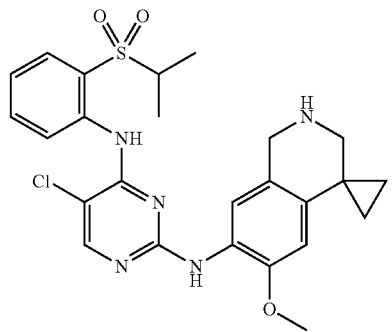 [SMILES: COc1cc2c(cc1Nc1ncc(Cl)c(Nc3ccccc3S(=O)(=O)C(C)C)n1)CNCC21CC1]

The title compound was obtained by performing the same method as Example 70 except that

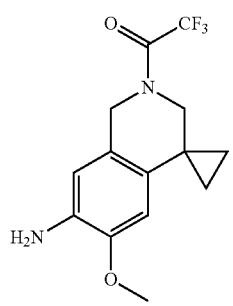 [SMILES: COc1cc2c(cc1N)CN(C(=O)C(F)(F)F)CC21CC1]

was used instead of using the 1-(6-amino-7-isopropoxy-3,4-dihydroisoquinolin-2(1H)-yl)-2,2,2-trifluoroethane-1-one.

¹H NMR (500 MHz, CDCl₃) δ 9.49 (s, br, 1H), 8.52 (d, J=8.3 Hz, 1H), 8.17 (s, 1H), 7.95 (d, J=7.9 Hz, 1H), 7.91 (s, 1H), 7.69 (t, J=7.1 Hz, 1H), 7.56 (s, br, 1H), 7.30 (t, J=7.6 Hz, 1H), 6.21 (s, 1H), 3.94 (s, 2H), 3.85 (s, 3H), 3.27 (sept, J=6.9 Hz, 1H), 2.93 (s, 2H), 1.86 (s, br, 1H), 1.33 (d, J=6.9 Hz, 6H), 0.98 (t, J=6.3 Hz, 2H), 0.86 (t, J=5.8 Hz, 2H);
LC/MS 514.2 [M⁺+H].

EXAMPLE 97

Preparation of 10-((5-chloro-4-(2-(isopropylsulfonyl)phenyl)aminopyrimidin-2-yl)amino)-9-methoxy-1,2,3,6,7,11b-hexahydro-4H-pyrazino[2,1-a]isoquinoline)-4-one

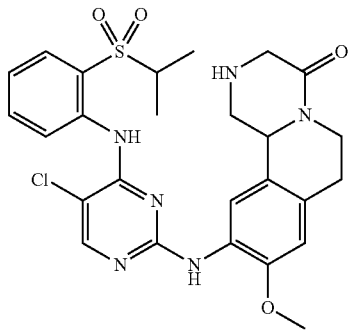 [SMILES: COc1cc2c(cc1Nc1ncc(Cl)c(Nc3ccccc3S(=O)(=O)C(C)C)n1)C1CNCC(=O)N1CC2]

The title compound was obtained by performing the same method as Example 70 except that 10-amino-9-methoxy-2-(2,2,2-trifluoroacetyl)-2,3,6,7-tetrahydro-1H-pyrazino[2,1-a]isoquinoline-4(11bH)-one

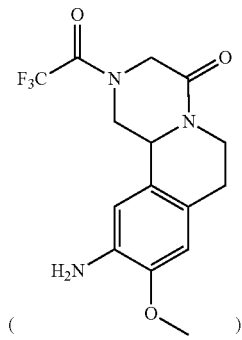 [SMILES: COc1cc2c(cc1N)C1CN(C(=O)C(F)(F)F)CC(=O)N1CC2]

as used instead of using the 1-(6-amino-7-isopropoxy-3,4-dihydroisoquinolin-2(1H)-yl)-2,2,2-trifluoroethane-1-one.

¹H NMR (300 MHz, CDCl₃) δ 9.51 (s, br, 1H), 9.48 (d, J=8.4 Hz, 1H), 8.18 (s, 1H), 8.17 (s, 1H), 7.96 (d, J=8.1 Hz, 1H), 7.67 (t, J=8.4 Hz, 1H), 7.57 (s, br, 1H), 7.31 (t, J=7.8 Hz, 1H), 6.65 (s, 1H), 4.94-4.89 (m, 1H), 4.66-4.61 (m, 1H), 3.89 (s, 3H), 3.65-3.59 (m, 1H), 3.47-3.42 (m, 1H), 3.26 (sept, J=6.9 Hz, 1H), 3.19-3.17 (m, 1H), 3.00-2.89 (m, 1H), 2.83-2.74 (m, 1H), 2.69-2.59 (m, 2H), 1.59 (s, br, 1H), 1.34 (d, J=6.9 Hz, 3H), 1.29 (d, J=6.9 Hz, 3H);
LC/MS 557.2 [M⁺+H].

EXAMPLE 98

Preparation of 5-chloro-N4-(2-(isopropylsulfonyl)phenyl)-N2-(9-methoxy-1,3,4,6,7,11b-hexahydro-2H-pyrazino[2,1-a]isoquinolin-10-yl)pyrimidine-2,4-diamine

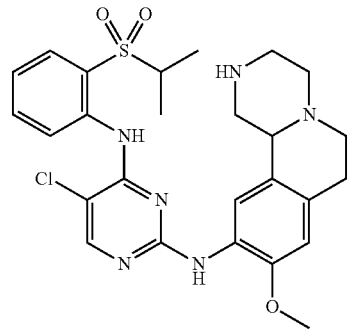 [SMILES: COc1cc2c(cc1Nc1ncc(Cl)c(Nc3ccccc3S(=O)(=O)C(C)C)n1)C1CNCCN1CC2]

The title compound was obtained by performing the same method as Example 70 except that 1-(10-amino-9-methoxy-3,4,6,7-tetrahydro-1H-pyrazino[2,1-a]isoquinolin-2(11bH)-yl)-2,2,2-trifluoroethanone

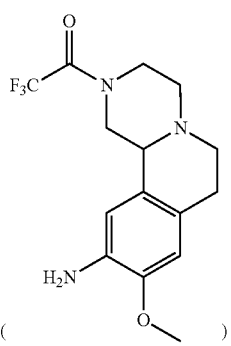 [SMILES: COc1cc2c(cc1N)C1CN(C(=O)C(F)(F)F)CCN1CC2]

was used instead of using the 1-(6-amino-7-isopropoxy-3,4-dihydroisoquinolin-2(1H)-yl)-2,2,2-trifluoroethane-1-one.

¹H NMR (500 MHz, CDCl₃) δ 9.54 (s, br, 1H), 8.54 (d, J=8.5 Hz, 1H), 8.17 (s, 1H), 8.12 (s, br, 1H), 7.95 (d, J=7.8 Hz, 1H), 7.69 (t, J=8.0 Hz, 1H), 7.49 (s, 1H), 7.31 (t, J=8.0 Hz, 1H), 6.63 (s, 1H), 3.88 (s, 3H), 3.51-3.39 (m, 1H), 3.28 (sept, J=6.9 Hz, 1H), 3.24-3.19 (m, 1H), 3.18-3.13 (m, 1.5H), 3.08-3.03 (m, 1H), 3.00-2.93 (m, 2.5H), 2.69-2.51 (m, 4H), 2.19-2.09 (m, 1H), 1.35 (d, J=6.9 Hz, 3H), 1.32 (d, J=6.9 Hz, 3H);
LC/MS 543.2 [M⁺+H].

EXAMPLE 99

Preparation of 5-chloro-N4-(2-(isopropylsulfonyl)phenyl)-N2-(7-ethoxy-1,1-dimethyl-1,2,3,4-tetrahydroisoquinolin-6-yl)pyrimidine-2,4-diamine

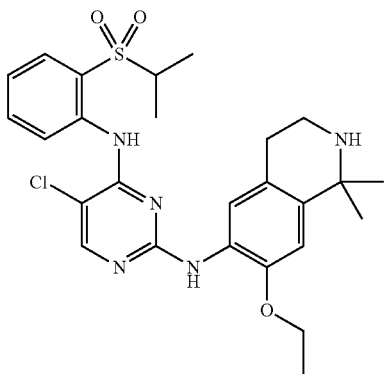 [SMILES: CCOc1cc2c(cc1Nc1ncc(Cl)c(Nc3ccccc3S(=O)(=O)C(C)C)n1)CCNC2(C)C]

The title compound was obtained by performing the same method as Example 70 except that 1-(6-amino-7-ethoxy-1,1-dimethyl-3,4-dihydroisoquinolin-2(1H)-yl)-2,2,2-trifluoroethanone

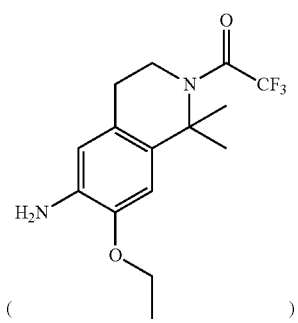 [SMILES: CCOc1cc2c(cc1N)CCN(C(=O)C(F)(F)F)C2(C)C]

was used instead of using the 1-(6-amino-7-isopropoxy-3,4-dihydroisoquinolin-2(1H)-yl)-2,2,2-trifluoroethane-1-one.

$^{1}$H NMR (300 MHz, CDCl$_3$) δ 9.48 (s, br, 1H), 8.54 (d, J=8.3 Hz, 1H), 8.16 (s, 1H), 7.93 (d, J=8.0 Hz, 2H), 7.64 (t, J=8.5 Hz, 1H), 7.56 (s, br, 1H), 7.26 (t, J=5.6 Hz, 1H), 6.68 (s, 1H), 4.10 (q, J=6.9 Hz, 2H), 3.26 (sept, J=6.9 Hz, 1H), 3.11 (t, J=5.8 Hz, 2H), 2.56 (t, J=5.7 Hz, 2H), 1.91 (s, br, 1H), 1.46 (t, J=7.0 Hz, 3H), 1.45 (s, 6H), 1.31 (d, J=6.9 Hz, 6H);

LC/MS 529.5 [M$^{+}$+H].

EXAMPLE 100

Preparation of 5-chloro-N4-(2-(isopropylsulfonyl)phenyl)-N2-(7-difluoromethoxy-1,1-dimethyl-1,2,3,4-tetrahydroisoquinolin-6-yl)pyrimidine-2,4-diamine

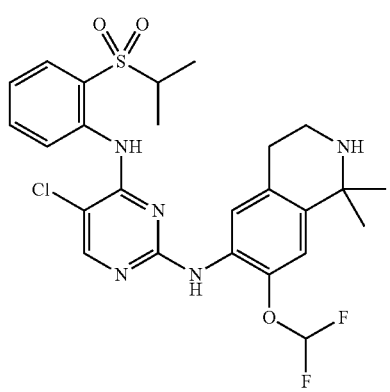 [SMILES: CC(C)S(=O)(=O)c1ccccc1Nc1nc(Nc2cc3c(cc2OC(F)F)C(C)(C)NCC3)ncc1Cl]

The title compound was obtained by performing the same method as Example 70 except that 1-(6-amino-7-difluoromethoxy-1,1-dimethyl-3,4-dihydroisoquinolin-2(1H)-yl)-2,2,2-trifluoroethanone

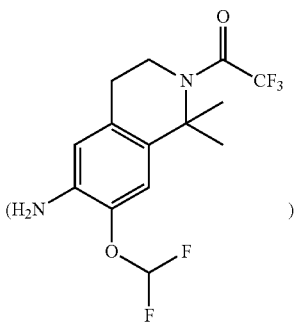

was used instead of using the 1-(6-amino-7-isopropoxy-3,4-dihydroisoquinolin-2(1H)-yl)-2,2,2-trifluoroethane-1-one.

$^{1}$H NMR (300 MHz, CDCl$_3$) δ 9.56 (s, br, 1H), 8.50 (d, J=8.3 Hz, 1H), 8.17 (s, 1H), 7.96 (s, 1H), 7.93 (d, J=8.0 Hz, 1H), 7.62 (t, J=8.4 Hz, 1H), 7.48 (s, br, 1H), 7.29-7.25 (m, 2H), 6.97 (s, 1H), 6.49 (t, J=73.6 Hz, 1H), 3.25 (sept, J=6.9 Hz, 1H), 3.12 (t, J=5.8 Hz, 2H), 2.63 (t, J=5.7 Hz, 2H), 2.01 (s, br, 1H), 1.45 (s, 6H), 1.32 (d, J=6.9 Hz, 6H);

LC/MS 551.5 [M$^{+}$+H].

EXAMPLE 101

Preparation of 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine hydrochloride

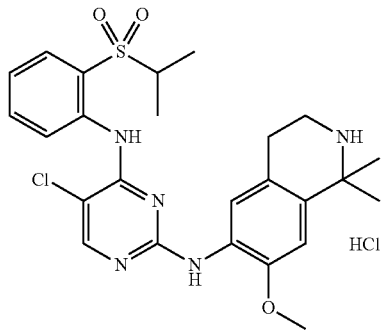 [SMILES: COc1cc2c(cc1Nc1ncc(Cl)c(Nc3ccccc3S(=O)(=O)C(C)C)n1)CCNC2(C)C ; Cl]

The 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine (52 mg, 0.1 mmol) obtained in Example 33 was dissolved in dichloromethane (3 mL), 3 mL of dioxane in which 4M HCl was dissolved was added thereto, and the reaction mixture was stirred at room temperature for 3 hours. After completion of the reaction, the HCl solution was removed under reduced pressure to obtain the title compound.

$^1$H NMR (300 MHz, DMSO-$d_6$) δ 9.75 (s, br, 1H), 9.65 (s, br, 2H), 8.75 (s, 1H), 8.35-8.32 (m, 2H), 7.88 (d, J=7.9 Hz, 1H), 7.77 (t, J=8.1 Hz, 1H), 7.47-7.42 (m, 2H), 7.01 (s, 1H), 3.82 (s, 3H), 3.47 (sept, J=6.6 Hz, 1H), 3.34-3.32 (m, 2H), 2.78 (t, J=5.4 Hz, 2H), 1.69 (s, 6H), 1.15 (d, J=6.9 Hz, 6H);

LC/MS 515.5 [M$^+$+H].

EXAMPLE 102

Preparation of 5-chloro-N4-(2-(isopropylsulfonyl)phenyl)-N2-(7-methoxy-1-propyl-1,2,3,4-tetrahydroisoquinolin-6-yl)pyrimidine-2,4-diamine

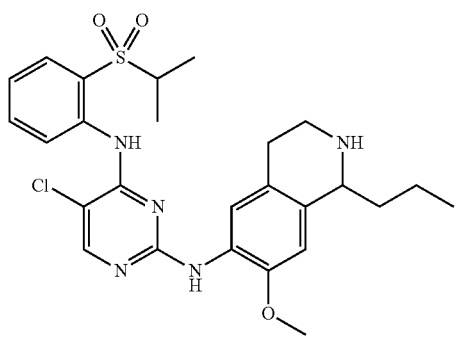 [SMILES: CCCC1NCCc2cc(Nc3ncc(Cl)c(Nc4ccccc4S(=O)(=O)C(C)C)n3)c(OC)cc21]

The title compound was obtained by performing the same method as Example 70 except that 1-(6-amino-7-methoxy-1-propyl-3,4-dihydroisoquinolin-2(1H)-yl)-2,2,2-trifluoroethanone

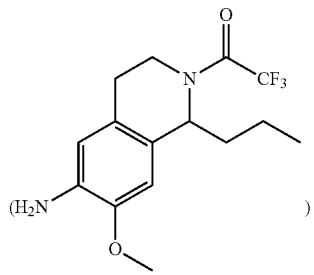

was used instead of using the 1-(6-amino-7-isopropoxy-3,4-dihydroisoquinolin-2(1H)-yl)-2,2,2-trifluoroethane-1-one.

$^1$H NMR (CDCl$_3$, 300 MHz) δ 9.50 (s, 1H), 8.53 (d, J=8.2 Hz, 1H), 8.19 (s, 1H), 8.05 (d, J=8.07 Hz, 1H), 7.94 (d, J=7.95 Hz, 1H) 7.64-7.54 (m, 2H), 7.30-7.27 (m, 1H), 6.62 (s, 1H), 5.52-5.47 (m, 1H), 4.04-3.97 (m, 1H), 3.87 (s, 3H), 3.64-3.56 (m, 1H), 3.29-3.22 (m, 1H), 2.88-2.83 (m, 1H), 2.66 (d, J=1.5 Hz, 1H) 1.89-1.78 (m, 2H), 1.48-1.23 (m, 8H), 0.97 (t, J=7.4, 3H);

LC/MS 530.2 [M$^+$+H].

EXAMPLE 103

Preparation of 6-((5-chloro-4-((2-(isopropylsulfonyl)phenyl)amino)pyridin-2-yl)amino)-7-methoxy-2,2-dimethyl-1,2,3,4-tetrahydroisoquinolin-2-ium iodide

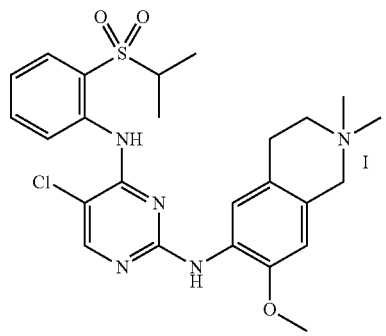

The 5-chloro-N4-(2-(isopropylsulfonyl)phenyl)-N2-(7-methoxy-2-methyl-1,2,3,4-tetrahydroisoquinolin-6-yl)pyrimidine-2,4-diamine obtained in Example 3 was dissolved in ethanol (1 mL), diisopropylamine (0.04 mL, 0.25 mmol) and methyl iodide (0.01 mL, 0.15 mmol) were added at 0° C., followed by stirring at room temperature for 18 hours. The reaction solution was diluted with water, extracted three times with dichloromethane, and then washed with a saturated aqueous sodium chloride solution. The organic layer was dried over anhydrous magnesium sulfate, concentrated under reduced pressure, and purified by column chromatography to obtain the title compound.

$^1$H NMR (300 MHz, CDCl$_3$) δ 9.59 (s, 1H), 8.51 (d, J=8.4 Hz, 1H), 8.26 (s, 1H), 8.19 (s, 1H), 7.94 (d, J=7.8 Hz, 1H), 7.73 (t, J=7.3 Hz, 1H), 7.62 (s, 1H), 7.35 (t, J=7.7 Hz, 1H), 6.68 (s, 1H), 4.85 (s, 2H), 4.00 (t, J=6.1 Hz, 2H), 3.91 (s, 3H), 3.61 (s, 6H), 3.32-3.16 (m, 1H), 3.08 (t, J=6.5 Hz, 2H), 1.32 (d, J=6.8 Hz, 6H);

LC/MS (ESI) m/z 516.2 [M-127 (I$^-$)]$^+$

EXAMPLE 104

Preparation of 5-chloro-N4-(2-(isopropylsulfonyl)phenyl)-N2-(8-methoxy-1,1-dimethyl-2,3,4,5-tetrahydro-1H-benzo[c]azepin-7-yl)pyrimidine-2,4-diamine

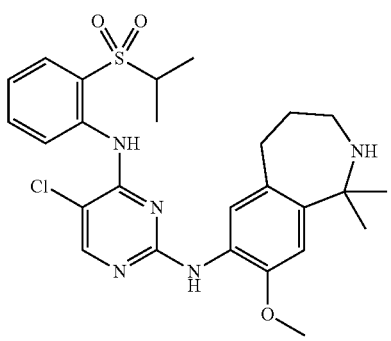 [SMILES: COc1cc2c(cc1Nc1ncc(Cl)c(Nc3ccccc3S(=O)(=O)C(C)C)n1)CCCNC2(C)C]

The title compound was obtained by performing the same method as Example 70 except that 1-(7-amino-8-methoxy-1,1-dimethyl-4,5-dihydro-1H-benzo[c]azepin-2(3H)-yl)-2,2,2-trifluoroethanone

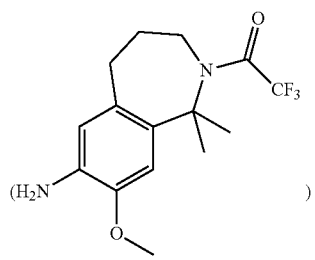

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.48 (s, 1H), 8.55 (d, J=8.4 Hz, 1H), 8.16 (s, 2H), 8.03-7.88 (m, 2H), 7.64 (t, J=7.9 Hz, 1H), 7.50 (s, 1H), 7.30-7.21 (m, 1H), 6.83 (s, 1H), 3.88 (s, 3H), 3.36-3.20 (m, 1H), 3.09 (t, J=6.2 Hz, 2H), 2.85-2.75 (m, 2H), 1.88-1.70 (m, 3H), 1.52 (s, 6H), 1.31 (d, J=6.8 Hz, 6H);

LC/MS (ESI) m/z 530.2 [M$^+$+H].

EXAMPLE 105

Preparation of 5-chloro-N4-(2-(isopropylsulfonyl)phenyl)-N2-(8-methoxy-1,1-dimethyl-2,3,4,5-tetrahydro-1H-benzo[d]azepin-7-yl)pyrimidine-2,4-diamine

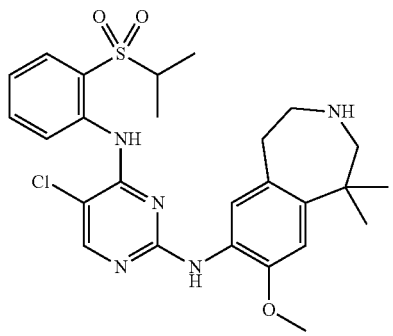 [SMILES: COc1cc2c(cc1Nc1ncc(Cl)c(Nc3ccccc3S(=O)(=O)C(C)C)n1)CCNCC2(C)C]

The title compound was obtained by performing the same method as Example 70 except that 1-(7-amino-8-methoxy-1,1-dimethyl-1,2,4,5-tetrahydrobenzo[d]azepin-3-yl)-2,2,2-trifluoroethanone

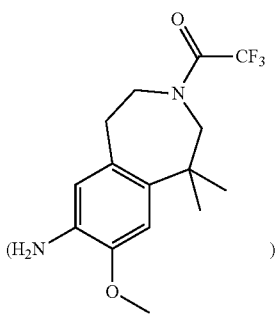

was used instead of using the 1-(6-amino-7-isopropoxy-3,4-dihydroisoquinolin-2(1H)-yl)-2,2,2-trifluoroethane-1-one.

$^1$H NMR (CDCl$_3$, 300 MHz) δ 9.48 (s, 1H), 8.55 (d, J=8.4, 1H), 8.15 (s, 1H), 7.95-7.91 (m, 2H), 7.62 (t, J=7.05, 1H), 7.48 (s, 1H), 7.27-7.22 (m, 1H), 6.90 (s, 1H), 3.89 (s, 3H), 3.30-3.21 (m, 1H), 2.99-2.96 (m, 2H), 2.93 (s, 2H), 2.89-2.85 (m, 2H), 1.93-1.72 (m, 4H), 1.36 (s, 6H), 1.30 (d, J=15.3, 6H);

LC/MS (ESI) m/z 530.2 [M$^+$+H].

EXAMPLE 106

Preparation of 5-chloro-N4-(2-(isopropylsulfonyl)phenyl)-N2-(6-methoxy-1,1-dimethylisoindolin-5-yl)pyrimidine-2,4-diamine

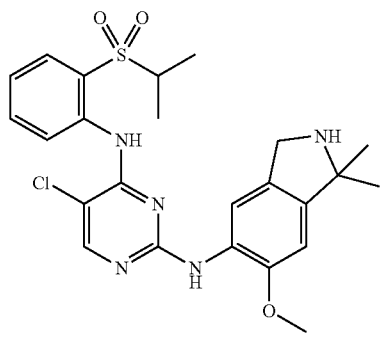 [SMILES: COc1cc2c(cc1Nc1ncc(Cl)c(Nc3ccccc3S(=O)(=O)C(C)C)n1)CNC2(C)C]

The title compound was obtained by performing the same method as Example 70 except that 1-(5-amino-6-methoxy-1,1-dimethylisoindolin-2-yl)-2,2,2-trifluoroethanone

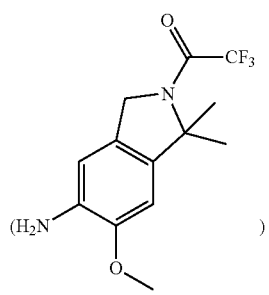

was used instead of using the 1-(6-amino-7-isopropoxy-3,4-dihydroisoquinolin-2(1H)-yl)-2,2,2-trifluoroethane-1-one.

$^1$H NMR (300 MHz, CDCl$_3$) δ 9.49 (s, 1H), 8.52 (d, J=8.4 Hz, 1H), 8.16 (s, 1H), 8.11 (s, 1H), 7.93 (dd, J=1.4 Hz, 8.0 Hz, 1H), 7.67-7.59 (m, 2H), 7.28 (t, J=6.6 Hz, 1H), 6.67 (s, 1H), 4.09 (s, 2H), 3.92 (s, 3H), 3.28-3.19 (m, 1H), 1.44 (s, 6H), 1.31 (d, J=6.9 Hz, 6H);

LC/MS 501.9 [M$^+$+H].

COMPARATIVE EXAMPLE 1

Preparation of Crizotinib

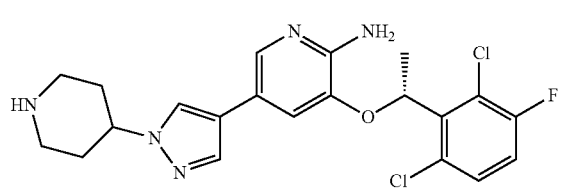 [SMILES: C[C@@H](Oc1cc(-c2cnn(C3CCNCC3)c2)cnc1N)c1c(Cl)ccc(F)c1Cl]

The Crizotinib was prepared by a known method.

COMPARATIVE EXAMPLE 2

Preparation of LDK-378

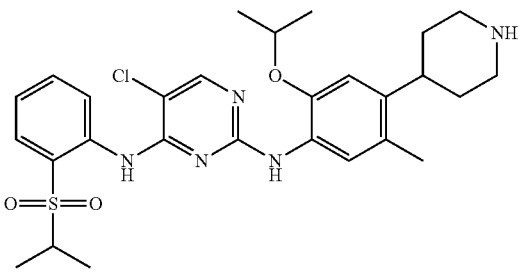 [SMILES: Cc1cc(Nc2ncc(Cl)c(Nc3ccccc3S(=O)(=O)C(C)C)n2)c(OC(C)C)cc1C1CCNCC1]

The LDK-378 was prepared by a known method.

The chemical structures of the compounds prepared in Examples 1-106 are summarized in Table 1 below.

TABLE 1

| Example | Chemical Structure |
|---|---|
| 1 | (structure) |
| 2 | (structure) |
| 3 | (structure) |

TABLE 1-continued
| Example | Chemical Structure |
|---|---|
| 4 | 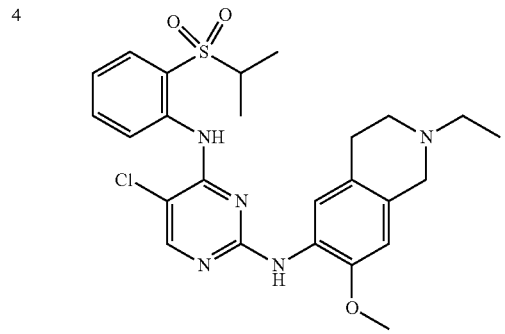 |
| 5 | 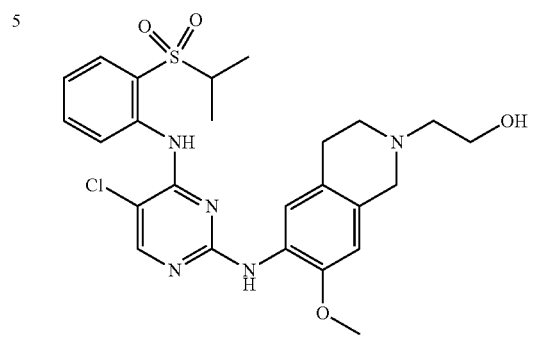 |
| 6 | 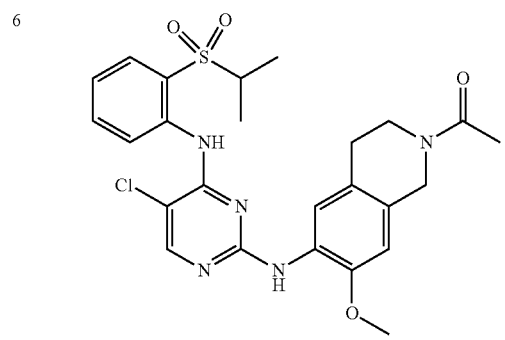 |
| 7 | 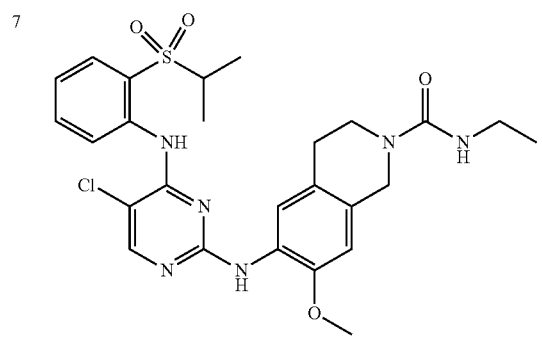 |
| 8 | 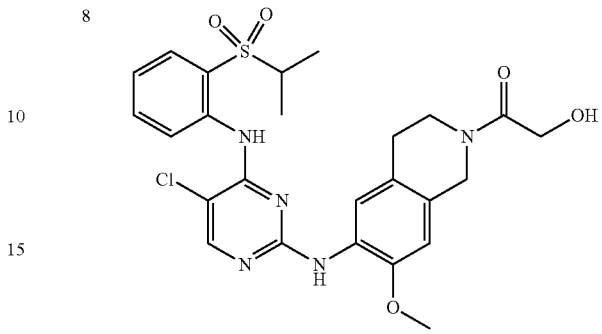 |
| 9 | 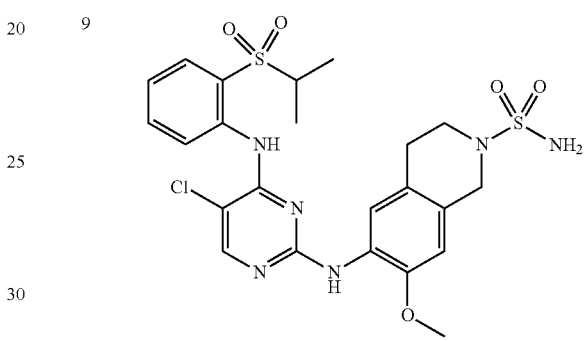 |
| 10 | 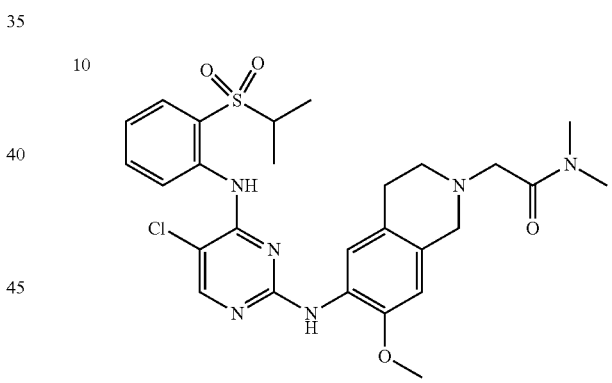 |
| 11 | 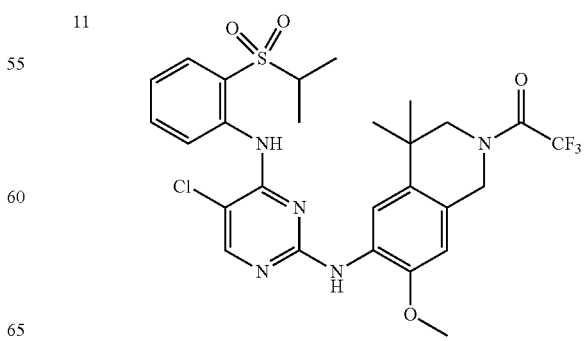 |

TABLE 1-continued
| Example | Chemical Structure |
|---|---|
| 12 | 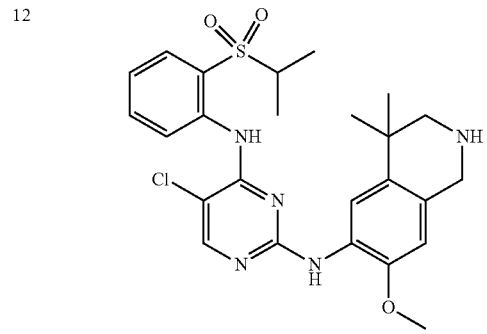 |
| 13 | 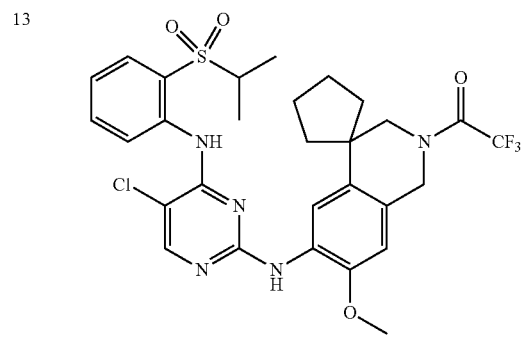 |
| 14 | 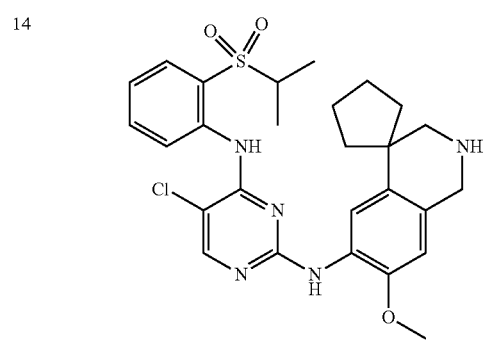 |
| 15 | 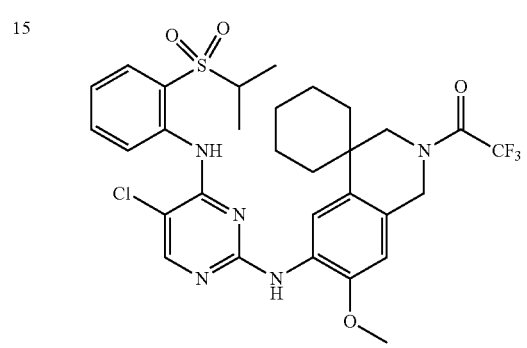 |
TABLE 1-continued
| Example | Chemical Structure |
|---|---|
| 16 | 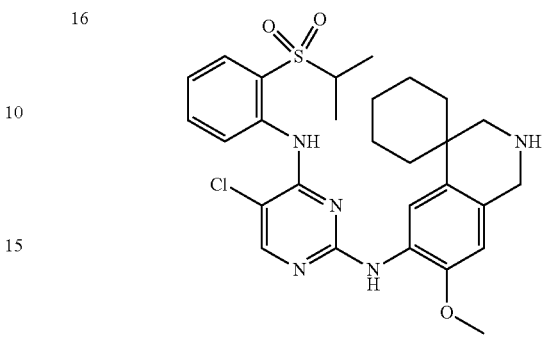 |
| 17 | 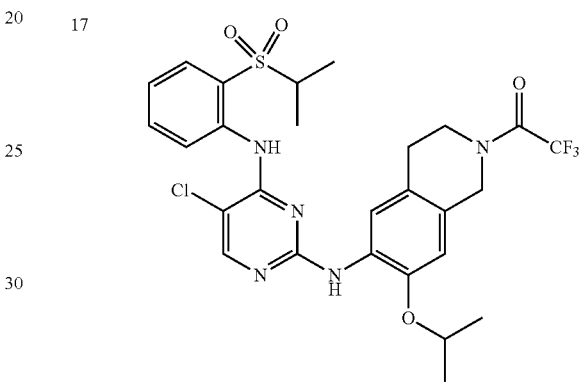 |
| 18 | 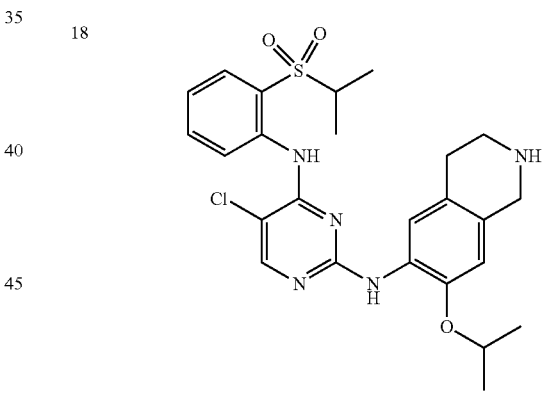 |
| 19 | 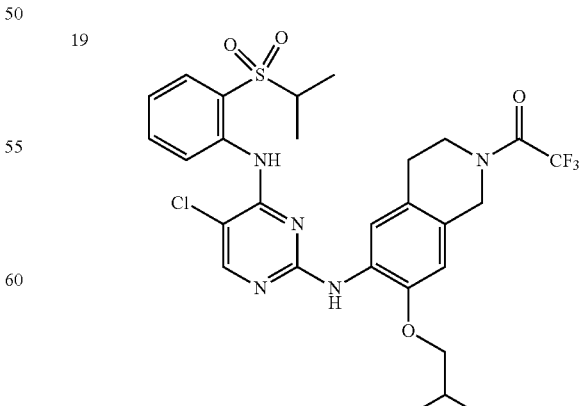 |

TABLE 1-continued

| Example | Chemical Structure |
|---|---|
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE 1-continued
| Example | Chemical Structure |
|---|---|
| 28 | 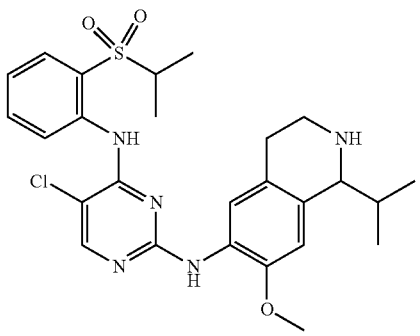 [SMILES: COc1cc2c(cc1Nc1ncc(Cl)c(Nc3ccccc3S(=O)(=O)C(C)C)n1)CCNC2C(C)C] |
| 29 | 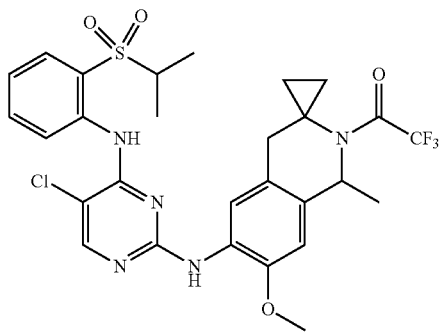 [SMILES: COc1cc2c(cc1Nc1ncc(Cl)c(Nc3ccccc3S(=O)(=O)C(C)C)n1)CC1(CC1)N(C(=O)C(F)(F)F)C2C] |
| 30 | 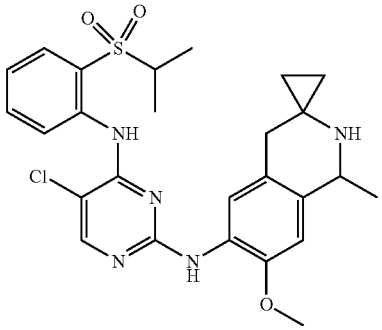 [SMILES: COc1cc2c(cc1Nc1ncc(Cl)c(Nc3ccccc3S(=O)(=O)C(C)C)n1)CC1(CC1)NC2C] |
| 31 | 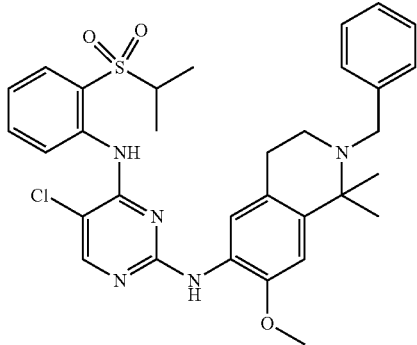 [SMILES: COc1cc2c(cc1Nc1ncc(Cl)c(Nc3ccccc3S(=O)(=O)C(C)C)n1)CCN(Cc1ccccc1)C2(C)C] |
TABLE 1-continued
| Example | Chemical Structure |
|---|---|
| 32 | 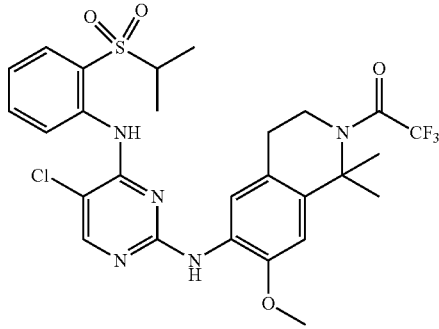 [SMILES: COc1cc2c(cc1Nc1ncc(Cl)c(Nc3ccccc3S(=O)(=O)C(C)C)n1)CCN(C(=O)C(F)(F)F)C2(C)C] |
| 33 | 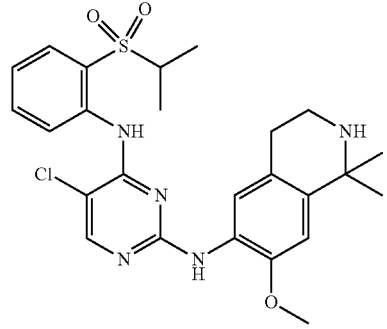 [SMILES: COc1cc2c(cc1Nc1ncc(Cl)c(Nc3ccccc3S(=O)(=O)C(C)C)n1)CCNC2(C)C] |
| 34 | 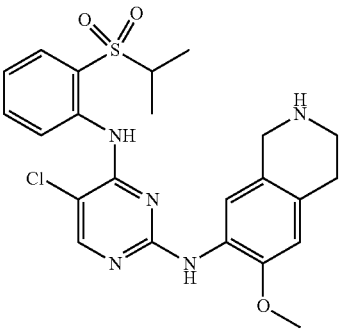 [SMILES: COc1cc2c(cc1Nc1ncc(Cl)c(Nc3ccccc3S(=O)(=O)C(C)C)n1)CNCC2] |
| 35 | 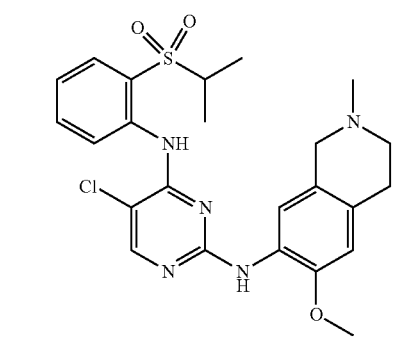 [SMILES: COc1cc2c(cc1Nc1ncc(Cl)c(Nc3ccccc3S(=O)(=O)C(C)C)n1)CN(C)CC2] |

TABLE 1-continued

| Example | Chemical Structure |
|---|---|
| 36 | (structure) |
| 37 | (structure) |
| 38 | (structure) |
| 39 | (structure) |
| 40 | (structure) |
| 41 | (structure) |
| 42 | (structure) |
| 43 | (structure) |

TABLE 1-continued
| Example | Chemical Structure |
|---|---|
| 44 | 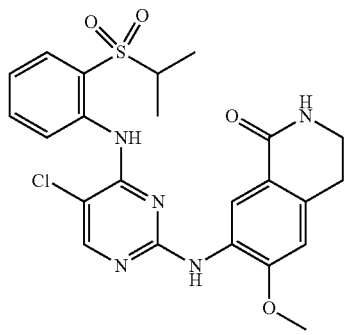 [SMILES: COc1cc2c(cc1Nc1ncc(Cl)c(Nc3ccccc3S(=O)(=O)C(C)C)n1)C(=O)NCC2] |
| 45 | 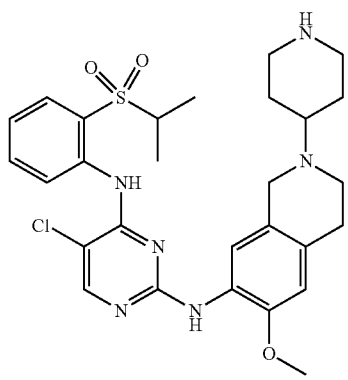 [SMILES: COc1cc2c(cc1Nc1ncc(Cl)c(Nc3ccccc3S(=O)(=O)C(C)C)n1)CN(C1CCNCC1)CC2] |
| 46 | 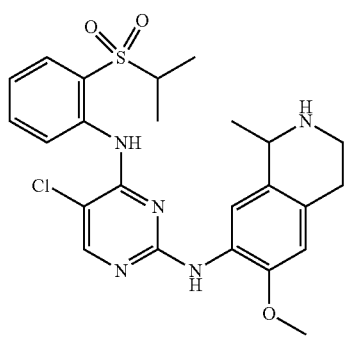 [SMILES: COc1cc2c(cc1Nc1ncc(Cl)c(Nc3ccccc3S(=O)(=O)C(C)C)n1)C(C)NCC2] |
| 47 | 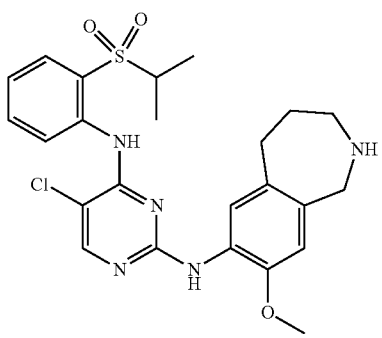 [SMILES: COc1cc2c(cc1Nc1ncc(Cl)c(Nc3ccccc3S(=O)(=O)C(C)C)n1)CCCNC2] |
TABLE 1-continued
| Example | Chemical Structure |
|---|---|
| 48 | 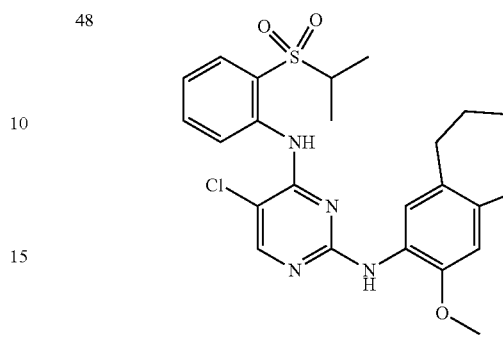 |
| 49 | 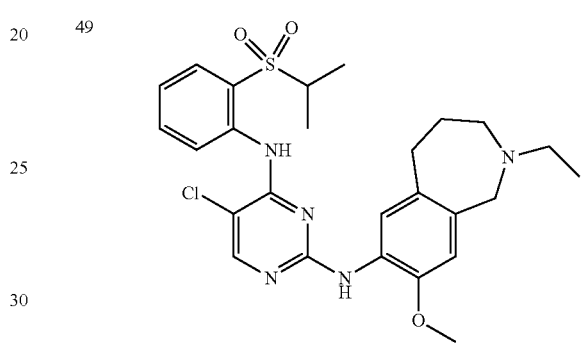 |
| 50 | 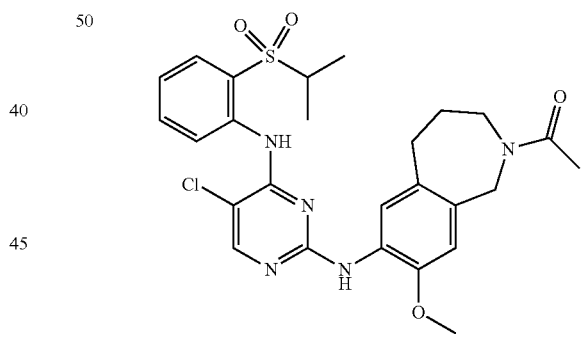 |
| 51 | 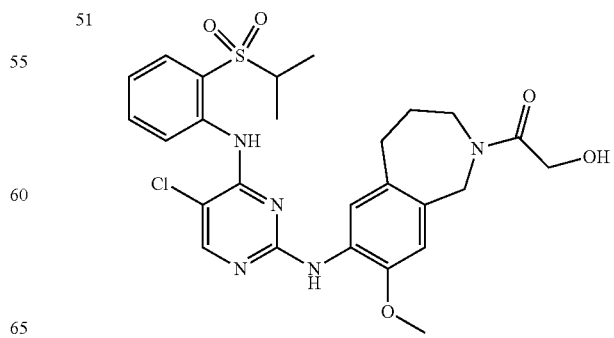 |

TABLE 1-continued
| Example | Chemical Structure |
|---|---|
| 52 | 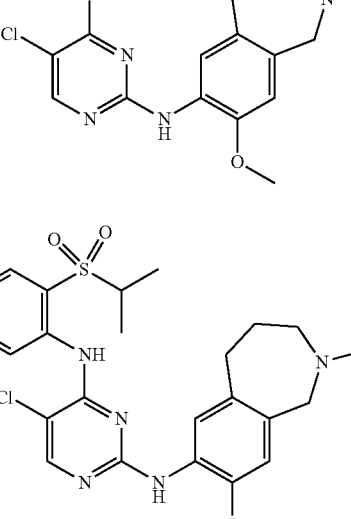 |
| 53 | 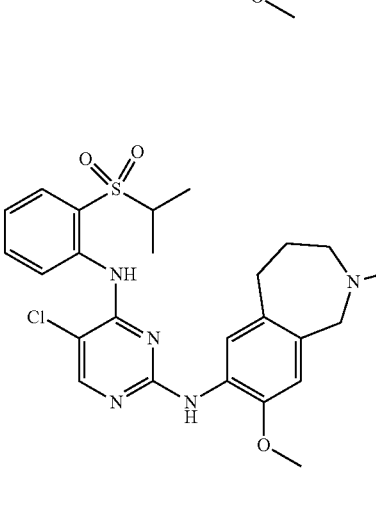 |
| 54 | 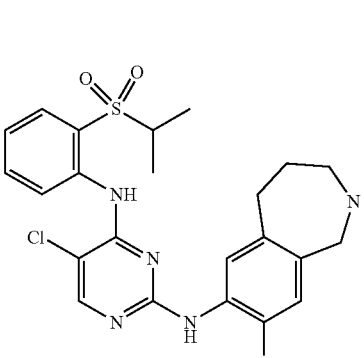 |
| 55 | 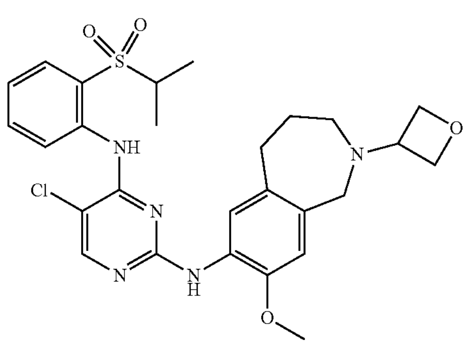 [SMILES: COc1cc2c(cc1Nc1ncc(Cl)c(Nc3ccccc3S(=O)(=O)C(C)C)n1)CCCN(C1COC1)C2] |
| 56 | 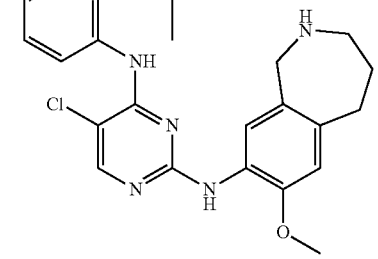 |
| 57 | 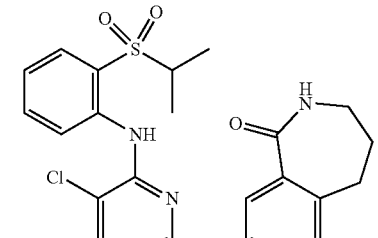 |
| 58 | 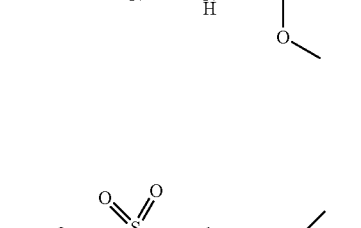 |
| 59 | 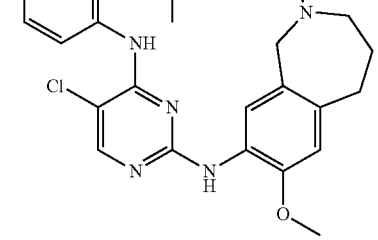 |

TABLE 1-continued

| Example | Chemical Structure |
|---|---|
| 60 | (structure) |
| 61 | (structure) |
| 62 | (structure) |
| 63 | (structure) |
| 64 | (structure) |
| 65 | (structure) |
| 66 | (structure) |
| 67 | (structure) |

TABLE 1-continued

| Example | Chemical Structure |
|---|---|
| 68 | (structure) |
| 69 | (structure) |
| 70 | (structure) |
| 71 | (structure) |
| 72 | (structure) |
| 73 | (structure) |
| 74 | (structure) |
| 75 | (structure) |

TABLE 1-continued
| Example | Chemical Structure |
|---|---|
| 76 | 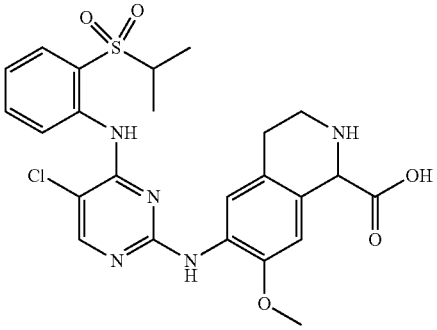 [SMILES: COc1cc2c(cc1Nc1ncc(Cl)c(Nc3ccccc3S(=O)(=O)C(C)C)n1)CCNC2C(=O)O] |
| 77 | 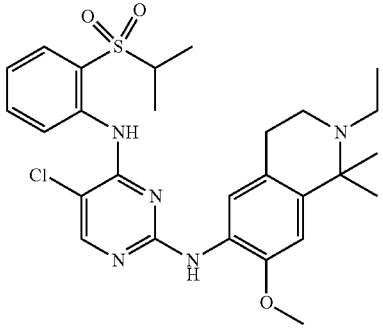 [SMILES: CCN1CCc2cc(Nc3ncc(Cl)c(Nc4ccccc4S(=O)(=O)C(C)C)n3)c(OC)cc2C1(C)C] |
| 78 | 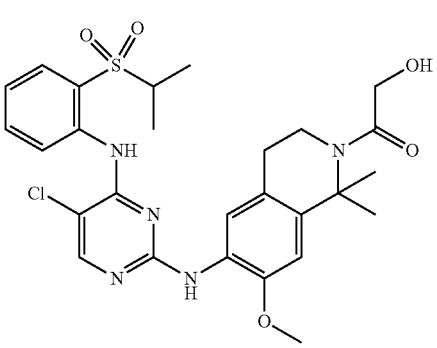 [SMILES: COc1cc2c(cc1Nc1ncc(Cl)c(Nc3ccccc3S(=O)(=O)C(C)C)n1)CCN(C(=O)CO)C2(C)C] |
| 79 | 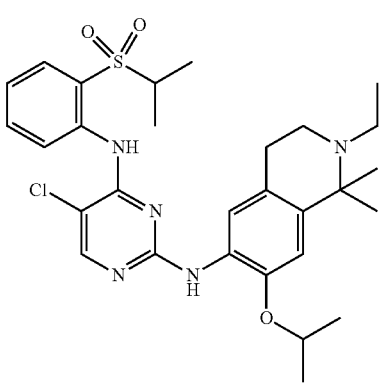 [SMILES: CCN1CCc2cc(Nc3ncc(Cl)c(Nc4ccccc4S(=O)(=O)C(C)C)n3)c(OC(C)C)cc2C1(C)C] |￼
| 80 | 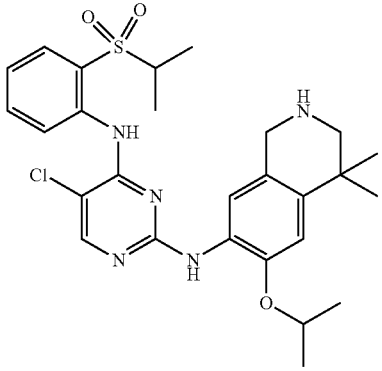 [SMILES: CC(C)Oc1cc2c(cc1Nc1ncc(Cl)c(Nc3ccccc3S(=O)(=O)C(C)C)n1)CNCC2(C)C] |
| 81 | 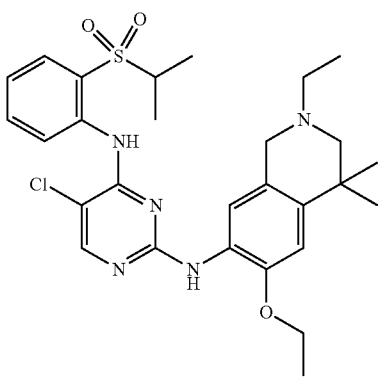 [SMILES: CCOc1cc2c(cc1Nc1ncc(Cl)c(Nc3ccccc3S(=O)(=O)C(C)C)n1)CN(CC)CC2(C)C] |
| 82 | 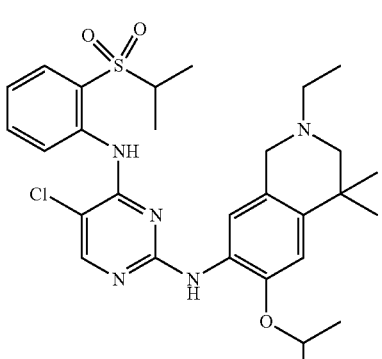 |
| 83 | 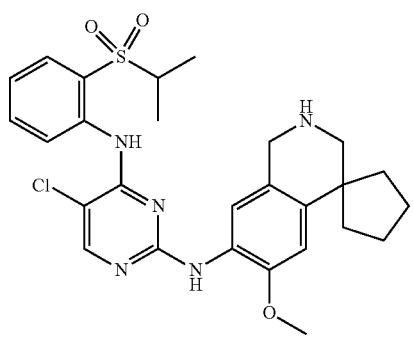 [SMILES: COc1cc2c(cc1Nc1ncc(Cl)c(Nc3ccccc3S(=O)(=O)C(C)C)n1)CNCC21CCCC1] |

TABLE 1-continued
| Example | Chemical Structure |
|---|---|
| 84 | 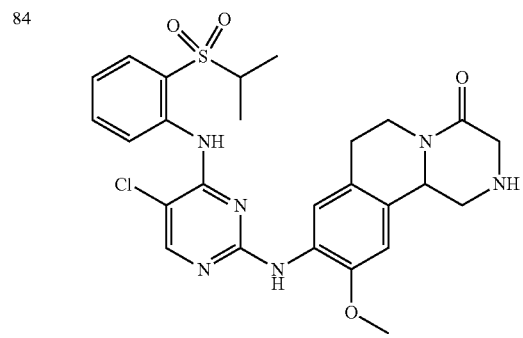 |
| 85 | 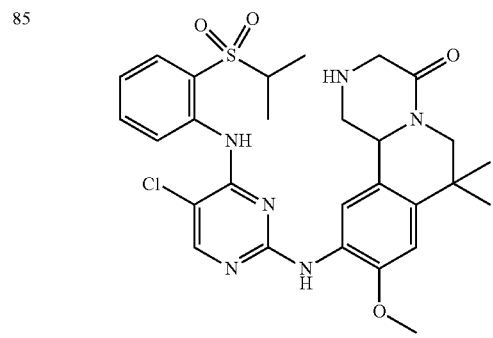 |
| 86 | 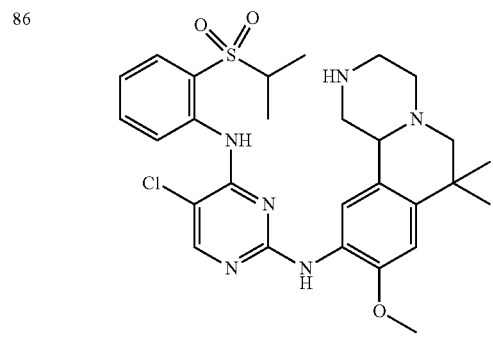 |
| 87 | 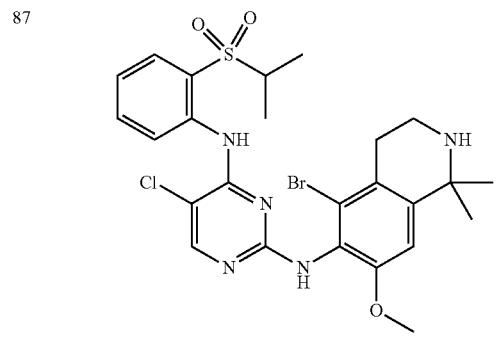 |
TABLE 1-continued
| Example | Chemical Structure |
|---|---|
| 88 | 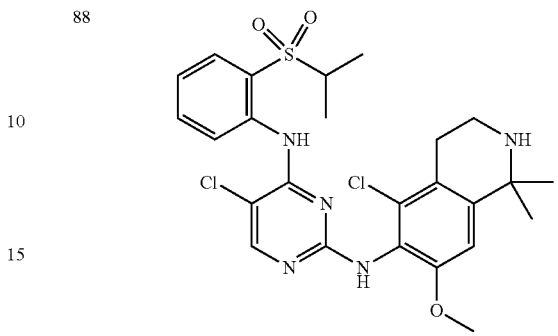 |
| 89 | 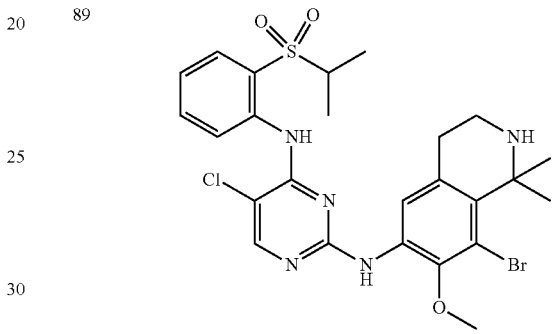 |
| 90 | 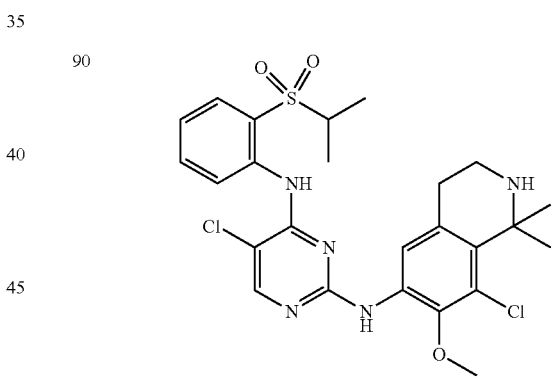 |
| 91 | 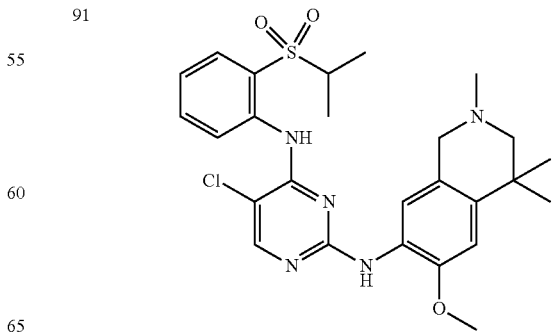 |

US 10,053,458 B2
133
TABLE 1-continued
| Example | Chemical Structure |
|---|---|
| 92 | 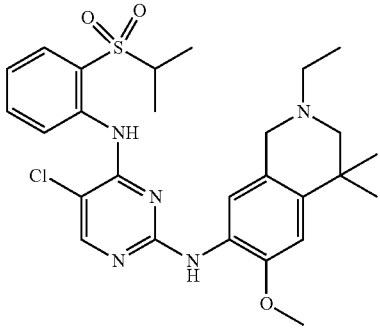 [SMILES: CCN1Cc2cc(Nc3ncc(Cl)c(Nc4ccccc4S(=O)(=O)C(C)C)n3)c(OC)cc2C(C)(C)C1] |
| 93 | 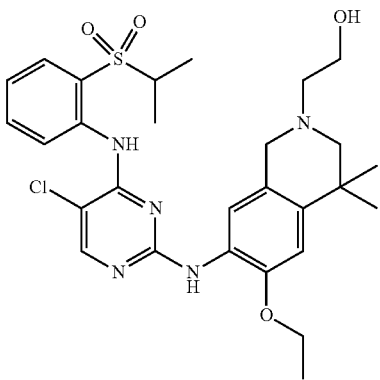 [SMILES: CCOc1cc2c(cc1Nc1ncc(Cl)c(Nc3ccccc3S(=O)(=O)C(C)C)n1)CN(CCO)CC2(C)C] |
| 94 | 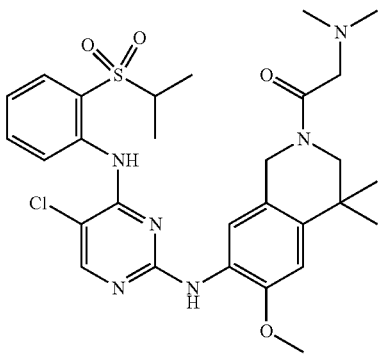 [SMILES: COc1cc2c(cc1Nc1ncc(Cl)c(Nc3ccccc3S(=O)(=O)C(C)C)n1)CN(C(=O)CN(C)C)CC2(C)C] |
| 95 | 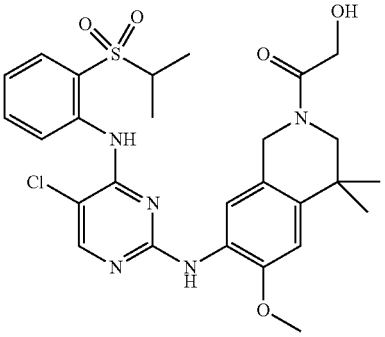 [SMILES: COc1cc2c(cc1Nc1ncc(Cl)c(Nc3ccccc3S(=O)(=O)C(C)C)n1)CN(C(=O)CO)CC2(C)C] |
134
TABLE 1-continued
| Example | Chemical Structure |
|---|---|
| 96 | 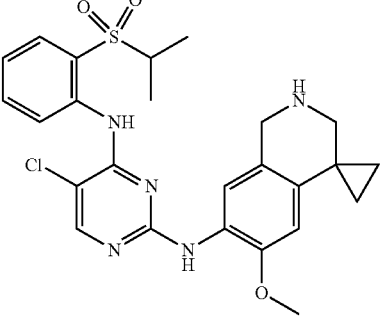 |
| 97 | 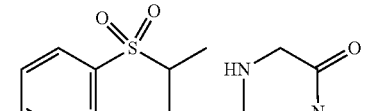 |
| 98 | 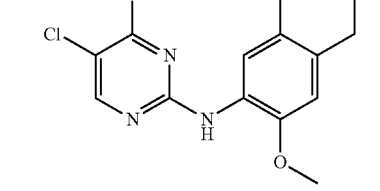 |
| 99 | 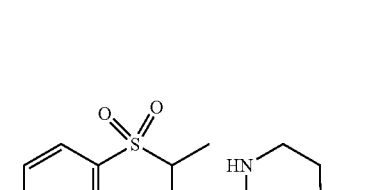 |

TABLE 1-continued

| Example | Chemical Structure |
|---|---|
| 100 | 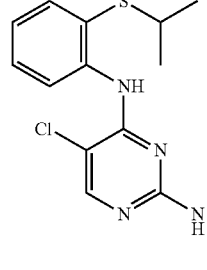 |
| 101 | 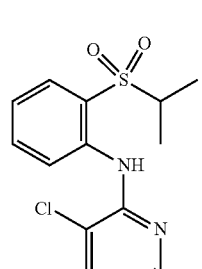 HCl |
| 102 | 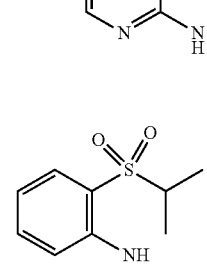 |
| 103 | 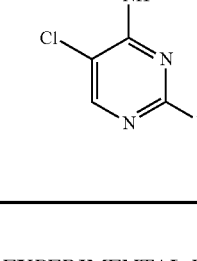 I |
| 104 | 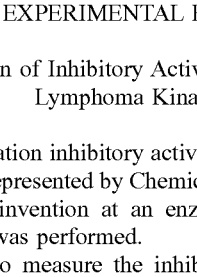 |
| 105 | 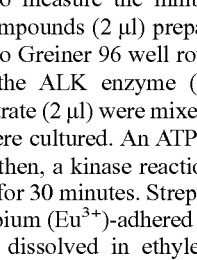 |
| 106 | 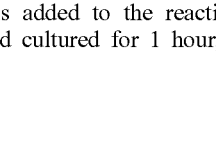 |

EXPERIMENTAL EXAMPLE 1

Evaluation of Inhibitory Activity Against Anaplastic Lymphoma Kinase (ALK)

A proliferation inhibitory activity against the ALK of the compound represented by Chemical Formula 1 according to the present invention at an enzyme level, the following experiment was performed.

In order to measure the inhibitory activity against the ALK, the compounds (2 μl) prepared in Examples 1 to 106 were added to Greiner 96 well round bottom plates, respectively, and the ALK enzyme (1 μl) and biotin-adhered peptide substrate (2 μl) were mixed for 15 minutes, and then, the plates were cultured. An ATP solution (5 μl) was added thereto, and then, a kinase reaction was performed at room temperature for 30 minutes. Streptavidin-adhered XL 665 (5 μl) and europium ($Eu^{3+}$)-adhered anti-phosphotyrosine antibody (5 μl) dissolved in ethylenediaminetetraacetic acid solution was added to the reaction solution to stop the reaction, and cultured for 1 hour, and analyzed by using homogeneous time-resolved fluorescence (HTRF, Cisbio) The compounds were read in a wavelength range of 615/665 nm using a Wallac Envision 2103 instrument. The $IC_{50}$ of each of the test compounds subjected to the above experiment was implemented using prism (version 5.01, GraphPad) software.

Accordingly, $IC_{50}$ of each of the compounds that reduce an ALK enzyme activity and a cell activity of L1196M (a non-small cell lung cancer cell including an ALK enzyme) to 50% was calculated, and as a result, it was found that all of the compounds prepared in Examples 1 to 106 according to the present invention had $IC_{50}$ values of 0.01 μM or less. In particular, specific results of the compounds of the Examples showing an $IC_{50}$ concentration that was equivalent or significantly lower than that of Comparative Example 2 (LDK-378) were shown in Table 2 below.

TABLE 2

| Example | ALK wt. $IC_{50}$ (μM) | ALK L1196M $IC_{50}$ (μM) |
| --- | --- | --- |
| Comparative Example 1 (crizotinib) | 0.036 | 0.22 |
| Comparative Example 2 (LDK-378) | 0.001 | 0.005 |
| 1 | <0.01 | <0.01 |
| 2 | 0.001 | <0.01 |
| 3 | <0.01 | <0.01 |
| 4 | <0.01 | <0.01 |
| 5 | 0.001 | <0.01 |
| 6 | <0.01 | <0.01 |
| 7 | <0.01 | <0.01 |
| 8 | 0.001 | <0.01 |
| 9 | <0.01 | <0.01 |
| 10 | <0.01 | <0.01 |
| 11 | <0.01 | <0.01 |
| 12 | <0.01 | <0.01 |
| 13 | <0.01 | 0.003 |
| 14 | 0.001 | 0.003 |
| 15 | <0.01 | <0.01 |
| 16 | <0.01 | <0.01 |
| 17 | <0.01 | <0.01 |
| 18 | 0.00021 | 0.0013 |
| 19 | <0.01 | <0.01 |
| 20 | <0.01 | 0.0012 |
| 21 | <0.01 | <0.01 |
| 22 | <0.01 | 0.0023 |
| 23 | <0.01 | <0.01 |
| 24 | <0.01 | <0.01 |
| 25 | 0.00024 | 0.0003 |
| 26 | <0.01 | <0.01 |
| 27 | 0.0003 | 0.0034 |
| 28 | <0.01 | <0.01 |
| 29 | <0.01 | <0.01 |
| 30 | <0.01 | <0.01 |
| 31 | <0.01 | <0.01 |
| 32 | <0.01 | <0.01 |
| 33 | 0.001 | 0.002 |
| 34 | 0.001 | <0.01 |
| 35 | <0.01 | <0.01 |
| 36 | <0.01 | <0.01 |
| 37 | <0.01 | <0.01 |
| 38 | <0.01 | <0.01 |
| 39 | <0.01 | <0.01 |
| 40 | <0.01 | <0.01 |
| 41 | 0.001 | <0.01 |
| 42 | <0.01 | <0.01 |
| 43 | <0.01 | <0.01 |
| 44 | <0.01 | <0.01 |
| 45 | 0.001 | 0.004 |
| 46 | <0.01 | 0.0013 |
| 47 | <0.01 | 0.003 |
| 48 | <0.01 | 0.003 |
| 49 | 0.00038 | 0.0013 |
| 50 | <0.01 | 0.0027 |
| 51 | 0.001 | 0.0012 |
| 52 | 0.00055 | 0.0007 |
| 53 | 0.00066 | 0.001 |
| 54 | 0.00078 | 0.0012 |
| 55 | <0.01 | 0.0023 |
| 56 | <0.01 | 0.001 |
| 57 | <0.01 | <0.01 |
| 58 | <0.01 | <0.01 |
| 59 | 0.001 | <0.01 |
| 60 | <0.01 | <0.01 |
| 61 | <0.01 | <0.01 |
| 62 | <0.01 | 0.0043 |
| 63 | 0.001 | <0.01 |
| 64 | <0.01 | 0.0033 |
| 65 | <0.01 | 0.003 |
| 66 | <0.01 | <0.01 |
| 67 | 0.00052 | <0.01 |
| 68 | <0.01 | <0.01 |
| 69 | <0.01 | <0.01 |
| 70 | <0.01 | <0.01 |
| 71 | <0.01 | <0.01 |
| 72 | <0.01 | <0.01 |
| 73 | <0.01 | <0.01 |
| 74 | <0.01 | <0.01 |
| 75 | <0.01 | <0.01 |
| 76 | <0.01 | <0.01 |
| 77 | <0.01 | <0.01 |
| 78 | <0.01 | <0.01 |
| 79 | <0.01 | <0.01 |
| 80 | <0.01 | <0.01 |
| 81 | <0.01 | <0.01 |
| 82 | <0.01 | <0.01 |
| 83 | <0.01 | <0.01 |
| 84 | <0.01 | <0.01 |
| 85 | <0.01 | <0.01 |
| 86 | <0.01 | <0.01 |
| 87 | <0.01 | <0.01 |
| 88 | <0.01 | <0.01 |
| 89 | <0.01 | <0.01 |
| 90 | <0.01 | <0.01 |
| 91 | <0.01 | <0.01 |
| 92 | <0.01 | <0.01 |
| 93 | <0.01 | <0.01 |
| 94 | <0.01 | <0.01 |
| 95 | <0.01 | <0.01 |
| 96 | <0.01 | <0.01 |
| 97 | <0.01 | <0.01 |
| 98 | <0.01 | <0.01 |
| 99 | <0.01 | <0.01 |
| 100 | <0.01 | <0.01 |
| 101 | <0.01 | <0.01 |
| 102 | <0.01 | <0.01 |
| 103 | <0.01 | <0.01 |
| 104 | <0.01 | <0.01 |
| 105 | <0.01 | <0.01 |
| 106 | <0.01 | <0.01 |

As shown in Table 2 above, it was shown that the compounds of the Examples according to the present invention had an excellent ability of inhibiting the ALK enzyme activity and the cell activity of L1196M which was the non-small cell lung cancer cell including the ALK enzyme.

Therefore, the compound represented by Chemical Formula 1 according to the present invention has an excellent effect of inhibiting the ALK activity, which may be effectively used not only as a composition for preventing or treating cancers such as non-small cell lung cancer, neuroblastoma, inflammatory myelofibroblastoma tumor, longitudinal rhabdomyosarcoma, myofibroblastoma, breast cancer, stomach cancer, lung cancer, melanoma, etc., but also as an inhibitor of the ALK activity.

EXPERIMENTAL EXAMPLE 2

Evaluation of Cancer Cell Proliferation Inhibition

The following experiment was performed to measure a cancer cell proliferation inhibitory ability of the compound represented by Chemical Formula 1 according to the present invention.

<2-1> Experimental Material

RPMI 1640 medium, fetal bovine serum (FBS) and trypsin used in cell culture were purchased from Gibco (Grand Island, N.Y.), and sodium bicarbonate, amphotericin B and gentamycin were purchased from Sigma Chemical Company.

In addition, reagents such as sulforhodamine (SRB) B, trisma base, and trichloroacetic acid (TCA) used in the cytotoxicity measurement experiment were purchased from Sigma Chemical Company. For the MTS assay, CellTiter $96^R$ Aqueous Non-Radioactive Cell Proliferation Assay product was purchased from Promega.

Further, a T-25 culture container, a 96-well plate used for cell culture, and disposable glasses used for other cell cultures were manufactured from Falcon (Lincoln Park, N.J).

<2-2> Used Equipment

The ELISA reader (microplate reader) for cytotoxicity measurement was E-max or SpectraMax 250 from Molecular Devices (Sunnyvale, Calif.).

<2-3> Experimental Method

Step 1: Cell Culture

The final dimethyl sulfoxide concentration was adjusted to be 0.5% or less.

Cancer cell lines used in the experiments were all human-derived cancer cell lines, specifically H2228 and H3122, which are non-small cell lung cancer cell lines.

The cells were cultured in RPMI 1640 medium supplemented with 10% fetal bovine serum (FBS) at 37° C. and 5% $CO_2$ incubator, and kept in subculture every 3 to 4 days.

Step 2: Evaluation of Proliferation Inhibitory Activity According to Compound Treatment $1 \times 10^4$ cells were plated into each well of a 96-well flat-bottom microplate, cultured for 24 hours so that the cells were adhered to the bottom surface, and then the culture medium was removed. To each well, the culture medium in which each of the compounds of Examples 1 to 106 was diluted was added and cultured for 72 hours. After completion of the culturing with the compound, the cytotoxicity was measured using a protein staining reagent (SRB), or by MTS assay. After completion of the culturing with the compounds of Examples 1 to 106, the culture medium was removed, cold TCA solution was treated in each well, and the cells were allowed to stand at 4° C. for 1 hour to be fixed. After the TCA solution was removed, the resultant product was dried at room temperature. Then, a staining solution in which 0.4% SRB was dissolved in 1% acetic acid solution was added, and the resultant product was left at room temperature for 30 minutes to stain the cells. Extra SRB that was not bound to the cells was washed away with 1% acetic acid solution, and 10 mM Tris buffer (Trisma base; unbuffered, and pH of 10.3 to 10.5) was added to the stained cells to elute SRB. The absorbance of each well was measured in a wavelength range of 520 nM using an ELISA reader (microplate reader).

From the OD values of the well (C) to which the drug was not added, each well (T) to which the drug was added, and the well (Tz) to which the drug was first added, the cytotoxicity of the drug was calculated by Equation: [(T−Tz)/(C−Tz)]100 when Tz=T, and Equation: [(T−Tz)/(Tz)]100 when Tz>T.

The cancer cell proliferation inhibition was measured using the MTS assay as follows. Specifically, after completion of the culturing with the compounds prepared in Examples 1 to 106, the PMS solution and the MTS solution constituting the product of CellTiter $96^R$ Aqueous Non-Radioactive Cell Proliferation Assay (Promega) were mixed, and 20 μL of the mixture was added to each well. Each culture medium was placed in an incubator for 4 hours, taken out and left at room temperature for 10 minutes. The absorbance at 490 nM was measured using a SpectraMax250 from Molecular Device, and then, $GI_{50}$ (Growth Inhibition 50%) indicating a proliferation inhibitory effect was calculated. As a result, it was found that all of the compounds prepared in Examples 1 to 106 according to the present invention had $GI_{50}$ values of 0.05 μM or less. In particular, specific results of the compounds of Examples showing the significantly low $GI_{50}$ than that of Comparative Example 2 (LDK-378) were shown in Table 3 below.

TABLE 3

| Example | H2228 $GI_{50}$ (μM) | H3122 $GI_{50}$ (μM) |
|---|---|---|
| Comparative Example 1 (crizotinib) | 0.085 | 0.28 |
| Comparative Example 2 (LDK-378) | 0.025 | 0.023 |
| 1 | 0.015 | <0.05 |
| 2 | 0.01 | 0.008 |
| 3 | <0.05 | <0.05 |
| 4 | <0.05 | <0.05 |
| 5 | <0.05 | <0.05 |
| 6 | <0.05 | <0.05 |
| 7 | <0.05 | <0.05 |
| 8 | 0.009 | <0.05 |
| 9 | <0.05 | <0.05 |
| 10 | <0.05 | <0.05 |
| 11 | <0.05 | <0.05 |
| 12 | <0.05 | <0.05 |
| 13 | <0.05 | <0.05 |
| 14 | <0.05 | <0.05 |
| 15 | <0.05 | <0.05 |
| 16 | <0.05 | <0.05 |
| 17 | <0.05 | <0.05 |
| 18 | 0.0052 | 0.0049 |
| 19 | <0.05 | <0.05 |
| 20 | <0.05 | <0.05 |
| 21 | <0.05 | <0.05 |
| 22 | <0.05 | <0.05 |
| 23 | <0.05 | <0.05 |
| 24 | <0.05 | <0.05 |
| 25 | <0.05 | 0.0089 |
| 26 | <0.05 | <0.05 |
| 27 | <0.05 | 0.0084 |
| 28 | <0.05 | 0.021 |
| 29 | <0.05 | <0.05 |
| 30 | <0.05 | <0.05 |
| 31 | <0.05 | <0.05 |
| 32 | <0.05 | <0.05 |
| 33 | 0.018 | 0.011 |
| 34 | 0.005 | 0.008 |
| 35 | <0.05 | <0.05 |
| 36 | 0.007 | <0.05 |
| 37 | <0.05 | <0.05 |
| 38 | <0.05 | <0.05 |
| 39 | 0.01 | <0.05 |
| 40 | 0.02 | <0.05 |
| 41 | 0.01 | 0.02 |
| 42 | <0.05 | <0.05 |
| 43 | <0.05 | <0.05 |
| 44 | <0.05 | <0.05 |
| 45 | <0.05 | <0.05 |

TABLE 3-continued

| Example | H2228 GI$_{50}$ (μM) | H3122 GI$_{50}$ (μM) |
|---|---|---|
| 46 | <0.05 | <0.05 |
| 47 | 0.02 | <0.05 |
| 48 | <0.05 | <0.05 |
| 49 | <0.05 | <0.05 |
| 50 | <0.05 | <0.05 |
| 51 | <0.05 | <0.05 |
| 52 | <0.05 | <0.05 |
| 53 | <0.05 | <0.05 |
| 54 | <0.05 | <0.05 |
| 55 | <0.05 | <0.05 |
| 56 | <0.05 | <0.05 |
| 57 | <0.05 | <0.05 |
| 58 | <0.05 | <0.05 |
| 59 | <0.05 | <0.05 |
| 60 | <0.05 | <0.05 |
| 61 | <0.05 | <0.05 |
| 62 | <0.05 | <0.05 |
| 63 | <0.05 | <0.05 |
| 64 | <0.05 | <0.05 |
| 65 | 0.015 | <0.05 |
| 66 | <0.05 | <0.05 |
| 67 | <0.05 | <0.05 |
| 68 | <0.05 | <0.05 |
| 69 | <0.05 | <0.05 |
| 70 | <0.05 | <0.05 |
| 71 | <0.05 | <0.05 |
| 72 | <0.05 | <0.05 |
| 73 | <0.05 | <0.05 |
| 74 | <0.05 | <0.05 |
| 75 | <0.05 | <0.05 |
| 76 | <0.05 | <0.05 |
| 77 | <0.05 | <0.05 |
| 78 | <0.05 | <0.05 |
| 79 | <0.05 | <0.05 |
| 80 | <0.05 | <0.05 |
| 81 | <0.05 | <0.05 |
| 82 | <0.05 | <0.05 |
| 83 | <0.05 | <0.05 |
| 84 | <0.05 | <0.05 |
| 85 | <0.05 | <0.05 |
| 86 | <0.05 | <0.05 |
| 87 | <0.05 | <0.05 |
| 88 | <0.05 | <0.05 |
| 89 | <0.05 | <0.05 |
| 90 | <0.05 | <0.05 |
| 91 | <0.05 | <0.05 |
| 92 | <0.05 | <0.05 |
| 93 | <0.05 | <0.05 |
| 94 | <0.05 | <0.05 |
| 95 | <0.05 | <0.05 |
| 96 | <0.05 | <0.05 |
| 97 | <0.05 | <0.05 |
| 98 | <0.05 | <0.05 |
| 99 | <0.05 | <0.05 |
| 100 | <0.05 | <0.05 |
| 101 | <0.05 | <0.05 |
| 102 | <0.05 | <0.05 |
| 103 | <0.05 | <0.05 |
| 104 | <0.05 | <0.05 |
| 105 | <0.05 | <0.05 |
| 106 | <0.05 | <0.05 |

As shown in Table 3, it was found that the compounds of the Examples according to the present invention had an excellent ability of inhibiting the ALKs of H2228 and H3122 which were non-small cell lung cancer cell lines, thereby reducing a proliferation activity thereof.

Therefore, the compound represented by Chemical Formula 1 according to the present invention has an excellent effect of inhibiting the ALK activity, which may be effectively used not only as a composition for preventing or treating cancers such as non-small cell lung cancer, neuroblastoma, inflammatory myelofibroblastoma tumor, longitudinal rhabdomyosarcoma, myofibroblastoma, breast cancer, stomach cancer, lung cancer, melanoma, etc., but also as an inhibitor of the ALK activity.

EXPERIMENTAL EXAMPLE 3

Evaluation of Cytotoxicity of BaF3 Cell Transfected with EML4-ALK

The following experiment was performed to measure cytotoxicity of the compound represented by Chemical Formula 1 according to the present invention on the BaF3 EML4-ALK L1196M and the BaF3 EML4-ALK WT cells.

Specifically, the EML4-ALK WT gene of the BaF3 cell was infected with lentivirus, thereby preparing the BaF3 EML4-ALK WT cell line in which the EML4-ALK WT was stably expressed. Further, the EML4-ALK L1196M gene of the BaF3 cell was infected with lentivirus, thereby preparing the BaF3 EML4-ALK L1196M cell line in which the EML4-ALK L1196M was stably expressed. The number of cells of two cell lines were measured, and 4,000 cells were placed in each well of 96-well plate with a volume of 90 μl. Then, the compounds prepared in the Examples were added to each well at concentrations of 10 μM, 2 μM, 0.4 μM, 0.08 μM, 0.016 μM, 0.0032 μM, 0.00064 μM and 0 μM, and put in a cell incubator at 37° C. for 3 days. After 3 days, 10 μl of WST-1 solution was added to each well, and when the color of the solution in each well was changed, the absorbance was measured at 450 nm using an ELISA (manufacturer: Molecular Devices, model name: EMax Endpoint ELISA Microplate reader). The measured values were used to calculate the amount of cells, and the IC$_{50}$ of the cytotoxicity of each compound was calculated. As a result, it was shown that all of the compounds prepared in Examples 1 to 106 according to the present invention had the IC$_{50}$ value of 0.05 μM or less. In particular, specific results of the compounds of the Examples showing the significantly lower IC$_{50}$ than that of Comparative Example 2 (LDK-378) were shown in Table 4 below.

TABLE 4

| Example | BaF3 EML4-ALK L1196M (μM) | BaF3 EML4-ALK WT (μM) |
|---|---|---|
| Comparative Example 1 (crizotinib) | 0.88 | 0.06 |
| Comparative Example 2 (LDK-378) | 0.041 | 0.019 |
| 1 | <0.05 | <0.05 |
| 2 | 0.036 | 0.0055 |
| 3 | <0.05 | <0.05 |
| 4 | <0.05 | <0.05 |
| 5 | <0.05 | <0.05 |
| 6 | <0.05 | <0.05 |
| 7 | <0.05 | <0.05 |
| 8 | 0.04 | 0.0091 |
| 9 | <0.05 | 0.0027 |
| 10 | <0.05 | <0.05 |
| 11 | <0.05 | <0.05 |
| 12 | <0.05 | <0.05 |
| 13 | <0.05 | <0.05 |
| 14 | <0.05 | <0.05 |
| 15 | <0.05 | <0.05 |
| 16 | <0.05 | <0.05 |
| 17 | <0.05 | <0.05 |
| 18 | 0.0085 | 0.004 |
| 19 | <0.05 | <0.05 |
| 20 | <0.05 | <0.05 |
| 21 | <0.05 | <0.05 |
| 22 | <0.05 | <0.05 |
| 23 | <0.05 | <0.05 |

TABLE 4-continued

| Example | BaF3 EML4-ALK L1196M (μM) | BaF3 EML4-ALK WT (μM) |
|---|---|---|
| 24 | <0.05 | <0.05 |
| 25 | 0.0037 | 0.0047 |
| 26 | <0.05 | <0.05 |
| 27 | 0.02 | 0.004 |
| 28 | <0.05 | 0.013 |
| 29 | <0.05 | <0.05 |
| 30 | <0.05 | 0.005 |
| 31 | <0.05 | <0.05 |
| 32 | <0.05 | <0.05 |
| 33 | 0.0097 | <0.05 |
| 34 | 0.02 | 0.0053 |
| 35 | <0.05 | <0.05 |
| 36 | 0.03 | 0.0084 |
| 37 | <0.05 | <0.05 |
| 38 | <0.05 | <0.05 |
| 39 | <0.05 | <0.05 |
| 40 | <0.05 | <0.05 |
| 41 | 0.04 | 0.011 |
| 42 | <0.05 | <0.05 |
| 43 | <0.05 | <0.05 |
| 44 | <0.05 | <0.05 |
| 45 | 0.033 | <0.05 |
| 46 | 0.023 | <0.05 |
| 47 | 0.03 | 0.018 |
| 48 | <0.05 | <0.05 |
| 49 | <0.05 | <0.05 |
| 50 | <0.05 | <0.05 |
| 51 | <0.05 | <0.05 |
| 52 | <0.05 | <0.05 |
| 53 | <0.05 | <0.05 |
| 54 | <0.05 | 0.016 |
| 55 | <0.05 | <0.05 |
| 56 | <0.05 | <0.05 |
| 57 | <0.05 | <0.05 |
| 58 | <0.05 | <0.05 |
| 59 | <0.05 | <0.05 |
| 60 | <0.05 | <0.05 |
| 61 | <0.05 | <0.05 |
| 62 | <0.05 | <0.05 |
| 63 | <0.05 | <0.05 |
| 64 | <0.05 | <0.05 |
| 65 | 0.03 | <0.05 |
| 66 | <0.05 | <0.05 |
| 67 | <0.05 | <0.05 |
| 68 | <0.05 | <0.05 |
| 69 | <0.05 | <0.05 |
| 70 | <0.05 | <0.05 |
| 71 | <0.05 | <0.05 |
| 72 | <0.05 | <0.05 |
| 73 | <0.05 | <0.05 |
| 74 | <0.05 | <0.05 |
| 75 | <0.05 | <0.05 |
| 76 | <0.05 | <0.05 |
| 77 | <0.05 | <0.05 |
| 78 | <0.05 | <0.05 |
| 79 | <0.05 | <0.05 |
| 80 | <0.05 | <0.05 |
| 81 | <0.05 | <0.05 |
| 82 | <0.05 | <0.05 |
| 83 | <0.05 | <0.05 |
| 84 | <0.05 | <0.05 |
| 85 | <0.05 | <0.05 |
| 86 | <0.05 | <0.05 |
| 87 | <0.05 | <0.05 |
| 88 | <0.05 | <0.05 |
| 89 | <0.05 | <0.05 |
| 90 | <0.05 | <0.05 |
| 91 | <0.05 | <0.05 |
| 92 | <0.05 | <0.05 |
| 93 | <0.05 | <0.05 |
| 94 | <0.05 | <0.05 |
| 95 | <0.05 | <0.05 |
| 96 | <0.05 | <0.05 |
| 97 | <0.05 | <0.05 |
| 98 | <0.05 | <0.05 |
| 99 | <0.05 | <0.05 |
| 100 | <0.05 | <0.05 |
| 101 | <0.05 | <0.05 |
| 102 | <0.05 | <0.05 |
| 103 | <0.05 | <0.05 |
| 104 | <0.05 | <0.05 |
| 105 | <0.05 | <0.05 |
| 106 | <0.05 | <0.05 |

As shown in Table 4, it was found that most of the compounds of the Examples according to the present invention had low cytotoxic $IC_{50}$ values in the BaF3 EML4-ALK WT (wild-type) cell and the BaF3 EML4-ALK L1196M cell that was resistant to crizotinib.

Therefore, the compound represented by Chemical Formula 1 according to the present invention has an excellent effect of inhibiting the ALK activity, which may be effectively used not only as a composition for preventing or treating cancers such as non-small cell lung cancer, neuroblastoma, inflammatory myelofibroblastoma tumor, longitudinal rhabdomyosarcoma, myofibroblastoma, breast cancer, stomach cancer, lung cancer, melanoma, etc., but also as an inhibitor of the ALK activity.

Meanwhile, the compound represented by Chemical Formula 1 according to the present invention is able to be formulated in a variety of forms depending on purposes.

Some examples of formulation methods in which the compound represented by Chemical Formula 1 according to the present invention is contained as an effective ingredient are provided as follows, but the present invention is not limited thereto.

FORMULATION EXAMPLE 1

Preparation of Pharmaceutical Formulation 1-1. Preparation of Powder
Compound represented by Chemical Formula 1: 500 mg
Lactose: 100 mg
Talc: 10 mg
These ingredients were mixed with each other and filled in an air-tight container to prepare powder.

1-2. Preparation of Tablet
Compound represented by Chemical Formula 1: 500 mg
Corn starch: 100 mg
Lactose: 100 mg
Magnesium stearate: 2 mg
These ingredients were mixed with each other and pressed according to the general tablet preparation method to prepare a tablet.

1-3. Preparation of Capsule
Compound represented by Chemical Formula 1 500 mg
Corn starch: 100 mg
Lactose: 100 mg
Magnesium stearate: 2 mg
According to the general capsule preparation method, these ingredients were mixed with each other and filled in a gelatin capsule to prepare a capsule.

1-4. Preparation of Injection
Compound represented by Chemical Formula 1: 500 mg
Sterilized distilled water for injection: Suitable amount
pH adjuster: Suitable amount The injection was prepared with the contents per 1 ampoule (2 ml) according to the general injection preparation method.

1-5. Preparation of Liquid Formulation

Compound represented by Chemical Formula 1 100 mg
Isomerized sugar: 10 g
Mannitol: 5 g
Purified water: Suitable amount Each ingredient was added and dissolved in purified water according to the general formulation method of liquid formulation, and a suitable amount of lemon scent was added, and the above-described ingredients were mixed. Then, the total amount was adjusted to 100 ml by adding purified water, and the mixture was filled in a brown bottle and sterilized to prepare a liquid formulation.

INDUSTRIAL APPLICABILITY

The compound according to the present invention has the remarkably excellent effect of inhibiting the activity of the anaplastic lymphoma kinase (ALK) to have an improved therapeutic effect on cancer cells having the ALK fusion protein such as EML4-ALK, NPM-ALK, etc., and to be effectively used in preventing recurrence of cancer. Therefore, the compound of the present invention may be useful as a pharmaceutical composition for preventing or treating cancer.

The invention claimed is:

1. A compound represented by Chemical Formula 1 below, an optical isomer thereof, or a pharmaceutically acceptable salt thereof:

[Chemical Formula 1]

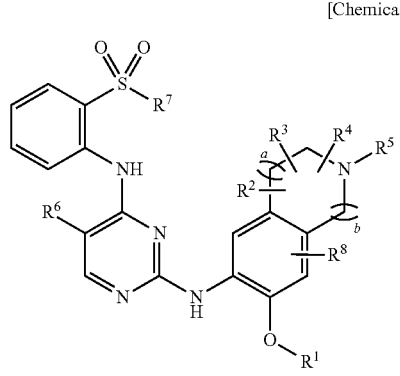

in Chemical Formula 1, a is an integer of 0 or 1, when a is 0, then b is 2, and when a is 1, then b is 1;

$R^1$ is $C_{1-10}$ straight or branched chain alkyl unsubstituted or substituted with at least one halogen;

$R^2$, $R^3$, $R^4$ are $R^5$ are independently —H, $C_{1-10}$ straight or branched chain alkyl unsubstituted or substituted with at least one halogen, $C_{1-10}$ straight or branched chain alkyl unsubstituted or substituted with at least one hydroxy group, unsubstituted 3-10 membered heterocycloalkyl including at least one heteroatom selected from the group consisting of N, O, and S, $C_{1-10}$ straight or branched chain alkyl substituted with unsubstituted $C_{6-10}$ aryl, —C(=O)$R^9$, —C(=O)NH$R^{10}$, —C(=O)(CH$_2$)$_r$OH, —SO$_2$N$R^{11}R^{12}$, —(CH$_2$)$_p$N$R^{13}R^{14}$, —(CH$_2$)$_q$C(=O)N$R^{15}R^{16}$ or —C(=O)(CH$_2$)$_k$N$R^{17}R^{18}$, wherein the $R^9$, $R^{10}$, $R^{11}$, $R^{12}$, $R^{13}$, $R^{14}$, $R^{15}$, $R^{16}$, $R^{17}$ and $R^{18}$ are independently —H or $C_{1-10}$ straight or branched chain alkyl unsubstituted or substituted with at least one halogen, the r, p, q and k are independently an integer of 0 to 10;

two substituents of the $R^2$, $R^3$, $R^4$, and $R^5$ may be simultaneously substituted on carbon atoms at the same position to form unsubstituted $C_{3-10}$ cycloalkyl, together with the carbon atoms to which they are connected;

two substituents of the $R^2$, $R^3$, $R^4$, and $R^5$ may be each substituted on adjacent atoms to form unsubstituted 5-10 membered heterocycloalkyl including at least one heteroatom selected from the group consisting of N, O, and S, together with the atoms to which they are connected;

$R^6$ is halogen;

$R^7$ is $C_{1-10}$ straight or branched chain alkyl; and $R^8$ is —H or halogen.

2. The compound, optical isomer thereof, or pharmaceutically acceptable salt thereof of claim 1, wherein a is an integer of 0 or 1, when a is 0, then b is 2, and when a is 1, then b is 1;

$R^1$ is $C_{1-5}$ straight or branched chain alkyl unsubstituted or substituted with at least one halogen;

$R^2$, $R^3$, $R^4$ are $R^5$ are independently —H, $C_{1-5}$ straight or branched chain alkyl unsubstituted or substituted with at least one halogen, $C_{1-5}$ straight or branched chain alkyl unsubstituted or substituted with at least one hydroxy group, unsubstituted 3-8 membered heterocycloalkyl including at least one heteroatom selected from the group consisting of N, O, and S, $C_{1-5}$ straight or branched chain alkyl substituted with unsubstituted $C_{6-8}$ aryl, —C(=O)$R^9$, —C(=O)NH$R^{10}$, —C(=O)(CH$_2$)$_r$OH, —SO$_2$N$R^{11}R^{12}$, —(CH$_2$)$_p$N$R^{13}R^{14}$, —(CH$_2$)$_q$C(=O)N$R^{15}R^{16}$ or —C(=O)(CH$_2$)$_k$N$R^{17}R^{18}$, wherein the $R^9$, $R^{10}$, $R^{11}$, $R^{12}$, $R^{13}$, $R^{14}$, $R^{15}$, $R^{16}$, $R^{17}$ and $R^{18}$ are independently —H or $C_{1-5}$ straight or branched chain alkyl unsubstituted or substituted with at least one halogen, the r, p, q and k are independently an integer of 0 to 5;

two substituents of the $R^2$, $R^3$, $R^4$, and $R^5$ may be simultaneously substituted on carbon atoms at the same position to form unsubstituted $C_{3-8}$ cycloalkyl, together with the carbon atoms to which they are connected;

two substituents of the $R^2$, $R^3$, $R^4$, and $R^5$ may be each substituted on adjacent atoms to form unsubstituted 5-8 membered heterocycloalkyl including at least one heteroatom selected from the group consisting of N, O, and S, together with the atoms to which they are connected;

$R^6$ is halogen;

$R^7$ is $C_{1-5}$ straight or branched chain alkyl; and $R^8$ is —H, —F, —Cl or —Br.

3. The compound, optical isomer thereof, or pharmaceutically acceptable salt thereof of claim 1, wherein a is an integer of 0 or 1, when a is 0, then b is 2, and when a is 1, then b is 1;

$R^1$ is methyl, difluoromethyl, ethyl, isopropyl, isobutyl or sec-butyl;

$R^2$, $R^3$, $R^4$ and $R^5$ are independently —H, methyl, ethyl, n-propyl, isopropyl, trifluoromethyl, benzyl,

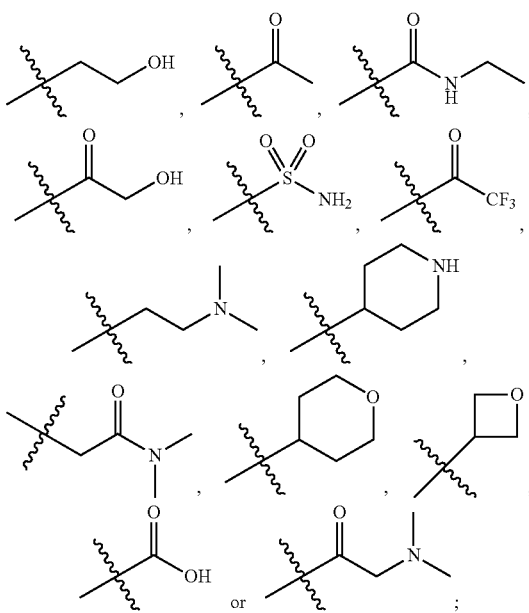

two substituents of the R², R³, R⁴, and R⁵ may be simultaneously substituted on carbon atoms at the same position to form unsubstituted cyclopropyl, cyclopentyl or cyclohexyl, together with the carbon atoms to which they are connected;

two substituents of the R², R³, R⁴, and R⁵ may be each substituted on adjacent atoms to form unsubstituted 6 membered heterocycloalkyl including at least one heteroatom selected from the group consisting of N, O, and S, together with the atoms to which they are connected;

R⁶ is —Cl;
R⁷ is isopropyl; and
R⁸ is —H, —Cl or —Br.

4. The compound, optical isomer thereof, or pharmaceutically acceptable salt thereof of claim 1, wherein the compound represented by Chemical Formula 1 is any one selected from the group consisting of compounds below:

(2) 5-chloro-N4-(2-(isopropylsulfonyl)phenyl)-N2-(7-methoxy-1,2,3,4-tetrahydroisoguinolin-6-yl)pyrimidine-2,4-diamine;
(3) 5-chloro-N4-(2-(isopropylsulfonyl)phenyl)-N2-(7-methoxy-2-methyl-1,2,3,4-tetrahydroisoguinolin-6-yl)pyrimidine-2,4-diamine;
(4) 5-chloro-N4-(2-(isopropylsulfonyl)phenyl)-N2-(7-methoxy-2-ethyl-1,2,3,4-tetrahydroisoguinolin-6-yl)pyrimidine-2,4-diamine;
(5) 5-chloro-N4-(2-(isopropylsulfonyl)phenyl)-N2-(7-methoxy-2-hydroxyethyl-1,2,3,4-tetrahydroisoguinolin-6-yl)pyrimidine-2,4-diamine;
(6) 5-chloro-N4-(2-(isopropylsulfonyl)phenyl)-N2-(7-methoxy-2-acetyl-1,2,3,4-tetrahydroisoguinolin-6-yl)pyrimidine-2,4-diamine;
(7) 6-(5-chloro-4-(2-(isopropylsulfonyl)phenylamino)pyrimidin-2-yl)amino-N-ethyl-7-methoxy-3,4-dihydroisoguinoline-2(1H)-carboxamide;
(8) 1-6-(5-chloro-4-(2-(isopropylsulfonyl)phenylamino)pyrimidin-2-yl)amino-7-methoxy-3,4-dihydroisoguinolin-2(1H)-yl-2-hydroxyethane-1-one;
(9) 6-(5-chloro-4-(2-(isopropylsulfonyl)phenylamino)pyrimidin-2-yl)amino-7-methoxy-3,4-dihydroisoquinoline-2(1H)-sulfonamide;
(10) 2-(6-(5-chloro-4-(2-(isopropylsulfonyl)phenylamino)pyrimidin-2-yl)amino-7-methoxy-3,4-dihydroisoquinolin-2(1H)-yl)-N,N-dimethylacetamide;
(11) 1-(6-(5-chloro-4-(2-(isopropylsulfonyl)phenylamino)pyrimidin-2-yl)amino-7-methoxy-4,4-dimethyl-3,4-dihydroisoquinolin-2(1H)-yl)-2,2,2-trifluoroethane-1-one;
(12) 5-chloro-N4-(2-(isopropylsulfonyl)phenyl)-N2-(7-methoxy-4,4-dimethyl-1,2,3,4-tetrahydroisoquinolin-6-yl)pyrimidine-2,4-diamine;
(13) 1-(6'-(5-chloro-4-(2-(isopropylsulfonyl)phenylamino)pyrimidin-2-yl)amino-7-methoxy-1'H-spiro[cyclopentane-1,4'-isoquinoline]-2'(3'H)-yl)-2,2,2-trifluoroethane-1-one;
(14) 5-chloro-N4-(2-(isopropylsulfonyl)phenyl)-N2-(7-methoxy-2',3'-dihydro-1'H-spiro[cyclopentane-1,4'-isoquinoline]-6'-yl)pyrimidine-2,4-diamine;
(15) 1-(6-(5-chloro-4-(2-(isopropylsulfonyl)phenylamino)pyrimidin-2-yl)amino-7-methoxy-1'H-spiro[cyclohexane-1,4'-isoquinoline]-2'(3'H)-yl)-2,2,2-trifluoroethane-1-one;
(16) 5-chloro-N4-(2-(isopropylsulfonyl)phenyl)-N2-(7-methoxy-2',3'-dihydro-1'H-spiro[cyclohexane-1,4'-isoquinoline]-6'-yl)pyrimidine-2,4-diamine;
(17) 1-(6-(5-chloro-4-(2-(isopropylsulfonyl)phenylamino)pyrimidin-2-yl)amino-7-isopropoxy-3,4-dihydroisoquinolin-2(1H)-yl)-2,2,2-trifluoroethane-1-one;
(18) 5-chloro-N4-(2-(isopropylsulfonyl)phenyl)-N2-(7-isopropoxy-1,2,3,4-tetrahydroisoquinolin-6-yl)pyrimidine-2,4-diamine;
(19) 1-(6-(5-chloro-4-(2-(isopropylsulfonyl)phenylamino)pyrimidine-2-yl)amino-7-isobutoxy-3,4-dihydroisoquinolin-2(1H)-yl)-2,2,2-trifluoroethane-1-one;
(20) 5-chloro-N4-(2-(isopropylsulfonyl)phenyl)-N2-(7-isobutoxy-1,2,3,4-tetrahydroisoquinolin-6-yl)pyrimidine-2,4-diamine;
(21) 1-(7-(sec-butoxy)-6-(5-chloro-4-(2-(isopropylsulfonyl)phenylamino)pyrimidin-2-yl)amino-3,4-dihydroisoquinolin-2(1H)-yl)-2,2,2-trifluoroethane-1-one;
(22) 5-chloro-N2-(7-(sec-butoxy)-1,2,3,4-tetrahydroisoquinolin-6-yl)-N4-(2-(isopropylsulfonyl)phenyl)pyrimidine-2,4-diamine;
(23) 5-chloro-N2-(2-(2-(dimethylaminoethyl)-7-methoxy-1,2,3,4-tetrahydroisoquinolin-6-yl)-N4-2-(isopropylsulfonyl)phenyl)pyrimidine-2,4-diamine;
(24) 5-chloro-N4-2-(isopropylsulfonyl)phenyl)-N2-(7-methoxy-2-(piperidine-4-yl)-1,2,3,4-tetrahydroisoquinolin-6-yl)pyrimidine-2,4-diamine;
(25) 5-chloro-N4-(2-(isopropylsulfonyl)phenyl)-N2-(7-methoxy-1-methyl-1,2,3,4-tetrahydroisoquinolin-6-yl)pyrimidine-2,4-diamine;
(26) 5-chloro-N4-(2-(isopropylsulfonyl)phenyl)-N2-(7-methoxy-1-trifluoromethyl-1,2,3,4-tetrahydroisoquinolin-6-yl)pyrimidine-2,4-diamine;
(27) 5-chloro-N4-2-(isopropylsulfonyl)phenyl)-N2-(7-methoxy-1-ethyl-1,2,3,4-tetrahydroisoquinolin-6-yl)pyrimidine-2,4-diamine;
(28) 5-chloro-N4-2-(isopropylsulfonyl)phenyl)-N2-(7-methoxy-1-isopropyl-1,2,3,4-tetrahydroisoquinolin-6-yl)pyrimidine-2,4-diamine;
(29) 1-(6'-(5-chloro-4-(2-(isopropylsulfonyl)phenylamino)pyrimidin-2-yl)amino-7'-methoxy-1'- methyl-1',4'-dihydro-2'H-spiro[cyclopropane-1,3'-isoquinoline]-2'-yl)-2,2,2-trifluoroethane-1-one;
(30) 5-chloro-N4-(2-(isopropylsulfonyl)phenyl)-N2-(7-methoxy-1'methyl-1',4'-dihydro-2'H-spiro[cyclopropane-1,3'-isoquinoline]-6'-yl)pyrimidine-2,4-diamine;
(31) 5-chloro-N4-(2-(isopropylsulfonyl)phenyl)-N2-(2-benzyl-7-methoxy-1,1-dimethyl-1,2,3,4-tetrahydroisoquinolin-6-yl)pyrimidine-2,4-diamine;
(32) 1-(6-(5-chloro-4-(2-(isopropylsulfonyl)phenylamino)pyrimidin-2-yl)amino-7-methoxy-1,1-dimethyl-3,4-dihydroisoquinolin-2(1H)-yl)-2,2,2-trifluoroethane-1-one;
(33) 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine;
(34) 5-chloro-N4-(2-(isopropylsulfonyl)phenyl)-N2-(6-methoxy-1,2,3,4-tetrahydroisoquinolin-7-yl)pyrimidine-2,4-diamine;
(35) 5-chloro-N4-(2-(isopropylsulfonyl)phenyl)-N2-(6-methoxy-2-methyl-1,2,3,4-tetrahydroisoquinolin-7-yl)pyrimidine-2,4-diamine;
(36) 2-(7-(5-chloro-4-(2-(isopropylsulfonyl)phenylamino)pyrimidin-2-yl)amino)-6-methoxy-3,4-dihydroisoquinolin-2(1H)-yl)-ethane-1-ol;
(37) 1-(7-(5-chloro-4-(2-(isopropylsulfonyl)phenylamino)pyrimidin-2-yl)amino)-6-methoxy-3,4-dihydroisoquinolin-2(1H)-yl)ethane-1-one;
(38) 7-(5-chloro-4-(2-(isopropylsulfonyl)phenylamino)pyrimidin-2-yl)amino)-N-ethyl-6-methoxy-3,4-dihydroisoquinolin-2(1H)-carboxamide;
(39) 1-(7-(5-chloro-4-(2-(isopropylsulfonyl)phenylamino)pyrimidin-2-yl)amino)-6-methoxy-3,4-dihydroisoquinolin-2(1H)-yl)-2-hydroxyethane-1-one;
(40) 7-(5-chloro-4-(2-(isopropylsulfonyl)phenylamino)pyrimidin-2-yl)amino)-6-methoxy-3,4-dihydroisoquinoline-2(1H)-sulfonamide;
(41) 5-chloro-N4-(2-(isopropylsulfonyl)phenyl)-N2-(6-methoxy-2-ethyl-1,2,3,4-tetrahydroisoquinolin-7-yl)pyrimidine-2,4-diamine;
(42) 2-(7-(5-chloro-4-(2-(isopropylsulfonyl)phenylamino)pyrimidin-2-yl)amino)-6-methoxy-3,4-dihydroisoquinolin-2(1H)-yl)-N,N-dimethylacetamide;
(43) 5-chloro-N4-(2-(isopropylsulfonyl)phenyl)-N2-(2-(2-(dimethylaminoethyl)-6-methoxy-1,2,3,4-tetrahydroquinolin-7-yl)pyrimidine-2,4-diamine;
(45) 5-chloro-N4-(2-(isopropylsulfonyl)phenyl)-N2-(6-methoxy-2-(piperidine-4-yl)-1,2,3,4-tetrahydroquinolin-7-yl)pyrimidine-2,4-diamine;
(46) 5-chloro-N4-(2-(isopropylsulfonyl)phenyl)-N2-(6-methoxy-1-methyl-1,2,3,4-tetrahydroquinolin-7-yl)pyrimidine-2,4-diamine;
(70) 5-chloro-N4-(2-(isopropylsulfonyl)phenyl)-N2-(7-isopropoxy-1-methyl-1,2,3,4-tetrahydroisoquinolin-6-yl)pyrimidine-2,4-diamine;
(71) 5-chloro-N4-(2-(isopropylsulfonyl)phenyl)-N2-(7-isopropoxy-1,1-dimethyl-1,2,3,4-tetrahydroisoquinolin-6-yl)pyrimidine-2,4-diamine;
(72) 5-chloro-N4-(2-(isopropylsulfonyl)phenyl)-N2-(6-methoxy-1,1-dimethyl-1,2,3,4-tetrahydroisoquinolin-7-yl)pyrimidine-2,4-diamine;
(73) 5-chloro-N4-(2-(isopropylsulfonyl)phenyl)-N2-(1-ethyl-7-methoxy-1-methyl-1,2,3,4-tetrahydroisoquinolin-6-yl)pyrimidine-2,4-diamine;
(74) 5-chloro-N4-(2-(isopropylsulfonyl)phenyl)-N2-(1,1-diethyl-7-methoxy-1,2,3,4-tetrahydroisoquinolin-6-yl)pyrimidine-2,4-diamine;
(75) 5-chloro-N4-(2-(isopropylsulfonyl)phenyl)-N2-(6-methoxy-4,4-dimethyl-1,2,3,4-tetrahydroisoquinolin-7-yl)pyrimidine-2,4-diamine;
(76) 6-(5-chloro-4-(2-(isopropylsulfonyl)phenylamino)pyrimidin-2-yl)amino-7-methoxy-1,2,3,4-dihydroisoquinoline-1-carboxylic acid;
(77) 5-chloro-N4-(2-(isopropylsulfonyl)phenyl)-N2-(2-ethyl-7-methoxy-1,1-dimethyl-1,2,3,4-tetrahydroisoquinolin-6-yl)pyrimidine-2,4-diamine;
(78) 1-6-(5-chloro-4-(2-(isopropylsulfonyl)phenylamino)pyrimidin-2-yl)amino-7-methoxy-1,1-dimethyl-3,4-dihydroisoquinolin-2(1H)-yl-2-hydroxyethane-1-one;
(79) 5-chloro-N4-(2-(isopropylsulfonyl)phenyl)-N2-(2-ethyl-7-isopropoxy-1,1-dimethyl-1,2,3,4-tetrahydroisoquinolin-6-yl)pyrimidine-2,4-diamine;
(80) 5-chloro-N4-(2-(isopropylsulfonyl)phenyl)-N2-(6-isopropoxy-4,4-dimethyl-1,2,3,4-tetrahydroisoquinolin-7-yl)pyrimidine-2,4-diamine;
(81) 5-chloro-N4-(2-(isopropylsulfonyl)phenyl)-N2-(6-ethoxy-2-ethyl-4,4-dimethyl-1,2,3,4-tetrahydroisoquinolin-7-yl)pyrimidine-2,4-diamine;
(82) 5-chloro-N4-(2-(isopropylsulfonyl)phenyl)-N2-(2-ethyl-6-isopropoxy-4,4-dimethyl-1,2,3,4-tetrahydroisoquinolin-7-yl)pyrimidine-2,4-diamine;
(83) 5-chloro-N4-(2-(isopropylsulfonyl)phenyl)-N2-(6-methoxy-2,3-dihydro-1H-spiro(cyclopentane-1,4-isoquinoline)-7-yl)pyrimidine-2,4-diamine;
(86) 5-chloro-N4-(2-(isopropylsulfonyl)phenyl)-N2-(9-methoxy-7,7-dimethyl-1,3,4,6,7,11b-hexahydro-2H-pyrazino[2,1-a]isoquinolin-10-yl)pyrimidine-2,4-diamine;
(87) 5-chloro-N4-(2-(isopropylsulfonyl)phenyl)-N2-(5-bromo-7-methoxy-1,1-dimethyl-1,2,3,4-tetrahydroisoquinolin-6-yl)pyrimidine-2,4-diamine;
(88) 5-chloro-N4-(2-(isopropylsulfonyl)phenyl)-N2-(5-chloro-7-methoxy-1,1-dimethyl-1,2,3,4-tetrahydroisoquinolin-6-yl)pyrimidine-2,4-diamine;
(89) 5-chloro-N4-(2-(isopropylsulfonyl)phenyl)-N2-(8-bromo-7-methoxy-1,1-dimethyl-1,2,3,4-tetrahydroisoquinolin-6-yl)pyrimidine-2,4-diamine;
(90) 5-chloro-N4-(2-(isopropylsulfonyl)phenyl)-N2-(8-chloro-7-methoxy-1,1-dimethyl-1,2,3,4-tetrahydroisoquinolin-6-yl)pyrimidine-2,4-diamine;
(91) 5-chloro-N4-(2-(isopropylsulfonyl)phenyl)-N2-(6-methoxy-2,4,4-trimethyl-1,2,3,4-tetrahydroisoquinolin-7-yl)pyrimidine-2,4-diamine;
(92) 5-chloro-N4-(2-(isopropylsulfonyl)phenyl)-N2-(2-ethyl-6-methoxy-4,4-trimethyl-1,2,3,4-tetrahydroisoquinolin-7-yl)pyrimidine-2,4-diamine;
(93) 2-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)ethane-1-ol;
(94) 1-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)-2-(dimethylamino)ethane-1-one;
(95) 1-(7-((5-chloro-4-((2-(isopropylsulfonyl)phenylamino)pyrimidin-2-yl)amino)-6-methoxy-4,4-dimethyl-3,4-dihydroisoquinolin-2(1H)-yl)-2- hydroxyethane-1-one;
(96) 5-chloro-N4-(2-(isopropylsulfonyl)phenyl)-N2-(6-methoxy-2,3-dihydro-1H-spiro(cyclopropane-1,4-isoquinoline)-7-yl)pyrimidine-2,4-diamine;
(98) 5-chloro-N4-(2-(isopropylsulfonyl)phenyl)-N2-(9-methoxy-1,3,4,6,7-11b -hexahydro-2H-pyrazino[2,1-a]isoquinolin-10-yl)pyrimidine-2,4-diamine;
(99) 5-chloro-N4-(2-(isopropylsulfonyl)phenyl)-N2-(7-ethoxy-1,1-dimethyl-1,2,3,4-tetrahydroisoquinolin-6-yl)pyrimidine-2,4-diamine;
(100) 5-chloro-N4-(2-(isopropylsulfonyl)phenyl)-N2-(7-difluoromethoxy-1,1-dimethyl-1,2,3,4-tetrahydroisoquinolin-6-yl)pyrimidine-2,4-diamine;

(101) 5-chloro-N4-(2-(isopropylsulfonyl)phenyl)-N2-(7-methoxy-1,1-dimethyl-1,2,3,4-tetrahydroisoquinolin-6-yl)pyrimidine-2,4-diamine hydrochloride;
(102) 5-chloro-N4-(2-(isopropylsulfonyl)phenyl)-N2-(7-methoxy-1-propyl-1,2,3,4-tetrahydroisoquinolin-6-yl)pyrimidine-2,4-diamine; and
(103) 6-((5-chloro-4-((2-(isopropylsulfonyl)phenyl)amino)pyridin-2-yl)amino)-7-methoxy-2,2-dimethyl-1,2,3,4-tetrahydroisoquinolin-2-ium iodide.

5. A pharmaceutical composition for treating cancer comprising:
compound represented by Chemical Formula 1 of claim 1, an optical isomer thereof, or a pharmaceutically acceptable salt thereof, as an effective ingredient.

6. The pharmaceutical composition of claim 5, wherein the pharmaceutical composition inhibits an activity of anaplastic lymphoma kinase (ALK) to inhibit expression and growth of cancer cells.

7. The pharmaceutical composition of claim 5, wherein the cancer is non-small cell lung cancer, neuroblastoma, inflammatory myelofibroblastoma tumor, longitudinal rhabdomyosarcoma, myofibroblastoma, breast cancer, stomach cancer, lung cancer, melanoma, large B-cell lymphoma, systemic histiocytosis, inflammatory myofibroblastic sarcoma, or esophageal squamous cell carcinoma.

8. A pharmaceutical composition for treating diseases caused by an anaplastic lymphoma kinase (ALK) hyperactivity, the pharmaceutical composition comprising:
compound represented by Chemical Formula 1 of claim 1, an optical isomer thereof, or a pharmaceutically acceptable salt thereof, as an effective ingredient.

9. An anaplastic lymphoma kinase (ALK) inhibitor comprising:
compound represented by Chemical Formula 1 of claim 1, an optical isomer thereof, or a pharmaceutically acceptable salt thereof, as an effective ingredient.

10. A method of preparing a compound represented by Chemical Formula 1 as shown in Reaction Scheme 1 below, the method comprising:
reacting a compound represented by Chemical Formula 2 with a compound represented by Chemical Formula 3 to prepare a compound represented by Chemical Formula 4 (Step 1);
substituting a -Boc group of the compound represented by Chemical Formula 4 obtained in step 1 with hydrogen to prepare a compound represented by Chemical Formula 5 (Step 2); and
reacting the compound represented by Chemical Formula 5 obtained in step 2 with a compound represented by Chemical Formula 6 to prepare the compound represented by Chemical Formula 1 (Step 3):

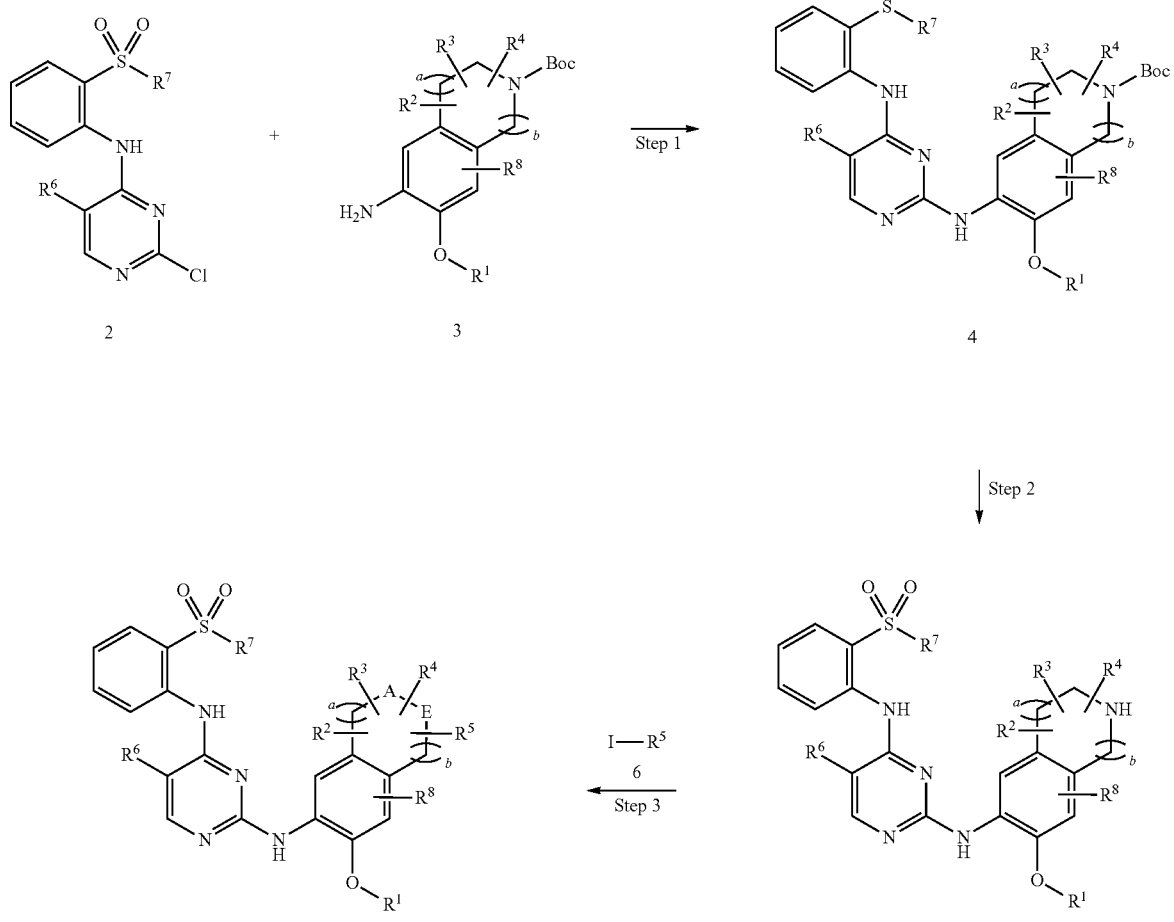

[Reaction Scheme 1]

in Reaction Scheme 1,
-Boc is
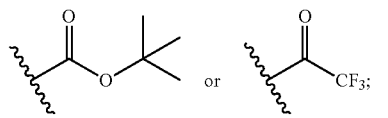
and
$R^1$, $R^2$, $R^3$, $R^4$, $R^5$, $R^6$, $R^7$, $R^8$, A, E, a, and b are the same as defined in Chemical Formula 1 of claim 1.
* * * * *